US010508275B2

(12) United States Patent
Roberts

(10) Patent No.: US 10,508,275 B2
(45) Date of Patent: Dec. 17, 2019

(54) METHOD FOR THE CONSTRUCTION OF SPECIFIC PROMOTERS

(75) Inventor: Michael L. Roberts, Dalkeith (GB)

(73) Assignee: Synpromics Ltd., Edinburgh (GB)

( * ) Notice: Subject to any disclaimer, the term of this patent is extended or adjusted under 35 U.S.C. 154(b) by 1143 days.

(21) Appl. No.: 13/981,894

(22) PCT Filed: Jan. 25, 2012

(86) PCT No.: PCT/EP2012/051174
§ 371 (c)(1),
(2), (4) Date: Jul. 25, 2013

(87) PCT Pub. No.: WO2012/101191
PCT Pub. Date: Aug. 2, 2012

(65) Prior Publication Data
US 2013/0324440 A1    Dec. 5, 2013

(30) Foreign Application Priority Data
Jan. 25, 2011    (EP) .................................... 11000572

(51) Int. Cl.
C12N 15/10      (2006.01)
C12N 15/79      (2006.01)
C12N 15/113     (2010.01)
C12N 15/85      (2006.01)

(52) U.S. Cl.
CPC ........ *C12N 15/1086* (2013.01); *C12N 15/113* (2013.01); *C12N 15/79* (2013.01); *C12N 15/85* (2013.01)

(58) Field of Classification Search
None
See application file for complete search history.

(56) References Cited

U.S. PATENT DOCUMENTS

2005/0227246 A1    10/2005    Hahm
2006/0085138 A1    4/2006     Klingenhoff

FOREIGN PATENT DOCUMENTS

JP      2007334769 A      12/2007
JP      2008516590 A      5/2008
WO      WO-2008/107725   9/2008

OTHER PUBLICATIONS

Odagiri et al (1996 JBC 271:1909-15).*
Blanchette et al., "Genome-wide computational prediction of transcriptional regulatory modules reveals new insights into human gene expression," Genome Res (2006) 16(5):656-668.
Blanco et al., "ABS: a database of Annotated regulatory Binding Sites from orthologous promoters," Nucleic Acids Res (2006) 34:D63-D67.
Bussemaker et al., "Regulatory element detection using correlation with expression," Nat Genet (2001) 27(2):167-171.
Dai et al., "Identification of synthetic endothelial cell-specific promoters by use of a high-throughput screen," J Virol (2004) 78(12):6209-6221.
Davuluri et al., "Computational identification of promoters and first exons in the human genome," Nat Genet (2001) 29(4):412-417.
Dieterich et al., "CORG: a database for COmparative Regulatory Genomics," Nucleic Acids Res (2003) 31(1):55-57.
Dubchak et al., "Vista family of computational tools for comparative analysis of DNA sequences and whole genomes," Methods Mol Biol (2006) 338:69-89.
Edelman et al., "Synthetic promoter elements obtained by nucleotide sequence variation and selection for activity," Proc Natl Acad Sci USA (2000) 97(7):3038-3043.
European Search Report for EP2479278, dated Oct. 6, 2011, 4 pages.
Ferretti et al., "PReMod: a database of genome-wide mammalian cis-regulatory module predictions," Nucleic Acids Res (2007) 35:D122-D126.
International Preliminary Report on Patentability for PCT/EP2012/051174, dated Jul. 30, 2013, 7 pages.
International Search Report and Written Opinion for PCT/EP2012/051174, dated Apr. 3, 2012, 11 pages.
Jagannathan et al., "HTPSELEX—a database of high-throughput SELEX libraries for transcription factor binding sites," (2006) 34:D90-D94.
Jegga et al., "CisMols Analyzer: identification of compositionally similar cis-element clusters in ortholog conserved regions of coordinately expressed genes," Nucleic Acids Res (2005) 33:W408-W411.
Jegga et al., "Detection and visualization of compositionally similar cis-regulatory element clusters in orthologous and coordinately controlled genes," Genome Res (2002) 12(9):1408-1417.
Jensen et al., "Automatic discovery of regulatory patterns in promoter regions based on whole cell expression data and functional annotation," Bioinformatics (2000) 16(4):326-333.
Karanam et al., "CONFAC: automated application of comparative genomic promoter analysis to DNA microarray datasets," Nucleic Acids Res (2004) 32:W475-W484.
Kel-Margoulis et al., "TRANSCompel: a database on composite regulatory elements in eukaryotic genes," Nucleic Acids Res (2002) 30(1):332-334.
Lardenois et al., "PromAn: an integrated knowledge-based web server dedicated to promoter analysis," Nucleic Acids Res (2006) 34:W578-W583.
La Rosa et al., "VAMP: visualization and analysis of array-CGH, transcriptome and other molecular profiles," Bioinformatics (2006) 22(17):2066-2073.
Lenhard et al., "Identification of conserved regulatory regions by comparative genome analysis," J Biol (2003) 2:13.1-13.11.

(Continued)

*Primary Examiner* — Christopher M Gross
(74) *Attorney, Agent, or Firm* — Marshall, Gerstein & Borun LLP

(57) ABSTRACT

The present application relates to a system for designing promoters for selective expression of genes. Thereby identified transcription regulatory elements are selected according to a specific methodology and used to create a library of transcription regulatory elements, which are then used to construct specific promoters, especially tissue-specific promoters.

11 Claims, 9 Drawing Sheets

Specification includes a Sequence Listing.

(56) References Cited

OTHER PUBLICATIONS

Li et al., "Synthetic muscle promoters: activities exceeding naturally occurring regulatory sequences," Nat Biotechnol (1999) 17(3):241-245.

Liu et al., "CRSD: a comprehensive web server for composite regulatory signature discovery," Nucleic Acids Res (2006) 34:W571-577.

Matys et al., "TRANSFAC: transcriptional regulation, from patterns to profiles," Nucleic Acids Res (2003) 31(1):374-378.

Needleman and Wunsch, "A general method applicable to the search for similarities in the amino acid sequence of two proteins," J Mol Biol (1970) 48(3):443-453.

Rebeiz et al., "SCORE: a computational approach to the identification of cis-regulatory modules and target genes in whole-genome sequence data. Site clustering over random expectation," Proc Natl Acad Sci USA (2002) 99(15):9888-9893.

Rhodes et al., "Large-scale meta-analysis of cancer microarray data identifies common transcriptional profiles of neoplastic transformation and progression," Proc Natl Acad Sci USA (2004) 101(25):9309-9314.

Rhodes et al., "Mining for regulatory programs in the cancer transcriptome," Nat Genet (2005) 37(6):579-583.

Roth et al., "Finding DNA regulatory motifs within unaligned noncoding sequences clustered by whole-genome mRNA quantitation," Nat Biotechnol (1998) 16(10):939-945.

Sandelin et al., "JASPAR: an open-access database for eukaryotic transcription factor binding profiles," (2004) 32:D91-D94.

Segal et al., "Module networks: identifying regulatory modules and their condition-specific regulators from gene expression data," Nat Genet (2003) 34(2):166-176.

Segal et al., "A module map showing conditional activity of expression modules in cancer," Nat Genet (2004) 36(10):1090-1098.

Sharov et al., "CisView: a browser and database of cis-regulatory modules predicted in the mouse genome," DNA Res (2006) 13(3):123-134.

Sinha et al., "Discovery of novel transcription factor binding sites by statistical overrepresentation," Nucleic Acids Res (2002) 30(24):5549-5560.

Sinha et al., "YMF: A program for discovery of novel transcription factor binding sites by statistical overrepresentation," Nucleic Acids Res (2003) 31(13):3568-3588.

Sun et al., "MPromDb: an integrated resource for annotation and visualization of mammalian gene promoters and ChIP-chip experimental data," Nucleic Acids Res (2006) 34:D98-D103.

Suzuki et al., "DBTSS: DataBase of human Transcriptional Start Sites and full-length cDNAs," Nucleic Acids Res (2002) 30(1):328-331.

Suzuki et al., "DBTSS, DataBase of Transcriptional Start Sites: progress report 2004," Nucleic Acids Res (2004) 32:D78-D81.

Vega et al., "BEARR: Batch Extraction and Analysis of cis-Regulatory Regions," Nucleic Acids Res (2004) 32:W257-W260.

Wingender, "Compilation of transcription regulating proteins," Nucleic Acids Res (1988) 16(5):1879-1902.

Zhao et al., "TRED: a Transcriptional Regulatory Element Database and a platform for in silico gene regulation studies," Nucleic Acids Res (2005) 33:D103-D107.

\* cited by examiner

HT29

NEURO2A

CMV-beta       Mucin-1        CRCSE

SEQUENCE LISTING

<160> NUMBER OF SEQ ID NOS: 253

<210> SEQ ID NO 1
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="DNA"
      /organism="Homo sapiens"

<400> SEQUENCE: 1
gctgggatta caggtgtgag                                        20

<210> SEQ ID NO 2
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="DNA"

/note="description of artifical sequence: Primer for pSmoothy
vectorSYN1S"
/organism="Artificial Sequence"

<400> SEQUENCE: 2
tatctgcagt aggcgccgga attc                                          24

<210> SEQ ID NO 3
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="DNA"
       /note="Description of artificial sequence: primer for pSmoothy
       vectorSYN1AS"
       /organism="Artificial Sequence"

<400> SEQUENCE: 3
gcaatccatg gtggtggtga aatg                                          24

<210> SEQ ID NO 4
<211> LENGTH: 6773
<212> TYPE: DNA
<213> ORGANISM: Artificial Sequence
<220> FEATURE:
<221> NAME/KEY: source
<222> LOCATION: 1..6773
<223> OTHER INFORMATION: /mol_type="DNA"
       /note="Description for artificial sequence: pSmoothy vector
       sequence"
       /organism="Artificial Sequence"

<400> SEQUENCE: 4

| | | | | | |
|---|---|---|---|---|---|
| gttaccttct | gctctgcaga | atggccaacc | tttaacgtcg | gatggccgcg | agacggcacc | 60 |
| tttaaccgag | acctcatcac | ccaggttaag | atcaaggtct | tttcacctgg | cccgcatgga | 120 |
| cacccagacc | aggtccccta | catcgtgacc | tgggaagcct | tggcttttga | ccccctccc | 180 |
| tgggtcaagc | cctttgtaca | ccctaagcct | ccgcctcctc | ttcctccatc | cgccccgtct | 240 |
| ctcccccttg | aacctcctcg | ttcgaccccg | cctcgatcct | cccttatcc | agccctcact | 300 |
| ccttctctag | gcgccggaat | tcgttaactc | gagctcaagc | ttcgaattct | gcagtcgacg | 360 |
| gtaccgcggg | cccgggatcc | accggtataa | agcggtaggc | gcctgtgccc | gctccacctc | 420 |
| tcaagcagcc | agcgcctgcc | tgaatctgtt | ctgcccctc | cccacccatt | tcaccaccac | 480 |
| catggtgagc | aagggcgagg | agctgttcac | cggggtggtg | cccatcctgg | tcgagctgga | 540 |
| cggcgacgta | aacggccaca | agttcagcgt | gtccggcgag | ggcgagggcg | atgccaccta | 600 |
| cggcaagctg | accctgaagt | tcatctgcac | caccggcaag | ctgcccgtgc | cctggcccac | 660 |
| cctcgtgacc | accctgacct | acggcgtgca | gtgcttcagc | cgctaccccg | accacatgaa | 720 |
| gcagcacgac | ttcttcaagt | ccgccatgcc | cgaaggctac | gtccaggagc | gcaccatctt | 780 |
| cttcaaggac | gacggcaact | acaagacccg | cgccgaggtg | aagttcgagg | gcgacaccct | 840 |
| ggtgaaccgc | atcgagctga | agggcatcga | cttcaaggag | gacggcaaca | tcctggggca | 900 |
| caagctggag | tacaactaca | acagccacaa | cgtctatatc | atggccgaca | agcagaagaa | 960 |
| cggcatcaag | gtgaacttca | agatccgcca | caacatcgag | gacggcagcg | tgcagctcgc | 1020 |
| cgaccactac | cagcagaaca | cccccatcgg | cgacggcccc | gtgctgctgc | ccgacaacca | 1080 |
| ctacctgagc | acccagtccg | ccctgagcaa | agacccaac | gagaagcgcg | atcacatggt | 1140 |
| cctgctggag | ttcgtgaccg | ccgccgggat | cactctcggc | atggacgagc | tgtacaagta | 1200 |

```
aagcggccga tccactagta acggccgcca gaattccgcc cctctccctc ccccccccct   1260
aacgttactg gccgaagccg cttggaataa ggccggtgtg cgtttgtcta tatgtgattt   1320
tccaccatat tgccgtcttt tggcaatgtg agggcccgga aacctggccc tgtcttcttg   1380
acgagcattc ctagggtct ttcccctctc gccaaaggaa tgcaaggtct gttgaatgtc    1440
gtgaaggaag cagttcctct ggaagcttct tgaagacaaa caacgtctgt agcgacccTT   1500
tgcaggcagc ggaaccccc acctggcgac aggtgcctct gcggccaaaa gccacgtgta    1560
taagatacac ctgcaaaggc ggcacaaccc cagtgccacg ttgtgagttg atagttgtg    1620
gaaagagtca aatggctctc ctcaagcgta ttcaacaagg ggctgaagga tgcccagaag   1680
gtaccccatt gtatgggatc tgatctgggg cctcggtgca catgctttac atgtgtttag   1740
tcgaggttaa aaaacgtct aggcccccg aaccacgggg acgtggtttt cctttgaaaa     1800
acacgatgat aatatgggat cggccattga acaagatgga ttgcacgcag gttctccggc   1860
cgcttgggtg gagaggctat tcggctatga ctgggcacaa cagacaatcg gctgctctga   1920
tgccgccgtg ttccggctgt cagcgcaggg gcgcccggtt cttttgtca agaccgacct    1980
gtccggtgcc ctgaatgaac tgcaggacga ggcagcgcgg ctatcgtggc tggccacgac   2040
gggcgttcct tgcgcagctg tgctcgacgt tgtcactgaa gcgggaaggg actggctgct   2100
attgggcgaa gtgccgggc aggatctcct gtcatctcac cttgctcctg ccagaaaagt    2160
atccatcatg gctgatgcaa tgcggcggct gcatacgctt gatccggcta cctgcccatt   2220
cgaccaccaa gcgaaacatc gcatcgagcg agcacgtact cggatggaag ccggtcttgt   2280
cgatcaggat gatctggacg aagagcatca ggggctcgcg ccagccgaac tgttcgccag   2340
gctcaaggcg cgcatgcccg acggcgagga tctcgtcgtg acccatggcg atgcctgctt   2400
gccgaatatc atggtggaaa atggccgctt ttctggattc atcgactgtg gccggctggg   2460
tgtggcggac cgctatcagg acatagcgtt ggctacccgt gatattgctg aagagcttgg   2520
cggcgaatgg gctgaccgct tcctcgtgct ttacggtatc gccgctcccg attcgcagcg   2580
catcgccttc tatcgccttc ttgacgagtt cttctgagcg ggactctggg gttcgataaa   2640
ataaagatt ttatttagtc tccagaaaaa gggggaatg aaagacccca cctgtaggtt     2700
tggcaagcta gagaaccatc agatgttttc agggtgcccc aaggacctga atgaccctg    2760
tgccttattt gaactaacca atcagttcgc ttctcgcttc tgttcgcgcg cttctgctcc   2820
ccgagctcaa taaagagcc cacaaccct cactcggggc gccagtcctc cgattgactg     2880
agtcgcccgg gtacccgtgt atccaataaa ccctcttgca gttgcatccg acttgtggtc   2940
tcgctgttcc ttgggagggt ctcctctgag tgattgacta cccgtcagcg ggggtctttc   3000
atttgggggc tcgtccggga tcgggagacc cctgcccagg gaccaccgac ccaccaccgg   3060
gaggtaagct ggctgcctcg cgcgtttcgg tgatgacggt gaaaacctct gacacatgca   3120
gctcccggag acggtcacag cttgtctgta agcggatgcc gggagcagac aagcccgtca   3180
gggcgcgtca gcgggtgttg gcgggtgtcg gggcgcagcc atgacccagt cacgtagcga   3240
tagcggagtg tatactggct taactatgcg gcatcagagc agattgtact gagagtgcac   3300
catatgcggt gtgaaatacc gcacagatgc gtaaggagaa ataccgcat caggcgctct    3360
tccgcttcct cgctcactga ctcgctgcgc tcggtcgttc ggctgcggcg agcggtatca   3420
gctcactcaa aggcggtaat acggttatcc acagaatcag gggataaacgc aggaaagaac   3480
atgtgagcaa aaggccagca aaaggccagg aaccgtaaaa aggccgcgtt gctggcgttt   3540
```

```
ttccataggc tccgccccccc tgacgagcat cacaaaaatc gacgctcaag tcagaggtgg    3600
cgaaacccga caggactata aagataccag gcgtttcccc ctggaagctc cctcgtgcgc    3660
tctcctgttc cgaccctgcc gcttaccgga tacctgtccg cctttctccc ttcgggaagc    3720
gtggcgcttt ctcatagctc acgctgtagg tatctcagtt cggtgtaggt cgttcgctcc    3780
aagctgggct gtgtgcacga acccccgtt cagcccgacc gctgcgcctt atccggtaac    3840
tatcgtcttg agtccaaccc ggtaagacac gacttatcgc cactggcagc agccactggt    3900
aacaggatta gcagagcgag gtatgtaggc ggtgctacag agttcttgaa gtggtggcct    3960
aactacggct acactagaag gacagtattt ggtatctgcg ctctgctgaa gccagttacc    4020
ttcggaaaaa gagttggtag ctcttgatcc ggcaaacaaa ccaccgctgg tagcggtggt    4080
tttttttgttt gcaagcagca gattacgcgc agaaaaaaag gatctcaaga agatcctttg    4140
atcttttcta cggggtctga cgctcagtgg aacgaaaact cacgttaagg gattttggtc    4200
atgagattat caaaaggat cttcacctag atcctttaa attaaaaatg aagttttaaa    4260
tcaatctaaa gtatatatga gtaaacttgg tctgacagtt accaatgctt aatcagtgag    4320
gcacctatct cagcgatctg tctatttcgt tcatccatag ttgcctgact ccccgtcgtg    4380
tagataacta cgatacggga gggcttacca tctggcccca gtgctgcaat gataccgcga    4440
gacccacgct caccggctcc agatttatca gcaataaacc agccagccgg aagggccgag    4500
cgcagaagtg gtcctgcaac tttatccgcc tccatccagt ctattaattg ttgccgggaa    4560
gctagagtaa gtagttcgcc agttaatagt ttgcgcaacg ttgttgccat tgctgcaggc    4620
atcgtggtgt cacgctcgtc gtttggtatg gcttcattca gctccggttc ccaacgatca    4680
aggcgagtta catgatcccc catgttgtgc aaaaaagcgg ttagctcctt cggtcctccg    4740
atcgttgtca gaagtaagtt ggccgcagtg ttatcactca tggttatggc agcactgcat    4800
aattctctta ctgtcatgcc atccgtaaga tgcttttctg tgactggtga gtactcaacc    4860
aagtcattct gagaatagtg tatgcggcga ccgagttgct cttgcccggc gtcaacacgg    4920
gataataccg cgccacatag cagaacttta aaagtgctca tcattggaaa acgttcttcg    4980
gggcgaaaac tctcaaggat cttaccgctg ttgagatcca gttcgatgta acccactcgt    5040
gcacccaact gatcttcagc atcttttact ttcaccagcg tttctgggtg agcaaaaaca    5100
ggaaggcaaa atgccgcaaa aaagggaata agggcgacac ggaaatgttg aatactcata    5160
ctcttccttt ttcaatatta ttgaagcatt tatcagggtt attgtctcat gagcggatac    5220
atatttgaat gtatttagaa aaataaacaa ataggggttc cgcgcacatt tccccgaaaa    5280
gtgccacctg acgtctaaga aaccattatt atcatgacat taacctataa aaataggcgt    5340
atcacgaggc cctttcgtct tcaagaatta gcttggccat tgcatacgtt gtatccatat    5400
cataatatgt acatttatat tggctcatgt ccaacattac cgccatgttg acattgatta    5460
ttgactagtt attaatagta atcaattacg gggtcattag ttcatagccc atatatggag    5520
ttccgcgtta cataacttac ggtaaatggc ccgcctggct gaccgcccaa cgacccccgc    5580
ccattgacgt caataatgac gtatgttccc atagtaacgc caatagggac tttccattga    5640
cgtcaatggg tggagtattt acggtaaact gcccacttgg cagtacatca agtgtatcat    5700
atgccaagta cgcccctat tgacgtcaat gacggtaaat ggcccgcctg gcattatgcc    5760
cagtacatga ccttatggga ctttcctact tggcagtaca tctacgtatt agtcatcgct    5820
attaccatgg tgatgcggtt ttggcagtac atcaatgggc gtggatagcg gtttgactca    5880
cggggatttc caagtctcca ccccattgac gtcaatggga gtttgttttg gcaccaaaat    5940
```

```
caacgggact ttccaaaatg tcgtaacaac tccgccccat tgacgcaaat gggcggtagg    6000
cgtgtacggt gggaggtcta tataagcaga gctcaataaa agagcccaca acccctcact    6060
cggcgcgcca gtcttccgat agactgcgtc gcccgggtac ccgtattccc aataaagcct    6120
cttgctgttt gcatccgaat cgtggtctcg ctgttccttg ggagggtctc ctctgagtga    6180
ttgactaccc acgacggggg tctttcattt ggggctcgt ccgggatttg agacccctg      6240 cccagggacc accgacccac caccgggagg taagctggcc agcaacttat ctgtgtctgt    6300
ccgattgtct agtgtctatg tttgatgtta tgcgcctgcg tctgtactag ttagctaact    6360
agctctgtat ctggcggacc cgtggtgaa ctgacgagtt ctgaacaccc ggccgcaacc     6420
ctgggagacg tcccagggac tttggggcc gttttttgtgg cccgacctga ggaagggagt    6480
cgatgtggaa tccgaccccg tcaggatatg tggttctggt aggagacgag aacctaaaac   6540
agttcccgcc tccgtctgaa ttttgcttt cggtttggaa ccgaagccgc gcgtcttgtc     6600
tgctgcagcg ctgcagcatc gttctgtgtt gtctctgtct gactgtgttt ctgtatttgt    6660
ctgaaaatta gggccagact gttaccactc ccttaagttt gaccttaggt cactggaaag    6720
atgtcgagcg gatcgctcac aaccagtcgg tagatgtcaa gaagagacgt tgg           6773

<210> SEQ ID NO 5
<211> LENGTH: 272
<212> TYPE: DNA
<213> ORGANISM: Artificial Sequence
<220> FEATURE:
<221> NAME/KEY: source
<222> LOCATION: 1..272
<223> OTHER INFORMATION: /mol_type="DNA"
      /note="SEQ SYN 001 Sense strand"
      /organism="Artificial Sequence"
<220> FEATURE:
<221> NAME/KEY: promoter
<222> LOCATION: 162..265
<223> OTHER INFORMATION: /note="mucin minimal promoter"

<400> SEQUENCE: 5
tttatctgca gtaggcgccg gaattcgtta actcgatcac cactttgtac aagaaagctg     60
ggtctcgatc tcacacctgt aatcccagcg tcgagagcct gctttttgt acaaacttgt     120 gatcgaattc tgcagtcgac ggtaccgcgg gcccgggatc caccggtata aagcggtagg    180
cgcctgtgcc cgctccacct ctcaagcagc cagcgcctgc ctgaatctgt tctgccccct    240
ccccacccat ttcaccacca ccatggattg ca                                  272

<210> SEQ ID NO 6
<211> LENGTH: 336
<212> TYPE: DNA
<213> ORGANISM: Artificial Sequence
<220> FEATURE:
<221> NAME/KEY: source
<222> LOCATION: 1..336
<223> OTHER INFORMATION: /mol_type="DNA"
      /note="SEQ SYN 102 sense"
      /organism="Artificial Sequence"
<220> FEATURE:
<221> NAME/KEY: promoter
<222> LOCATION: 226..329
<223> OTHER INFORMATION: /note="mucin minimal promoter"

<400> SEQUENCE: 6
tatctgcagt aggcgccgga attcgttaac tcgatcacca ctttgtacaa gaaagctggg    60
tctcgacctt tgatatcgat ctcacaccag taatcccagc gtcgacttca agatcgact    120
```

```
gagtcaatcg atccccgccg tcgatatgca aatgtcgaga gcctgctttt ttgtacaaac    180
ttgtgatcga attctgcagt cgacggtacc gcgggcccgg gatccaccgg tataaagcgg    240
taggcgcctg tgcccgctcc acctctcaag cagccagcgc ctgcctgaat ctgttctgcc    300
ccctccccac ccatttcacc accaccatgg attgca                             336
```

```
<210> SEQ ID NO 7
<211> LENGTH: 300
<212> TYPE: DNA
<213> ORGANISM: artificial sequences
<220> FEATURE:
<221> NAME/KEY: source
<222> LOCATION: 1..300
<223> OTHER INFORMATION: /mol_type="DNA"
      /note="seq syn 103 sense"
      /organism="artificial sequences"
<220> FEATURE:
<221> NAME/KEY: promoter
<222> LOCATION: 192..295
<223> OTHER INFORMATION: /note="mucin minimal promoter"

<400> SEQUENCE: 7
```

```
cctgcagggc ccactagtat ctgcagtagg cgccggaatt cgttaactcg atcaccactt    60
tgtacaagaa agctgggtct cgattttggg agggtcgatt gagtcagtcg atctttgaag   120
tcgagagcct gctttttgt acaaacttgt gatcgaattc tgcagtcgac ggtaccgcgg   180
gcccgggatc caccggtata aagcggtagg cgcctgtgcc cgctccacct ctcaagcagc   240
cagcgcctgc ctgaatctgt tctgccccct ccccacccat ttcaccacca ccatggattg   300
```

```
<210> SEQ ID NO 8
<211> LENGTH: 351
<212> TYPE: DNA
<213> ORGANISM: Artificial Sequence
<220> FEATURE:
<221> NAME/KEY: source
<222> LOCATION: 1..351
<223> OTHER INFORMATION: /mol_type="DNA"
      /note="seq syn 105 sense"
      /organism="Artificial Sequence"
<220> FEATURE:
<221> NAME/KEY: promoter
<222> LOCATION: 241..344
<223> OTHER INFORMATION: /note="mucin minimal promoter"

<400> SEQUENCE: 8
```

```
tgcactttgt ggcagaggct gcagtaggcg ccggaattcg ttaactcgat caccactttg    60
tacaagaaag ctgggtctcg acggcgggga tcgatctttg aagtcgacgg cggggatcga   120
catttgcata tcgacctttg atatcgacat ttgcatatcg tatcaaaggt cgagagcctg   180
cttttttgta caaacttgtg atcgaattct gcagtcgacg gtaccgcggg cccgggatcc   240
accggtataa agcggtaggc gcctgtgccc gctccacctc tcaagcagcc agcgcctgcc   300
tgaatctgtt ctgccccctc cccacccatt tcaccaccac catggattgc a            351
```

```
<210> SEQ ID NO 9
<211> LENGTH: 298
<212> TYPE: DNA
<213> ORGANISM: Artificial Sequence
<220> FEATURE:
<221> NAME/KEY: source
<222> LOCATION: 1..298
<223> OTHER INFORMATION: /mol_type="DNA"
      /note="seq syn 106 sense"
      /organism="Artificial Sequence"
<220> FEATURE:
<221> NAME/KEY: promoter
```

```
<222> LOCATION: 188..291
<223> OTHER INFORMATION: /note="mucin minmal promoter"

<400> SEQUENCE: 9
tgcactttgt ggcagaggag caggactgag gataagaatt gagtttcaga aaaggggcc      60 tgagtggccc cggaattcgt taactcgatc accactttgt acaagaaagc tgggtctcga    120
gagcctgctt ttttgtacaa acttgtgatc gaattctgca gtcgacggta ccgcgggccc    180
gggatccacc ggtataaagc ggtaggcgcc tgtgcccgct ccacctctca agcagccagc   240
gcctgcctga atctgttctg cccctcccc acccatttca ccaccaccat ggattgca      298

<210> SEQ ID NO 10
<211> LENGTH: 243
<212> TYPE: DNA
<213> ORGANISM: Artificial Sequence
<220> FEATURE:
<221> NAME/KEY: source
<222> LOCATION: 1..243
<223> OTHER INFORMATION: /mol_type="DNA"
      /note="seq syn 108 sense"
      /organism="Artificial Sequence"
<220> FEATURE:
<221> NAME/KEY: promoter
<222> LOCATION: 133..236
<223> OTHER INFORMATION: /note="mucin minimal promoter"

<400> SEQUENCE: 10
ctgcagggcc ggcgccggaa ttcgttaact cgatcaccac tttgtacaag aaagctgggt    60
ctcgagagcc tgcttttttg tacaaacttg tgatcgaatt ctgcagtcga cggtaccgcg   120
ggcccgggat ccaccggtat aaagcggtag gcgcctgtgc ccgctccacc tctcaagcag   180
ccagcgcctg cctgaatctg ttctgccccc tccccaccca tttcaccacc accatggatt   240
gca                                                                  243

<210> SEQ ID NO 11
<211> LENGTH: 278
<212> TYPE: DNA
<213> ORGANISM: artificial sequences
<220> FEATURE:
<221> NAME/KEY: source
<222> LOCATION: 1..278
<223> OTHER INFORMATION: /mol_type="DNA"
      /note="Promoter Pro_200 sense"
      /organism="artificial sequences"
<220> FEATURE:
<221> NAME/KEY: promoter
<222> LOCATION: 178..271
<223> OTHER INFORMATION: /note="Muc-1 minimal promoter"

<400> SEQUENCE: 11
cgttaactcg atcaccactt tgtacaagaa agctgggtct cgacaacaaa gatcgatatt    60
tgcatgtcga ctgagtcaat cgatctttgt tgtcgactga catcaatcga gagcctgctt   120
ttttgtacaa acttgtgatc gaattctgca gtcgacggta ccgcgggccc gggatccacc   180
ggtataaagc ggtaggcgcc tgtgcccgct ccacctctca agcagccagc gcctgcctga   240
atctgttctg cccctcccc acccatttca ccacaca                              278

<210> SEQ ID NO 12
<211> LENGTH: 265
<212> TYPE: DNA
<213> ORGANISM: artificial sequences
<220> FEATURE:
<221> NAME/KEY: source
<222> LOCATION: 1..265
```

```
<223> OTHER INFORMATION: /mol_type="DNA"
      /note="Promoter Pro_201 sense"
      /organism="artificial sequences"
<220> FEATURE:
<221> NAME/KEY: promoter
<222> LOCATION: 166..259
<223> OTHER INFORMATION: /note="Muc-1 minimal promoter"

<400> SEQUENCE: 12
cgttaactcg atcaccactt tgtacaagaa agctgggtct cgattgatgt cagtcgacaa     60
caaagatcga tatgcaaatg tcgatatttg catgtcgaga gcctgctttt ttgtacaaac    120
ttgtgatcga attctgcagt cgacggtacc gcgggcccgg gatccaccgg tataaagcgg    180
taggcgcctg tgcccgctcc acctctcaag cagccagcgc ctgcctgaat ctgttctgcc    240
ccctccccac ccatttcacc accac                                          265

<210> SEQ ID NO 13
<211> LENGTH: 330
<212> TYPE: DNA
<213> ORGANISM: artificial sequences
<220> FEATURE:
<221> NAME/KEY: source
<222> LOCATION: 1..330
<223> OTHER INFORMATION: /mol_type="DNA"
      /note="Promoter Pro_202 sense"
      /organism="artificial sequences"
<220> FEATURE:
<221> NAME/KEY: promoter
<222> LOCATION: 231..324
<223> OTHER INFORMATION: /note="Muc-1 minimal promoter"

<400> SEQUENCE: 13
cgttaactcg atcaccactt tgtacaggaa agctgggtct cgacaacaaa gatcgattga     60
gtcagtcgac tgactcaatc gacatttgca tatcgaccct cccaaaatcg attgactcag    120
tcgacaacaa agatcgacct ttgatatcga tctttgaagt cgagagcctg cttttttgta    180
caaacttgtg atcgaattct gcagtcgacg gtaccgcggg cccgggatcc accggtataa    240
agcggtaggc gcctgtgccc gctccacctc tcaagcagcc agcgcctgcc tgaatctgtt    300 ctgcccccctc cccacccatt tcaccaccac                                    330

<210> SEQ ID NO 14
<211> LENGTH: 222
<212> TYPE: DNA
<213> ORGANISM: artificial sequences
<220> FEATURE:
<221> NAME/KEY: source
<222> LOCATION: 1..222
<223> OTHER INFORMATION: /mol_type="DNA"
      /note="Promoter Pro_203 sense"
      /organism="artificial sequences"
<220> FEATURE:
<221> NAME/KEY: promoter
<222> LOCATION: 124..217
<223> OTHER INFORMATION: /note="Muc-1 minimal promoter"

<400> SEQUENCE: 14
cgttaactcg atcaccactt tgtacaagaa agctgggtct cgacaacaaa gatcgagagc     60 ctgcttttttt gtacaaactt gtgatcgaat tctgcagtcg acggtaccgc gggcccggga    120
tccaccggta taaagcggta ggcgcctgtg cccgctccac ctctcaagca gccagcgcct    180
gcctgaatct gttctgcccc ctccccaccc atttcaccac cc                        222

<210> SEQ ID NO 15
<211> LENGTH: 251
```

```
<212> TYPE: DNA
<213> ORGANISM: artificial sequences
<220> FEATURE:
<221> NAME/KEY: source
<222> LOCATION: 1..251
<223> OTHER INFORMATION: /mol_type="DNA"
      /note="Promoter Pro_204 sense"
      /organism="artificial sequences"
<220> FEATURE:
<221> NAME/KEY: promoter
<222> LOCATION: 153..246
<223> OTHER INFORMATION: /note="Muc-1 minimal promoter"

<400> SEQUENCE: 15
cgttaactcg atcaccactt tgtacaagaa agctgggtct cgattttggg agggtcgata      60
tgcaaatgtc gactgagtca atcgagagcc tgctttttg tacaaacttg tgatcgaatt      120
ctgcagtcga cggtaccgcg ggcccgggat ccaccggtat aaagcggtag gcgcctgtgc     180
ccgctccacc tctcaagcag ccagcgcctg cctgaatctg ttctgccccc tccccaccca    240
tttcaccacc a                                                          251

<210> SEQ ID NO 16
<211> LENGTH: 250
<212> TYPE: DNA
<213> ORGANISM: artificial sequences
<220> FEATURE:
<221> NAME/KEY: source
<222> LOCATION: 1..250
<223> OTHER INFORMATION: /mol_type="DNA"
      /note="Promoter Pro_205 sense"
      /organism="artificial sequences"
<220> FEATURE:
<221> NAME/KEY: promoter
<222> LOCATION: 150..243
<223> OTHER INFORMATION: /note="Muc-1 minimal promoter"

<400> SEQUENCE: 16
cgttaactcg atcaccactt tgtacaagaa agctgggtct cgactgactc aatcgatctc      60
acacctgtaa tcccagcgtc gagagcctgc tttttgtac aaacttgtga tcgaattctg      120
cagtcgacgg taccgcgggc ccgggatcca ccggtataaa gcggtaggcg cctgtgcccg     180
ctccacctct caagcagcca gcgcctgcct gaatctgttc tgccccctcc ccacccattt    240
caccaccaca                                                            250

<210> SEQ ID NO 17
<211> LENGTH: 263
<212> TYPE: DNA
<213> ORGANISM: artificial sequences
<220> FEATURE:
<221> NAME/KEY: source
<222> LOCATION: 1..263
<223> OTHER INFORMATION: /mol_type="DNA"
      /note="Promoter Pro_206 sense"
      /organism="artificial sequences"
<220> FEATURE:
<221> NAME/KEY: promoter
<222> LOCATION: 163..256
<223> OTHER INFORMATION: /note="Muc-1 minimal promoter"

<400> SEQUENCE: 17
cgttaactcg atcaccactt tgtacaagaa agctgggtct cgatctttga agtcgacaac      60
aaagatcgat ctcacacctg taatcccagc gtcgagagcc tgctttttg tacaaacttg     120 tgatcgaatt ctgcagtcga cggtaccgcg ggcccgggat ccaccggtat aaagcggtag    180
gcgcctgtgc ccgctccacc tctcaagcag ccagcgcctg cctgaatctg ttctgccccc   240
```
tccccaccca tttcaccacc aca                                           263

<210> SEQ ID NO 18
<211> LENGTH: 237
<212> TYPE: DNA
<213> ORGANISM: artificial sequences
<220> FEATURE:
<221> NAME/KEY: source
<222> LOCATION: 1..237
<223> OTHER INFORMATION: /mol_type="DNA"
      /note="Promoter Pro_207 sense"
      /organism="artificial sequences"
<220> FEATURE:
<221> NAME/KEY: promoter
<222> LOCATION: 137..230
<223> OTHER INFORMATION: /note="Muc-1 minimal promoter"

<400> SEQUENCE: 18
cgttaactcg atcaccactt tgtacaagaa agctgggtct cgatctcaca cctgtaatcc    60
cagcgtcgag agcctgcttt tttgtacaaa cttgtgatcg aattctgcag tcgacggtac   120
cgcgggcccg ggatccaccg gtataaagcg gtaggcgcct gtgcccgctc cacctctcaa   180
gcagccagcg cctgcctgaa tctgttctgc cccctcccca cccatttcac caccaca      237

<210> SEQ ID NO 19
<211> LENGTH: 240
<212> TYPE: DNA
<213> ORGANISM: artificial sequences
<220> FEATURE:
<221> NAME/KEY: source
<222> LOCATION: 1..240
<223> OTHER INFORMATION: /mol_type="DNA"
      /note="Promoter Pro_208 sense"
      /organism="artificial sequences"
<220> FEATURE:
<221> NAME/KEY: promoter
<222> LOCATION: 140..233
<223> OTHER INFORMATION: /note="Muc-1 minimal promoter"

<400> SEQUENCE: 19
cgttaactcg atcaccactt tgtacaagaa agctgggtct cgattttggg agggtcgatt    60
gatgtcagtc gagagcctgc ttttttgtac aaacttgtga tcgaattctg cagtcgacgg   120
taccgcgggc ccgggatcca ccggtataaa gcggtaggcg cctgtgcccg ctccacctct   180
caagcagcca gcgcctgcct gaatctgttc tgcccccctcc ccacccattt caccaccaca  240

<210> SEQ ID NO 20
<211> LENGTH: 270
<212> TYPE: DNA
<213> ORGANISM: Homo sapiens
<220> FEATURE:
<221> NAME/KEY: source
<222> LOCATION: 1..270
<223> OTHER INFORMATION: /mol_type="DNA"
      /note="Promoter Pro_209 sense"
      /organism="Homo sapiens"
<220> FEATURE:
<221> NAME/KEY: promoter
<222> LOCATION: 155..248
<223> OTHER INFORMATION: /note="Muc-1 minimal promoter"

<400> SEQUENCE: 20
tagtggatcc cccgggctgc aggaattcga ttcgacttca aagatcgcac tttgatatcg    60
acgctgggat tacaggtgtg agatcgagag cctgcttttt tgtacaaact tgtgatcgaa   120
ttctgcagtc gacggtaccg cgggcccggg atcaccggt ataaagcggt aggcgcctgt    180
gcccgctcca cctctcaagc agccagcgcc tgcctgaatc tgttctgccc cctccccacc   240
catttcacca ccacatcaag cttatcgata 270

<210> SEQ ID NO 21
<211> LENGTH: 238
<212> TYPE: DNA
<213> ORGANISM: artificial sequences
<220> FEATURE:
<221> NAME/KEY: source
<222> LOCATION: 1..238
<223> OTHER INFORMATION: /mol_type="DNA"
      /note="Promoter Pro_210 sense"
      /organism="artificial sequences"
<220> FEATURE:
<221> NAME/KEY: promoter
<222> LOCATION: 138..231
<223> OTHER INFORMATION: /note="Muc-1 minimal promoter"

<400> SEQUENCE: 21
cgttaactcg atcaccactt tgtacaagaa agctgggtct cgacggcggg gatcgacatt    60
tgcatatcga gagcctgctt ttttgtacaa acttgtgatc gaattctgca gtcgacggta   120
ccgcgggccc gggatccacc ggtataaagc ggtaggcgcc tgtgcccgct ccacctctca   180
agcagccagc gcctgcctga atctgttctg ccccctcccc acccatttca ccaccaca    238

<210> SEQ ID NO 22
<211> LENGTH: 237
<212> TYPE: DNA
<213> ORGANISM: artificial sequences
<220> FEATURE:
<221> NAME/KEY: source
<222> LOCATION: 1..237
<223> OTHER INFORMATION: /mol_type="DNA"
      /note="Promoter Pro_211 sense"
      /organism="artificial sequences"
<220> FEATURE:
<221> NAME/KEY: promoter
<222> LOCATION: 137..230
<223> OTHER INFORMATION: /note="Muc-1 minimal promoter"

<400> SEQUENCE: 22
cgttaactcg atcaccactt tgtacaagaa agctgggtct cgactgactc aatcgatctt    60
tgttgtcgag agcctgcttt tttgtacaaa cttgtgatcg aattctgcag tcgacggtac   120
cgcgggcccg ggatccaccg gtataaagcg gtaggcgcct gtgcccgctc cacctctcaa   180
gcagccagcg cctgcctgaa tctgttctgc ccctcccca cccatttcac caccaca      237

<210> SEQ ID NO 23
<211> LENGTH: 224
<212> TYPE: DNA
<213> ORGANISM: artificial sequences
<220> FEATURE:
<221> NAME/KEY: source
<222> LOCATION: 1..224
<223> OTHER INFORMATION: /mol_type="DNA"
      /note="Promoter Pro_212 sense"
      /organism="artificial sequences"
<220> FEATURE:
<221> NAME/KEY: promoter
<222> LOCATION: 126..219
<223> OTHER INFORMATION: /note="Muc-1 minimal promoter"

<400> SEQUENCE: 23
cgttaactcg atcaccactt tgtacaagaa agctgggtct cgaccctccc aaaatcgaga    60
gcctgctttt ttgtacaaac ttgtgatcga attctgcagt cgacggtacc gcgggcccgg   120
gatccaccgg tataaagcgg taggcgcctg tgcccgctcc acctctcaag cagccagcgc   180

```
ctgcctgaat ctgttctgcc ccctccccac ccatttcacc acca              224
```

```
<210> SEQ ID NO 24
<211> LENGTH: 324
<212> TYPE: DNA
<213> ORGANISM: artificial sequences
<220> FEATURE:
<221> NAME/KEY: source
<222> LOCATION: 1..324
<223> OTHER INFORMATION: /mol_type="DNA"
      /note="Promoter Pro_213 sense"
      /organism="artificial sequences"
<220> FEATURE:
<221> NAME/KEY: promoter
<222> LOCATION: 218..311
<223> OTHER INFORMATION: /note="Muc-1 minimal promoter"

<400> SEQUENCE: 24
cgttaactcg atcaccactt tgtacaagaa agctgggtct cgacaacaaa gatcgatctt    60
tgttgtcgat tttgggaggg tcgacgctgg gattacaggt gtgagatcga tatcaaaggt   120
cgattgactc agtcgacggc ggggatcgag agcctgcttt ttttgtacaa acttgtgatc   180
gaattctgca gtcgacggta ccgcgggccc gggatccacc ggtataaagc ggtaggcgcc   240
tgtgcccgct ccacctctca agcagccagc gcctgcctga atctgttctg ccccctcccc   300
acccatttca ccaccaccct tctc                                          324
```

```
<210> SEQ ID NO 25
<211> LENGTH: 268
<212> TYPE: DNA
<213> ORGANISM: artificial sequences
<220> FEATURE:
<221> NAME/KEY: source
<222> LOCATION: 1..268
<223> OTHER INFORMATION: /mol_type="DNA"
      /note="Promoter Pro_214 sense"
      /organism="artificial sequences"
<220> FEATURE:
<221> NAME/KEY: promoter
<222> LOCATION: 165..258
<223> OTHER INFORMATION: /note="Muc-1 minimal promoter"

<400> SEQUENCE: 25
cgttaactcg atcaccactt tgtacaagaa agctgggtct cgactgacat caatcgactt    60
caaagatcga tatgcaaatg tcgactgagt caatcgagag cctgcttttt tgtacaaact   120
tgtgatcgaa ttctgcagtc gacggtaccg cgggcccggg atccaccggt ataaagcggt   180
aggcgcctgt gcccgctcca cctctcaagc agccagcgcc tgcctgaatc tgttctgccc   240
cctccccacc catttcacca ccacaccg                                      268
```

```
<210> SEQ ID NO 26
<211> LENGTH: 291
<212> TYPE: DNA
<213> ORGANISM: artificial sequences
<220> FEATURE:
<221> NAME/KEY: source
<222> LOCATION: 1..291
<223> OTHER INFORMATION: /mol_type="DNA"
      /note="Promoter Pro_215 sense"
      /organism="artificial sequences"
<220> FEATURE:
<221> NAME/KEY: promoter
<222> LOCATION: 194..287
<223> OTHER INFORMATION: /note="Muc-1 minimal promoter"

<400> SEQUENCE: 26
cgttaactcg atcaccactt tgtacaagaa agctgggtct cgacggcggg gatcgacaac    60
```

```
aaagatcgac atttgcatat cgactgacat caatcgatat ttgcatgtcg accctcccaa      120
aatcgagagc ctgcttttt gtacaaactt gtgatcgaat tctgcagtcg acggtaccgc       180
gggcccggga tccaccggta taaagcggta ggcgcctgtg cccgctccac ctctcaagca      240
gccagcgcct gcctgaatct gttctgcccc ctccccaccc atttcaccac c               291
```

<210> SEQ ID NO 27
<211> LENGTH: 289
<212> TYPE: DNA
<213> ORGANISM: artificial sequences
<220> FEATURE:
<221> NAME/KEY: source
<222> LOCATION: 1..289
<223> OTHER INFORMATION: /mol_type="DNA"
      /note="Promoter Pro_216 sense"
      /organism="artificial sequences"
<220> FEATURE:
<221> NAME/KEY: promoter
<222> LOCATION: 189..282
<223> OTHER INFORMATION: /note="Muc-1 minimal promoter"

<400> SEQUENCE: 27

```
cgttaactcg atcaccactt tgtacaagaa agctgggtct cgatatgcaa atgtcgattg      60
agtcagtcga cttcaaagat cgattgagtc agtcgatctc acactgtaat cccagcgtcg     120
agagcctgct tttttgtaca aacttgtgat cgaattctgc agtcgacggt accgcgggcc     180
cgggatccac cggtataaag cggtaggcgc ctgtgcccgc tccacctctc aagcagccag    240
cgcctgcctg aatctgttct gcccctccc cacccatttc accaccacc                  289
```

<210> SEQ ID NO 28
<211> LENGTH: 291
<212> TYPE: DNA
<213> ORGANISM: artificial sequences
<220> FEATURE:
<221> NAME/KEY: source
<222> LOCATION: 1..291
<223> OTHER INFORMATION: /mol_type="DNA"
      /note="Promoter Pro_217 sense"
      /organism="artificial sequences"
<220> FEATURE:
<221> NAME/KEY: promoter
<222> LOCATION: 191..284
<223> OTHER INFORMATION: /note="Muc-1 minimal promoter"

<400> SEQUENCE: 28

```
cgttaactcg atcaccactt tgtacaagaa agctgggtct cgacgctggg attacaggtg      60
tgagatcgac aacaaagatc gattgagtca gtcgatcttt gaagtcgatt ttgggagggt     120
cgagagcctg cttttttgta caaacttgtg atcgaattct gcagtcgacg gtaccgcggg    180
cccgggatcc accggtataa agcggtaggc gcctgtgccc gctccacctc tcaagcagcc    240
agcgcctgcc tgaatctgtt ctgccccctc cccacccatt tcaccaccac a              291
```

<210> SEQ ID NO 29
<211> LENGTH: 237
<212> TYPE: DNA
<213> ORGANISM: artificial sequences
<220> FEATURE:
<221> NAME/KEY: source
<222> LOCATION: 1..237
<223> OTHER INFORMATION: /mol_type="DNA"
      /note="Promoter Pro_218 sense"
      /organism="artificial sequences"
<220> FEATURE:
<221> NAME/KEY: promoter
<222> LOCATION: 137..230

<223> OTHER INFORMATION: /note="Muc-1 minimal promoter"

<400> SEQUENCE: 29

```
cgttaactcg atcaccactt tgtacaagaa agctgggtct cgacggcggg gatcgatctt      60
tgttgtcgag agcctgcttt tttgtacaaa cttgtgatcg aattctgcag tcgacggtac     120
cgcgggcccg ggatccaccg gtataaagcg gtaggcgcct gtgcccgctc cacctctcaa     180
gcagccagcg cctgcctgaa tctgttctgc cccctcccca cccatttcac caccaca       237
```

<210> SEQ ID NO 30
<211> LENGTH: 280
<212> TYPE: DNA
<213> ORGANISM: artificial sequences
<220> FEATURE:
<221> NAME/KEY: source
<222> LOCATION: 1..280
<223> OTHER INFORMATION: /mol_type="DNA"
      /note="Promoter Pro_219 sense"
      /organism="artificial sequences"
<220> FEATURE:
<221> NAME/KEY: promoter
<222> LOCATION: 180..273
<223> OTHER INFORMATION: /note="Muc-1 minimal promoter"

<400> SEQUENCE: 30

```
cgttaactcg atcaccactt tgtacaagaa agctgggtct cgactgacat caatcgatat      60
caaaggtcga ttttgggagg gtcgacttca aagatcgact tcaaagatcg agagcctgct     120
ttttgtaca aacttgtgat cgaattctgc agtcgacggt accgcgggcc cggggatcca     180
ccggtataaa gcggtaggcg cctgtgcccg ctccacctct caagcagcca gcgcctgcct     240
gaatctgttc tgcccctcc ccacccattt caccaccaca                          280
```

<210> SEQ ID NO 31
<211> LENGTH: 224
<212> TYPE: DNA
<213> ORGANISM: artificial sequences
<220> FEATURE:
<221> NAME/KEY: source
<222> LOCATION: 1..224
<223> OTHER INFORMATION: /mol_type="DNA"
      /note="Promoter Pro_220 sense"
      /organism="artificial sequences"
<220> FEATURE:
<221> NAME/KEY: promoter
<222> LOCATION: 124..217
<223> OTHER INFORMATION: /note="Muc-1 minimal promoter"

<400> SEQUENCE: 31

```
cgttaactcg atcaccactt tgtacaagaa agctgggtct cgactgactc aatcgagagc      60
ctgctttttt gtacaaactt gtgatcgaat tctgcagtcg atggtaccgc gggcccggga     120
tccaccggta taaagcggta ggcgcctgtg cccgctccac ctctcaagca gccagcgcct     180
gcctgaatct gttctgcccc ctccccaccc atttccacca caca                     224
```

<210> SEQ ID NO 32
<211> LENGTH: 235
<212> TYPE: DNA
<213> ORGANISM: artificial sequences
<220> FEATURE:
<221> NAME/KEY: source
<222> LOCATION: 1..235
<223> OTHER INFORMATION: /mol_type="DNA"
      /note="Promoter Pro_221 sense"
      /organism="artificial sequences"
<220> FEATURE:
<221> NAME/KEY: promoter

```
<222> LOCATION: 138..231
<223> OTHER INFORMATION: /note="Muc-1 minimal promoter"

<400> SEQUENCE: 32
cgttaactcg atcaccactt tgtacaagaa agctgggtct cgactgagtc aatcgacatg    60
caaatatcga gagcctgctt ttttgtacaa acttgtgatc gaattctgca gtcgagggga   120 ccggggcgc gggatccacc ggtataaagc ggtaggcgcc tgtgcccgct ccacctctca    180
agcagccagc gcctgcctga atctgttctg ccccctcccc acgcatttca ccacc        235

<210> SEQ ID NO 33
<211> LENGTH: 303
<212> TYPE: DNA
<213> ORGANISM: artificial sequences
<220> FEATURE:
<221> NAME/KEY: source
<222> LOCATION: 1..303
<223> OTHER INFORMATION: /mol_type="DNA"
      /note="Promoter Pro_222 sense"
      /organism="artificial sequences"
<220> FEATURE:
<221> NAME/KEY: promoter
<222> LOCATION: 203..296
<223> OTHER INFORMATION: /note="Muc-1 minimal promoter"

<400> SEQUENCE: 33
cgttaactcg atcaccactt tgtacaagaa agctgggtct cgacctttga tatcgatctc    60
acaccagtaa tcccagcgtc gacttcaaag atcgactgag tcaatcgatc cccgccgtcg   120
atatgcaaat gtcgagagcc tgcttttttg tacaaacttg tgatcgaatt ctgcagtcga   180
cggtaccgcg ggcccgggat ccaccggtat aaagcggtag gcgcctgtgc ccgctccacc   240
tctcaagcag ccagcgcctg cctgaatctg ttctgccccc tccccaccca tttcaccacc   300
aca                                                                303

<210> SEQ ID NO 34
<211> LENGTH: 318
<212> TYPE: DNA
<213> ORGANISM: artificial sequences
<220> FEATURE:
<221> NAME/KEY: source
<222> LOCATION: 1..318
<223> OTHER INFORMATION: /mol_type="DNA"
      /note="Promoter Pro_223 sense"
      /organism="artificial sequences"
<220> FEATURE:
<221> NAME/KEY: promoter
<222> LOCATION: 205..298
<223> OTHER INFORMATION: /note="Muc-1 minimal promoter"

<400> SEQUENCE: 34
cgttaactcg atcaccactt tgtacaagaa agctgggtct cgattgatgt cagtcgacct    60
ttgatatcga ttgactcagt cgattgagtc agtcgacatt tgcatatcga tatgcaaatg   120
tcgactgagt caatcgagag cctgcttttt tgtacaaact tgtgatcgaa ttctgcagtc   180
gacggtaccg cgggcccggg atccaccggt ataaagcggt aggcgcctgt gcccgctcca   240
cctctcaagc agccagcgcc tgcctgaatc tgttctgccc cctccccacc catttcacca   300
ccacatcaag cttatcga                                                318

<210> SEQ ID NO 35
<211> LENGTH: 251
<212> TYPE: DNA
<213> ORGANISM: artificial sequences
<220> FEATURE:
```

```
<221> NAME/KEY: source
<222> LOCATION: 1..251
<223> OTHER INFORMATION: /mol_type="DNA"
      /note="Promoter Pro_224 sense"
      /organism="artificial sequences"
<220> FEATURE:
<221> NAME/KEY: promoter
<222> LOCATION: 151..244
<223> OTHER INFORMATION: /note="Muc-1 minimal promoter"

<400> SEQUENCE: 35
cgttaactcg atcaccactt tgtacaagaa agctgggtct cgattgatgt cagtcgatcc      60
ccgccgtcga ttgagtcagt cgagagcctg cttttttgta caaacttgtg atcgaattct    120
gcagtcgacg gtaccgcggg cccgggatcc accggtataa agcggtaggc gcctgtgccc    180
gctccacctc tcaagcagcc agcgcctgcc tgaatctgtt ctgcccccctc cccacccatt    240 tcaccaccac a                                                          251

<210> SEQ ID NO 36
<211> LENGTH: 286
<212> TYPE: DNA
<213> ORGANISM: artificial sequences
<220> FEATURE:
<221> NAME/KEY: source
<222> LOCATION: 1..286
<223> OTHER INFORMATION: /mol_type="DNA"
      /note="Promoter Pro_225 sense"
      /organism="artificial sequences"
<220> FEATURE:
<221> NAME/KEY: promoter
<222> LOCATION: 179..272
<223> OTHER INFORMATION: /note="Muc-1 minimal promoter"

<400> SEQUENCE: 36
cgttaactcg atcaccactt tgtacaagaa agctgggtct cgatctttga agtcgatctt      60
tgttgtcgac atgcaaatat cgactgactc aatcgatttt gggagggtcg agagcctgct    120
tttttgtaca aacttgtgat cgaattctgc agtcgacggt accgcgggcc cgggatccac    180
cggtataaag cggtaggcgc ctgtgcccgc tccacctctc aagcagccag cgcctgcctg    240
aatctgttct gcccccctccc cacccatttc accaccacat caagct                  286

<210> SEQ ID NO 37
<211> LENGTH: 315
<212> TYPE: DNA
<213> ORGANISM: artificial sequences
<220> FEATURE:
<221> NAME/KEY: source
<222> LOCATION: 1..315
<223> OTHER INFORMATION: /mol_type="DNA"
      /note="Promoter Pro_226 sense"
      /organism="artificial sequences"
<220> FEATURE:
<221> NAME/KEY: promoter
<222> LOCATION: 215..308
<223> OTHER INFORMATION: /note="Muc-1 minimal promoter"

<400> SEQUENCE: 37
cgttaactcg atcaccactt tgtacaagaa agctgggtct cgacttcaaa gatcgatctt      60
tgttgtcgac ttcaaagatc gatcccgcc gtcgacttca agatcgaca acaaagatcg      120 attgagtcag tcgatatcaa aggtcgagag cctgcttttt tgtacaaact tgtgatcgaa    180
ttctgcagtc gacggtaccg cgggcccggg atccaccggt ataaagcggt aggcgcctgt    240
gcccgctcca cctctcaagc agccagcgcc tgcctgaatc tgttctgccc cctcccacc    300 catttcacca ccaca                                                     315
```

```
<210> SEQ ID NO 38
<211> LENGTH: 277
<212> TYPE: DNA
<213> ORGANISM: artificial sequences
<220> FEATURE:
<221> NAME/KEY: source
<222> LOCATION: 1..277
<223> OTHER INFORMATION: /mol_type="DNA"
      /note="Promoter Pro_227 sense"
      /organism="artificial sequences"
<220> FEATURE:
<221> NAME/KEY: promoter
<222> LOCATION: 179..272
<223> OTHER INFORMATION: /note="Muc-1 minimal promoter"

<400> SEQUENCE: 38
cgttaactcg atcaccactt tgtacaagaa agctgggtct cgatatttgc atgtcgattg      60
agtcagtcga tctttgttgt cgattgatgt cagtcgacat ttgcatatcg agagcctgct     120
tttttgtaca aacttgtgat cgaattctgc agtcgacggt accgcgggcc cgggatccac     180
cggtataaag cggtaggcgc ctgtgcccgc tccacctctc aagcagccag cgcctgcctg     240
aatctgttyt gccccctccc cacccatttc accaca                               277

<210> SEQ ID NO 39
<211> LENGTH: 262
<212> TYPE: DNA
<213> ORGANISM: artificial sequences
<220> FEATURE:
<221> NAME/KEY: source
<222> LOCATION: 1..262
<223> OTHER INFORMATION: /mol_type="DNA"
      /note="Promoter Pro_228 sense"
      /organism="artificial sequences"
<220> FEATURE:
<221> NAME/KEY: promoter
<222> LOCATION: 165..258
<223> OTHER INFORMATION: /note="Muc-1 minimal promoter"

<400> SEQUENCE: 39
gttaactcga tcaccacttt gtacaagaaa gctgggtctc gaccctccca aaatcgactt      60
caaagatcga tccccgccgt cgactgacat caatcgagag cctgcttttt tgtacaaact     120
tgtgatcgaa ttctgcagtc gacggtaccg cgggcccggg atccaccggt ataaagcggt     180
aggcgcctgt gcccgctcca cctctcaagc agccagcgcc tgcctgaatc tgttctgccc     240
cctccccacc catttcacca cc                                              262

<210> SEQ ID NO 40
<211> LENGTH: 264
<212> TYPE: DNA
<213> ORGANISM: artificial sequences
<220> FEATURE:
<221> NAME/KEY: source
<222> LOCATION: 1..264
<223> OTHER INFORMATION: /mol_type="DNA"
      /note="Promoter Pro_229 sense"
      /organism="artificial sequences"
<220> FEATURE:
<221> NAME/KEY: promoter
<222> LOCATION: 164..257
<223> OTHER INFORMATION: /note="Muc-1 minimal promoter"

<400> SEQUENCE: 40
cgttaactcg atcaccactt tgtacaagaa agctgggtct cgattgagtc agtcgactga      60
gtcaatcgac atttgcatat cgacttcaaa gatcgagagc ctgcttttt gtacaaactt     120
```

```
gtgatcgaat tctgcagtcg acggtaccgc gggcccggga tccaccggta taaagcggta    180
ggcgcctgtg cccgctccac ctctcaagca gccagcgcct gcctgaatct gttctgcccc    240
ctccccaccc atttcaccac caca                                           264
```

<210> SEQ ID NO 41
<211> LENGTH: 266
<212> TYPE: DNA
<213> ORGANISM: artificial sequences
<220> FEATURE:
<221> NAME/KEY: source
<222> LOCATION: 1..266
<223> OTHER INFORMATION: /mol_type="DNA"
      /note="Promoter Pro_230 sense"
      /organism="artificial sequences"
<220> FEATURE:
<221> NAME/KEY: promoter
<222> LOCATION: 166..259
<223> OTHER INFORMATION: /note="Muc-1 minimal promoter"

<400> SEQUENCE: 41

```
cgttaactcg atcaccactt tgtacaggaa agctgggtct cgacatttgc atatcgacat     60
ttgcatatcg attgagtcag tcgatatgca aatgtcgaga gcctgctttt ttgtacaaac    120
ttgtgatcga attctgcagt cgacggtacc gcgggcccgg gatccaccgg tataaagcgg    180
taggcgcctg tgcccgctcc acctctcaag cagccagcgc tgcctgaat ctgttctgcc     240 ccctccccac ccatttcacc accaca                                         266
```

<210> SEQ ID NO 42
<211> LENGTH: 279
<212> TYPE: DNA
<213> ORGANISM: artificial sequences
<220> FEATURE:
<221> NAME/KEY: source
<222> LOCATION: 1..279
<223> OTHER INFORMATION: /mol_type="DNA"
      /note="Promoter Pro_231 sense"
      /organism="artificial sequences"
<220> FEATURE:
<221> NAME/KEY: promoter
<222> LOCATION: 180..273

<400> SEQUENCE: 42

```
cgttaactcg atcaccactt tgtacaagaa agctgggtct cgattgatgt cagtcgatct     60
ttgttgtcga tatgcaaatg tcgactgact caatcgattt tgggagggtc gagagcctgc    120
ttttttgtac aaacttgtga tcgaattctg cagtcgacgg taccgcgggc ccgggatcca    180
ccggtataaa gcggtaggcg cctgtgcccg ctccacctct caagcagcca gcgcctgcct    240
gaatctgttc tgcccctcc ccacccattt caccaccac                            279
```

<210> SEQ ID NO 43
<211> LENGTH: 311
<212> TYPE: DNA
<213> ORGANISM: artificial sequences
<220> FEATURE:
<221> NAME/KEY: source
<222> LOCATION: 1..311
<223> OTHER INFORMATION: /mol_type="DNA"
      /note="Promoter Pro_232 sense"
      /organism="artificial sequences"
<220> FEATURE:
<221> NAME/KEY: promoter
<222> LOCATION: 186..279
<223> OTHER INFORMATION: /note="Muc-1 minimal promoter"

<400> SEQUENCE: 43

```
ccggaattcg ttaactcgat caccactttg tacaagaaag ctgggtctcg acatttgcat      60
atcgacattt gcatatcgat ccccgccgtc gatctttgaa gtcgattgac tcagtcgaga     120
gcctgctttt ttgtacaaac ttgtgatcga attctgcagt cgacggtacc gcgggcccgg     180
gatccaccgg tataaagcgg taggcgcctg tgcccgctcc acctctcaag cagccagcgc     240
ctgcctgaat ctgttctgcc cctccccac ccatttcacc accacatcga attcctgcag      300
cccgggggat c                                                         311
```

```
<210> SEQ ID NO 44
<211> LENGTH: 264
<212> TYPE: DNA
<213> ORGANISM: artificial sequences
<220> FEATURE:
<221> NAME/KEY: source
<222> LOCATION: 1..264
<223> OTHER INFORMATION: /mol_type="DNA"
      /note="Promoter Pro_233 sense"
      /organism="artificial sequences"
<220> FEATURE:
<221> NAME/KEY: promoter
<222> LOCATION: 164..264
<223> OTHER INFORMATION: /note="Muc-1 minimal promoter"

<400> SEQUENCE: 44
cgttaactcg atcaccactt tgtacaggaa agctgggtct cgacaacaaa gatcgatatg      60
caaatgtcga caacaaagat cgatctttga agtcgagagc ctgctttttt gtacaaactt     120
gtgatcgaat tctgcagtcg acggtaccgc gggcccggga tccaccggta taaagcggta     180
ggcgcctgtg cccgctccac ctctcaagca gccagcgcct gcctgaatct gttctgcccc     240
ctcccaaccc atttcaccac caca                                            264
```

```
<210> SEQ ID NO 45
<211> LENGTH: 310
<212> TYPE: DNA
<213> ORGANISM: artificial sequences
<220> FEATURE:
<221> NAME/KEY: source
<222> LOCATION: 1..310
<223> OTHER INFORMATION: /mol_type="DNA"
      /note="Promoter Pro_234 sense"
      /organism="artificial sequences"
<220> FEATURE:
<221> NAME/KEY: promoter
<222> LOCATION: 210..310
<223> OTHER INFORMATION: /note="Muc-1 minimal promoter"

<400> SEQUENCE: 45
aattcgttaa ctcgatcacc actttgtaca agaaagctgg gtctcgactg agtcaatcga      60
ttgactcagt cgatccccgc cgtcgaccct cccaaaatcg actgagtcaa tcgactgaca     120
tcaatcgatt gatgtcagtc gagagcctgc ttttttgtac aaacttgtga tcgaattctg     180
cagtcgacgg taccgcgggc ccgggatcca ccggtataaa gcggtaggcg cctgtgcccg     240
ctccacctct caagcagcca gcgcctgcct gaatctgttc tgccccctcc cacccattt      300 caccaccaca                                                            310
```

```
<210> SEQ ID NO 46
<211> LENGTH: 277
<212> TYPE: DNA
<213> ORGANISM: artificial sequences
<220> FEATURE:
<221> NAME/KEY: source
<222> LOCATION: 1..277
<223> OTHER INFORMATION: /mol_type="DNA"
```

```
        /note="Promoter Pro_235 sense"
        /organism="artificial sequences"
<220> FEATURE:
<221> NAME/KEY: promoter
<222> LOCATION: 177..277
<223> OTHER INFORMATION: /note="Muc-1 minimal promoter"

<400> SEQUENCE: 46
cgttaactcg atcaccactt tgtacaagaa agctgggtct cgacatttgc atatcgattg    60
agtcagtcga tctttgttgt cgactgagtc aatcgattga gtcagtcgag agcctgcttt   120
tttgtacaaa cttgtgatcg aattctgcag tcgacggtac cgcgggcccg ggatccaccg   180
gtataaagcg gtaggcgcct gtgcccgctc cacctctcaa gcagccagcg cctgcctgaa   240
tctgttctgc ccccgcccca cccatttcac caccaca                            277

<210> SEQ ID NO 47
<211> LENGTH: 252
<212> TYPE: DNA
<213> ORGANISM: artificial sequences
<220> FEATURE:
<221> NAME/KEY: source
<222> LOCATION: 1..252
<223> OTHER INFORMATION: /mol_type="DNA"
        /note="Promoter Pro_236 sense"
        /organism="artificial sequences"
<220> FEATURE:
<221> NAME/KEY: promoter
<222> LOCATION: 152..252
<223> OTHER INFORMATION: /note="Muc-1 minimal promoter"

<400> SEQUENCE: 47
cgttaactcg atcaccactt tgtacaagaa agctgggtct cgattgatgt cagtcgactg    60
agtcaatcga tatgcaaatg tcgagagcct gcttttttgt acaaacttgt gatcgaattc   120
tgcagtcgac ggtaccgcgg gcccgggatc caccggtata aagcggtagg cgcctgtgcc   180
cgctccacct ctcaagcagc cagcgcctgc ctgaatctgt tctgcccccc tccccacccat  240 ttcaccacca ca                                                        252

<210> SEQ ID NO 48
<211> LENGTH: 346
<212> TYPE: DNA
<213> ORGANISM: artificial sequences
<220> FEATURE:
<221> NAME/KEY: source
<222> LOCATION: 1..346
<223> OTHER INFORMATION: /mol_type="DNA"
        /note="Promoter Pro_237 sense"
        /organism="artificial sequences"
<220> FEATURE:
<221> NAME/KEY: promoter
<222> LOCATION: 246..346
<223> OTHER INFORMATION: /note="Muc-1 minimal promoter"

<400> SEQUENCE: 48
gaaagctggg tctcgacaac aaagatcgat tgactcagtc gattgagtca gtcgatattt    60
gcatgtcgac atttgcatat cgactgacat caatcgattg actcagtcga ctgacatcaa   120
tcgacttcaa agatcgatct cacacctgta atcccagcgt cgaccctccc aaaatcgaga   180
gcctgctttt ttgtacaaac ttgtgatcga attctgcagt cgacggtacc gcgggcccgg   240
gatccaccgg tataaagcgg taggcgcctg tgcccgctcc acctctcaag cagccagcgc   300
ctgcctgaat ctgttctgcc ccctccccac ccatttcacc accaca                   346

<210> SEQ ID NO 49
```

```
<211> LENGTH: 238
<212> TYPE: DNA
<213> ORGANISM: artificial sequences
<220> FEATURE:
<221> NAME/KEY: source
<222> LOCATION: 1..238
<223> OTHER INFORMATION: /mol_type="DNA"
      /note="Promoter Pro_238 sense"
      /organism="artificial sequences"
<220> FEATURE:
<221> NAME/KEY: promoter
<222> LOCATION: 138..238
<223> OTHER INFORMATION: /note="Muc-1 minimal promoter"

<400> SEQUENCE: 49
cgttaactcg atcaccactt tgtacaagaa agctggctct cgatctttga agtcgatatg    60
caaatgtcga gagcctgctt ttttgtacaa acttgtgatc gaattctgca gtcgacggta   120
ccgcgggccc gggatccacc ggtataaagc ggtaggcgcc tgtgcccgct ccacctctca   180
agcagccagc gcctgcctga atctgttctg ccccctcccc acccatttca ccaccaca    238

<210> SEQ ID NO 50
<211> LENGTH: 318
<212> TYPE: DNA
<213> ORGANISM: artificial sequences
<220> FEATURE:
<221> NAME/KEY: source
<222> LOCATION: 1..318
<223> OTHER INFORMATION: /mol_type="DNA"
      /note="Promoter Pro_239 sense"
      /organism="artificial sequences"
<220> FEATURE:
<221> NAME/KEY: promoter
<222> LOCATION: 217..318
<223> OTHER INFORMATION: /note="Muc-1 minimal promoter"

<400> SEQUENCE: 50
gaaagctggg tctcgatctt tgttgtcgac tgagtcaatc gacaacaaag atcgatatca    60
aaggtcgatc cccgccgtcg attgactcgg tcgacatttg catatcgacg tttgcatatc   120
gacatgcaaa tgtcgatccc gccgtcgag agcctgcttt tttgtgcaaa cttgtgatcg   180
aattctgcag tcgacggtac cgcgggcccg ggatccaccg gtataaagcg gtaggcgcct   240
gtgcccgctc cacctctcaa gcagccagcg cctgcctgaa tctgttctgc ccctcccca   300 cccatttcac caccaccc                                                 318

<210> SEQ ID NO 51
<211> LENGTH: 272
<212> TYPE: DNA
<213> ORGANISM: artificial sequences
<220> FEATURE:
<221> NAME/KEY: source
<222> LOCATION: 1..272
<223> OTHER INFORMATION: /mol_type="DNA"
      /note="Promoter Pro_240 sense"
      /organism="artificial sequences"
<220> FEATURE:
<221> NAME/KEY: promoter
<222> LOCATION: 172..272
<223> OTHER INFORMATION: /note="Muc-1 minimal promoter"

<400> SEQUENCE: 51
gctgggtctc gacgctggga ttacaggtgt gagatcgcgg cggggatcga cgctgggatt    60
acaggtgtga gatcgatatt tgcatgtcga ctgacatcaa tcgagagcct gcttttttgt   120
acaaacttgt gatcgaattc tgcagtcgac ggtaccgcgg gccgggatc caccggtata   180 aagcggtagg cgcctgtgcc cgctccacct ctcaagcagc cagcgcctgc ctgaatctgt   240
```

```
tctgcccct ccccacccat ttcaccacca ca                                     272
```

<210> SEQ ID NO 52
<211> LENGTH: 236
<212> TYPE: DNA
<213> ORGANISM: artificial sequences
<220> FEATURE:
<221> NAME/KEY: source
<222> LOCATION: 1..236
<223> OTHER INFORMATION: /mol_type="DNA"
      /note="Promoter Pro_241 sense"
      /organism="artificial sequences"
<220> FEATURE:
<221> NAME/KEY: promoter
<222> LOCATION: 137..236
<223> OTHER INFORMATION: /note="Muc-1 minimal promoter"

<400> SEQUENCE: 52

```
cgttaactcg atcaccactt tgtacaagaa agctgggtct cgatcccgc cgtcgatatc       60 aaaggtcgag agcctgcttt tttgtacaaa cttgtgatcg aattctgcag tcgacggtac     120
cgcgggcccg ggatccaccg gtataaagcg gtaggcgcct gtgcccgctc cacctctcaa    180
gcagccagcg cctgcctgaa tctgttctgc cccctcccca cccatttcac caccac          236
```

<210> SEQ ID NO 53
<211> LENGTH: 301
<212> TYPE: DNA
<213> ORGANISM: artificial sequences
<220> FEATURE:
<221> NAME/KEY: source
<222> LOCATION: 1..301
<223> OTHER INFORMATION: /mol_type="DNA"
      /note="Promoter Pro_242 sense"
      /organism="artificial sequences"
<220> FEATURE:
<221> NAME/KEY: promoter
<222> LOCATION: 200..301
<223> OTHER INFORMATION: /note="Muc-1 minimal promoter"

<400> SEQUENCE: 53

```
cgttaactcg atcaccactt tgtacaagaa agctgggtct cgacggcggg gatcgactga      60
ctcaatcgat atgcaaatgt cgactgagtc aatcgactga ctcaatcgat tgatgtcagc    120
tgagtcaatc gagagcctgc ttttttgtac aaacttgtga tcgaattctg cagtcgacgg    180
taccgcgggc ccgggatcca ccggtataaa gcggtaggcg cctgtgcccg ctccacctct    240
caagcagcca gcgcctgcct gaatctgttc tgccccctcc cacccatttc accaccacc    300 c                                                                      301
```

<210> SEQ ID NO 54
<211> LENGTH: 239
<212> TYPE: DNA
<213> ORGANISM: artificial sequences
<220> FEATURE:
<221> NAME/KEY: source
<222> LOCATION: 1..239
<223> OTHER INFORMATION: /mol_type="DNA"
      /note="Promoter Pro_243 sense"
      /organism="artificial sequences"
<220> FEATURE:
<221> NAME/KEY: promoter
<222> LOCATION: 139..239
<223> OTHER INFORMATION: /note="Muc-1 minimal promoter"

<400> SEQUENCE: 54

```
cgttaactcg atcaccactt tgtacaggaa agctgggtct cgatatttgc atgtcgacat      60
```

```
gcaaatatcg agagcctgct tttttgtaca aacttgtgat cgaattctgc agtcgacggt    120
accgcgggcc cgggatccac cggtataaag cggtaggcgc ctgtgcccgc tccacctctc    180
aagcagccag cgcctgcctg aatctgttct gcccccctccc cacccatttc accaccaca   239
```

<210> SEQ ID NO 55
<211> LENGTH: 240
<212> TYPE: DNA
<213> ORGANISM: artificial sequences
<220> FEATURE:
<221> NAME/KEY: source
<222> LOCATION: 1..240
<223> OTHER INFORMATION: /mol_type="DNA"
      /note="Promoter Pro_244 sense"
      /organism="artificial sequences"
<220> FEATURE:
<221> NAME/KEY: promoter
<222> LOCATION: 140..240
<223> OTHER INFORMATION: /note="Muc-1 minimal promoter"

<400> SEQUENCE: 55

```
cgttaactcg atcaccactt tgtacaagaa agctgggtct cgattttggg agggtcgata     60
tttgcatgtc gagagcctgc ttttttgtac aaacttgtga tcgaattctg cagtcgacgg    120
taccgcgggc ccgggatcca ccggtataaa gcggtaggcg cctgtgcccg ctccacctct    180
caagcagcca gcgcctgcct gaatctgttc tgccccctcc ccacccattt caccaccaca   240
```

<210> SEQ ID NO 56
<211> LENGTH: 251
<212> TYPE: DNA
<213> ORGANISM: artificial sequences
<220> FEATURE:
<221> NAME/KEY: source
<222> LOCATION: 1..251
<223> OTHER INFORMATION: /mol_type="DNA"
      /note="Promoter Pro_245 sense"
      /organism="artificial sequences"
<220> FEATURE:
<221> NAME/KEY: promoter
<222> LOCATION: 151..251
<223> OTHER INFORMATION: /note="Muc-1 minimal promoter"

<400> SEQUENCE: 56

```
cgttaactcg atcaccactt tgtacaagaa agctgggtct cgattgatgt cagtcgactt     60
caaagatcga tctttgaagt cgagagcctg cttttttgta caaacttgtg atcgaattct    120
gcagtcgacg gtaccgcggg cccgggatcc accggtataa agcggtaggc gcctgtgccc    180
gctccacctc tcaagcagcc agcgcctgcc tgaatctgtt ctgccccctc cccacccatt    240
tcaccaccac a                                                         251
```

<210> SEQ ID NO 57
<211> LENGTH: 280
<212> TYPE: DNA
<213> ORGANISM: artificial sequences
<220> FEATURE:
<221> NAME/KEY: source
<222> LOCATION: 1..280
<223> OTHER INFORMATION: /mol_type="DNA"
      /note="Promoter Pro_246 sense"
      /organism="artificial sequences"
<220> FEATURE:
<221> NAME/KEY: promoter
<222> LOCATION: 180..280
<223> OTHER INFORMATION: /note="Muc-1 minimal promoter"

<400> SEQUENCE: 57

```
cgttaactcg atcaccactt tgtacaagaa agctgggcct cgacggcggg gatcgacatt     60
```

```
tgcatatcga ttttgggagg gtcgatatgc aaatgtcgac tgactcaatc gagagcctgc      120 tttttgtac aaacttgtga tcgaattctg cagtcgacgg taccgcgggc ccgggatcca        180
ccggtataaa gcggtaggcg cctgtgcccg ctccacctct caagcagcca gcgcctgcct       240
gaatctgttc tgcccctcc ccacccattt caccaccaca                              280
```

<210> SEQ ID NO 58
<211> LENGTH: 306
<212> TYPE: DNA
<213> ORGANISM: artificial sequences
<220> FEATURE:
<221> NAME/KEY: source
<222> LOCATION: 1..306
<223> OTHER INFORMATION: /mol_type="DNA"
      /note="Promoter Pro_247 sense"
      /organism="artificial sequences"
<220> FEATURE:
<221> NAME/KEY: promoter
<222> LOCATION: 206..306
<223> OTHER INFORMATION: /note="Muc-1 minimal promoter"

<400> SEQUENCE: 58

```
cgttaactcg atcaccactt tgtacaagaa agctgggtct cgatctttgt tgtcgatctt        60
tgaagtcgat tttgggaggg tcgactgacg tcaatcgaca tttgcatatc gatatcaaag      120
gtcgacaaca aagatcgaga gcctgctttt ttgtacaaac ttgtgatcga attctgcagt      180
cgacggtacc gcgggcccgg gatccaccgg tataaagcgg taggcgcctg tgcccgctcc      240
acctctcaag cagccagcgc ctgcctgaat ctgttctgcc cctcccccac ccatttcacc      300
accaca                                                                  306
```

<210> SEQ ID NO 59
<211> LENGTH: 329
<212> TYPE: DNA
<213> ORGANISM: artificial sequences
<220> FEATURE:
<221> NAME/KEY: source
<222> LOCATION: 1..329
<223> OTHER INFORMATION: /mol_type="DNA"
      /note="Promoter Pro_248 sense"
      /organism="artificial sequences"
<220> FEATURE:
<221> NAME/KEY: promoter
<222> LOCATION: 229..329
<223> OTHER INFORMATION: /note="Muc-1 minimal promoter"

<400> SEQUENCE: 59

```
cgttaactcg atcaccactt tgtacaagaa agctgggtct cgatatttgc atgtcgacgc        60
tgggattaca ggtgtgagat cgatctttga agtcgacaac aaagatcgat tgagtcagtc      120
gactgactca atcgacaaca aagatcgata tcaaaggtcg agagcctgct tttttgtaca      180
aacttgtgat cgaattctgc agtcgacggt accgcgggcc cgggatccac cggtataaag      240
cggtaggcgc ctgtgcccgc tccacctctc aagcagccag cgcctgcctg aatctgttct      300
gccccctccc cacccatttc accaccaca                                         329
```

<210> SEQ ID NO 60
<211> LENGTH: 250
<212> TYPE: DNA
<213> ORGANISM: artificial sequences
<220> FEATURE:
<221> NAME/KEY: source
<222> LOCATION: 1..250
<223> OTHER INFORMATION: /mol_type="DNA"
      /note="Promoter Pro_249 sense"

/organism="artificial sequences"
<220> FEATURE:
<221> NAME/KEY: promoter
<222> LOCATION: 150..250
<223> OTHER INFORMATION: /note="Muc-1 minimal promoter"

<400> SEQUENCE: 60
cgttaactcg atcaccactt tgtacaagaa agctgggtct cgacggcggg gatcgactga      60
gtcaatcgac ctttgatatc gagagcctgc ttttttgtac aaacttgtga tcgaattctg     120
cagtcgacgg taccgcgggc ccgggatcca ccggtataaa gcggtaggcg cctgtgcccg     180
ctccacctct caagcagcca gcgcctgcct gaatctgttc tgcccctcc ccacccattt      240 caccaccaca                                                            250

<210> SEQ ID NO 61
<211> LENGTH: 289
<212> TYPE: DNA
<213> ORGANISM: artificial sequences
<220> FEATURE:
<221> NAME/KEY: source
<222> LOCATION: 1..289
<223> OTHER INFORMATION: /mol_type="DNA"
        /note="Promoter Pro_250 sense"
        /organism="artificial sequences"
<220> FEATURE:
<221> NAME/KEY: promoter
<222> LOCATION: 189..289
<223> OTHER INFORMATION: /note="Muc-1 minimal promoter"

<400> SEQUENCE: 61
cgttaactcg atcaccactt tgtacaagaa agctgggtct cgacttcaaa gatcgactga      60
ctcaatcgac ctttgatatc gatctttgtt gtcgatctca cctgtaat cccagcgtcg      120 agagcctgct ttttgtaca aacttgtgat cgaattctgc agtcgacggt accgcgggcc     180
cgggatccac cggtataaag cggtaggcgc ctgtgcccgc tccacctctc aagcagccag     240
cgcctgcctg aatctgttct gcccctccc cacccatttc accaccaca                 289

<210> SEQ ID NO 62
<211> LENGTH: 234
<212> TYPE: DNA
<213> ORGANISM: artificial sequences
<220> FEATURE:
<221> NAME/KEY: source
<222> LOCATION: 1..234
<223> OTHER INFORMATION: /mol_type="DNA"
        /note="Promoter Pro_251 sense"
        /organism="artificial sequences"
<220> FEATURE:
<221> NAME/KEY: promoter
<222> LOCATION: 136..229
<223> OTHER INFORMATION: /note="Muc-1 minimal promoter"

<400> SEQUENCE: 62
gttaactcga tcaccacttt gtacaagaaa gctgggtctc gatctcacac ctgtaatccc      60
agcgtcgaga gcctgctttt ttgtacaaac ttgtgatcga attctgcagt cgacggtacc     120
gcgggcccgg gatccaccgg tataaagcgg taggcgccgg tgcccgctcc acctctcaag     180
cagccagcgc ctgcctgaat ctgttctgcc cctccccac ccatttcacc acca            234

<210> SEQ ID NO 63
<211> LENGTH: 298
<212> TYPE: DNA
<213> ORGANISM: artificial sequences
<220> FEATURE:
<221> NAME/KEY: source

```
<222> LOCATION: 1..298
<223> OTHER INFORMATION: /mol_type="DNA"
      /note="Promoter Pro_252 sense"
      /organism="artificial sequences"
<220> FEATURE:
<221> NAME/KEY: promoter
<222> LOCATION: 202..295
<223> OTHER INFORMATION: /note="Muc-1 minimal promoter"

<400> SEQUENCE: 63
gttaactcga tcaccacttt gtacaagaaa gctgggtctc gacctttgat atcgatctca      60
caccagtaat cccagcgtcg acttcaaaga tcgactgagt caatcgatcc cgccgtcga     120 tatgcaaatg tcgagagcct gcttttttgt acaaacttgt gatcgaattc tgcagtcgac    180
ggtaccgcgg gcccgggatc caccggtata aagcggtagg cgcctgtgcc cgctccacct    240
ctcaagcagc cagcgcctgc ctgaatctgt tctgcccct ccccacccat ttccaccac     298

<210> SEQ ID NO 64
<211> LENGTH: 214
<212> TYPE: DNA
<213> ORGANISM: artificial sequences
<220> FEATURE:
<221> NAME/KEY: source
<222> LOCATION: 1..214
<223> OTHER INFORMATION: /mol_type="DNA"
      /note="Promoter Pro_253 sense"
      /organism="artificial sequences"
<220> FEATURE:
<221> NAME/KEY: promoter
<222> LOCATION: 152..214
<223> OTHER INFORMATION: /note="Muc-1 minimal promoter"

<400> SEQUENCE: 64
cgttaactcg atcaccactt tgtacaagaa agctgggtct cgattttggg agggtcgatt      60
gagtcagtcg atctttgaag tcgagagcct gcttttttgt acaaacttgt gatcgaattc    120
tgcagtcgac ggtaccgcgg gcccgggatc caccggtata aagcggtagg cgcctgtgcc    180
cgctccacct ctcaagcagc cagcgcctgc cgaa                                214

<210> SEQ ID NO 65
<211> LENGTH: 270
<212> TYPE: DNA
<213> ORGANISM: artificial sequences
<220> FEATURE:
<221> NAME/KEY: source
<222> LOCATION: 1..270
<223> OTHER INFORMATION: /mol_type="DNA"
      /note="Promoter Pro_254 sense"
      /organism="artificial sequences"
<220> FEATURE:
<221> NAME/KEY: promoter
<222> LOCATION: 203..270
<223> OTHER INFORMATION: /note="Muc-1 minimal promoter"

<400> SEQUENCE: 65
cgttaactcg atcaccactt tgtacaagaa agctgggtct cgacggcggg gatcgatctt      60
tgaagtcgac ggcggggatc gacatttgca tatcgacctt tgatatcgac atttgcatat    120
cgtatcaaag gtcgagagcc tgcttttttg tacaaacttg tgatcgaatt ctgcagtcga    180
cggtaccgcg ggcccgggat ccaccggtat aaagcggtag gcgcctgtgc ccgctccacc    240
tctcaagcag ccagcgcctg ccgaatcatt                                    270

<210> SEQ ID NO 66
<211> LENGTH: 211
<212> TYPE: DNA
```

```
<213> ORGANISM: artificial sequences
<220> FEATURE:
<221> NAME/KEY: source
<222> LOCATION: 1..211
<223> OTHER INFORMATION: /mol_type="DNA"
      /note="Promoter Pro_255 sense"
      /organism="artificial sequences"
<220> FEATURE:
<221> NAME/KEY: promoter
<222> LOCATION: 111..211
<223> OTHER INFORMATION: /note="Muc-1 minimal promoter"

<400> SEQUENCE: 66
cgttaactcg atcaccactt tgtacaagaa agctgggtct cgagagcctg cttttttgta      60
caaacttgtg atcgaattct gcagtcgacg gtaccgcggg cccgggatcc accggtataa    120
agcggtaggc gcctgtgccc gctccacctc tcaagcagcc agcgcctgcc tgaatctgtt    180 ctgccccac cccacccatt tcaccaccac a                                    211

<210> SEQ ID NO 67
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="DNA"
      /organism="Homo sapiens"

<400> SEQUENCE: 67
ctcacacctg taatcccagc                                                 20

<210> SEQ ID NO 68
<211> LENGTH: 272
<212> TYPE: DNA
<213> ORGANISM: Artificial Sequence
<220> FEATURE:
<221> NAME/KEY: source
<222> LOCATION: 1..272
<223> OTHER INFORMATION: /mol_type="DNA"
      /note="SEQ SYN 001 antisense"
      /organism="Artificial Sequence"

<400> SEQUENCE: 68
tgcaatccat ggtggtggtg aaatgggtgg ggaggggca gaacagattc aggcaggcgc      60
tggctgcttg agaggtggag cgggcacagg cgcctaccgc tttataccgg tggatcccgg    120
gcccgcggta ccgtcgactg cagaattcga tcacaagttt gtacaaaaaa gcaggctctc    180
gacgctggga ttacaggtgt gagatcgaga cccagctttc ttgtacaaag tggtgatcga    240
gttaacgaat tccggcgcct actgcagata aa                                  272

<210> SEQ ID NO 69
<211> LENGTH: 336
<212> TYPE: DNA
<213> ORGANISM: Artificial Sequence
<220> FEATURE:
<221> NAME/KEY: source
<222> LOCATION: 1..336
<223> OTHER INFORMATION: /mol_type="DNA"
      /note="seq syn 102 antisense"
      /organism="Artificial Sequence"

<400> SEQUENCE: 69
tgcaatccat ggtggtggtg aaatgggtgg ggaggggca gaacagattc aggcaggcgc      60
tggctgcttg agaggtggag cgggcacagg cgcctaccgc tttataccgg tggatcccgg    120
```

```
gcccgcggta ccgtcgactg cagaattcga tcacaagttt gtacaaaaaa gcaggctctc    180
gacatttgca tatcgacggc ggggatcgat tgactcagtc gatctttgaa gtcgacgctg    240
ggattactgg tgtgagatcg atatcaaagg tcgagaccca gctttcttgt acaaagtggt    300
gatcgagtta acgaattccg gcgcctactg cagata                              336
```

<210> SEQ ID NO 70
<211> LENGTH: 300
<212> TYPE: DNA
<213> ORGANISM: Artificial Sequence
<220> FEATURE:
<221> NAME/KEY: source
<222> LOCATION: 1..300
<223> OTHER INFORMATION: /mol_type="DNA"
    /note="seq syn 103 antisense"
    /organism="Artificial Sequence"

<400> SEQUENCE: 70

```
caatccatgg tggtggtgaa atgggtgggg aggggcaga acagattcag gcaggcgctg      60
gctgcttgag aggtggagcg ggcacaggcg cctaccgctt tataccggtg gatcccgggc    120
ccgcggtacc gtcgactgca gaattcgatc acaagtttgt acaaaaaagc aggctctcga    180
cttcaaagat cgactgactc aatcgaccct cccaaaatcg agaccagct ttcttgtaca     240 aagtggtgat cgagttaacg aattccggcg cctactgcag atactagtgg gccctgcagg    300
```

<210> SEQ ID NO 71
<211> LENGTH: 351
<212> TYPE: DNA
<213> ORGANISM: Artificial Sequence
<220> FEATURE:
<221> NAME/KEY: source
<222> LOCATION: 1..351
<223> OTHER INFORMATION: /mol_type="DNA"
    /note="seq syn 105 antisense"
    /organism="Artificial Sequence"

<400> SEQUENCE: 71

```
tgcaatccat ggtggtggtg aaatgggtgg ggaggggca gaacagattc aggcaggcgc      60
tggctgcttg agaggtggag cgggcacagg cgcctaccgc tttataccgg tggatcccgg    120
gcccgcggta ccgtcgactg cagaattcga tcacaagttt gtacaaaaaa gcaggctctc    180
gacctttgat acgatatgca aatgtcgata tcaaaggtcg atatgcaaat gtcgatcccc    240
gccgtcgact tcaaagatcg atccccgccg tcgagaccca gctttcttgt acaaagtggt    300
gatcgagtta acgaattccg gcgcctactg cagcctctgc acaaagtgc a              351
```

<210> SEQ ID NO 72
<211> LENGTH: 298
<212> TYPE: DNA
<213> ORGANISM: Artificial Sequence
<220> FEATURE:
<221> NAME/KEY: source
<222> LOCATION: 1..298
<223> OTHER INFORMATION: /mol_type="DNA"
    /note="seq syn 106 antisense"
    /organism="Artificial Sequence"

<400> SEQUENCE: 72

```
tgcaatccat ggtggtggtg aaatgggtgg ggaggggca gaacagattc aggcaggcgc      60
tggctgcttg agaggtggag cgggcacagg cgcctaccgc tttataccgg tggatcccgg    120
gcccgcggta ccgtcgactg cagaattcga tcacaagttt gtacaaaaaa gcaggctctc    180
gagacccagc tttcttgtac aaagtggtga tcgagttaac gaattccggg ccactcagg    240
```

```
cccccttttc tgaaactcaa ttcttatcct cagtcctgct cctctgccac aaagtgca        298
```

<210> SEQ ID NO 73
<211> LENGTH: 243
<212> TYPE: DNA
<213> ORGANISM: Artificial Sequence
<220> FEATURE:
<221> NAME/KEY: source
<222> LOCATION: 1..243
<223> OTHER INFORMATION: /mol_type="DNA"
      /note="seq syn 108 antisense"
      /organism="Artificial Sequence"

<400> SEQUENCE: 73

```
tgcaatccat ggtggtggtg aaatgggtgg ggaggggggca gaacagattc aggcaggcgc      60
tggctgcttg agaggtggag cgggcacagg cgcctaccgc tttataccgg tggatcccgg      120
gcccgcggta ccgtcgactg cagaattcga tcacaagttt gtacaaaaaa gcaggctctc      180
gagacccagc tttcttgtac aaagtggtga tcgagttaac gaattccggc gccggccctg      240
cag                                                                   243
```

<210> SEQ ID NO 74
<211> LENGTH: 278
<212> TYPE: DNA
<213> ORGANISM: artificial sequences
<220> FEATURE:
<221> NAME/KEY: source
<222> LOCATION: 1..278
<223> OTHER INFORMATION: /mol_type="DNA"
      /note="Pro_200 antisense"
      /organism="artificial sequences"

<400> SEQUENCE: 74

```
tgtggtggtg aaatgggtgg ggaggggggca gaacagattc aggcaggcgc tggctgcttg      60
agaggtggag cgggcacagg cgcctaccgc tttataccgg tggatcccgg gcccgcggta      120
ccgtcgactg cagaattcga tcacaagttt gtacaaaaaa gcaggctctc gattgatgtc      180
agtcgacaac aaagatcgat tgactcagtc gacatgcaaa tatcgatctt tgttgtcgag      240
acccagcttt cttgtacaaa gtggtgatcg agttaacg                              278
```

<210> SEQ ID NO 75
<211> LENGTH: 265
<212> TYPE: DNA
<213> ORGANISM: artificial sequences
<220> FEATURE:
<221> NAME/KEY: source
<222> LOCATION: 1..265
<223> OTHER INFORMATION: /mol_type="DNA"
      /note="Pro_201 antisense"
      /organism="artificial sequences"

<400> SEQUENCE: 75

```
gtggtggtga aatgggtggg gaggggggcag aacagattca ggcaggcgct ggctgcttga      60
gaggtggagc gggcacaggc gcctaccgct ttataccggt ggatcccggg cccgcggtac      120
cgtcgactgc agaattcgat cacaagtttg tacaaaaaag caggctctcg acatgcaaat      180
atcgacattt gcatatcgat ctttgttgtc gactgacatc aatcgagacc cagctttctt      240
gtacaaagtg gtgatcgagt taacg                                           265
```

<210> SEQ ID NO 76
<211> LENGTH: 330
<212> TYPE: DNA

```
<213> ORGANISM: artificial sequences
<220> FEATURE:
<221> NAME/KEY: source
<222> LOCATION: 1..330
<223> OTHER INFORMATION: /mol_type="DNA"
      /note="Pro_202 antisense"
      /organism="artificial sequences"

<400> SEQUENCE: 76
gtggtggtga atgggtggg gaggggcag aacagattca ggcaggcgct ggctgcttga      60
gaggtggagc gggcacaggc gcctaccgct ttataccggt ggatcccggg cccgcggtac   120
cgtcgactgc agaattcgat cacaagtttg tacaaaaaag caggctctcg acttcaaaga   180
tcgatatcaa aggtcgatct ttgttgtcga ctgagtcaat cgattttggg agggtcgata   240
tgcaaatgtc gattgagtca gtcgactgac tcaatcgatc tttgttgtcg agacccagct   300
ttcctgtaca aagtggtgat cgagttaacg                                    330

<210> SEQ ID NO 77
<211> LENGTH: 222
<212> TYPE: DNA
<213> ORGANISM: artificial sequences
<220> FEATURE:
<221> NAME/KEY: source
<222> LOCATION: 1..222
<223> OTHER INFORMATION: /mol_type="DNA"
      /note="Pro_203 antisense"
      /organism="artificial sequences"

<400> SEQUENCE: 77
gggtggtgaa atgggtgggg aggggcaga acagattcag gcaggcgctg gctgcttgag      60
aggtggagcg ggcacaggcg cctaccgctt tataccggtg gatcccgggc ccgcggtacc   120
gtcgactgca gaattcgatc acaagtttgt acaaaaaagc aggctctcga tctttgttgt   180
cgagacccag ctttcttgta caaagtggtg atcgagttaa cg                      222

<210> SEQ ID NO 78
<211> LENGTH: 251
<212> TYPE: DNA
<213> ORGANISM: artificial sequences
<220> FEATURE:
<221> NAME/KEY: source
<222> LOCATION: 1..251
<223> OTHER INFORMATION: /mol_type="DNA"
      /note="Pro_204 antisense"
      /organism="artificial sequences"

<400> SEQUENCE: 78
tggtggtgaa atgggtgggg aggggcaga acagattcag gcaggcgctg gctgcttgag      60
aggtggagcg ggcacaggcg cctaccgctt tataccggtg gatcccgggc ccgcggtacc   120
gtcgactgca gaattcgatc acaagtttgt acaaaaaagc aggctctcga ttgactcagt   180
cgacatttgc atatcgaccc tcccaaaatc gagacccagc tttcttgtac aaagtggtga   240
tcgagttaac g                                                        251

<210> SEQ ID NO 79
<211> LENGTH: 250
<212> TYPE: DNA
<213> ORGANISM: artificial sequences
<220> FEATURE:
<221> NAME/KEY: source
<222> LOCATION: 1..250
<223> OTHER INFORMATION: /mol_type="DNA"
      /note="Pro_205 antisense"
      /organism="artificial sequences"
```

<400> SEQUENCE: 79

```
tgtggtggtg aaatgggtgg ggaggggggca gaacagattc aggcaggcgc tggctgcttg    60
agaggtggag cgggcacagg cgcctaccgc tttataccgg tggatcccgg gcccgcggta   120
ccgtcgactg cagaattcga tcacaagttt gtacaaaaaa gcaggctctc gacgctggga   180
ttacaggtgt gagatcgatt gagtcagtcg agacccagct ttcttgtaca aagtggtgat   240
cgagttaacg                                                         250
```

<210> SEQ ID NO 80
<211> LENGTH: 263
<212> TYPE: DNA
<213> ORGANISM: artificial sequences
<220> FEATURE:
<221> NAME/KEY: source
<222> LOCATION: 1..263
<223> OTHER INFORMATION: /mol_type="DNA"
   /note="Pro_206 antisense"
   /organism="artificial sequences"

<400> SEQUENCE: 80

```
tgtggtggtg aaatgggtgg ggaggggggca gaacagattc aggcaggcgc tggctgcttg    60
agaggtggag cgggcacagg cgcctaccgc tttataccgg tggatcccgg gcccgcggta   120
ccgtcgactg cagaattcga tcacaagttt gtacaaaaaa gcaggctctc gacgctggga   180
ttacaggtgt gagatcgatc tttgttgtcg acttcaaaga tcgagaccca gctttcttgt   240
acaaagtggt gatcgagtta acg                                          263
```

<210> SEQ ID NO 81
<211> LENGTH: 237
<212> TYPE: DNA
<213> ORGANISM: artificial sequences
<220> FEATURE:
<221> NAME/KEY: source
<222> LOCATION: 1..237
<223> OTHER INFORMATION: /mol_type="DNA"
   /note="Pro_207 antisense"
   /organism="artificial sequences"

<400> SEQUENCE: 81

```
tgtggtggtg aaatgggtgg ggaggggggca gaacagattc aggcaggcgc tggctgcttg    60
agaggtggag cgggcacagg cgcctaccgc tttataccgg tggatcccgg gcccgcggta   120
ccgtcgactg cagaattcga tcacaagttt gtacaaaaaa gcaggctctc gacgctggga   180
ttacaggtgt gagatcgaga cccagctttc ttgtacaaag tggtgatcga gttaacg     237
```

<210> SEQ ID NO 82
<211> LENGTH: 240
<212> TYPE: DNA
<213> ORGANISM: artificial sequences
<220> FEATURE:
<221> NAME/KEY: source
<222> LOCATION: 1..240
<223> OTHER INFORMATION: /mol_type="DNA"
   /note="Pro_208 antisense"
   /organism="artificial sequences"

<400> SEQUENCE: 82

```
tgtggtggtg aaatgggtgg ggaggggggca gaacagattc aggcaggcgc tggctgcttg    60
agaggtggag cgggcacagg cgcctaccgc tttataccgg tggatcccgg gcccgcggta   120
ccgtcgactg cagaattcga tcacaagttt gtacaaaaaa gcaggctctc gactgacatc   180
```
aatcgaccct cccaaaatcg agacccagct ttcttgtaca aagtggtgat cgagttaacg    240

<210> SEQ ID NO 83
<211> LENGTH: 270
<212> TYPE: DNA
<213> ORGANISM: artificial sequences
<220> FEATURE:
<221> NAME/KEY: source
<222> LOCATION: 1..270
<223> OTHER INFORMATION: /mol_type="DNA"
    /note="Pro_209 antisense"
    /organism="artificial sequences"

<400> SEQUENCE: 83
tatcgataag cttgatgtgg tggtgaaatg ggtggggagg gggcagaaca gattcaggca    60
ggcgctggct gcttgagagg tggagcgggc acaggcgcct accgctttat accggtggat    120
cccgggcccg cggtaccgtc gactgcagaa ttcgatcaca gtttgtaca aaaaagcagg    180 ctctcgatct cacacctgta atcccagcgt cgatatcaaa gtgcgatctt tgaagtcgaa    240
tcgaattcct gcagcccggg ggatccacta    270

<210> SEQ ID NO 84
<211> LENGTH: 238
<212> TYPE: DNA
<213> ORGANISM: artificial sequences
<220> FEATURE:
<221> NAME/KEY: source
<222> LOCATION: 1..238
<223> OTHER INFORMATION: /mol_type="DNA"
    /note="Pro_210 antisense"
    /organism="artificial sequences"

<400> SEQUENCE: 84
tgtggtggtg aaatgggtgg ggaggggggca gaacagattc aggcaggcgc tggctgcttg    60
agaggtggag cgggcacagg cgcctaccgc tttataccgg tggatcccgg gcccgcggta    120
ccgtcgactg cagaattcga tcacaagttt gtacaaaaaa gcaggctctc gatatgcaaa    180
tgtcgatccc cgccgtcgag acccagcttt cttgtacaaa gtggtgatcg agttaacg    238

<210> SEQ ID NO 85
<211> LENGTH: 237
<212> TYPE: DNA
<213> ORGANISM: artificial sequences
<220> FEATURE:
<221> NAME/KEY: source
<222> LOCATION: 1..237
<223> OTHER INFORMATION: /mol_type="DNA"
    /note="Pro_211 antisense"
    /organism="artificial sequences"

<400> SEQUENCE: 85
tgtggtggtg aaatgggtgg ggaggggggca gaacagattc aggcaggcgc tggctgcttg    60
agaggtggag cgggcacagg cgcctaccgc tttataccgg tggatcccgg gcccgcggta    120
ccgtcgactg cagaattcga tcacaagttt gtacaaaaaa gcaggctctc gacaacaaag    180
atcgattgag tcagtcgaga cccagctttc ttgtacaaag tggtgatcga gttaacg    237

<210> SEQ ID NO 86
<211> LENGTH: 224
<212> TYPE: DNA
<213> ORGANISM: artificial sequences
<220> FEATURE:
<221> NAME/KEY: source
<222> LOCATION: 1..224
<223> OTHER INFORMATION: /mol_type="DNA"

/note="Pro_212 antisense"
/organism="artificial sequences"

<400> SEQUENCE: 86
tggtggtgaa atgggtgggg aggggggcaga acagattcag gcaggcgctg gctgcttgag    60
aggtggagcg ggcacaggcg cctaccgctt tataccggtg gatcccgggc ccgcggtacc   120
gtcgactgca gaattcgatc acaagtttgt acaaaaaagc aggctctcga ttttgggagg   180
gtcgagaccc agctttcttg tacaaagtgg tgatcgagtt aacg                    224

<210> SEQ ID NO 87
<211> LENGTH: 324
<212> TYPE: DNA
<213> ORGANISM: artificial sequences
<220> FEATURE:
<221> NAME/KEY: source
<222> LOCATION: 1..324
<223> OTHER INFORMATION: /mol_type="DNA"
      /note="Pro_213 antisense"
      /organism="artificial sequences"

<400> SEQUENCE: 87
gagaagggtg gtggtgaaat gggtggggag ggggcagaac agattcaggc aggcgctggc    60
tgcttgagag gtggagcggg cacaggcgcc taccgcttta taccggtgga tcccgggccc   120
gcggtaccgt cgactgcaga attcgatcac aagtttgtac aaaaaagca ggctctcgat    180 ccccgccgtc gactgagtca atcgaccttt gatatcgatc tcacacctgt aatcccagcg   240
tcgaccctcc caaaatcgac aacaaagatc gatctttgtt gtcgagaccc agctttcttg   300
tacaaagtgg tgatcgagtt aacg                                         324

<210> SEQ ID NO 88
<211> LENGTH: 268
<212> TYPE: DNA
<213> ORGANISM: artificial sequences
<220> FEATURE:
<221> NAME/KEY: source
<222> LOCATION: 1..268
<223> OTHER INFORMATION: /mol_type="DNA"
      /note="Pro_214 antisense"
      /organism="artificial sequences"

<400> SEQUENCE: 88
cggtgtggtg gtgaaatggg tggggagggg gcagaacaga ttcaggcagg cgctggctgc    60
ttgagaggtg gagcgggcac aggcgcctac cgctttatac cggtggatcc cgggcccgcg   120
gtaccgtcga ctgcagaatt cgatcacaag tttgtacaaa aaagcaggct ctcgattgac   180
tcagtcgaca tttgcatatc gatctttgaa gtcgattgat gtcagtcgag acccagcttt   240
cttgtacaaa gtggtgatcg agttaacg                                     268

<210> SEQ ID NO 89
<211> LENGTH: 291
<212> TYPE: DNA
<213> ORGANISM: artificial sequences
<220> FEATURE:
<221> NAME/KEY: source
<222> LOCATION: 1..291
<223> OTHER INFORMATION: /mol_type="DNA"
      /note="Pro_215 antisense"
      /organism="artificial sequences"

<400> SEQUENCE: 89
ggtggtgaaa tgggtgggga ggggcagaa cagattcagg caggcgctgg ctgcttgaga    60

```
ggtggagcgg gcacaggcgc ctaccgcttt ataccggtgg atcccgggcc cgcggtaccg    120
tcgactgcag aattcgatca caagtttgta caaaaaagca ggctctcgat tttgggaggg    180
tcgacatgca aatatcgatt gatgtcagtc gatatgcaaa tgtcgatctt tgttgtcgat    240
ccccgccgtc gagacccagc tttcttgtac aaagtggtga tcgagttaac g            291

<210> SEQ ID NO 90
<211> LENGTH: 289
<212> TYPE: DNA
<213> ORGANISM: artificial sequences
<220> FEATURE:
<221> NAME/KEY: source
<222> LOCATION: 1..289
<223> OTHER INFORMATION: /mol_type="DNA"
      /note="Pro_216 antisense"
      /organism="artificial sequences"

<400> SEQUENCE: 90
ggtggtggtg aaatgggtgg ggaggggggca gaacagattc aggcaggcgc tggctgcttg    60
agaggtggag cgggcacagg cgcctaccgc tttataccgg tggatcccgg gcccgcggta   120
ccgtcgactg cagaattcga tcacaagttt gtacaaaaaa gcaggctctc gacgctggga   180
ttacagtgtg agatcgactg actcaatcga tctttgaagt cgactgactc aatcgacatt   240
tgcatatcga gacccagctt tcttgtacaa agtggtgatc gagttaacg              289

<210> SEQ ID NO 91
<211> LENGTH: 291
<212> TYPE: DNA
<213> ORGANISM: artificial sequences
<220> FEATURE:
<221> NAME/KEY: source
<222> LOCATION: 1..291
<223> OTHER INFORMATION: /mol_type="DNA"
      /note="Pro_217 antisense"
      /organism="artificial sequences"

<400> SEQUENCE: 91
tgtggtggtg aaatgggtgg ggaggggggca gaacagattc aggcaggcgc tggctgcttg    60
agaggtggag cgggcacagg cgcctaccgc tttataccgg tggatcccgg gcccgcggta   120
ccgtcgactg cagaattcga tcacaagttt gtacaaaaaa gcaggctctc gaccctccca   180
aaatcgactt caaagatcga ctgactcaat cgatctttgt tgtcgatctc acacctgtaa   240
tcccagcgtc gagacccagc tttcttgtac aaagtggtga tcgagttaac g            291

<210> SEQ ID NO 92
<211> LENGTH: 237
<212> TYPE: DNA
<213> ORGANISM: artificial sequences
<220> FEATURE:
<221> NAME/KEY: source
<222> LOCATION: 1..237
<223> OTHER INFORMATION: /mol_type="DNA"
      /note="Pro_218 antisense"
      /organism="artificial sequences"

<400> SEQUENCE: 92
tgtggtggtg aaatgggtgg ggaggggggca gaacagattc aggcaggcgc tggctgcttg    60
agaggtggag cgggcacagg cgcctaccgc tttataccgg tggatcccgg gcccgcggta   120
ccgtcgactg cagaattcga tcacaagttt gtacaaaaaa gcaggctctc gacaacaaag   180
atcgatcccc gccgtcgaga cccagctttc ttgtacaaag tggtgatcga gttaacg      237
```

```
<210> SEQ ID NO 93
<211> LENGTH: 280
<212> TYPE: DNA
<213> ORGANISM: artificial sequences
<220> FEATURE:
<221> NAME/KEY: source
<222> LOCATION: 1..280
<223> OTHER INFORMATION: /mol_type="DNA"
      /note="Pro_219 antisense"
      /organism="artificial sequences"

<400> SEQUENCE: 93
tgtggtggtg aaatgggtgg ggaggggggca gaacagattc aggcaggcgc tggctgcttg    60
agaggtggag cgggcacagg cgcctaccgc tttataccgg tggatccccg ggcccgcggt   120
accgtcgact gcagaattcg atcacaagtt tgtacaaaaa agcaggctct cgatctttga   180
agtcgatctt tgaagtcgac cctcccaaaa tcgacctttg atatcgattg atgtcagtcg   240
agacccagct ttcttgtaca aagtggtgat cgagttaacg                         280

<210> SEQ ID NO 94
<211> LENGTH: 224
<212> TYPE: DNA
<213> ORGANISM: artificial sequences
<220> FEATURE:
<221> NAME/KEY: source
<222> LOCATION: 1..224
<223> OTHER INFORMATION: /mol_type="DNA"
      /note="Pro_220 antisense"
      /organism="artificial sequences"

<400> SEQUENCE: 94
tgtggtggtg aaatgggtgg ggaggggggca gaacagattc aggcaggcgc tggctgcttg    60
agaggtggag cgggcacagg cgcctaccgc tttataccgg tggatcccgg gcccgcggta   120
ccatcgactg cagaattcga tcacaagttt gtacaaaaaa gcaggctctc gattgagtca   180
gtcgagaccc agctttcttg tacaaagtgg tgatcgagtt aacg                    224

<210> SEQ ID NO 95
<211> LENGTH: 235
<212> TYPE: DNA
<213> ORGANISM: artificial sequences
<220> FEATURE:
<221> NAME/KEY: source
<222> LOCATION: 1..235
<223> OTHER INFORMATION: /mol_type="DNA"
      /note="Pro_221 antisense"
      /organism="artificial sequences"

<400> SEQUENCE: 95
ggtggtgaaa tgcgtgggga gggggcagaa cagattcagg caggcgctgg ctgcttgaga    60
ggtggagcgg gcacaggcgc ctaccgcttt ataccggtgg atcccgcgcc cccggtcccc   120
tcgactgcag aattcgatca caagtttgta caaaaaagca ggctctcgat atttgcatgt   180
cgattgactc agtcgagacc cagctttctt gtacaaagtg gtgatcgagt taacg        235

<210> SEQ ID NO 96
<211> LENGTH: 303
<212> TYPE: DNA
<213> ORGANISM: artificial sequences
<220> FEATURE:
<221> NAME/KEY: source
<222> LOCATION: 1..303
<223> OTHER INFORMATION: /mol_type="DNA"
      /note="Pro_222 antisense"
      /organism="artificial sequences"
```

<400> SEQUENCE: 96

| | | | | | |
|---|---|---|---|---|---|
| tgtggtggtg | aaatgggtgg | ggaggggggca | gaacagattc | aggcaggcgc | tggctgcttg | 60 |
| agaggtggag | cgggcacagg | cgcctaccgc | tttataccgg | tggatcccgg | gcccgcggta | 120 |
| ccgtcgactg | cagaattcga | tcacaagttt | gtacaaaaaa | gcaggctctc | gacatttgca | 180 |
| tatcgacggc | ggggatcgat | tgactcagtc | gatctttgaa | gtcgacgctg | ggattactgg | 240 |
| tgtgagatcg | atatcaaagg | tcgagaccca | gctttcttgt | acaaagtggt | gatcgagtta | 300 |
| acg | | | | | | 303 |

<210> SEQ ID NO 97
<211> LENGTH: 318
<212> TYPE: DNA
<213> ORGANISM: artificial sequences
<220> FEATURE:
<221> NAME/KEY: source
<222> LOCATION: 1..318
<223> OTHER INFORMATION: /mol_type="DNA"
    /note="Pro_223 antisense"
    /organism="artificial sequences"

<400> SEQUENCE: 97

| | | | | | |
|---|---|---|---|---|---|
| tcgataagct | tgatgtggtg | gtgaaatggg | tggggagggg | gcagaacaga | ttcaggcagg | 60 |
| cgctggctgc | ttgagaggtg | gagcgggcac | aggcgcctac | cgctttatac | cggtggatcc | 120 |
| cgggcccgcg | gtaccgtcga | ctgcagaatt | cgatcacaag | tttgtacaaa | aaagcaggct | 180 |
| ctcgattgac | tcagtcgaca | tttgcatatc | gatatgcaaa | tgtcgactga | ctcaatcgac | 240 |
| tgagtcaatc | gatatcaaag | gtcgactgac | atcaatcgag | acccagcttt | cttgtacaaa | 300 |
| gtggtgatcg | agttaacg | | | | | 318 |

<210> SEQ ID NO 98
<211> LENGTH: 251
<212> TYPE: DNA
<213> ORGANISM: artificial sequences
<220> FEATURE:
<221> NAME/KEY: source
<222> LOCATION: 1..251
<223> OTHER INFORMATION: /mol_type="DNA"
    /note="Pro_224 antisense"
    /organism="artificial sequences"

<400> SEQUENCE: 98

| | | | | | |
|---|---|---|---|---|---|
| tgtggtggtg | aaatgggtgg | ggaggggggca | gaacagattc | aggcaggcgc | tggctgcttg | 60 |
| agaggtggag | cgggcacagg | cgcctaccgc | tttataccgg | tggatcccgg | gcccgcggta | 120 |
| ccgtcgactg | cagaattcga | tcacaagttt | gtacaaaaaa | gcaggctctc | gactgactca | 180 |
| atcgacggcg | gggatcgact | gacatcaatc | gagacccagc | tttcttgtac | aaagtggtga | 240 |
| tcgagttaac | g | | | | | 251 |

<210> SEQ ID NO 99
<211> LENGTH: 286
<212> TYPE: DNA
<213> ORGANISM: artificial sequences
<220> FEATURE:
<221> NAME/KEY: source
<222> LOCATION: 1..286
<223> OTHER INFORMATION: /mol_type="DNA"
    /note="Pro_225 antisense"
    /organism="artificial sequences"

<400> SEQUENCE: 99

| | | | | | |
|---|---|---|---|---|---|
| agcttgatgt | ggtggtgaaa | tgggtgggga | ggggcagaa | cagattcagg | caggcgctgg | 60 |

-continued
ctgcttgaga ggtggagcgg gcacaggcgc ctaccgcttt ataccggtgg atcccgggcc 120
cgcggtaccg tcgactgcag aattcgatca caagtttgta caaaaaagca ggctctcgac 180
cctcccaaaa tcgattgagt cagtcgatat ttgcatgtcg acaacaaaga tcgacttcaa 240
agatcgagac ccagctttct tgtacaaagt ggtgatcgag ttaacg 286

<210> SEQ ID NO 100
<211> LENGTH: 315
<212> TYPE: DNA
<213> ORGANISM: artificial sequences
<220> FEATURE:
<221> NAME/KEY: source
<222> LOCATION: 1..315
<223> OTHER INFORMATION: /mol_type="DNA"
/note="Pro_226 antisense"
/organism="artificial sequences"

<400> SEQUENCE: 100
tgtggtggtg aaatgggtgg ggagggggca gaacagattc aggcaggcgc tggctgcttg 60
agaggtggag cgggcacagg cgcctaccgc tttataccgg tggatcccgg gcccgcggta 120
ccgtcgactg cagaattcga tcacaagttt gtacaaaaaa gcaggctctc gacctttgat 180
atcgactgac tcaatcgatc tttgttgtcg atctttgaag tcgacggcgg ggatcgatct 240
ttgaagtcga caacaaagat cgatctttga agtcgagacc cagctttctt gtacaaagtg 300
gtgatcgagt taacg 315

<210> SEQ ID NO 101
<211> LENGTH: 277
<212> TYPE: DNA
<213> ORGANISM: artificial sequences
<220> FEATURE:
<221> NAME/KEY: source
<222> LOCATION: 1..277
<223> OTHER INFORMATION: /mol_type="DNA"
/note="Pro_227 antisense"
/organism="artificial sequences"

<400> SEQUENCE: 101
tggtggtgaa atgggtgggg agggggcara acagattcag gcaggcgctg gctgcttgag 60
aggtggagcg ggcacaggcg cctaccgctt tataccggtg gatcccgggc ccgcggtacc 120
gtcgactgca gaattcgatc acaagtttgt acaaaaaagc aggctctcga tatgcaaatg 180
tcgactgaca tcaatcgaca acaaagatcg actgactcaa tcgacatgca aatatcgaga 240
cccagctttc ttgtacaaag tggtgatcga gttaacg 277

<210> SEQ ID NO 102
<211> LENGTH: 262
<212> TYPE: DNA
<213> ORGANISM: artificial sequences
<220> FEATURE:
<221> NAME/KEY: source
<222> LOCATION: 1..262
<223> OTHER INFORMATION: /mol_type="DNA"
/note="Pro_228 antisense"
/organism="artificial sequences"

<400> SEQUENCE: 102
ggtggtgaaa tgggtgggga gggggcagaa cagattcagg caggcgctgg ctgcttgaga 60
ggtggagcgg gcacaggcgc ctaccgcttt ataccggtgg atcccgggcc cgcggtaccg 120
tcgactgcag aattcgatca caagtttgta caaaaaagca ggctctcgat tgatgtcagt 180
cgacggcggg gatcgatctt tgaagtcgat tttgggaggg tcgagaccca gctttcttgt     240
acaaagtggt gatcgagtta ac     262

<210> SEQ ID NO 103
<211> LENGTH: 264
<212> TYPE: DNA
<213> ORGANISM: artificial sequences
<220> FEATURE:
<221> NAME/KEY: source
<222> LOCATION: 1..264
<223> OTHER INFORMATION: /mol_type="DNA"
      /note="Pro_229 antisense"
      /organism="artificial sequences"

<400> SEQUENCE: 103
tgtggtggtg aaatgggtgg ggaggggca gaacagattc aggcaggcgc tggctgcttg     60
agaggtggag cgggcacagg cgcctaccgc tttataccgg tggatcccgg gcccgcggta     120
ccgtcgactg cagaattcga tcacaagttt gtacaaaaaa gcaggctctc gatctttgaa     180
gtcgatatgc aaatgtcgat tgactcagtc gactgactca atcgagaccc agctttcttg     240
tacaaagtgg tgatcgagtt aacg     264

<210> SEQ ID NO 104
<211> LENGTH: 266
<212> TYPE: DNA
<213> ORGANISM: artificial sequences
<220> FEATURE:
<221> NAME/KEY: source
<222> LOCATION: 1..266
<223> OTHER INFORMATION: /mol_type="DNA"
      /note="Pro_230 antisense"
      /organism="artificial sequences"

<400> SEQUENCE: 104
tgtggtggtg aaatgggtgg ggaggggca gaacagattc aggcaggcgc tggctgcttg     60
agaggtggag cgggcacagg cgcctaccgc tttataccgg tggatcccgg gcccgcggta     120
ccgtcgactg cagaattcga tcacaagttt gtacaaaaaa gcaggctctc gacatttgca     180
tatcgactga ctcaatcgat atgcaaatgt cgatatgcaa atgtcgagac ccagctttcc     240
tgtacaaagt ggtgatcgag ttaacg     266

<210> SEQ ID NO 105
<211> LENGTH: 279
<212> TYPE: DNA
<213> ORGANISM: artificial sequences
<220> FEATURE:
<221> NAME/KEY: source
<222> LOCATION: 1..279
<223> OTHER INFORMATION: /mol_type="DNA"
      /note="Pro_231 antisense"
      /organism="artificial sequences"

<400> SEQUENCE: 105
gtggtggtga aatgggtggg gagggggcag aacagattca ggcaggcgct ggctgcttga     60
gaggtggagc gggcacaggc gcctaccgct ttataccggt ggatcccggg cccgcggtac     120
cgtcgactgc agaattcgat cacaagtttg tacaaaaaag caggctctcg accctcccaa     180
aatcgattga gtcagtcgac atttgcatat cgacaacaaa gatcgactga catcaatcga     240
gacccagctt tcttgtacaa agtggtgatc gagttaacg     279

<210> SEQ ID NO 106
<211> LENGTH: 311

```
<212> TYPE: DNA
<213> ORGANISM: artificial sequences
<220> FEATURE:
<221> NAME/KEY: source
<222> LOCATION: 1..311
<223> OTHER INFORMATION: /mol_type="DNA"
      /note="Pro_232 antisense"
      /organism="artificial sequences"

<400> SEQUENCE: 106 gatccccgg gctgcaggaa ttcgatgtgg tggtgaaatg ggtggggagg gggcagaaca      60
gattcaggca ggcgctggct gcttgagagg tggagcgggc acaggcgcct accgctttat     120
accggtggat cccgggcccg cggtaccgtc gactgcagaa ttcgatcaca gtttgtaca     180 aaaaagcagg ctctcgactg agtcaatcga cttcaaagat cgacggcggg gatcgatatg    240
caaatgtcga tatgcaaatg tcgagaccca gctttcttgt acaaagtggt gatcgagtta    300
acgaattccg g                                                          311

<210> SEQ ID NO 107
<211> LENGTH: 264
<212> TYPE: DNA
<213> ORGANISM: artificial sequences
<220> FEATURE:
<221> NAME/KEY: source
<222> LOCATION: 1..264
<223> OTHER INFORMATION: /mol_type="DNA"
      /note="Pro_233 antisense"
      /organism="artificial sequences"

<400> SEQUENCE: 107
tgtggtggtg aaatgggttg ggaggggca gaacagattc aggcaggcgc tggctgcttg      60
agaggtggag cgggcacagg cgcctaccgc tttataccgg tggatcccgg gcccgcggta    120
ccgtcgactg cagaattcga tcacaagttt gtacaaaaaa gcaggctctc gacttcaaag    180
atcgatcttt gttgtcgaca tttgcatatc gatctttgtt gtcgagaccc agctttcctg    240
tacaaagtgg tgatcgagtt aacg                                            264

<210> SEQ ID NO 108
<211> LENGTH: 310
<212> TYPE: DNA
<213> ORGANISM: artificial sequences
<220> FEATURE:
<221> NAME/KEY: source
<222> LOCATION: 1..310
<223> OTHER INFORMATION: /mol_type="DNA"
      /note="Pro_234 antisense"
      /organism="artificial sequences"

<400> SEQUENCE: 108
tgtggtggtg aaatgggtgg ggaggggca gaacagattc aggcaggcgc tggctgcttg      60
agaggtggag cgggcacagg cgcctaccgc tttataccgg tggatcccgg gcccgcggta    120
ccgtcgactg cagaattcga tcacaagttt gtacaaaaaa gcaggctctc gactgacatc    180
aatcgattga tgtcagtcga ttgactcagt cgattttggg agggtcgacg gcggggatcg    240
actgagtcaa tcgattgact cagtcgagac ccagctttct tgtacaaagt ggtgatcgag    300
ttaacgaatt                                                            310

<210> SEQ ID NO 109
<211> LENGTH: 277
<212> TYPE: DNA
<213> ORGANISM: artificial sequences
<220> FEATURE:
```

```
<221> NAME/KEY: source
<222> LOCATION: 1..277
<223> OTHER INFORMATION: /mol_type="DNA"
      /note="Pro_225 antisense"
      /organism="artificial sequences"

<400> SEQUENCE: 109
tgtggtggtg aaatgggtgg ggcgggggca gaacagattc aggcaggcgc tggctgcttg      60
agaggtggag cgggcacagg cgcctaccgc tttataccgg tggatcccgg gcccgcggta     120
ccgtcgactg cagaattcga tcacaagttt gtacaaaaaa gcaggctctc gactgactca     180
atcgattgac tcagtcgaca acaaagatcg actgactcaa tcgatatgca aatgtcgaga     240
cccagctttc ttgtacaaag tggtgatcga gttaacg                              277

<210> SEQ ID NO 110
<211> LENGTH: 252
<212> TYPE: DNA
<213> ORGANISM: artificial sequences
<220> FEATURE:
<221> NAME/KEY: source
<222> LOCATION: 1..252
<223> OTHER INFORMATION: /mol_type="DNA"
      /note="Pro_236 antisense"
      /organism="artificial sequences"

<400> SEQUENCE: 110
tgtggtggtg aaatgggtgg ggaggggggca gaacagattc aggcaggcgc tggctgcttg     60
agaggtggag cgggcacagg cgcctaccgc tttataccgg tggatcccgg gcccgcggta    120
ccgtcgactg cagaattcga tcacaagttt gtacaaaaaa gcaggctctc gacatttgca    180
tatcgattga ctcagtcgac tgacatcaat cgagacccag ctttcttgta caaagtggtg    240
atcgagttaa cg                                                         252

<210> SEQ ID NO 111
<211> LENGTH: 346
<212> TYPE: DNA
<213> ORGANISM: artificial sequences
<220> FEATURE:
<221> NAME/KEY: source
<222> LOCATION: 1..346
<223> OTHER INFORMATION: /mol_type="DNA"
      /note="Pro_237 antisense"
      /organism="artificial sequences"

<400> SEQUENCE: 111
tgtggtggtg aaatgggtgg ggaggggggca gaacagattc aggcaggcgc tggctgcttg     60
agaggtggag cgggcacagg cgcctaccgc tttataccgg tggatcccgg gcccgcggta    120
ccgtcgactg cagaattcga tcacaagttt gtacaaaaaa gcaggctctc gattttggga    180
gggtcgacgc tgggattaca ggtgtgagat cgatctttga agtcgattga tgtcagtcga    240
ctgagtcaat cgattgatgt cagtcgatat gcaaatgtcg acatgcaaat atcgactgac    300
tcaatcgact gagtcaatcg atctttgttg tcgagaccca gctttc                   346

<210> SEQ ID NO 112
<211> LENGTH: 238
<212> TYPE: DNA
<213> ORGANISM: artificial sequences
<220> FEATURE:
<221> NAME/KEY: source
<222> LOCATION: 1..238
<223> OTHER INFORMATION: /mol_type="DNA"
      /note="Pro_238 antisense"
      /organism="artificial sequences"
```

<400> SEQUENCE: 112

```
tgtggtggtg aaatgggtgg ggaggggggca gaacagattc aggcaggcgc tggctgcttg      60
agaggtggag cgggcacagg cgcctaccgc tttataccgg tggatcccgg gcccgcggta     120
ccgtcgactg cagaattcga tcacaagttt gtacaaaaaa gcaggctctc gacatttgca     180
tatcgacttc aaagatcgag agccagcttt cttgtacaaa gtggtgatcg agttaacg      238
```

<210> SEQ ID NO 113
<211> LENGTH: 318
<212> TYPE: DNA
<213> ORGANISM: artificial sequences
<220> FEATURE:
<221> NAME/KEY: source
<222> LOCATION: 1..318
<223> OTHER INFORMATION: /mol_type="DNA"
    /note="Pro_239 antisense"
    /organism="artificial sequences"

<400> SEQUENCE: 113

```
gggtggtggt gaaatgggtg gggaggggggc agaacagatt caggcaggcg ctggctgctt      60
gagaggtgga gcgggcacag gcgcctaccg ctttataccg gtggatcccg ggcccgcggt     120
accgtcgact gcagaattcg atcacaagtt tgcacaaaaa agcaggctct cgacggcggg     180
gatcgacatt tgcatgtcga tatgcaaacg tcgatatgca aatgtcgacc gagtcaatcg     240
acggcgggga tcgacctttg atatcgatct ttgttgtcga ttgactcagt cgacaacaaa     300
gatcgagacc cagcttttc                                                   318
```

<210> SEQ ID NO 114
<211> LENGTH: 272
<212> TYPE: DNA
<213> ORGANISM: artificial sequences
<220> FEATURE:
<221> NAME/KEY: source
<222> LOCATION: 1..272
<223> OTHER INFORMATION: /mol_type="DNA"
    /note="Pro_240 antisense"
    /organism="artificial sequences"

<400> SEQUENCE: 114

```
tgtggtggtg aaatgggtgg ggaggggggca gaacagattc aggcaggcgc tggctgcttg      60
agaggtggag cgggcacagg cgcctaccgc tttataccgg tggatcccgg gcccgcggta     120
ccgtcgactg cagaattcga tcacaagttt gtacaaaaaa gcaggctctc gattgatgtc     180
agtcgacatg caaatatcga tctcacacct gtaatcccag cgtcgatccc cgccgcgatc     240
tcacacctgt aatcccagcg tcgagaccca gc                                    272
```

<210> SEQ ID NO 115
<211> LENGTH: 236
<212> TYPE: DNA
<213> ORGANISM: artificial sequences
<220> FEATURE:
<221> NAME/KEY: source
<222> LOCATION: 1..236
<223> OTHER INFORMATION: /mol_type="DNA"
    /note="Pro_241 antisense"
    /organism="artificial sequences"

<400> SEQUENCE: 115

```
gtggtggtga aatgggtggg gagggggcag aacagattca ggcaggcgct ggctgcttga      60
gaggtggagc gggcacaggc gcctaccgct ttataccggt ggatcccggg cccgcggtac     120
```

```
cgtcgactgc agaattcgat cacaagtttg tacaaaaaag caggctctcg acctttgata    180
tcgacggcgg ggatcgagac ccagctttct tgtacaaagt ggtgatcgag ttaacg        236
```

<210> SEQ ID NO 116
<211> LENGTH: 301
<212> TYPE: DNA
<213> ORGANISM: artificial sequences
<220> FEATURE:
<221> NAME/KEY: source
<222> LOCATION: 1..301
<223> OTHER INFORMATION: /mol_type="DNA"
      /note="Pro_242 antisense"
      /organism="artificial sequences"

<400> SEQUENCE: 116

```
gggtggtggt gaaatgggtg gggaggggggc agaacagatt caggcaggcg ctggctgctt    60
gagaggtgga gcgggcacag gcgcctaccg ctttataccg gtggatcccg ggcccgcggt   120
accgtcgact gcagaattcg atcacaagtt tgtacaaaaa agcaggctct cgattgactc   180
agctgacatc aatcgattga gtcagtcgat tgactcagtc gacatttgca tatcgattga   240
gtcagtcgat ccccgccgtc gagacccagc tttcttgtac aaagtggtga tcgagttaac   300
g                                                                   301
```

<210> SEQ ID NO 117
<211> LENGTH: 239
<212> TYPE: DNA
<213> ORGANISM: artificial sequences
<220> FEATURE:
<221> NAME/KEY: source
<222> LOCATION: 1..239
<223> OTHER INFORMATION: /mol_type="DNA"
      /note="Pro_243 antisense"
      /organism="artificial sequences"

<400> SEQUENCE: 117

```
tgtggtggtg aaatgggtgg ggaggggggca gaacagattc aggcaggcgc tggctgcttg    60
agaggtggag cgggcacagg cgcctaccgc tttataccgg tggatcccgg gcccgcggta   120
ccgtcgactg cagaattcga tcacaagttt gtacaaaaaa gcaggctctc gatatttgca   180
tgtcgacatg caaatatcga gacccagctt cctgtacaa agtggtgatc gagttaacg     239
```

<210> SEQ ID NO 118
<211> LENGTH: 240
<212> TYPE: DNA
<213> ORGANISM: artificial sequences
<220> FEATURE:
<221> NAME/KEY: source
<222> LOCATION: 1..240
<223> OTHER INFORMATION: /mol_type="DNA"
      /note="Pro_234 antisense"
      /organism="artificial sequences"

<400> SEQUENCE: 118

```
tgtggtggtg aaatgggtgg ggaggggggca gaacagattc aggcaggcgc tggctgcttg    60
agaggtggag cgggcacagg cgcctaccgc tttataccgg tggatcccgg gcccgcggta   120
ccgtcgactg cagaattcga tcacaagttt gtacaaaaaa gcaggctctc gacatgcaaa   180
tatcgaccct cccaaaatcg agacccagct ttccttgtaca agtggtgat cgagttaacg   240
```

<210> SEQ ID NO 119
<211> LENGTH: 251
<212> TYPE: DNA
<213> ORGANISM: artificial sequences

```
<220> FEATURE:
<221> NAME/KEY: source
<222> LOCATION: 1..251
<223> OTHER INFORMATION: /mol_type="DNA"
      /note="Pro_235 antisense"
      /organism="artificial sequences"

<400> SEQUENCE: 119
tgtggtggtg aaatgggtgg ggaggggggca gaacagattc aggcaggcgc tggctgcttg      60
agaggtggag cgggcacagg cgcctaccgc tttataccgg tggatcccgg gcccgcggta     120
ccgtcgactg cagaattcga tcacaagttt gtacaaaaaa gcaggctctc gacttcaaag     180
atcgatcttt gaagtcgact gacatcaatc gagacccagc tttcttgtac aaagtggtga     240
tcgagttaac g                                                          251

<210> SEQ ID NO 120
<211> LENGTH: 280
<212> TYPE: DNA
<213> ORGANISM: artificial sequences
<220> FEATURE:
<221> NAME/KEY: source
<222> LOCATION: 1..280
<223> OTHER INFORMATION: /mol_type="DNA"
      /note="Pro_246 antisense"
      /organism="artificial sequences"

<400> SEQUENCE: 120
tgtggtggtg aaatgggtgg ggaggggggca gaacagattc aggcaggcgc tggctgcttg      60
agaggtggag cgggcacagg cgcctaccgc tttataccgg tggatcccgg gcccgcggta     120
ccgtcgactg cagaattcga tcacaagttt gtacaaaaaa gcaggctctc gattgagtca     180
gtcgacattt gcatatcgac cctcccaaaa tcgatatgca aatgtcgatc cccgccgtcg     240
aggcccagct ttcttgtaca aagtggtgat cgagttaacg                           280

<210> SEQ ID NO 121
<211> LENGTH: 306
<212> TYPE: DNA
<213> ORGANISM: artificial sequences
<220> FEATURE:
<221> NAME/KEY: source
<222> LOCATION: 1..306
<223> OTHER INFORMATION: /mol_type="DNA"
      /note="Pro_247 antisense"
      /organism="artificial sequences"

<400> SEQUENCE: 121
tgtggtggtg aaatgggtgg ggaggggggca gaacagattc aggcaggcgc tggctgcttg      60
agaggtggag cgggcacagg cgcctaccgc tttataccgg tggatcccgg gcccgcggta     120
ccgtcgactg cagaattcga tcacaagttt gtacaaaaaa gcaggctctc gatctttgtt     180 gtcgacctttt gatatcgata tgcaaatgtc gattgacgtc agtcgaccct cccaaaatcg     240
acttcaaaga tcgacaacaa agatcgagac ccagctttct tgtacaaagt ggtgatcgag     300
ttaacg                                                                306

<210> SEQ ID NO 122
<211> LENGTH: 329
<212> TYPE: DNA
<213> ORGANISM: artificial sequences
<220> FEATURE:
<221> NAME/KEY: source
<222> LOCATION: 1..329
<223> OTHER INFORMATION: /mol_type="DNA"
      /note="Pro_248 antisense"
```

/organism="artificial sequences"

<400> SEQUENCE: 122

```
tgtggtggtg aaatgggtgg ggaggggca  gaacagattc aggcaggcgc tggctgcttg      60
agaggtggag cgggcacagg cgcctaccgc tttataccgg tggatcccgg gcccgcggta     120
ccgtcgactg cagaattcga tcacaagttt gtacaaaaaa gcaggctctc gacctttgat    180
atcgatcttt gttgtcgatt gagtcagtcg actgactcaa tcgatctttg ttgtcgactt    240
caaagatcga tctcacacct gtaatcccag cgtcgacatg caaatatcga gacccagctt    300
tcttgtacaa agtggtgatc gagttaacg                                      329
```

<210> SEQ ID NO 123
<211> LENGTH: 250
<212> TYPE: DNA
<213> ORGANISM: artificial sequences
<220> FEATURE:
<221> NAME/KEY: source
<222> LOCATION: 1..250
<223> OTHER INFORMATION: /mol_type="DNA"
    /note="Pro_249 antisense"
    /organism="artificial sequences"

<400> SEQUENCE: 123

```
tgtggtggtg aaatgggtgg ggagggggca gaacagattc aggcaggcgc tggctgcttg      60
agaggtggag cgggcacagg cgcctaccgc tttataccgg tggatcccgg gcccgcggta     120
ccgtcgactg cagaattcga tcacaagttt gtacaaaaaa gcaggctctc gatatcaaag    180
gtcgattgac tcagtcgatc cccgccgtcg agacccagct tcttgtaca  aagtggtgat    240
cgagttaacg                                                           250
```

<210> SEQ ID NO 124
<211> LENGTH: 289
<212> TYPE: DNA
<213> ORGANISM: artificial sequences
<220> FEATURE:
<221> NAME/KEY: source
<222> LOCATION: 1..289
<223> OTHER INFORMATION: /mol_type="DNA"
    /note="Pro_250 antisense"
    /organism="artificial sequences"

<400> SEQUENCE: 124

```
tgtggtggtg aaatgggtgg ggagggggca gaacagattc aggcaggcgc tggctgcttg      60
agaggtggag cgggcacagg cgcctaccgc tttataccgg tggatcccgg gcccgcggta     120
ccgtcgactg cagaattcga tcacaagttt gtacaaaaaa gcaggctctc gacgctggga    180
ttacaggtgt gagatcgaca acaaagatcg atatcaaagg tcgattgagt cagtcgatct    240
ttgaagtcga gacccagctt tcttgtacaa agtggtgatc gagttaacg                289
```

<210> SEQ ID NO 125
<211> LENGTH: 234
<212> TYPE: DNA
<213> ORGANISM: artificial sequences
<220> FEATURE:
<221> NAME/KEY: source
<222> LOCATION: 1..234
<223> OTHER INFORMATION: /mol_type="DNA"
    /note="Pro_251 antisense"
    /organism="artificial sequences"

<400> SEQUENCE: 125
tggtggtgaa atgggtgggg aggggcaga  acagattcag gcaggcgctg gctgcttgag     60
```

```
aggtggagcg ggcaccggcg cctaccgctt tataccggtg gatcccgggc ccgcggtacc    120
gtcgactgca gaattcgatc acaagtttgt acaaaaaagc aggctctcga cgctgggatt    180
acaggtgtga gatcgagacc cagctttctt gtacaaagtg gtgatcgagt taac          234
```

<210> SEQ ID NO 126
<211> LENGTH: 298
<212> TYPE: DNA
<213> ORGANISM: artificial sequences
<220> FEATURE:
<221> NAME/KEY: source
<222> LOCATION: 1..298
<223> OTHER INFORMATION: /mol_type="DNA"
      /note="Pro_252 antisense"
      /organism="artificial sequences"

<400> SEQUENCE: 126

```
gtggtgaaat gggtggggag ggggcagaac agattcaggc aggcgctggc tgcttgagag    60
gtggagcggg cacaggcgcc taccgcttta taccggtgga tcccgggccc gcggtaccgt   120
cgactgcaga attcgatcac aagtttgtac aaaaaagcag gctctcgaca tttgcatatc   180
gacggcgggg atcgattgac tcagtcgatc tttgaagtcg acgctgggat tactggtgtg   240
agatcgatat caaaggtcga gacccagctt tcttgtacaa agtggtgatc gagttaac    298
```

<210> SEQ ID NO 127
<211> LENGTH: 214
<212> TYPE: DNA
<213> ORGANISM: artificial sequences
<220> FEATURE:
<221> NAME/KEY: source
<222> LOCATION: 1..214
<223> OTHER INFORMATION: /mol_type="DNA"
      /note="Pro_253 antisense"
      /organism="artificial sequences"

<400> SEQUENCE: 127

```
ttcggcaggc gctggctgct tgagaggtgg agcgggcaca ggcgcctacc gctttatacc    60
ggtggatccc gggcccgcgg taccgtcgac tgcagaattc gatcacaagt tgtacaaaa   120 aagcaggctc tcgacttcaa agatcgactg actcaatcga ccctcccaaa atcgagaccc   180
agctttcttg tacaaagtgg tgatcgagtt aacg                              214
```

<210> SEQ ID NO 128
<211> LENGTH: 270
<212> TYPE: DNA
<213> ORGANISM: artificial sequences
<220> FEATURE:
<221> NAME/KEY: source
<222> LOCATION: 1..270
<223> OTHER INFORMATION: /mol_type="DNA"
      /note="Pro_254 antisense"
      /organism="artificial sequences"

<400> SEQUENCE: 128

```
aatgattcgg caggcgctgg ctgcttgaga ggtggagcgg gcacaggcgc ctaccgcttt    60
ataccggtgg atcccgggcc cgcggtaccg tcgactgcag aattcgatca caagtttgta   120
caaaaaagca ggctctcgac ctttgatacg atatgcaaat gtcgatatca aaggtcgata   180
tgcaaatgtc gatccccgcc gtcgacttca agatcgatc cccgccgtcg agacccagct   240
ttcttgtaca agtggtgat cgagttaacg                                    270
```

<210> SEQ ID NO 129

<211> LENGTH: 211
<212> TYPE: DNA
<213> ORGANISM: artificial sequences
<220> FEATURE:
<221> NAME/KEY: source
<222> LOCATION: 1..211
<223> OTHER INFORMATION: /mol_type="DNA"
      /note="Pro_255 antisense"
      /organism="artificial sequences"

<400> SEQUENCE: 129
tgtggtggtg aaatgggtgg ggtgggggca gaacagattc aggcaggcgc tggctgcttg      60
agaggtggag cgggcacagg cgcctaccgc tttataccgg tggatcccgg gcccgcggta     120
ccgtcgactg cagaattcga tcacaagttt gtacaaaaaa gcaggctctc gagacccagc    180
tttcttgtac aaagtggtga tcgagttaac g                                    211

<210> SEQ ID NO 130
<211> LENGTH: 161
<212> TYPE: DNA
<213> ORGANISM: artificial sequences
<220> FEATURE:
<221> NAME/KEY: source
<222> LOCATION: 1..161
<223> OTHER INFORMATION: /mol_type="DNA"
      /note="No. 001 no muc sense"
      /organism="artificial sequences"

<400> SEQUENCE: 130
tttatctgca gtaggcgccg gaattcgtta actcgatcac cactttgtac aagaaagctg      60
ggtctcgatc tcacacctgt aatcccagcg tcgagagcct gcttttttgt acaaacttgt    120
gatcgaattc tgcagtcgac ggtaccgcgg gcccgggatc c                         161

<210> SEQ ID NO 131
<211> LENGTH: 225
<212> TYPE: DNA
<213> ORGANISM: artificial sequences
<220> FEATURE:
<221> NAME/KEY: source
<222> LOCATION: 1..225
<223> OTHER INFORMATION: /mol_type="DNA"
      /note="SEQ SYN 102 no muc sense"
      /organism="artificial sequences"

<400> SEQUENCE: 131
tatctgcagt aggcgccgga attcgttaac tcgatcacca ctttgtacaa gaaagctggg      60
tctcgacctt tgatatcgat ctcacaccag taatcccagc gtcgacttca agatcgact     120 gagtcaatcg atccccgccg tcgatatgca aatgtcgaga gcctgctttt ttgtacaaac    180
ttgtgatcga attctgcagt cgacggtacc gcgggcccgg gatcc                     225

<210> SEQ ID NO 132
<211> LENGTH: 191
<212> TYPE: DNA
<213> ORGANISM: artificial sequences
<220> FEATURE:
<221> NAME/KEY: source
<222> LOCATION: 1..191
<223> OTHER INFORMATION: /mol_type="DNA"
      /note="seq syn 103 no muc sense"
      /organism="artificial sequences"

<400> SEQUENCE: 132
cctgcagggc ccactagtat ctgcagtagg cgccggaatt cgttaactcg atcaccactt      60
tgtacaagaa agctgggtct cgattttggg agggtcgatt gagtcagtcg atctttgaag    120

```
tcgagagcct gcttttttgt acaaacttgt gatcgaattc tgcagtcgac ggtaccgcgg      180
gcccgggatc c                                                          191
```

<210> SEQ ID NO 133
<211> LENGTH: 240
<212> TYPE: DNA
<213> ORGANISM: artificial sequences
<220> FEATURE:
<221> NAME/KEY: source
<222> LOCATION: 1..240
<223> OTHER INFORMATION: /mol_type="DNA"
      /note="seq syn 105 no muc sense"
      /organism="artificial sequences"

<400> SEQUENCE: 133

```
tgcactttgt ggcagaggct gcagtaggcg ccggaattcg ttaactcgat caccactttg      60
tacaagaaag ctgggtctcg acggcgggga tcgatctttg aagtcgacgg cggggatcga     120
catttgcata tcgaccttTg atatcgacat ttgcatatcg tatcaaaggt cgagagcctg     180
cttttttgta caaacttgtg atcgaattct gcagtcgacg gtaccgcggg cccgggatcc     240
```

<210> SEQ ID NO 134
<211> LENGTH: 187
<212> TYPE: DNA
<213> ORGANISM: artificial sequences
<220> FEATURE:
<221> NAME/KEY: source
<222> LOCATION: 1..187
<223> OTHER INFORMATION: /mol_type="DNA"
      /note="seq syn 106 no muc sense"
      /organism="artificial sequences"

<400> SEQUENCE: 134

```
tgcactttgt ggcagaggag caggactgag gataagaatt gagtttcaga aaagggggcc      60
tgagtggccc cggaattcgt taactcgatc accactttgt acaagaaagc tgggtctcga     120
gagcctgctt ttttgtacaa acttgtgatc gaattctgca gtcgacggta ccgcgggccc     180
gggatcc                                                              187
```

<210> SEQ ID NO 135
<211> LENGTH: 132
<212> TYPE: DNA
<213> ORGANISM: artificial sequences
<220> FEATURE:
<221> NAME/KEY: source
<222> LOCATION: 1..132
<223> OTHER INFORMATION: /mol_type="DNA"
      /note="seq syn 108 no muc sense"
      /organism="artificial sequences"

<400> SEQUENCE: 135

```
ctgcagggcc ggcgccggaa ttcgttaact cgatcaccac tttgtacaag aaagctgggt      60
ctcgagagcc tgcttttttg tacaaacttg tgatcgaatt ctgcagtcga cggtaccgcg     120
ggcccgggat cc                                                        132
```

<210> SEQ ID NO 136
<211> LENGTH: 177
<212> TYPE: DNA
<213> ORGANISM: artificial sequences
<220> FEATURE:
<221> NAME/KEY: source
<222> LOCATION: 1..177
<223> OTHER INFORMATION: /mol_type="DNA"
      /note="Pro_200 no_muc sense"

/organism="artificial sequences"

<400> SEQUENCE: 136

```
cgttaactcg atcaccactt tgtacaagaa agctgggtct cgacaacaaa gatcgatatt      60
tgcatgtcga ctgagtcaat cgatctttgt tgtcgactga catcaatcga gagcctgctt     120
ttttgtacaa acttgtgatc gaattctgca gtcgacggta ccgcgggccc gggatcc        177
```

<210> SEQ ID NO 137
<211> LENGTH: 165
<212> TYPE: DNA
<213> ORGANISM: artificial sequences
<220> FEATURE:
<221> NAME/KEY: source
<222> LOCATION: 1..165
<223> OTHER INFORMATION: /mol_type="DNA"
    /note="Pro_201 no_muc sense"
    /organism="artificial sequences"

<400> SEQUENCE: 137

```
cgttaactcg atcaccactt tgtacaagaa agctgggtct cgattgatgt cagtcgacaa      60
caaagatcga tatgcaaatg tcgatatttg catgtcgaga gcctgctttt ttgtacaaac     120
ttgtgatcga attctgcagt cgacggtacc gcgggcccgg gatcc                     165
```

<210> SEQ ID NO 138
<211> LENGTH: 230
<212> TYPE: DNA
<213> ORGANISM: artificial sequences
<220> FEATURE:
<221> NAME/KEY: source
<222> LOCATION: 1..230
<223> OTHER INFORMATION: /mol_type="DNA"
    /note="Pro_202 no_muc sense"
    /organism="artificial sequences"

<400> SEQUENCE: 138

```
cgttaactcg atcaccactt tgtacaggaa agctgggtct cgacaacaaa gatcgattga      60
gtcagtcgac tgactcaatc gacatttgca tatcgaccct cccaaaatcg attgactcag     120
tcgacaacaa agatcgacct tgatatcga tctttgaagt cgagagcctg cttttttgta     180
caaacttgtg atcgaattct gcagtcgacg gtaccgcggg cccgggatcc                230
```

<210> SEQ ID NO 139
<211> LENGTH: 123
<212> TYPE: DNA
<213> ORGANISM: artificial sequences
<220> FEATURE:
<221> NAME/KEY: source
<222> LOCATION: 1..123
<223> OTHER INFORMATION: /mol_type="DNA"
    /note="Pro_203 no_muc sense"
    /organism="artificial sequences"

<400> SEQUENCE: 139

```
cgttaactcg atcaccactt tgtacaagaa agctgggtct cgacaacaaa gatcgagagc      60 ctgcttttttt gtacaaactt gtgatcgaat tctgcagtcg acggtaccgc gggcccggga    120
tcc                                                                   123
```

<210> SEQ ID NO 140
<211> LENGTH: 152
<212> TYPE: DNA
<213> ORGANISM: artificial sequences
<220> FEATURE:
<221> NAME/KEY: source

```
<222> LOCATION: 1..152
<223> OTHER INFORMATION: /mol_type="DNA"
      /note="Pro_204 no_muc sense"
      /organism="artificial sequences"

<400> SEQUENCE: 140
cgttaactcg atcaccactt tgtacaagaa agctgggtct cgatttggg agggtcgata      60 tgcaaatgtc gactgagtca atcgagagcc tgcttttttg tacaaacttg tgatcgaatt     120
ctgcagtcga cggtaccgcg ggcccgggat cc                                   152

<210> SEQ ID NO 141
<211> LENGTH: 149
<212> TYPE: DNA
<213> ORGANISM: artificial sequences
<220> FEATURE:
<221> NAME/KEY: source
<222> LOCATION: 1..149
<223> OTHER INFORMATION: /mol_type="DNA"
      /note="Pro_205 no_muc sense"
      /organism="artificial sequences"

<400> SEQUENCE: 141
cgttaactcg atcaccactt tgtacaagaa agctgggtct cgactgactc aatcgatctc      60
acacctgtaa tcccagcgtc gagagcctgc tttttgtac aaacttgtga tcgaattctg      120
cagtcgacgg taccgcgggc ccgggatcc                                       149

<210> SEQ ID NO 142
<211> LENGTH: 162
<212> TYPE: DNA
<213> ORGANISM: artificial sequences
<220> FEATURE:
<221> NAME/KEY: source
<222> LOCATION: 1..162
<223> OTHER INFORMATION: /mol_type="DNA"
      /note="Pro_206 no_muc sense"
      /organism="artificial sequences"

<400> SEQUENCE: 142
cgttaactcg atcaccactt tgtacaagaa agctgggtct cgatctttga agtcgacaac      60
aaagatcgat ctcacacctg taatcccagc gtcgagagcc tgcttttttg tacaaacttg    120
tgatcgaatt ctgcagtcga cggtaccgcg ggcccgggat cc                        162

<210> SEQ ID NO 143
<211> LENGTH: 136
<212> TYPE: DNA
<213> ORGANISM: artificial sequences
<220> FEATURE:
<221> NAME/KEY: source
<222> LOCATION: 1..136
<223> OTHER INFORMATION: /mol_type="DNA"
      /note="Pro_207 no_muc sense"
      /organism="artificial sequences"

<400> SEQUENCE: 143
cgttaactcg atcaccactt tgtacaagaa agctgggtct cgatctcaca cctgtaatcc      60
cagcgtcgag agcctgcttt tttgtacaaa cttgtgatcg aattctgcag tcgacggtac    120
cgcgggcccg ggatcc                                                     136

<210> SEQ ID NO 144
<211> LENGTH: 139
<212> TYPE: DNA
<213> ORGANISM: artificial sequences
<220> FEATURE:
```

<221> NAME/KEY: source
<222> LOCATION: 1..139
<223> OTHER INFORMATION: /mol_type="DNA"
      /note="Pro_208 no_muc sense"
      /organism="artificial sequences"

<400> SEQUENCE: 144
cgttaactcg atcaccactt tgtacaagaa agctgggtct cgattttggg agggtcgatt    60
gatgtcagtc gagagcctgc ttttttgtac aaacttgtga tcgaattctg cagtcgacgg    120
taccgcgggc ccgggatcc                                                 139

<210> SEQ ID NO 145
<211> LENGTH: 168
<212> TYPE: DNA
<213> ORGANISM: artificial sequences
<220> FEATURE:
<221> NAME/KEY: source
<222> LOCATION: 1..168
<223> OTHER INFORMATION: /mol_type="DNA"
      /note="Pro_209 no_muc sense"
      /organism="artificial sequences"

<400> SEQUENCE: 145
tagtggatcc cccgggctgc aggaattcga ttcgacttca aagatcgcac tttgatatcg    60
acgctgggat tacaggtgtg agatcgagag cctgcttttt tgtacaaact tgtgatcgaa    120
ttctgcagtc gacggtaccg cgggcccggg atcccaagct tatcgata                168

<210> SEQ ID NO 146
<211> LENGTH: 137
<212> TYPE: DNA
<213> ORGANISM: artificial sequences
<220> FEATURE:
<221> NAME/KEY: source
<222> LOCATION: 1..137
<223> OTHER INFORMATION: /mol_type="DNA"
      /note="Pro_210 no_muc sense"
      /organism="artificial sequences"

<400> SEQUENCE: 146
cgttaactcg atcaccactt tgtacaagaa agctgggtct cgacggcggg gatcgacatt    60
tgcatatcga gagcctgctt ttttgtacaa acttgtgatc gaattctgca gtcgacggta    120
ccgcgggccc gggatcc                                                   137

<210> SEQ ID NO 147
<211> LENGTH: 136
<212> TYPE: DNA
<213> ORGANISM: artificial sequences
<220> FEATURE:
<221> NAME/KEY: source
<222> LOCATION: 1..136
<223> OTHER INFORMATION: /mol_type="DNA"
      /note="Pro_211 no_muc sense"
      /organism="artificial sequences"

<400> SEQUENCE: 147
cgttaactcg atcaccactt tgtacaagaa agctgggtct cgactgactc aatcgatctt    60
tgttgtcgag agcctgcttt tttgtacaaa cttgtgatcg aattctgcag tcgacggtac    120
cgcgggcccg ggatcc                                                    136

<210> SEQ ID NO 148
<211> LENGTH: 125
<212> TYPE: DNA
<213> ORGANISM: artificial sequences

```
<220> FEATURE:
<221> NAME/KEY: source
<222> LOCATION: 1..125
<223> OTHER INFORMATION: /mol_type="DNA"
      /note="Pro_212 no_muc sense"
      /organism="artificial sequences"

<400> SEQUENCE: 148
cgttaactcg atcaccactt tgtacaagaa agctgggtct cgaccctccc aaaatcgaga      60
gcctgctttt ttgtacaaac ttgtgatcga attctgcagt cgacggtacc gcgggcccgg    120
gatcc                                                                125

<210> SEQ ID NO 149
<211> LENGTH: 217
<212> TYPE: DNA
<213> ORGANISM: artificial sequences
<220> FEATURE:
<221> NAME/KEY: source
<222> LOCATION: 1..217
<223> OTHER INFORMATION: /mol_type="DNA"
      /note="Pro_213 no_muc sense"
      /organism="artificial sequences"

<400> SEQUENCE: 149
cgttaactcg atcaccactt tgtacaagaa agctgggtct cgacaacaaa gatcgatctt     60
tgttgtcgat tttgggaggg tcgacgctgg gattacaggt gtgagatcga tatcaaaggt    120
cgattgactc agtcgacggc ggggatcgag agcctgcttt ttttgtacaa acttgtgatc    180
gaattctgca gtcgacggta ccgcgggccc gggatcc                             217

<210> SEQ ID NO 150
<211> LENGTH: 164
<212> TYPE: DNA
<213> ORGANISM: artificial sequences
<220> FEATURE:
<221> NAME/KEY: source
<222> LOCATION: 1..164
<223> OTHER INFORMATION: /mol_type="DNA"
      /note="Pro_214 no_muc sense"
      /organism="artificial sequences"

<400> SEQUENCE: 150
cgttaactcg atcaccactt tgtacaagaa agctgggtct cgactgacat caatcgactt     60
caaagatcga tatgcaaatg tcgactgagt caatcgagag cctgcttttt tgtacaaact   120
tgtgatcgaa ttctgcagtc gacggtaccg cgggcccggg atcc                    164

<210> SEQ ID NO 151
<211> LENGTH: 193
<212> TYPE: DNA
<213> ORGANISM: artificial sequences
<220> FEATURE:
<221> NAME/KEY: source
<222> LOCATION: 1..193
<223> OTHER INFORMATION: /mol_type="DNA"
      /note="Pro_215 no_muc sense"
      /organism="artificial sequences"

<400> SEQUENCE: 151
cgttaactcg atcaccactt tgtacaagaa agctgggtct cgacggcggg gatcgacaac     60
aaagatcgac atttgcatat cgactgacat caatcgatat tgcatgtcg accctcccaa   120 aatcgagagc ctgctttttt gtacaaactt gtgatcgaat tctgcagtcg acggtaccgc   180
gggcccggga tcc                                                      193
```

```
<210> SEQ ID NO 152
<211> LENGTH: 188
<212> TYPE: DNA
<213> ORGANISM: artificial sequences
<220> FEATURE:
<221> NAME/KEY: source
<222> LOCATION: 1..188
<223> OTHER INFORMATION: /mol_type="DNA"
      /note="Pro_216 no_muc sense"
      /organism="artificial sequences"

<400> SEQUENCE: 152
cgttaactcg atcaccactt tgtacaagaa agctgggtct cgatatgcaa atgtcgattg      60
agtcagtcga cttcaaagat cgattgagtc agtcgatctc acactgtaat cccagcgtcg     120
agagcctgct tttttgtaca aacttgtgat cgaattctgc agtcgacggt accgcgggcc     180
cgggatcc                                                              188

<210> SEQ ID NO 153
<211> LENGTH: 190
<212> TYPE: DNA
<213> ORGANISM: artificial sequences
<220> FEATURE:
<221> NAME/KEY: source
<222> LOCATION: 1..190
<223> OTHER INFORMATION: /mol_type="DNA"
      /note="Pro_217 no_muc sense"
      /organism="artificial sequences"

<400> SEQUENCE: 153
cgttaactcg atcaccactt tgtacaagaa agctgggtct cgacgctggg attacaggtg      60
tgagatcgac aacaaagatc gattgagtca gtcgatcttt gaagtcgatt ttgggagggt     120
cgagagcctg cttttttgta caaacttgtg atcgaattct gcagtcgacg gtaccgcggg     180
cccgggatcc                                                            190

<210> SEQ ID NO 154
<211> LENGTH: 136
<212> TYPE: DNA
<213> ORGANISM: artificial sequences
<220> FEATURE:
<221> NAME/KEY: source
<222> LOCATION: 1..136
<223> OTHER INFORMATION: /mol_type="DNA"
      /note="Pro_218 no_muc sense"
      /organism="artificial sequences"

<400> SEQUENCE: 154
cgttaactcg atcaccactt tgtacaagaa agctgggtct cgacggcggg gatcgatctt      60
tgttgtcgag agcctgcttt tttgtacaaa cttgtgatcg aattctgcag tcgacggtac     120
cgcgggcccg ggatcc                                                     136

<210> SEQ ID NO 155
<211> LENGTH: 179
<212> TYPE: DNA
<213> ORGANISM: artificial sequences
<220> FEATURE:
<221> NAME/KEY: source
<222> LOCATION: 1..179
<223> OTHER INFORMATION: /mol_type="DNA"
      /note="Pro_219 no_muc sense"
      /organism="artificial sequences"

<400> SEQUENCE: 155
cgttaactcg atcaccactt tgtacaagaa agctgggtct cgactgacat caatcgatat      60
```

```
caaaggtcga ttttgggagg gtcgacttca aagatcgact tcaaagatcg agagcctgct    120
tttttgtaca aacttgtgat cgaattctgc agtcgacggt accgcgggcc cggggatcc     179
```

<210> SEQ ID NO 156
<211> LENGTH: 123
<212> TYPE: DNA
<213> ORGANISM: artificial sequences
<220> FEATURE:
<221> NAME/KEY: source
<222> LOCATION: 1..123
<223> OTHER INFORMATION: /mol_type="DNA"
      /note="Pro_220 no_muc sense"
      /organism="artificial sequences"

<400> SEQUENCE: 156

```
cgttaactcg atcaccactt tgtacaagaa agctgggtct cgactgactc aatcgagagc    60
ctgctttttt gtacaaactt gtgatcgaat tctgcagtcg atggtaccgc gggcccggga   120
tcc                                                                 123
```

<210> SEQ ID NO 157
<211> LENGTH: 137
<212> TYPE: DNA
<213> ORGANISM: artificial sequences
<220> FEATURE:
<221> NAME/KEY: source
<222> LOCATION: 1..137
<223> OTHER INFORMATION: /mol_type="DNA"
      /note="Pro_221 no_muc sense"
      /organism="artificial sequences"

<400> SEQUENCE: 157

```
cgttaactcg atcaccactt tgtacaagaa agctgggtct cgactgagtc aatcgacatg    60
caaatatcga gagcctgctt ttttgtacaa acttgtgatc gaattctgca gtcgagggga   120
ccgggggcgc gggatcc                                                  137
```

<210> SEQ ID NO 158
<211> LENGTH: 202
<212> TYPE: DNA
<213> ORGANISM: artificial sequences
<220> FEATURE:
<221> NAME/KEY: source
<222> LOCATION: 1..202
<223> OTHER INFORMATION: /mol_type="DNA"
      /note="Pro_222 no_muc sense"
      /organism="artificial sequences"

<400> SEQUENCE: 158

```
cgttaactcg atcaccactt tgtacaagaa agctgggtct cgacctttga tatcgatctc    60
acaccagtaa tcccagcgtc gacttcaaag atcgactgag tcaatcgatc cccgccgtcg   120
atatgcaaat gtcgagagcc tgctttttg tacaaacttg tgatcgaatt ctgcagtcga   180
cggtaccgcg ggcccgggat cc                                            202
```

<210> SEQ ID NO 159
<211> LENGTH: 204
<212> TYPE: DNA
<213> ORGANISM: artificial sequences
<220> FEATURE:
<221> NAME/KEY: source
<222> LOCATION: 1..204
<223> OTHER INFORMATION: /mol_type="DNA"
      /note="Pro_223 no_muc sense"
      /organism="artificial sequences"

<400> SEQUENCE: 159

```
cgttaactcg atcaccactt tgtacaagaa agctgggtct cgattgatgt cagtcgacct      60
ttgatatcga ttgactcagt cgattgagtc agtcgacatt tgcatatcga tatgcaaatg    120
tcgactgagt caatcgagag cctgctttt tgtacaaact tgtgatcgaa ttctgcagtc     180
gacggtaccg cgggcccggg atcc                                             204
```

<210> SEQ ID NO 160
<211> LENGTH: 150
<212> TYPE: DNA
<213> ORGANISM: artificial sequences
<220> FEATURE:
<221> NAME/KEY: source
<222> LOCATION: 1..150
<223> OTHER INFORMATION: /mol_type="DNA"
    /note="Pro_224 no_muc sense"
    /organism="artificial sequences"

<400> SEQUENCE: 160

```
cgttaactcg atcaccactt tgtacaagaa agctgggtct cgattgatgt cagtcgatcc      60
ccgccgtcga ttgagtcagt cgagagcctg ctttttgta caaacttgtg atcgaattct     120
gcagtcgacg gtaccgcggg cccgggatcc                                       150
```

<210> SEQ ID NO 161
<211> LENGTH: 178
<212> TYPE: DNA
<213> ORGANISM: artificial sequences
<220> FEATURE:
<221> NAME/KEY: source
<222> LOCATION: 1..178
<223> OTHER INFORMATION: /mol_type="DNA"
    /note="Pro_225 no_muc sense"
    /organism="artificial sequences"

<400> SEQUENCE: 161

```
cgttaactcg atcaccactt tgtacaagaa agctgggtct cgatctttga agtcgatctt      60
tgttgtcgac atgcaaatat cgactgactc aatcgatttt gggagggtcg agagcctgct    120
tttttgtaca aacttgtgat cgaattctgc agtcgacggt accgcgggcc cgggatcc       178
```

<210> SEQ ID NO 162
<211> LENGTH: 214
<212> TYPE: DNA
<213> ORGANISM: artificial sequences
<220> FEATURE:
<221> NAME/KEY: source
<222> LOCATION: 1..214
<223> OTHER INFORMATION: /mol_type="DNA"
    /note="Pro_226 no_muc sense"
    /organism="artificial sequences"

<400> SEQUENCE: 162

```
cgttaactcg atcaccactt tgtacaagaa agctgggtct cgacttcaaa gatcgatctt      60
tgttgtcgac ttcaaagatc gatccccgcc gtcgacttca aagatcgaca acaaagatcg    120
attgagtcag tcgatatcaa aggtcgagag cctgctttt tgtacaaact tgtgatcgaa    180
ttctgcagtc gacggtaccg cgggcccggg atcc                                  214
```

<210> SEQ ID NO 163
<211> LENGTH: 178
<212> TYPE: DNA
<213> ORGANISM: artificial sequences
<220> FEATURE:
<221> NAME/KEY: source

```
<222> LOCATION: 1..178
<223> OTHER INFORMATION: /mol_type="DNA"
      /note="Pro_227 no_muc sense"
      /organism="artificial sequences"

<400> SEQUENCE: 163
cgttaactcg atcaccactt tgtacaagaa agctgggtct cgatatttgc atgtcgattg      60
agtcagtcga tctttgttgt cgattgatgt cagtcgacat ttgcatatcg agagcctgct     120
tttttgtaca aacttgtgat cgaattctgc agtcgacgg accgcgggcc cgggatcc       178

<210> SEQ ID NO 164
<211> LENGTH: 164
<212> TYPE: DNA
<213> ORGANISM: artificial sequences
<220> FEATURE:
<221> NAME/KEY: source
<222> LOCATION: 1..164
<223> OTHER INFORMATION: /mol_type="DNA"
      /note="Pro_228 no_muc sense"
      /organism="artificial sequences"

<400> SEQUENCE: 164
gttaactcga tcaccacttt gtacaagaaa gctgggtctc gaccctccca aaatcgactt      60
caaagatcga tccccgccgt cgactgacat caatcgagag cctgcttttt tgtacaaact    120
tgtgatcgaa ttctgcagtc gacggtaccg cgggcccggg atcc                     164

<210> SEQ ID NO 165
<211> LENGTH: 163
<212> TYPE: DNA
<213> ORGANISM: artificial sequences
<220> FEATURE:
<221> NAME/KEY: source
<222> LOCATION: 1..163
<223> OTHER INFORMATION: /mol_type="DNA"
      /note="Pro_229 no_muc sense"
      /organism="artificial sequences"

<400> SEQUENCE: 165
cgttaactcg atcaccactt tgtacaagaa agctgggtct cgattgagtc agtcgactga      60
gtcaatcgac atttgcatat cgacttcaaa gatcgagagc ctgcttttt gtacaaactt     120 gtgatcgaat tctgcagtcg acggtaccgc gggcccggga tcc                      163

<210> SEQ ID NO 166
<211> LENGTH: 165
<212> TYPE: DNA
<213> ORGANISM: artificial sequences
<220> FEATURE:
<221> NAME/KEY: source
<222> LOCATION: 1..165
<223> OTHER INFORMATION: /mol_type="DNA"
      /note="Pro_230 no_muc sense"
      /organism="artificial sequences"

<400> SEQUENCE: 166
cgttaactcg atcaccactt tgtacaggaa agctgggtct cgacatttgc atatcgacat      60
ttgcatatcg attgagtcag tcgatatgca aatgtcgaga gcctgctttt tgtacaaac     120 ttgtgatcga attctgcagt cgacggtacc gcgggcccgg gatcc                    165

<210> SEQ ID NO 167
<211> LENGTH: 179
<212> TYPE: DNA
<213> ORGANISM: artificial sequences
<220> FEATURE:
```

```
<221> NAME/KEY: source
<222> LOCATION: 1..179
<223> OTHER INFORMATION: /mol_type="DNA"
      /note="Pro_231 no_muc sense"
      /organism="artificial sequences"

<400> SEQUENCE: 167
cgttaactcg atcaccactt tgtacaagaa agctgggtct cgattgatgt cagtcgatct      60
ttgttgtcga tatgcaaatg tcgactgact caatcgattt tgggagggtc gagagcctgc     120 tttttttgtac aaacttgtga tcgaattctg cagtcgacgg taccgcgggc ccgggatcc    179

<210> SEQ ID NO 168
<211> LENGTH: 185
<212> TYPE: DNA
<213> ORGANISM: artificial sequences
<220> FEATURE:
<221> NAME/KEY: source
<222> LOCATION: 1..185
<223> OTHER INFORMATION: /mol_type="DNA"
      /note="Pro_232 no_muc sense"
      /organism="artificial sequences"

<400> SEQUENCE: 168
ccggaattcg ttaactcgat caccactttg tacaagaaag ctgggtctcg acatttgcat      60
atcgacattt gcatatcgat ccccgccgtc gatctttgaa gtcgattgac tcagtcgaga    120
gcctgctttt tgtacaaac ttgtgatcga attctgcagt cgacggtacc gcgggcccgg     180
gatcc                                                                185

<210> SEQ ID NO 169
<211> LENGTH: 163
<212> TYPE: DNA
<213> ORGANISM: artificial sequences
<220> FEATURE:
<221> NAME/KEY: source
<222> LOCATION: 1..163
<223> OTHER INFORMATION: /mol_type="DNA"
      /note="Pro_233 no_muc sense"
      /organism="artificial sequences"

<400> SEQUENCE: 169
cgttaactcg atcaccactt tgtacaggaa agctgggtct cgacaacaaa gatcgatatg      60
caaatgtcga caacaaagat cgatctttga agtcgagagc ctgctttttt gtacaaactt    120
gtgatcgaat tctgcagtcg acggtaccgc gggcccggga tcc                      163

<210> SEQ ID NO 170
<211> LENGTH: 209
<212> TYPE: DNA
<213> ORGANISM: artificial sequences
<220> FEATURE:
<221> NAME/KEY: source
<222> LOCATION: 1..209
<223> OTHER INFORMATION: /mol_type="DNA"
      /note="Pro_234 no_muc sense"
      /organism="artificial sequences"

<400> SEQUENCE: 170
aattcgttaa ctcgatcacc actttgtaca agaaagctgg gtctcgactg agtcaatcga      60
ttgactcagt cgatccccgc cgtcgaccct cccaaaatcg actgagtcaa tcgactgaca    120
tcaatcgatt gatgtcagtc gagagcctgc tttttttgtac aaacttgtga tcgaattctg    180
cagtcgacgg taccgcgggc ccgggatcc                                      209
```

```
<210> SEQ ID NO 171
<211> LENGTH: 176
<212> TYPE: DNA
<213> ORGANISM: artificial sequences
<220> FEATURE:
<221> NAME/KEY: source
<222> LOCATION: 1..176
<223> OTHER INFORMATION: /mol_type="DNA"
      /note="Pro_235 no_muc sense"
      /organism="artificial sequences"

<400> SEQUENCE: 171
cgttaactcg atcaccactt tgtacaagaa agctgggtct cgacatttgc atatcgattg    60
agtcagtcga tctttgttgt cgactgagtc aatcgattga gtcagtcgag agcctgcttt   120
tttgtacaaa cttgtgatcg aattctgcag tcgacggtac cgcgggcccg ggatcc       176

<210> SEQ ID NO 172
<211> LENGTH: 151
<212> TYPE: DNA
<213> ORGANISM: artificial sequences
<220> FEATURE:
<221> NAME/KEY: source
<222> LOCATION: 1..151
<223> OTHER INFORMATION: /mol_type="DNA"
      /note="Pro_236 no_muc sense"
      /organism="artificial sequences"

<400> SEQUENCE: 172
cgttaactcg atcaccactt tgtacaagaa agctgggtct cgattgatgt cagtcgactg    60
agtcaatcga tatgcaaatg tcgagagcct gcttttttgt acaaacttgt gatcgaattc   120
tgcagtcgac ggtaccgcgg gcccgggatc c                                  151

<210> SEQ ID NO 173
<211> LENGTH: 245
<212> TYPE: DNA
<213> ORGANISM: artificial sequences
<220> FEATURE:
<221> NAME/KEY: source
<222> LOCATION: 1..245
<223> OTHER INFORMATION: /mol_type="DNA"
      /note="Pro_237 no_muc sense"
      /organism="artificial sequences"

<400> SEQUENCE: 173
gaaagctggg tctcgacaac aaagatcgat tgactcagtc gattgagtca gtcgatattt    60
gcatgtcgac atttgcatat cgactgacat caatcgattg actcagtcga ctgacatcaa   120
tcgacttcaa agatcgatct cacacctgta atcccagcgt cgaccctccc aaaatcgaga   180
gcctgctttt ttgtacaaac ttgtgatcga attctgcagt cgacggtacc gcgggcccgg   240
gatcc                                                               245

<210> SEQ ID NO 174
<211> LENGTH: 137
<212> TYPE: DNA
<213> ORGANISM: artificial sequences
<220> FEATURE:
<221> NAME/KEY: source
<222> LOCATION: 1..137
<223> OTHER INFORMATION: /mol_type="DNA"
      /note="Pro_238 no_muc sense"
      /organism="artificial sequences"

<400> SEQUENCE: 174
cgttaactcg atcaccactt tgtacaagaa agctggctct cgatctttga agtcgatatg    60
```

```
caaatgtcga gagcctgctt ttttgtacaa acttgtgatc gaattctgca gtcgacggta    120
ccgcgggccc gggatcc                                                   137
```

<210> SEQ ID NO 175
<211> LENGTH: 216
<212> TYPE: DNA
<213> ORGANISM: artificial sequences
<220> FEATURE:
<221> NAME/KEY: source
<222> LOCATION: 1..216
<223> OTHER INFORMATION: /mol_type="DNA"
      /note="Pro_239 no_muc sense"
      /organism="artificial sequences"

<400> SEQUENCE: 175

```
gaaagctggg tctcgatctt tgttgtcgac tgagtcaatc gacaacaaag atcgatatca    60
aaggtcgatc cccgccgtcg attgactcgg tcgacatttg catatcgacg tttgcatatc   120
gacatgcaaa tgtcgatccc cgccgtcgag agcctgcttt tttgtgcaaa cttgtgatcg   180
aattctgcag tcgacggtac cgcgggcccg ggatcc                             216
```

<210> SEQ ID NO 176
<211> LENGTH: 171
<212> TYPE: DNA
<213> ORGANISM: artificial sequences
<220> FEATURE:
<221> NAME/KEY: source
<222> LOCATION: 1..171
<223> OTHER INFORMATION: /mol_type="DNA"
      /note="Pro_240 no_muc sense"
      /organism="artificial sequences"

<400> SEQUENCE: 176

```
gctgggtctc gacgctggga ttacaggtgt gagatcgcgg cggggatcga cgctgggatt    60
acaggtgtga gatcgatatt tgcatgtcga ctgacatcaa tcgagagcct gctttttttgt   120 acaaacttgt gatcgaattc tgcagtcgac ggtaccgcgg gcccgggatc c             171
```

<210> SEQ ID NO 177
<211> LENGTH: 136
<212> TYPE: DNA
<213> ORGANISM: artificial sequences
<220> FEATURE:
<221> NAME/KEY: source
<222> LOCATION: 1..136
<223> OTHER INFORMATION: /mol_type="DNA"
      /note="Pro_241 no_muc sense"
      /organism="artificial sequences"

<400> SEQUENCE: 177

```
cgttaactcg atcaccactt tgtacaagaa agctgggtct cgatcccgc cgtcgatatc     60 aaaggtcgag agcctgcttt tttgtacaaa cttgtgatcg aattctgcag tcgacggtac   120
cgcgggcccg ggatcc                                                    136
```

<210> SEQ ID NO 178
<211> LENGTH: 199
<212> TYPE: DNA
<213> ORGANISM: artificial sequences
<220> FEATURE:
<221> NAME/KEY: source
<222> LOCATION: 1..199
<223> OTHER INFORMATION: /mol_type="DNA"
      /note="Pro_242 no_muc sense"
      /organism="artificial sequences"

<400> SEQUENCE: 178
cgttaactcg atcaccactt tgtacaagaa agctgggtct cgacggcggg gatcgactga    60
ctcaatcgat atgcaaatgt cgactgagtc aatcgactga ctcaatcgat tgatgtcagc   120
tgagtcaatc gagagcctgc ttttttgtac aaacttgtga tcgaattctg cagtcgacgg   180
taccgcgggc ccgggatcc                                                199

<210> SEQ ID NO 179
<211> LENGTH: 138
<212> TYPE: DNA
<213> ORGANISM: artificial sequences
<220> FEATURE:
<221> NAME/KEY: source
<222> LOCATION: 1..138
<223> OTHER INFORMATION: /mol_type="DNA"
      /note="Pro_243 no_muc sense"
      /organism="artificial sequences"

<400> SEQUENCE: 179
cgttaactcg atcaccactt tgtacaggaa agctgggtct cgatatttgc atgtcgacat    60
gcaaatatcg agagcctgct tttttgtaca aacttgtgat cgaattctgc agtcgacggt   120
accgcgggcc cgggatcc                                                 138

<210> SEQ ID NO 180
<211> LENGTH: 139
<212> TYPE: DNA
<213> ORGANISM: artificial sequences
<220> FEATURE:
<221> NAME/KEY: source
<222> LOCATION: 1..139
<223> OTHER INFORMATION: /mol_type="DNA"
      /note="Pro_244 no_muc sense"
      /organism="artificial sequences"

<400> SEQUENCE: 180
cgttaactcg atcaccactt tgtacaagaa agctgggtct cgattttggg agggtcgata    60
tttgcatgtc gagagcctgc ttttttgtac aaacttgtga tcgaattctg cagtcgacgg   120
taccgcgggc ccgggatcc                                                139

<210> SEQ ID NO 181
<211> LENGTH: 150
<212> TYPE: DNA
<213> ORGANISM: artificial sequences
<220> FEATURE:
<221> NAME/KEY: source
<222> LOCATION: 1..150
<223> OTHER INFORMATION: /mol_type="DNA"
      /note="Pro_245 no_muc sense"
      /organism="artificial sequences"

<400> SEQUENCE: 181
cgttaactcg atcaccactt tgtacaagaa agctgggtct cgattgatgt cagtcgactt    60
caaagatcga tctttgaagt cgagagcctg cttttttgta caaacttgtg atcgaattct   120
gcagtcgacg gtaccgcggg cccgggatcc                                    150

<210> SEQ ID NO 182
<211> LENGTH: 179
<212> TYPE: DNA
<213> ORGANISM: artificial sequences
<220> FEATURE:
<221> NAME/KEY: source
<222> LOCATION: 1..179
<223> OTHER INFORMATION: /mol_type="DNA"
      /note="Pro_246 no_muc sense"

/organism="artificial sequences"

<400> SEQUENCE: 182

| cgttaactcg atcaccactt tgtacaagaa agctgggcct cgacggcggg gatcgacatt | 60 |
| tgcatatcga ttttgggagg gtcgatatgc aaatgtcgac tgactcaatc gagagcctgc | 120 |
| tttttgtac aaacttgtga tcgaattctg cagtcgacgg taccgcgggc ccgggatcc | 179 |

<210> SEQ ID NO 183
<211> LENGTH: 205
<212> TYPE: DNA
<213> ORGANISM: artificial sequences
<220> FEATURE:
<221> NAME/KEY: source
<222> LOCATION: 1..205
<223> OTHER INFORMATION: /mol_type="DNA"
      /note="Pro_247 no_muc sense"
      /organism="artificial sequences"

<400> SEQUENCE: 183

| cgttaactcg atcaccactt tgtacaagaa agctgggtct cgatctttgt tgtcgatctt | 60 |
| tgaagtcgat tttgggaggg tcgactgacg tcaatcgaca tttgcatatc gatatcaaag | 120 |
| gtcgacaaca aagatcgaga gcctgctttt ttgtacaaac ttgtgatcga attctgcagt | 180 |
| cgacggtacc gcgggcccgg gatcc | 205 |

<210> SEQ ID NO 184
<211> LENGTH: 228
<212> TYPE: DNA
<213> ORGANISM: artificial sequences
<220> FEATURE:
<221> NAME/KEY: source
<222> LOCATION: 1..228
<223> OTHER INFORMATION: /mol_type="DNA"
      /note="Pro_248 no_muc sense"
      /organism="artificial sequences"

<400> SEQUENCE: 184

| cgttaactcg atcaccactt tgtacaagaa agctgggtct cgatatttgc atgtcgacgc | 60 |
| tgggattaca ggtgtgagat cgatctttga agtcgacaac aaagatcgat tgagtcagtc | 120 |
| gactgactca atcgacaaca aagatcgata tcaaaggtcg agagcctgct tttttgtaca | 180 |
| aacttgtgat cgaattctgc agtcgacggt accgcgggcc cgggatcc | 228 |

<210> SEQ ID NO 185
<211> LENGTH: 149
<212> TYPE: DNA
<213> ORGANISM: artificial sequences
<220> FEATURE:
<221> NAME/KEY: source
<222> LOCATION: 1..149
<223> OTHER INFORMATION: /mol_type="DNA"
      /note="Pro_249 no_muc sense"
      /organism="artificial sequences"

<400> SEQUENCE: 185

| cgttaactcg atcaccactt tgtacaagaa agctgggtct cgacggcggg gatcgactga | 60 |
| gtcaatcgac ctttgatatc gagagcctgc tttttgtac aaacttgtga tcgaattctg | 120 |
| cagtcgacgg taccgcgggc ccgggatcc | 149 |

<210> SEQ ID NO 186
<211> LENGTH: 188
<212> TYPE: DNA
<213> ORGANISM: artificial sequences

```
<220> FEATURE:
<221> NAME/KEY: source
<222> LOCATION: 1..188
<223> OTHER INFORMATION: /mol_type="DNA"
      /note="Pro_250 no_muc sense"
      /organism="artificial sequences"

<400> SEQUENCE: 186
cgttaactcg atcaccactt tgtacaagaa agctgggtct cgacttcaaa gatcgactga      60
ctcaatcgac ctttgatatc gatctttgtt gtcgatctca cacctgtaat cccagcgtcg     120
agagcctgct tttttgtaca aacttgtgat cgaattctgc agtcgacggt accgcgggcc     180
cgggatcc                                                              188

<210> SEQ ID NO 187
<211> LENGTH: 135
<212> TYPE: DNA
<213> ORGANISM: artificial sequences
<220> FEATURE:
<221> NAME/KEY: source
<222> LOCATION: 1..135
<223> OTHER INFORMATION: /mol_type="DNA"
      /note="Pro_251 no_muc sense"
      /organism="artificial sequences"

<400> SEQUENCE: 187
gttaactcga tcaccacttt gtacaagaaa gctgggtctc gatctcacac ctgtaatccc      60
agcgtcgaga gcctgctttt ttgtacaaac ttgtgatcga attctgcagt cgacggtacc     120
gcgggcccgg gatcc                                                     135

<210> SEQ ID NO 188
<211> LENGTH: 201
<212> TYPE: DNA
<213> ORGANISM: artificial sequences
<220> FEATURE:
<221> NAME/KEY: source
<222> LOCATION: 1..201
<223> OTHER INFORMATION: /mol_type="DNA"
      /note="Pro_252 no_muc sense"
      /organism="artificial sequences"

<400> SEQUENCE: 188
gttaactcga tcaccacttt gtacaagaaa gctgggtctc gacctttgat atcgatctca      60
caccagtaat cccagcgtcg acttcaaaga tcgactgagt caatcgatcc ccgccgtcga    120
tatgcaaatg tcgagagcct gcttttttgt acaaacttgt gatcgaattc tgcagtcgac    180
ggtaccgcgg gcccgggatc c                                             201

<210> SEQ ID NO 189
<211> LENGTH: 151
<212> TYPE: DNA
<213> ORGANISM: artificial sequences
<220> FEATURE:
<221> NAME/KEY: source
<222> LOCATION: 1..151
<223> OTHER INFORMATION: /mol_type="DNA"
      /note="Pro_253 no_muc sense"
      /organism="artificial sequences"

<400> SEQUENCE: 189
cgttaactcg atcaccactt tgtacaagaa agctgggtct cgattttggg agggtcgatt      60
gagtcagtcg atctttgaag tcgagagcct gcttttttgt acaaacttgt gatcgaattc    120
tgcagtcgac ggtaccgcgg gcccgggatc c                                   151
```

<210> SEQ ID NO 190
<211> LENGTH: 202
<212> TYPE: DNA
<213> ORGANISM: artificial sequences
<220> FEATURE:
<221> NAME/KEY: source
<222> LOCATION: 1..202
<223> OTHER INFORMATION: /mol_type="DNA"
      /note="Pro_254 no_muc sense"
      /organism="artificial sequences"

<400> SEQUENCE: 190
cgttaactcg atcaccactt tgtacaagaa agctgggtct cgacggcggg gatcgatctt      60
tgaagtcgac ggcggggatc gacatttgca tatcgacctt tgatatcgac atttgcatat     120
cgtatcaaag gtcgagagcc tgcttttttg tacaaacttg tgatcgaatt ctgcagtcga     180
cggtaccgcg ggcccgggat cc                                              202

<210> SEQ ID NO 191
<211> LENGTH: 110
<212> TYPE: DNA
<213> ORGANISM: artificial sequences
<220> FEATURE:
<221> NAME/KEY: source
<222> LOCATION: 1..110
<223> OTHER INFORMATION: /mol_type="DNA"
      /note="Pro_255 no_muc sense"
      /organism="artificial sequences"

<400> SEQUENCE: 191
cgttaactcg atcaccactt tgtacaagaa agctgggtct cgagagcctg cttttttgta      60
caaacttgtg atcgaattct gcagtcgacg gtaccgcggg cccgggatcc                110

<210> SEQ ID NO 192
<211> LENGTH: 161
<212> TYPE: DNA
<213> ORGANISM: artificial sequences
<220> FEATURE:
<221> NAME/KEY: source
<222> LOCATION: 1..161
<223> OTHER INFORMATION: /mol_type="DNA"
      /note="No. 001 no muc antisense"
      /organism="artificial sequences"

<400> SEQUENCE: 192
ggatcccggg cccgcggtac cgtcgactgc agaattcgat cacaagtttg tacaaaaaag      60
caggctctcg acgctgggat tacaggtgtg agatcgagac ccagctttct tgtacaaagt     120
ggtgatcgag ttaacgaatt ccggcgccta ctgcagataa a                         161

<210> SEQ ID NO 193
<211> LENGTH: 225
<212> TYPE: DNA
<213> ORGANISM: artificial sequences
<220> FEATURE:
<221> NAME/KEY: source
<222> LOCATION: 1..225
<223> OTHER INFORMATION: /mol_type="DNA"
      /note="SEQ SYN 102 no muc antisense"
      /organism="artificial sequences"

<400> SEQUENCE: 193
ggatcccggg cccgcggtac cgtcgactgc agaattcgat cacaagtttg tacaaaaaag      60
caggctctcg acatttgcat atcgacggcg gggatcgatt gactcagtcg atctttgaag     120
tcgacgctgg gattactggt gtgagatcga tatcaaaggt cgagacccag ctttcttgta     180
caaagtggtg atcgagttaa cgaattccgg cgcctactgc agata        225

<210> SEQ ID NO 194
<211> LENGTH: 191
<212> TYPE: DNA
<213> ORGANISM: artificial sequences
<220> FEATURE:
<221> NAME/KEY: source
<222> LOCATION: 1..191
<223> OTHER INFORMATION: /mol_type="DNA"
      /note="seq syn 103 no muc antisense"
      /organism="artificial sequences"

<400> SEQUENCE: 194
ggatcccggg cccgcggtac cgtcgactgc agaattcgat cacaagtttg tacaaaaaag   60
caggctctcg acttcaaaga tcgactgact caatcgaccc tcccaaaatc gagacccagc  120
tttcttgtac aaagtggtga tcgagttaac gaattccggc gcctactgca gatactagtg  180
ggccctgcag g                                                       191

<210> SEQ ID NO 195
<211> LENGTH: 240
<212> TYPE: DNA
<213> ORGANISM: artificial sequences
<220> FEATURE:
<221> NAME/KEY: source
<222> LOCATION: 1..240
<223> OTHER INFORMATION: /mol_type="DNA"
      /note="seq syn 105 no muc antisense"
      /organism="artificial sequences"

<400> SEQUENCE: 195
ggatcccggg cccgcggtac cgtcgactgc agaattcgat cacaagtttg tacaaaaaag   60
caggctctcg acctttgata cgatatgcaa atgtcgatat caaggtcga tatgcaaatg  120 tcgatcccg ccgtcgactt caaagatcga tccccgccgt cgagacccag ctttcttgta  180
caaagtggtg atcgagttaa cgaattccgg cgcctactgc agcctctgcc acaaagtgca  240

<210> SEQ ID NO 196
<211> LENGTH: 187
<212> TYPE: DNA
<213> ORGANISM: artificial sequences
<220> FEATURE:
<221> NAME/KEY: source
<222> LOCATION: 1..187
<223> OTHER INFORMATION: /mol_type="DNA"
      /note="seq syn 106 no muc antisense"
      /organism="artificial sequences"

<400> SEQUENCE: 196
ggatcccggg cccgcggtac cgtcgactgc agaattcgat cacaagtttg tacaaaaaag   60
caggctctcg agacccagct ttcttgtaca aagtggtgat cgagttaacg aattccgggg  120
ccactcaggc cccctttct gaaactcaat tcttatcctc agtcctgctc ctctgccaca  180
aagtgca                                                            187

<210> SEQ ID NO 197
<211> LENGTH: 132
<212> TYPE: DNA
<213> ORGANISM: artificial sequences
<220> FEATURE:
<221> NAME/KEY: source
<222> LOCATION: 1..132
<223> OTHER INFORMATION: /mol_type="DNA"
      /note="seq syn 108 no muc antisense"

/organism="artificial sequences"

<400> SEQUENCE: 197
ggatcccggg cccgcggtac cgtcgactgc agaattcgat cacaagtttg tacaaaaaag   60
caggctctcg agacccagct ttcttgtaca aagtggtgat cgagttaacg aattccggcg   120
ccggccctgc ag   132

<210> SEQ ID NO 198
<211> LENGTH: 177
<212> TYPE: DNA
<213> ORGANISM: artificial sequences
<220> FEATURE:
<221> NAME/KEY: source
<222> LOCATION: 1..177
<223> OTHER INFORMATION: /mol_type="DNA"
      /note="Pro_200 no_muc antisense"
      /organism="artificial sequences"

<400> SEQUENCE: 198
ggatcccggg cccgcggtac cgtcgactgc agaattcgat cacaagtttg tacaaaaaag   60
caggctctcg attgatgtca gtcgacaaca aagatcgatt gactcagtcg acatgcaaat   120
atcgatcttt gttgtcgaga cccagctttc ttgtacaaag tggtgatcga gttaacg   177

<210> SEQ ID NO 199
<211> LENGTH: 165
<212> TYPE: DNA
<213> ORGANISM: artificial sequences
<220> FEATURE:
<221> NAME/KEY: source
<222> LOCATION: 1..165
<223> OTHER INFORMATION: /mol_type="DNA"
      /note="Pro_201 no_muc antisense"
      /organism="artificial sequences"

<400> SEQUENCE: 199
ggatcccggg cccgcggtac cgtcgactgc agaattcgat cacaagtttg tacaaaaaag   60
caggctctcg acatgcaaat atcgacattt gcatatcgat ctttgttgtc gactgacatc   120
aatcgagacc cagctttctt gtacaaagtg gtgatcgagt taacg   165

<210> SEQ ID NO 200
<211> LENGTH: 230
<212> TYPE: DNA
<213> ORGANISM: artificial sequences
<220> FEATURE:
<221> NAME/KEY: source
<222> LOCATION: 1..230
<223> OTHER INFORMATION: /mol_type="DNA"
      /note="Pro_202 no_muc antisense"
      /organism="artificial sequences"

<400> SEQUENCE: 200
ggatcccggg cccgcggtac cgtcgactgc agaattcgat cacaagtttg tacaaaaaag   60
caggctctcg acttcaaaga tcgatatcaa aggtcgatct tgttgtcga ctgagtcaat    120 cgattttggg agggtcgata tgcaaatgtc gattgagtca gtcgactgac tcaatcgatc   180
tttgttgtcg agacccagct ttcctgtaca aagtggtgat cgagttaacg   230

<210> SEQ ID NO 201
<211> LENGTH: 123
<212> TYPE: DNA
<213> ORGANISM: artificial sequences
<220> FEATURE:
<221> NAME/KEY: source

```
<222> LOCATION: 1..123
<223> OTHER INFORMATION: /mol_type="DNA"
      /note="Pro_203 no_muc antisense"
      /organism="artificial sequences"

<400> SEQUENCE: 201
ggatcccggg cccgcggtac cgtcgactgc agaattcgat cacaagtttg tacaaaaaag     60
caggctctcg atctttgttg tcgagaccca gctttcttgt acaaagtggt gatcgagtta    120
acg                                                                  123

<210> SEQ ID NO 202
<211> LENGTH: 152
<212> TYPE: DNA
<213> ORGANISM: artificial sequences
<220> FEATURE:
<221> NAME/KEY: source
<222> LOCATION: 1..152
<223> OTHER INFORMATION: /mol_type="DNA"
      /note="Pro_204 no_muc antisense"
      /organism="artificial sequences"

<400> SEQUENCE: 202
ggatcccggg cccgcggtac cgtcgactgc agaattcgat cacaagtttg tacaaaaaag     60
caggctctcg attgactcag tcgacatttg catatcgacc ctcccaaaat cgagacccag    120
ctttcttgta caaagtggtg atcgagttaa cg                                  152

<210> SEQ ID NO 203
<211> LENGTH: 149
<212> TYPE: DNA
<213> ORGANISM: artificial sequences
<220> FEATURE:
<221> NAME/KEY: source
<222> LOCATION: 1..149
<223> OTHER INFORMATION: /mol_type="DNA"
      /note="Pro_205 no_muc antisense"
      /organism="artificial sequences"

<400> SEQUENCE: 203
ggatcccggg cccgcggtac cgtcgactgc agaattcgat cacaagtttg tacaaaaaag     60
caggctctcg acgctgggat tacaggtgtg agatcgattg agtcagtcga gacccagctt    120
tcttgtacaa agtggtgatc gagttaacg                                      149

<210> SEQ ID NO 204
<211> LENGTH: 162
<212> TYPE: DNA
<213> ORGANISM: artificial sequences
<220> FEATURE:
<221> NAME/KEY: source
<222> LOCATION: 1..162
<223> OTHER INFORMATION: /mol_type="DNA"
      /note="Pro_206 no_muc antisense"
      /organism="artificial sequences"

<400> SEQUENCE: 204
ggatcccggg cccgcggtac cgtcgactgc agaattcgat cacaagtttg tacaaaaaag     60
caggctctcg acgctgggat tacaggtgtg agatcgatct tgttgtcga cttcaaagat    120 cgagacccag ctttcttgta caaagtggtg atcgagttaa cg                       162

<210> SEQ ID NO 205
<211> LENGTH: 136
<212> TYPE: DNA
<213> ORGANISM: artificial sequences
<220> FEATURE:
```

```
<221> NAME/KEY: source
<222> LOCATION: 1..136
<223> OTHER INFORMATION: /mol_type="DNA"
      /note="Pro_207 no_muc antisense"
      /organism="artificial sequences"

<400> SEQUENCE: 205
ggatcccggg cccgcggtac cgtcgactgc agaattcgat cacaagtttg tacaaaaaag      60
caggctctcg acgctgggat tacaggtgtg agatcgagac ccagctttct tgtacaaagt    120
ggtgatcgag ttaacg                                                     136

<210> SEQ ID NO 206
<211> LENGTH: 139
<212> TYPE: DNA
<213> ORGANISM: artificial sequences
<220> FEATURE:
<221> NAME/KEY: source
<222> LOCATION: 1..139
<223> OTHER INFORMATION: /mol_type="DNA"
      /note="Pro_208 no_muc antisense"
      /organism="artificial sequences"

<400> SEQUENCE: 206
ggatcccggg cccgcggtac cgtcgactgc agaattcgat cacaagtttg tacaaaaaag      60
caggctctcg actgacatca atcgaccctc ccaaaatcga gacccagctt tcttgtacaa    120
agtggtgatc gagttaacg                                                  139

<210> SEQ ID NO 207
<211> LENGTH: 168
<212> TYPE: DNA
<213> ORGANISM: artificial sequences
<220> FEATURE:
<221> NAME/KEY: source
<222> LOCATION: 1..168
<223> OTHER INFORMATION: /mol_type="DNA"
      /note="Pro_209 no_muc antisense"
      /organism="artificial sequences"

<400> SEQUENCE: 207
tatcgataag cttgggatcc cgggcccgcg gtaccgtcga ctgcagaatt cgatcacaag      60
tttgtacaaa aaagcaggct ctcgatctca cacctgtaat cccagcgtcg atatcaaagt    120
gcgatctttg aagtcgaatc gaattcctgc agcccggggg atccacta                 168

<210> SEQ ID NO 208
<211> LENGTH: 137
<212> TYPE: DNA
<213> ORGANISM: artificial sequences
<220> FEATURE:
<221> NAME/KEY: source
<222> LOCATION: 1..137
<223> OTHER INFORMATION: /mol_type="DNA"
      /note="Pro_210 no_muc antisense"
      /organism="artificial sequences"

<400> SEQUENCE: 208
ggatcccggg cccgcggtac cgtcgactgc agaattcgat cacaagtttg tacaaaaaag      60
caggctctcg atatgcaaat gtcgatcccc gccgtcgaga cccagctttc ttgtacaaag    120
tggtgatcga gttaacg                                                    137

<210> SEQ ID NO 209
<211> LENGTH: 136
<212> TYPE: DNA
<213> ORGANISM: artificial sequences
```

```
<220> FEATURE:
<221> NAME/KEY: source
<222> LOCATION: 1..136
<223> OTHER INFORMATION: /mol_type="DNA"
      /note="Pro_211 no_muc antisense"
      /organism="artificial sequences"

<400> SEQUENCE: 209
ggatcccggg cccgcggtac cgtcgactgc agaattcgat cacaagtttg tacaaaaaag     60
caggctctcg acaacaaaga tcgattgagt cagtcgagac ccagctttct tgtacaaagt    120
ggtgatcgag ttaacg                                                    136

<210> SEQ ID NO 210
<211> LENGTH: 125
<212> TYPE: DNA
<213> ORGANISM: artificial sequences
<220> FEATURE:
<221> NAME/KEY: source
<222> LOCATION: 1..125
<223> OTHER INFORMATION: /mol_type="DNA"
      /note="Pro_212 no_muc antisense"
      /organism="artificial sequences"

<400> SEQUENCE: 210
ggatcccggg cccgcggtac cgtcgactgc agaattcgat cacaagtttg tacaaaaaag     60
caggctctcg attttgggag ggtcgagacc cagctttctt gtacaaagtg gtgatcgagt    120
taacg                                                                125

<210> SEQ ID NO 211
<211> LENGTH: 217
<212> TYPE: DNA
<213> ORGANISM: artificial sequences
<220> FEATURE:
<221> NAME/KEY: source
<222> LOCATION: 1..217
<223> OTHER INFORMATION: /mol_type="DNA"
      /note="Pro_213 no_muc antisense"
      /organism="artificial sequences"

<400> SEQUENCE: 211
ggatcccggg cccgcggtac cgtcgactgc agaattcgat cacaagtttg tacaaaaaaa     60
gcaggctctc gatccccgcc gtcgactgag tcaatcgacc tttgatatcg atctcacacc    120
tgtaatccca gcgtcgaccc tcccaaaatc gacaacaaag atcgatcttt gttgtcgaga    180
cccagctttc ttgtacaaag tggtgatcga gttaacg                             217

<210> SEQ ID NO 212
<211> LENGTH: 164
<212> TYPE: DNA
<213> ORGANISM: artificial sequences
<220> FEATURE:
<221> NAME/KEY: source
<222> LOCATION: 1..164
<223> OTHER INFORMATION: /mol_type="DNA"
      /note="Pro_214 no_muc antisense"
      /organism="artificial sequences"

<400> SEQUENCE: 212
ggatcccggg cccgcggtac cgtcgactgc agaattcgat cacaagtttg tacaaaaaag     60
caggctctcg attgactcag tcgacatttg catatcgatc tttgaagtcg attgatgtca    120
gtcgagaccc agctttcttg tacaaagtgg tgatcgagtt aacg                     164

<210> SEQ ID NO 213
```

<210> SEQ ID NO 213
<211> LENGTH: 193
<212> TYPE: DNA
<213> ORGANISM: artificial sequences
<220> FEATURE:
<221> NAME/KEY: source
<222> LOCATION: 1..193
<223> OTHER INFORMATION: /mol_type="DNA"
    /note="Pro_215 no_muc antisense"
    /organism="artificial sequences"

<400> SEQUENCE: 213
ggatcccggg cccgcggtac cgtcgactgc agaattcgat cacaagtttg tacaaaaaag      60
caggctctcg attttgggag ggtcgacatg caaatatcga ttgatgtcag tcgatatgca     120
aatgtcgatc tttgttgtcg atccccgccg tcgagaccca gctttcttgt acaaagtggt     180
gatcgagtta acg                                                        193

<210> SEQ ID NO 214
<211> LENGTH: 188
<212> TYPE: DNA
<213> ORGANISM: artificial sequences
<220> FEATURE:
<221> NAME/KEY: source
<222> LOCATION: 1..188
<223> OTHER INFORMATION: /mol_type="DNA"
    /note="Pro_216 no_muc antisense"
    /organism="artificial sequences"

<400> SEQUENCE: 214
ggatcccggg cccgcggtac cgtcgactgc agaattcgat cacaagtttg tacaaaaaag      60
caggctctcg acgctgggat tacagtgtga gatcgactga ctcaatcgat ctttgaagtc     120
gactgactca atcgacattt gcatatcgag acccagcttt cttgtacaaa gtggtgatcg     180
agttaacg                                                              188

<210> SEQ ID NO 215
<211> LENGTH: 190
<212> TYPE: DNA
<213> ORGANISM: artificial sequences
<220> FEATURE:
<221> NAME/KEY: source
<222> LOCATION: 1..190
<223> OTHER INFORMATION: /mol_type="DNA"
    /note="Pro_217 no_muc antisense"
    /organism="artificial sequences"

<400> SEQUENCE: 215
ggatcccggg cccgcggtac cgtcgactgc agaattcgat cacaagtttg tacaaaaaag      60
caggctctcg accctcccaa aatcgacttc aaagatcgac tgactcaatc gatctttgtt     120
gtcgatctca cacctgtaat cccagcgtcg agacccagct tcttgtaca aagtggtgat     180 cgagttaacg                                                            190

<210> SEQ ID NO 216
<211> LENGTH: 136
<212> TYPE: DNA
<213> ORGANISM: artificial sequences
<220> FEATURE:
<221> NAME/KEY: source
<222> LOCATION: 1..136
<223> OTHER INFORMATION: /mol_type="DNA"
    /note="Pro_218 no_muc antisense"
    /organism="artificial sequences"

<400> SEQUENCE: 216
ggatcccggg cccgcggtac cgtcgactgc agaattcgat cacaagtttg tacaaaaaag      60
caggctctcg acaacaaaga tcgatccccg ccgtcgagac ccagctttct tgtacaaagt       120
ggtgatcgag ttaacg                                                       136

<210> SEQ ID NO 217
<211> LENGTH: 179
<212> TYPE: DNA
<213> ORGANISM: artificial sequences
<220> FEATURE:
<221> NAME/KEY: source
<222> LOCATION: 1..179
<223> OTHER INFORMATION: /mol_type="DNA"
      /note="Pro_219 no_muc antisense"
      /organism="artificial sequences"

<400> SEQUENCE: 217
ggatccccgg gcccgcggta ccgtcgactg cagaattcga tcacaagttt gtacaaaaaa       60
gcaggctctc gatctttgaa gtcgatcttt gaagtcgacc ctcccaaaat cgacctttga      120
tatcgattga tgtcagtcga gacccagctt tcttgtacaa agtggtgatc gagttaacg      179

<210> SEQ ID NO 218
<211> LENGTH: 123
<212> TYPE: DNA
<213> ORGANISM: artificial sequences
<220> FEATURE:
<221> NAME/KEY: source
<222> LOCATION: 1..123
<223> OTHER INFORMATION: /mol_type="DNA"
      /note="Pro_220 no_muc antisense"
      /organism="artificial sequences"

<400> SEQUENCE: 218
ggatcccggg cccgcggtac catcgactgc agaattcgat cacaagtttg tacaaaaaag       60
caggctctcg attgagtcag tcgagaccca gctttcttgt acaaagtggt gatcgagtta      120
acg                                                                    123

<210> SEQ ID NO 219
<211> LENGTH: 137
<212> TYPE: DNA
<213> ORGANISM: artificial sequences
<220> FEATURE:
<221> NAME/KEY: source
<222> LOCATION: 1..137
<223> OTHER INFORMATION: /mol_type="DNA"
      /note="Pro_221 no_muc antisense"
      /organism="artificial sequences"

<400> SEQUENCE: 219
ggatcccgcg cccccggtcc cctcgactgc agaattcgat cacaagtttg tacaaaaaag       60
caggctctcg atatttgcat gtcgattgac tcagtcgaga cccagctttc ttgtacaaag      120
tggtgatcga gttaacg                                                     137

<210> SEQ ID NO 220
<211> LENGTH: 202
<212> TYPE: DNA
<213> ORGANISM: artificial sequences
<220> FEATURE:
<221> NAME/KEY: source
<222> LOCATION: 1..202
<223> OTHER INFORMATION: /mol_type="DNA"
      /note="Pro_222 no_muc antisense"
      /organism="artificial sequences"

<400> SEQUENCE: 220

```
ggatcccggg cccgcggtac cgtcgactgc agaattcgat cacaagtttg tacaaaaaag    60
caggctctcg acatttgcat atcgacggcg gggatcgatt gactcagtcg atctttgaag   120
tcgacgctgg gattactggt gtgagatcga tatcaaaggt cgagacccag ctttcttgta   180
caaagtggtg atcgagttaa cg                                            202

<210> SEQ ID NO 221
<211> LENGTH: 204
<212> TYPE: DNA
<213> ORGANISM: artificial sequences
<220> FEATURE:
<221> NAME/KEY: source
<222> LOCATION: 1..204
<223> OTHER INFORMATION: /mol_type="DNA"
      /note="Pro_223 no_muc antisense"
      /organism="artificial sequences"

<400> SEQUENCE: 221
ggatcccggg cccgcggtac cgtcgactgc agaattcgat cacaagtttg tacaaaaaag    60
caggctctcg attgactcag tcgacatttg catatcgata tgcaaatgtc gactgactca   120
atcgactgag tcaatcgata tcaaaggtcg actgacatca atcgagaccc agctttcttg   180
tacaaagtgg tgatcgagtt aacg                                          204

<210> SEQ ID NO 222
<211> LENGTH: 150
<212> TYPE: DNA
<213> ORGANISM: artificial sequences
<220> FEATURE:
<221> NAME/KEY: source
<222> LOCATION: 1..150
<223> OTHER INFORMATION: /mol_type="DNA"
      /note="Pro_224 no_muc antisense"
      /organism="artificial sequences"

<400> SEQUENCE: 222
ggatcccggg cccgcggtac cgtcgactgc agaattcgat cacaagtttg tacaaaaaag    60
caggctctcg actgactcaa tcgacggcgg ggatcgactg acatcaatcg agacccagct   120
ttcttgtaca aagtggtgat cgagttaacg                                    150

<210> SEQ ID NO 223
<211> LENGTH: 178
<212> TYPE: DNA
<213> ORGANISM: artificial sequences
<220> FEATURE:
<221> NAME/KEY: source
<222> LOCATION: 1..178
<223> OTHER INFORMATION: /mol_type="DNA"
      /note="Pro_225 no_muc antisense"
      /organism="artificial sequences"

<400> SEQUENCE: 223
ggatcccggg cccgcggtac cgtcgactgc agaattcgat cacaagtttg tacaaaaaag    60
caggctctcg accctcccaa aatcgattga gtcagtcgat atttgcatgt cgacaacaaa   120
gatcgacttc aaagatcgag acccagcttt cttgtacaaa gtggtgatcg agttaacg    178

<210> SEQ ID NO 224
<211> LENGTH: 214
<212> TYPE: DNA
<213> ORGANISM: artificial sequences
<220> FEATURE:
<221> NAME/KEY: source
<222> LOCATION: 1..214
<223> OTHER INFORMATION: /mol_type="DNA"
```

/note="Pro_226 no_muc antisense"
/organism="artificial sequences"

<400> SEQUENCE: 224

```
ggatcccggg cccgcggtac cgtcgactgc agaattcgat cacaagtttg tacaaaaaag    60
caggctctcg acctttgata tcgactgact caatcgatct tgttgtcga tctttgaagt    120 cgacggcggg gatcgatctt tgaagtcgac aacaaagatc gatctttgaa gtcgagaccc   180
agctttcttg tacaaagtgg tgatcgagtt aacg                              214
```

<210> SEQ ID NO 225
<211> LENGTH: 178
<212> TYPE: DNA
<213> ORGANISM: artificial sequences
<220> FEATURE:
<221> NAME/KEY: source
<222> LOCATION: 1..178
<223> OTHER INFORMATION: /mol_type="DNA"
/note="Pro_227 no_muc antisense"
/organism="artificial sequences"

<400> SEQUENCE: 225

```
ggatcccggg cccgcggtac cgtcgactgc agaattcgat cacaagtttg tacaaaaaag    60
caggctctcg atatgcaaat gtcgactgac atcaatcgac aacaaagatc gactgactca   120
atcgacatgc aaatatcgag acccagcttt cttgtacaaa gtggtgatcg agttaacg    178
```

<210> SEQ ID NO 226
<211> LENGTH: 164
<212> TYPE: DNA
<213> ORGANISM: artificial sequences
<220> FEATURE:
<221> NAME/KEY: source
<222> LOCATION: 1..164
<223> OTHER INFORMATION: /mol_type="DNA"
/note="Pro_228 no_muc antisense"
/organism="artificial sequences"

<400> SEQUENCE: 226

```
ggatcccggg cccgcggtac cgtcgactgc agaattcgat cacaagtttg tacaaaaaag    60
caggctctcg attgatgtca gtcgacggcg gggatcgatc tttgaagtcg attttgggag   120
ggtcgagacc cagctttctt gtacaaagtg gtgatcgagt taac                   164
```

<210> SEQ ID NO 227
<211> LENGTH: 163
<212> TYPE: DNA
<213> ORGANISM: artificial sequences
<220> FEATURE:
<221> NAME/KEY: source
<222> LOCATION: 1..163
<223> OTHER INFORMATION: /mol_type="DNA"
/note="Pro_229 no_muc antisense"
/organism="artificial sequences"

<400> SEQUENCE: 227

```
ggatcccggg cccgcggtac cgtcgactgc agaattcgat cacaagtttg tacaaaaaag    60
caggctctcg atctttgaag tcgatatgca aatgtcgatt gactcagtcg actgactcaa   120
tcgagaccca gctttcttgt acaaagtggt gatcgagtta acg                    163
```

<210> SEQ ID NO 228
<211> LENGTH: 165
<212> TYPE: DNA
<213> ORGANISM: artificial sequences
<220> FEATURE:

```
<221> NAME/KEY: source
<222> LOCATION: 1..165
<223> OTHER INFORMATION: /mol_type="DNA"
      /note="Pro_230 no_muc antisense"
      /organism="artificial sequences"

<400> SEQUENCE: 228
ggatcccggg cccgcggtac cgtcgactgc agaattcgat cacaagtttg tacaaaaaag    60
caggctctcg acatttgcat atcgactgac tcaatcgata tgcaaatgtc gatatgcaaa   120
tgtcgagacc cagctttcct gtacaaagtg gtgatcgagt taacg                  165

<210> SEQ ID NO 229
<211> LENGTH: 179
<212> TYPE: DNA
<213> ORGANISM: artificial sequences
<220> FEATURE:
<221> NAME/KEY: source
<222> LOCATION: 1..179
<223> OTHER INFORMATION: /mol_type="DNA"
      /note="Pro_231 no_muc antisense"
      /organism="artificial sequences"

<400> SEQUENCE: 229
ggatcccggg cccgcggtac cgtcgactgc agaattcgat cacaagtttg tacaaaaaag    60
caggctctcg accctcccaa aatcgattga gtcagtcgac atttgcatat cgacaacaaa   120
gatcgactga catcaatcga gacccagctt tcttgtacaa agtggtgatc gagttaacg   179

<210> SEQ ID NO 230
<211> LENGTH: 185
<212> TYPE: DNA
<213> ORGANISM: artificial sequences
<220> FEATURE:
<221> NAME/KEY: source
<222> LOCATION: 1..185
<223> OTHER INFORMATION: /mol_type="DNA"
      /note="Pro_232 no_muc antisense"
      /organism="artificial sequences"

<400> SEQUENCE: 230
ggatcccggg cccgcggtac cgtcgactgc agaattcgat cacaagtttg tacaaaaaag    60
caggctctcg actgagtcaa tcgacttcaa agatcgacgg cggggatcga tatgcaaatg   120
tcgatatgca aatgtcgaga cccagctttc ttgtacaaag tggtgatcga gttaacgaat   180
tccgg                                                              185

<210> SEQ ID NO 231
<211> LENGTH: 163
<212> TYPE: DNA
<213> ORGANISM: artificial sequences
<220> FEATURE:
<221> NAME/KEY: source
<222> LOCATION: 1..163
<223> OTHER INFORMATION: /mol_type="DNA"
      /note="Pro_233 no_muc antisense"
      /organism="artificial sequences"

<400> SEQUENCE: 231
ggatcccggg cccgcggtac cgtcgactgc agaattcgat cacaagtttg tacaaaaaag    60
caggctctcg acttcaaaga tcgatctttg ttgtcgacat ttgcatatcg atctttgttg   120
tcgagaccca gctttcctgt acaaagtggt gatcgagtta acg                    163

<210> SEQ ID NO 232
<211> LENGTH: 209
```

```
<212> TYPE: DNA
<213> ORGANISM: artificial sequences
<220> FEATURE:
<221> NAME/KEY: source
<222> LOCATION: 1..209
<223> OTHER INFORMATION: /mol_type="DNA"
      /note="Pro_234 no_muc antisense"
      /organism="artificial sequences"

<400> SEQUENCE: 232
ggatcccggg cccgcggtac cgtcgactgc agaattcgat cacaagtttg tacaaaaaag        60
caggctctcg actgacatca atcgattgat gtcagtcgat tgactcagtc gattttggga       120
gggtcgacgg cggggatcga ctgagtcaat cgattgactc agtcgagacc cagcttcttt      180
gtacaaagtg gtgatcgagt taacgaatt                                         209

<210> SEQ ID NO 233
<211> LENGTH: 176
<212> TYPE: DNA
<213> ORGANISM: artificial sequences
<220> FEATURE:
<221> NAME/KEY: source
<222> LOCATION: 1..176
<223> OTHER INFORMATION: /mol_type="DNA"
      /note="Pro_235 no_muc antisense"
      /organism="artificial sequences"

<400> SEQUENCE: 233
ggatcccggg cccgcggtac cgtcgactgc agaattcgat cacaagtttg tacaaaaaag        60
caggctctcg actgactcaa tcgattgact cagtcgacaa caaagatcga ctgactcaat       120
cgatatgcaa atgtcgagac ccagctttct tgtacaaagt ggtgatcgag ttaacg           176

<210> SEQ ID NO 234
<211> LENGTH: 151
<212> TYPE: DNA
<213> ORGANISM: artificial sequences
<220> FEATURE:
<221> NAME/KEY: source
<222> LOCATION: 1..151
<223> OTHER INFORMATION: /mol_type="DNA"
      /note="Pro_236 no_muc antisense"
      /organism="artificial sequences"

<400> SEQUENCE: 234
ggatcccggg cccgcggtac cgtcgactgc agaattcgat cacaagtttg tacaaaaaag        60
caggctctcg acatttgcat atcgattgac tcagtcgact gacatcaatc gagacccagc       120
tttcttgtac aaagtggtga tcgagttaac g                                      151

<210> SEQ ID NO 235
<211> LENGTH: 245
<212> TYPE: DNA
<213> ORGANISM: artificial sequences
<220> FEATURE:
<221> NAME/KEY: source
<222> LOCATION: 1..245
<223> OTHER INFORMATION: /mol_type="DNA"
      /note="Pro_237 no_muc antisense"
      /organism="artificial sequences"

<400> SEQUENCE: 235
ggatcccggg cccgcggtac cgtcgactgc agaattcgat cacaagtttg tacaaaaaag        60
caggctctcg attttgggag ggtcgacgct gggattacag gtgtgagatc gatctttgaa      120
gtcgattgat gtcagtcgac tgagtcaatc gattgatgtc agtcgatatg caaatgtcga      180
```

```
catgcaaata tcgactgact caatcgactg agtcaatcga tctttgttgt cgagacccag    240
ctttc                                                               245
```

<210> SEQ ID NO 236
<211> LENGTH: 137
<212> TYPE: DNA
<213> ORGANISM: artificial sequences
<220> FEATURE:
<221> NAME/KEY: source
<222> LOCATION: 1..137
<223> OTHER INFORMATION: /mol_type="DNA"
      /note="Pro_238 no_muc antisense"
      /organism="artificial sequences"

<400> SEQUENCE: 236

```
ggatcccggg cccgcggtac cgtcgactgc agaattcgat cacaagtttg tacaaaaaag    60
caggctctcg acatttgcat atcgacttca aagatcgaga gccagctttc ttgtacaaag   120
tggtgatcga gttaacg                                                  137
```

<210> SEQ ID NO 237
<211> LENGTH: 216
<212> TYPE: DNA
<213> ORGANISM: artificial sequences
<220> FEATURE:
<221> NAME/KEY: source
<222> LOCATION: 1..216
<223> OTHER INFORMATION: /mol_type="DNA"
      /note="Pro_239 no_muc antisense"
      /organism="artificial sequences"

<400> SEQUENCE: 237

```
ggatcccggg cccgcggtac cgtcgactgc agaattcgat cacaagtttg cacaaaaaag    60
caggctctcg acggcgggga tcgacatttg catgtcgata tgcaaacgtc gatatgcaaa   120
tgtcgaccga gtcaatcgac ggcggggatc gacctttgat atcgatcttt gttgtcgatt   180
gactcagtcg acaacaaaga tcgagaccca gctttc                             216
```

<210> SEQ ID NO 238
<211> LENGTH: 171
<212> TYPE: DNA
<213> ORGANISM: artificial sequences
<220> FEATURE:
<221> NAME/KEY: source
<222> LOCATION: 1..171
<223> OTHER INFORMATION: /mol_type="DNA"
      /note="Pro_240 no_muc antisense"
      /organism="artificial sequences"

<400> SEQUENCE: 238

```
ggatcccggg cccgcggtac cgtcgactgc agaattcgat cacaagtttg tacaaaaaag    60
caggctctcg attgatgtca gtcgacatgc aaatatcgat ctcacacctg taatcccagc   120
gtcgatcccc gccgcgatct cacacctgta atcccagcgt cgagacccag c            171
```

<210> SEQ ID NO 239
<211> LENGTH: 136
<212> TYPE: DNA
<213> ORGANISM: artificial sequences
<220> FEATURE:
<221> NAME/KEY: source
<222> LOCATION: 1..136
<223> OTHER INFORMATION: /mol_type="DNA"
      /note="Pro_241 no_muc antisense"
      /organism="artificial sequences"

<400> SEQUENCE: 239

```
ggatcccggg cccgcggtac cgtcgactgc agaattcgat cacaagtttg tacaaaaaag     60
caggctctcg acctttgata tcgacggcgg ggatcgagac ccagctttct tgtacaaagt    120
ggtgatcgag ttaacg                                                    136
```

<210> SEQ ID NO 240
<211> LENGTH: 199
<212> TYPE: DNA
<213> ORGANISM: artificial sequences
<220> FEATURE:
<221> NAME/KEY: source
<222> LOCATION: 1..199
<223> OTHER INFORMATION: /mol_type="DNA"
      /note="Pro_242 no_muc antisense"
      /organism="artificial sequences"

<400> SEQUENCE: 240

```
ggatcccggg cccgcggtac cgtcgactgc agaattcgat cacaagtttg tacaaaaaag     60
caggctctcg attgactcag ctgacatcaa tcgattgagt cagtcgattg actcagtcga    120
catttgcata tcgattgagt cagtcgatcc ccgccgtcga gacccagctt tcttgtacaa    180
agtggtgatc gagttaacg                                                 199
```

<210> SEQ ID NO 241
<211> LENGTH: 138
<212> TYPE: DNA
<213> ORGANISM: artificial sequences
<220> FEATURE:
<221> NAME/KEY: source
<222> LOCATION: 1..138
<223> OTHER INFORMATION: /mol_type="DNA"
      /note="Pro_243 no_muc antisense"
      /organism="artificial sequences"

<400> SEQUENCE: 241

```
ggatcccggg cccgcggtac cgtcgactgc agaattcgat cacaagtttg tacaaaaaag     60
caggctctcg atatttgcat gtcgacatgc aaatatcgag acccagcttt cctgtacaaa    120
gtggtgatcg agttaacg                                                  138
```

<210> SEQ ID NO 242
<211> LENGTH: 139
<212> TYPE: DNA
<213> ORGANISM: artificial sequences
<220> FEATURE:
<221> NAME/KEY: source
<222> LOCATION: 1..139
<223> OTHER INFORMATION: /mol_type="DNA"
      /note="Pro_244 no_muc antisense"
      /organism="artificial sequences"

<400> SEQUENCE: 242

```
ggatcccggg cccgcggtac cgtcgactgc agaattcgat cacaagtttg tacaaaaaag     60
caggctctcg acatgcaaat atcgaccctc ccaaaatcga gacccagctt tcttgtacaa    120
agtggtgatc gagttaacg                                                 139
```

<210> SEQ ID NO 243
<211> LENGTH: 150
<212> TYPE: DNA
<213> ORGANISM: artificial sequences
<220> FEATURE:
<221> NAME/KEY: source
<222> LOCATION: 1..150
<223> OTHER INFORMATION: /mol_type="DNA"
      /note="Pro_245 no_muc antisense"

/organism="artificial sequences"

<400> SEQUENCE: 243

```
ggatcccggg cccgcggtac cgtcgactgc agaattcgat cacaagtttg tacaaaaaag    60
caggctctcg acttcaaaga tcgatctttg aagtcgactg acatcaatcg agacccagct   120
ttcttgtaca aagtggtgat cgagttaacg                                    150
```

<210> SEQ ID NO 244
<211> LENGTH: 179
<212> TYPE: DNA
<213> ORGANISM: artificial sequences
<220> FEATURE:
<221> NAME/KEY: source
<222> LOCATION: 1..179
<223> OTHER INFORMATION: /mol_type="DNA"
    /note="Pro_246 no_muc antisense"
    /organism="artificial sequences"

<400> SEQUENCE: 244

```
ggatcccggg cccgcggtac cgtcgactgc agaattcgat cacaagtttg tacaaaaaag    60
caggctctcg attgagtcag tcgacatttg catatcgacc ctcccaaaat cgatatgcaa   120
atgtcgatcc ccgccgtcga ggcccagctt tcttgtacaa agtggtgatc gagttaacg    179
```

<210> SEQ ID NO 245
<211> LENGTH: 205
<212> TYPE: DNA
<213> ORGANISM: artificial sequences
<220> FEATURE:
<221> NAME/KEY: source
<222> LOCATION: 1..205
<223> OTHER INFORMATION: /mol_type="DNA"
    /note="Pro_247 no_muc antisense"
    /organism="artificial sequences"

<400> SEQUENCE: 245

```
ggatcccggg cccgcggtac cgtcgactgc agaattcgat cacaagtttg tacaaaaaag    60
caggctctcg atctttgttg tcgacctttg atatcgatat gcaaatgtcg attgacgtca   120
gtcgaccctc ccaaaatcga cttcaaagat cgacaacaaa gatcgagacc cagctttctt   180
gtacaaagtg gtgatcgagt taacg                                         205
```

<210> SEQ ID NO 246
<211> LENGTH: 228
<212> TYPE: DNA
<213> ORGANISM: artificial sequences
<220> FEATURE:
<221> NAME/KEY: source
<222> LOCATION: 1..228
<223> OTHER INFORMATION: /mol_type="DNA"
    /note="Pro_248 no_muc antisense"
    /organism="artificial sequences"

<400> SEQUENCE: 246

```
ggatcccggg cccgcggtac cgtcgactgc agaattcgat cacaagtttg tacaaaaaag    60
caggctctcg acctttgata tcgatctttg ttgtcgattg agtcagtcga ctgactcaat   120
cgatctttgt tgtcgacttc aaagatcgat ctcacacctg taatcccagc gtcgacatgc   180
aaatatcgag acccagcttt cttgtacaaa gtggtgatcg agttaacg                228
```

<210> SEQ ID NO 247
<211> LENGTH: 149
<212> TYPE: DNA
<213> ORGANISM: artificial sequences

```
<220> FEATURE:
<221> NAME/KEY: source
<222> LOCATION: 1..149
<223> OTHER INFORMATION: /mol_type="DNA"
      /note="Pro_249 no_muc antisense"
      /organism="artificial sequences"

<400> SEQUENCE: 247
ggatcccggg cccgcggtac cgtcgactgc agaattcgat cacaagtttg tacaaaaaag    60
caggctctcg atatcaaagg tcgattgact cagtcgatcc ccgccgtcga gacccagctt   120
tcttgtacaa agtggtgatc gagttaacg                                     149

<210> SEQ ID NO 248
<211> LENGTH: 188
<212> TYPE: DNA
<213> ORGANISM: artificial sequences
<220> FEATURE:
<221> NAME/KEY: source
<222> LOCATION: 1..188
<223> OTHER INFORMATION: /mol_type="DNA"
      /note="Pro_250 no_muc antisense"
      /organism="artificial sequences"

<400> SEQUENCE: 248
ggatcccggg cccgcggtac cgtcgactgc agaattcgat cacaagtttg tacaaaaaag    60
caggctctcg acgctgggat tacaggtgtg agatcgacaa caaagatcga tatcaaaggt   120
cgattgagtc agtcgatctt tgaagtcgag acccagcttt cttgtacaaa gtggtgatcg   180
agttaacg                                                            188

<210> SEQ ID NO 249
<211> LENGTH: 135
<212> TYPE: DNA
<213> ORGANISM: artificial sequences
<220> FEATURE:
<221> NAME/KEY: source
<222> LOCATION: 1..135
<223> OTHER INFORMATION: /mol_type="DNA"
      /note="Pro_251 no_muc antisense"
      /organism="artificial sequences"

<400> SEQUENCE: 249
ggatcccggg cccgcggtac cgtcgactgc agaattcgat cacaagtttg tacaaaaaag    60
caggctctcg acgctgggat tacaggtgtg agatcgagac ccagctttct tgtacaaagt   120
ggtgatcgag ttaac                                                    135

<210> SEQ ID NO 250
<211> LENGTH: 201
<212> TYPE: DNA
<213> ORGANISM: artificial sequences
<220> FEATURE:
<221> NAME/KEY: source
<222> LOCATION: 1..201
<223> OTHER INFORMATION: /mol_type="DNA"
      /note="Pro_252 no_muc antisense"
      /organism="artificial sequences"

<400> SEQUENCE: 250
ggatcccggg cccgcggtac cgtcgactgc agaattcgat cacaagtttg tacaaaaaag    60
caggctctcg acatttgcat atcgacggcg gggatcgatt gactcagtcg atctttgaag   120
tcgacgctgg gattactggt gtgagatcga tatcaaaggt cgagacccag ctttcttgta   180
caaagtggtg atcgagttaa c                                             201
```

```
<210> SEQ ID NO 251
<211> LENGTH: 151
<212> TYPE: DNA
<213> ORGANISM: artificial sequences
<220> FEATURE:
<221> NAME/KEY: source
<222> LOCATION: 1..151
<223> OTHER INFORMATION: /mol_type="DNA"
      /note="Pro_253 no_muc antisense"
      /organism="artificial sequences"

<400> SEQUENCE: 251
ggatcccggg cccgcggtac cgtcgactgc agaattcgat cacaagtttg tacaaaaaag      60
caggctctcg acttcaaaga tcgactgact caatcgaccc tcccaaaatc gagacccagc     120
tttcttgtac aaagtggtga tcgagttaac g                                    151

<210> SEQ ID NO 252
<211> LENGTH: 202
<212> TYPE: DNA
<213> ORGANISM: artificial sequences
<220> FEATURE:
<221> NAME/KEY: source
<222> LOCATION: 1..202
<223> OTHER INFORMATION: /mol_type="DNA"
      /note="Pro_254 no_muc antisense"
      /organism="artificial sequences"

<400> SEQUENCE: 252
ggatcccggg cccgcggtac cgtcgactgc agaattcgat cacaagtttg tacaaaaaag      60
caggctctcg acctttgata cgatatgcaa atgtcgatat caaaggtcga tatgcaaatg     120
tcgatccccg ccgtcgactt caaagatcga tccccgccgt cgagacccag ctttcttgta     180
caaagtggtg atcgagttaa cg                                              202

<210> SEQ ID NO 253
<211> LENGTH: 110
<212> TYPE: DNA
<213> ORGANISM: artificial sequences
<220> FEATURE:
<221> NAME/KEY: source
<222> LOCATION: 1..110
<223> OTHER INFORMATION: /mol_type="DNA"
      /note="Pro_255 no_muc antisense"
      /organism="artificial sequences"

<400> SEQUENCE: 253
ggatcccggg cccgcggtac cgtcgactgc agaattcgat cacaagtttg tacaaaaaag      60
caggctctcg agacccagct tcttgtaca aagtggtgat cgagttaacg                 110
```

METHOD FOR THE CONSTRUCTION OF SPECIFIC PROMOTERS

CROSS-REFERENCE TO RELATED APPLICATIONS

This application is a U.S. National Phase Application of International Application No. PCT/EP2012/051174, filed Jan. 25, 2012, which claims priority to European Application No. 11000572.5, filed Jan. 25, 2011, the contents of each of which are incorporated in their entirety by reference herein.

FIELD OF THE INVENTION

The present application relates to a system for designing promoters for selective expression of genes.

DESCRIPTION OF RELATED ART

Cancer is a complex biological phenomenon that is thought to arise out of a multi-step process of genetic and epigenetic alterations in the cellular DNA, ultimately resulting in the transformation of the cell and its uncontrolled growth, division and migration. Identifying the aberrant molecular pathways that mediate cellular transformation has been a major challenge in understanding how malignancy develops.

The advent of functional genomics has given scientists the prospect of examining global changes in gene expression, providing molecular phenotypes that could potentially help in establishing more effective techniques of diagnosis and prognosis in a variety of cancers.

Utilising microarrays to decipher the molecular events that result in tumour progression has proven a more difficult task, particularly since microarray data only provides a snapshot into a cell's transcriptome at a specific point in time. As many cancers contain multiple genetic alterations, it is difficult to ascribe specific changes in gene expression profiles to particular alterations in the genome of the transformed cell.

However, progress in the past few years has revealed that microarray data can have wider applications in the study of cancer, particularly with the advent of comparative genomic microarray analysis. In this type of analysis, gene expression data can be mapped to chromosomes, revealing potential sites of chromosomal aberrations, e.g. amplifications or deletions, which may predominate in particular types of cancer.

There is also now a growing trend for researchers to analyse microarray data in terms of 'gene modules' instead of the presentation of differentially regulated gene lists. By grouping genes into functionally related modules it is possible to identify subtle changes in gene expression that may be biologically (if not statistically significantly) important, to more easily interpret molecular pathways that mediate a particular response and to compare many different microarray experiments from different tumour types in an effort to uncover the commonalities and differences in multiple clinical conditions.

Therefore, we are moving into a new era of functional genomics, where the large datasets generated by the evaluation of global gene expression studies can be more fully interpreted by improvements in computational methods. It is important in the study of cancer that these improved bioinformatics tools be applied to this complex disease in an effort to unravel the molecular processes that mediate the malignant phenotype, so that ultimately improved targeted therapeutics can be effectively designed.

SUMMARY

Among the objects of the present invention is to provide a method and compositions for the construction of specific promoters. Such promoters can be specific for a type of cell, tissue, or condition, such as a particular disease or environmental condition, e.g., presence of a biological or chemical agent or microbial pathogen. Preferably these are promoters for a tissue-specific expression.

In certain embodiments, this aim is achieved by the inventions as claimed in the independent claims. Certain advantageous embodiments are described in the dependent claims, with other embodiments described herein.

Even if no multiple back-referenced claims are drawn, all reasonable combinations of the features in the claims shall be disclosed.

In certain aspects, the object of the invention is achieved by a method. In what follows, individual steps of a method will be described in more detail. The steps do not necessarily have to be performed in the order given in the text. Also, further steps not explicitly stated may be part of the method.

Provided are methods for selecting promoter elements and selecting and making promoter cassettes for cell-, tissue- or condition-specific expression, such as transcription-enhancing combined promoter cassettes. Such methods generally include a step of identifying or providing transcription factor regulatory elements (TFREs), such as a plurality of TFREs. Each of the plurality of TFREs is typically associated with one or more of a plurality of genes. Each of the plurality of genes generally is differentially expressed, for example, aberrently expressed, e.g., up-regulated or down-regulated, in a particular cell type or tissue type, or under a particular condition, for example, compared to another cell type, tissue type, or condition, such as a normal, control, or standard cell type or tissue or in the absence of the specified condition.

Among the cell and tissue types are eukaryotic cells, including animals, plants, fungi, and other eukaryotic cells. For example, the cell or tissue type can be from a mammal, yeast, insect, bovine, porcine, murine, equine, canine, feline, avian, piscine, ovine, insect, simian, and/or human.

In some aspects, the cell or tissue type is a tissue or cell from the cerebrum, cerebellum, adrenal gland, ovary, pancreas, parathyroid gland, hypophysis, testis, thyroid gland, breast, spleen, tonsil, thymus, lymph node, bone marrow, lung, cardiac muscle, esophagus, stomach, small intestine, colon, liver, salivary gland, kidney, prostate, blood, or other cell or tissue type.

In some aspects, the condition is a disease condition, such as a cancer, inflammatory disease, infectious disease, genetic defect, or other disease. The cancer can be cancer of the cerebrum, cerebellum, adrenal gland, ovary, pancreas, parathyroid gland, hypophysis, testis, thyroid gland, breast, spleen, tonsil, thymus, lymph node, bone marrow, lung, cardiac muscle, esophagus, stomach, small intestine, colon, liver, salivary gland, kidney, prostate, blood, or other cell or tissue type, and can include multiple cancers. For example, in some cases, each of the plurality of genes is aberrently regulated or differentially expressed in a number of different cancers.

In some aspects, the condition is in the presence of a genetic defect, such as in the absence of a gene or portion thereof, in the presence of a particular genetic mutation, or in the absence of the function of a particular genetic pathway, such as in a genetically engineered cell or organism or in the presence of a naturally occurring mutation or genetic defect.

In other cases, the condition is an environmental condition. In some cases, the environmental condition is exposure to a particular drug, biological agent, chemical agent, or microbial pathogen. Such agents can include biologics, small molecules, antibodies and antibody fragments, fusion protein, recombinant proteins, nucleic acids, cytokines, ligands, and/or stimulatory materials derived or secreted from a particular cell culture or organism, such as from a tissue or fluid (e.g., blood or other bodily fluid) from a subject with a particular disease.

The determination that the plurality of genes is differentially expressed in the particular cell or tissue type or in the presence of the particular condition may be determined using well-known methods, such as the functional genomics applications described herein, including microarray or other analysis.

In one aspect, a TFRE is said to be associated with a given gene if it is within 20 kilobases, within 10 kilobases, within 5 kilobases, or within 4, 3, 2, or 1 kilobases of the gene; often, such TFREs are within the upstream region of the gene. In some aspects, each of the selected TFREs is within the upstream region of more than fifty percent of the plurality of genes. In some embodiments, a TFRE is considered associated with a given gene only if it is present in the sense strand or only if it is present in the antisense strand. In one embodiment, the TFRE is considered associated with a given gene only if it is present in the sense strand. If not otherwise specified, a TFRE is considered associated if present in the sense or antisense strand.

The methods typically further include selecting one or more TFRE from among the plurality of TFREs. In one aspect, each of the selected TFREs is within close proximity, such as within 20 kilobases, within 10 kilobases, within 5 kilobases, or within 4, 3, 2, or 1 kilobases, of more than fifty percent of the plurality of genes. In some aspects, each is within 10 kilobases or 5 kilobases, preferably within the upstream region of, more than 50 percent of the plurality of genes. In some aspects, each of the selected TFREs is within the upstream region of more than fifty percent of the plurality of genes.

The selection of TFREs is typically further based upon the frequency and length of the TFREs, and the relationship thereof.

Frequency of a TFRE relates to the frequency if its occurrence in association with the plurality of genes, as defined herein. In some cases, the frequency may be set forth in terms of the frequency within a given proximity to any of the plurality of genes, i.e., the number of occurrences of a given TFRE within such proximity to any of the plurality of genes, divided by the total number of TFRES within that proximity to any of the plurality of genes. For example, frequency of a given TFRE within 20 kilobases of the plurality of genes would be defined as the number of occurrences of that TFRE within 20 kilobases of any of the genes divided by the number of occurrences of all TFREs within 20 kilobases of any of the plurality of genes.

In some embodiments, the frequency is set forth in terms of association of the TFRE with the gene in the sense or antisense strand; in other embodiments, it is set forth in terms of the frequency of association of the TFRE with the gene in the sense strand. For example, in some embodiments, frequency is the frequency of a given TFRE within a given proximity, e.g., 20 kilobases, of a plurality of genes, in the sense strand; in other embodiments, frequency is the frequency of a given TFRE within a given proximity, e.g., 20 kilobases, of a plurality of genes, in the sense or antisense strand. Unless otherwise specified, frequency refers to the occurrence in either the sense or antisense strand.

Length refers to the length in nucleotides of a given TFRE.

Frequency and length generally are used to select TFREs according to the following equation:

$$\text{frequency}^{(1/length)}.$$

The value of this equation is called the SYN value. TFREs typically are selected based on their SYN values. In some embodiments, each of the selected TFREs has a SYN value (as defined by the above equation) of at least or larger than 0.1, 0.2, typically of at least or larger than 0.3, 0.4, 0.5, 0.6, 0.7, or 0.8, such as or at about 0.3, 0.4, 0.5, 0.6, 0.7, or 0.8, typically at least at or about or above 0.5 or 0.6. In other embodiments, SYN values are used to rank the TFREs, with the TFREs having the highest SYN values selected. In some aspects, each of the selected TFRES is within the TFREs having the top 1, 2, 3, 4, 5, 6, 7, 8, 9, 10, 11, 12, 13, 14, 15, 16, 17, 18, 19, 20, 25, or 50 SYN values of the plurality of TFRES, typically having a SYN value within the top 1, 2, 3, 4, 5, 6, 7, 8, 9, or 10.

In some embodiments, the methods include making or designing promoter-cassettes, such as a transcription-enhancing combined promoter cassette. In such embodiments, the methods can further include constructing a library of randomly combined selected TFREs or randomly combined elements. In one aspect, the library is made by mixing individual double stranded DNA sequence elements encoding at least the selected TFREs together under ligation reaction conditions. Such a library may be made by randomly ligating together double stranded DNA oligonucleotides, each of which may contain a DNA sequence element encoding at least the selected transcription factor regulatory elements, preferably the selected transcription factor regulatory elements, together under ligation conditions.

In some examples, the methods further include inserting combined TFREs or elements of the library into a vector or into multiple vectors, such as a vector with a minimum promoter and typically a reporter gene, thereby producing a combined promoter cassette. In some embodiments, multiple vectors are used, thereby producing a plurality of combined promoter cassettes. In one aspect, the reporter gene is LacZ or GFP. In some examples, the methods further include inserting the vector into a host cell.

In some aspects, elements present in the library and/or combined promoter cassette contain at least or more than 70, 75, 80. 85, 86, 87, 88, 89, 90, 91, 92, 93, 94, 95, 96, 97, 98, 99, or 100% identity to one of the selected TFREs, preferably 100% identity to one of the selected TFREs. In some aspects, the combined promoter cassettes contain at least 70, 75, 80, 85, 86, 87, 88, 89, 90, 91, 92, 93, 94, 95, 96, 97, 98, 99, or 100% identity to one of SEQ ID NOs: 130 to 191 or its complement. In some aspects, they contain at least 70, 75, 80, 85, 86, 87, 88, 89, 90, 91, 92, 93, 94, 95, 96, 97, 98, 99, or 100% identity to one of SEQ ID NOs: 5 to 66 or its complement.

In particular examples, the combined promoter cassettes or promoters contain at least 70, 75, 80, 85, 86, 87, 88, 89, 90, 91, 92, 93, 94, 95, 96, 97, 98, 99, or 100% identity to SEQ ID NO: 50, SEQ ID NO: 113, SEQ ID NO: 175, or SEQ ID NO: 237. In particular examples, the combined promoter cassettes or promoters contain at least 70, 75, 80, 85, 86, 87, 88, 89, 90, 91, 92, 93, 94, 95, 96, 97, 98, 99, or 100% identity to SEQ ID NO: 24, SEQ ID NO: 87, SEQ ID NO: 149, or SEQ ID NO: 211. In particular examples, the combined promoter cassettes or promoters contain at least 70, 75, 80, 85, 86, 87, 88, 89, 90, 91, 92, 93, 94, 95, 96, 97, 98, 99, or 100% identity to SEQ ID NO: 26, SEQ ID NO: 89, SEQ ID NO: 151, or SEQ ID NO: 213. In particular examples, the combined promoter cassettes or promoters contain at least 70, 75, 80, 85, 86, 87, 88, 89, 90, 91, 92, 93, 94, 95, 96, 97, 98, 99, or 100% identity to SEQ ID NO: 59, SEQ ID NO: 122, SEQ ID NO: 184, or SEQ ID NO: 246. In particular examples, the combined promoter cassettes or promoters contain at least 70, 75, 80, 85, 86, 87, 88, 89, 90, 91, 92, 93, 94, 95, 96, 97, 98, 99, or 100% identity to SEQ ID NO: 65, SEQ ID NO: 128, SEQ ID NO: 190, or SEQ ID NO: 252.

The randomly combined sequence elements may be cut with a restriction enzyme and cloned upstream of a reporter gene, which can be without limitation GFP or LacZ, and a library of plasmid DNA or viral vector may be generated. The library can be produced using without limitation retroviral vectors or adenoviral vectors.

In some examples, a plurality of host cells is produced. In such cases, the methods can further include screening for combined promoter cassettes made by the method, e.g., by screening for a host cell as produced in the method that shows enhanced expression of the reporter gene. Typically, such promoter cassettes are selected.

In certain aspects, the methods further include identifying the combined promoter cassette in the host cell produced by the method, or the host cell or cells selected by the screening step as described above. In some aspects, the identification includes determining the sequence or part of the sequence of the combined promoter cassette or the TFRE(s) therein.

In some cases, synthetic promoters and cassettes having a greater number of TFREs per promoter is advantageous, such as by generating a more effective promoter. Thus, in one embodiment, where a plurality of combined promoter cassettes are generated by the method, the method further includes selecting one or more of the combined promoter cassettes so produced. In one aspect, the number of TFREs per promoter in each of the selected combined promoter cassettes is greater than the average number of TFREs per promoter for the plurality of combined promoter cassettes originally generated by the method. In another example, the number of TFREs per promoter is greater than 1, 2, 3, 4, 5, 6, 7, 8, or more per promoter, or is 1, 2, 3, 4, 5, 6, 7, 8, or more per promoter preferably greater than 2, 3, 4, 5, 6, 7, or 8 or more per promoter or 2, 3, 4, 5, 6, 7, 8, or more per promoter. The TFRE can be present in the sense or the antisense strand of the promoter cassettes.

In one embodiment, the vector DNA containing the library of random sequence combinations cloned upstream of a minimum promoter followed by the reporter gene may be transfected or infected into the target cells and sorted with FACS (fluorescence activated cell sorting) for the selection of cells expressing high levels of the reporter gene. Sorted cells are then used to recover and amplify the vector DNA containing the desired high performing transcription regulatory element combination.

The vectors recovered and amplified from the sorted cells may be used for another round of screening for transcription regulatory element combinations with even higher performance and/or activity in a different type of host cell.

Upon the completion of repeated sorting and selection, recovered DNA vectors may further be screened individually in the target cells to test for their true promoter activity.

As a control, if cell-type specific promoters are desired, the selected vectors containing the transcription regulatory element combinations may also be tested in non-target cells for the purpose of eliminating vectors with substantial promoter activities in non-target cells.

Also provided are the combined promoter cassettes as produced by such methods, and vectors, libraries, and cells containing the same and methods for using the same. In some cases, the promoter cassettes include randomly combined TFREs, a minimum promoter, and a reporter gene. In some embodiments, each of the TFREs in the combined promoter cassette is within 20, 10, or 5 kilobases, preferably within the upstream region, of more than fifty percent of a plurality of genes identified as being differentially expressed in a particular cell type or tissue type or under a particular condition and has a SYN value larger than 0.3, 0.2. 0.1, 0.4, or 0.5, where the SYN value is defined as described above. The vector can be a plasmid, viral, transiently expressed, or integrated into the genome of a host cell.

Also provided are isolated promoters for driving and/or regulating expression. In some embodiments, such promoters contain an isolated nucleic acid as given in one of the SEQ ID Nos. 130 to 191 or the complement of one of SEQ ID Nos. 130 to 191. Thus, provided are promoters containing the nucleotide sequence set forth in any of SEQ ID NOs: 130-191 or the antisense sequence (i.e., complement) thereof. In other embodiments, they contain an isolated nucleic acid having at least or more than 70, 75, 80. 85, 86, 87, 88, 89, 90, 91, 92, 93, 94, 95, 96, 97, 98, 99, or 100% sequence identity, such as at least 90% sequence identity with, the sequence of any of SEQ ID Nos. 130 to 191. In other embodiments, they contain isolated nucleic acid capable of specifically hybridising under stringent conditions with a DNA sequence as given in one of SEQ ID Nos. 130 to 191. In other embodiments, such promoters can include such an isolated nucleic acid that is further interrupted by an intervening sequence or a fragment of such a nucleic acid sequence capable of driving and/or regulating expression.

The isolated promoters may comprise further a minimal promoter, like Muc-1 minimal promoter. In some embodiments, such promoters contain an isolated nucleic acid as given in one of the SEQ ID Nos. 5 to 66 or the complement of one of SEQ ID Nos. 5 to 66. Thus, provided are promoters containing the nucleotide sequence set forth in any of SEQ ID NOs: 5-6 or the antisense sequence (i.e., complement) thereof. In other embodiments, they contain an isolated nucleic acid having at least or more than 70, 75, 80. 85, 86, 87, 88, 89, 90, 91, 92, 93, 94, 95, 96, 97, 98, 99, or 100% sequence identity, such as at least 90% sequence identity with, the sequence of any of SEQ ID Nos. 130 to 191. In other embodiments, they contain isolated nucleic acid capable of specifically hybridising under stringent conditions with a DNA sequence as given in one of SEQ ID Nos. 5 to 66. In other embodiments, such promoters can include such an isolated nucleic acid that is further interrupted by an intervening sequence or a fragment of such a nucleic acid sequence capable of driving and/or regulating expression.

Also provided are genetic constructs including such isolated promoters, a heterologous nucleic acid sequence operatively linked to such a promoter. Such constructs can optionally include a 3' transcription terminator.

Also provided are host cells including any one or more of the vectors, isolated promoters, and/or genetic constructs described above.

Also provided are methods for driving and/or regulating expression using the provided promoters, constructs, vectors, and cells. In one aspect, such methods include driving or regulating expression of a nucleic acid in a cell. Such methods can be carried out by operably linking such nucleic acid to any of the isolated promoters described above or made using the described methods, and introducing the resultant genetic construct into a cell.

Also provided are uses of the above-described promoters to drive and/or regulate expression of an operably linked nucleic acid.

DETAILED DESCRIPTION OF THE INVENTION

Definitions

As used herein, "transcription regulatory element," "TRE," transcription factor regulatory element," and "TFRE" refer to a nucleotide sequence that is recognized by a transcription regulator, and is synonymous with "cis-acting sequence" or "cis-acting sequence element" or "cis-acting region", and sometimes expressed as "sequence element".

As used herein, "combined transcription regulatory element" refers to a double stranded DNA molecule that includes more than one transcription regulatory element. The combined transcription regulatory element may be created by ligating various double stranded transcription regulatory elements in a random fashion. Optionally, the combined sequence element may contain a spacer region and the length of the spacer nucleotides may be controlled by subjecting the double stranded DNA molecules to time-course exonuclease digestion before using them in random ligation reactions.

As used herein, "oligonucleotide" refers to a sequence that functionally includes a cis-acting region and perhaps up to about 25 or less extraneous nucleotides. Therefore, the number of nucleotides that are encompassed by the term "oligonucleotide" cannot be fixed, and therefore is not limited to any particular number of nucleotides.

As used herein, "promoter cassette" or "synthetic promoter cassette" refers to DNA segment that contains components for an efficient transcription of a gene, and may include one or more transcription regulatory element, a minimum promoter region, sequences from 5'-untranslated region or introns.

As used herein, "minimum promoter region" or "minimum promoter" refers to a short DNA segment which is inactive by itself, but can mediate strong transcription when combined with other transcription regulatory elements. Minimum promoter sequence can be derived from various different sources, including prokaryotic and eukaryotic genes. Examples of this are dopamine beta-hydroxylase gene minimum promoter and cytomegalovirus (CMV) immediate early gene minimum promoter.

As used herein, "combined promoter cassette" or "synthetic combined promoter cassette" refers to promoter cassettes containing combined transcription regulatory elements.

As used herein, a "transcription regulator" refers to any factor including proteins that bind to the cis-acting region and regulate either positively or negatively the expression of the gene. Transcription factors or repressors or co-activators or co-repressors are all included.

The advances in functional genomics made in recent years have resulted in the identification of many more cis-regulatory elements that can be directly related to the increased transcription of specific genes. Indeed, the ability to use bioinformatics to unravel complex transcriptional pathways active in diseased cells can actually serve to facilitate the process of choosing suitable cis-elements that can be used to design synthetic promoters in complex pathologies such as cancer.

In cancer the changes in the gene expression profile are often the result of alterations in the cell's transcription machinery induced by aberrant activation of signalling pathways that control growth, proliferation and migration. Such changes result in the activation of transcription regulatory networks that are not found in normal cells and provide us with an opportunity to design synthetic promoters that should only be active in cancerous cells.

If microarray technology is to truly result in the design of tailored therapies to individual cancers or even patients, as has been heralded, it is important that the functional genomics methodology that was designed for the identification of signalling and transcription networks be applied to the design of cancer-specific promoters so that effective gene therapeutic strategies can be formulated.

The development of bioinformatics algorithms for the analysis of microarray datasets has largely been applied in order to unravel the transcription networks operative under different disease and environmental conditions. To this date there has been no effort to use this type of approach to design synthetic promoters that are operative only under these certain disease or environmental conditions.

Described herein are methods whereby data obtained from functional genomics experiments, such as microarray analysis, are analysed using widely available bioinformatics software tools, which function to find over-represented cis promoter elements, in order to design synthetic promoters that are only active in cancer cells. This represents a major leap forward in the design of cancer-specific promoters that can subsequently be used in the study of cancer, or in the design of safe and effective genetic therapy of human malignancies.

Rational Promoter Selection and Design

In one aspect, the provided methods and compositions are based on the application of functional genomics in the development of synthetic promoters, for example, for the control of gene expression in specific environmental conditions, for example, in a disease- or tissue-specific manner, or in response to the introduction of an external agent, either chemical or biological. Synthetic promoters have been constructed for use in a number of systems, both prokaryotic and eukaryotic.

Available methods for designing synthetic promoters for eukaryotic systems involve the arbitrary selection of well-characterised cis-regulatory elements, spanning 50 to 100 nucleotides. Such elements then are included in synthetic promoter libraries created by random ligation and selected for in the cell type of interest (Li, X., Eastman, E. M., Schwartz, R. J., & Draghia-Akli, R. Synthetic muscle promoters: activities exceeding naturally occurring regulatory sequences. *Nat. Biotechnol.* 17, 241-245 (1999); Dai, C., McAninch, R. E., & Sutton, R. E. Identification of synthetic endothelial cell-specific promoters by use of a high-throughput screen. *J. Virol.* 78, 6209-6221 (2004)).

In one aspect, the provided methods and compositions apply functional genomics and advanced bioinformatics approaches to the sequence of the human genome to design synthetic promoters in a rational manner. Generally, in the provided methods, transcription factor regulatory elements (TFREs), such as cis-regulatory elements, are selected for inclusion in synthetic promoter libraries in a non-arbitrary fashion. In some aspects, the methods use information from global gene expression analyses to identify TFREs (e.g., cis-regulatory elements) associated with specific gene expression profiles, allowing for the weighting and ranking of regulatory elements and the development of improved methods of selection.

Thus, methods provided herein are advantageous compared to methods that arbitrarily select cis-elements for use in synthetic promoters. In some aspects, the provided methods are capable of selecting shorter cis-regulatory elements compared to those selected by available methods. In some aspects, the provided methods identify cis-elements that were previously not known to be involved in the transcriptional network for which cis-elements are being selected, or would not be selected using a random selection approach. In some aspects, the provided methods generate synthetic promoters that are shorter, more complex, and/or contain more cis-regulatory elements, compared to available methods.

The regulation of gene expression in eukaryotes is highly complex and often occurs through the coordinated action of multiple transcription factors. The use of trans-factor combinations in the control of gene expression allows a cell to employ a relatively small number of transcription factors in the regulation of disparate biological processes.

As discussed herein, a number of tools are available for use with the provided methods to utilise microarray data to identify TFREs, such as cis-regulatory elements. It is also possible to use this information to decipher the transcriptional networks that are active in cells under different environmental conditions. In yeast, the importance of the combinatorial nature of transcriptional regulation was established by specifically examining clusters of upregulated genes for the presence of combinations of cis-elements. By examining microarray data from yeast exposed to a variety of conditions, it is possible to construct a network of transcription revealing the functional associations between different regulatory elements. This approach resulted in the identification of key motifs with many interactions, suggesting that some factors serve as facilitator proteins assisting their gene-specific partners in their function.

Thus, a core number of transcription factors mediate such a vast array of biological responses by adopting multiple configurations. In one aspect, the provided methods use this observation to hijack the transcriptional programs that have gone awry in multifactorial diseases, such as cancer, to develop disease-specific or condition-specific regulatory elements. In cancer, for example, methods of interpreting cancer microarray data are continually evolving so that a more global picture of transcriptional regulation in transformed cells can now be painted.

Meta-analyses of cancer datasets has permitted the identification of gene modules, allowing for the reduction of complex cancer signatures to small numbers of activated transcription programs and even to the identification of common programs that are active in most types of cancer. This type of analysis can also help to identify specific transcription factors whose deregulation plays a key role in tumour development. For instance, in one study, the importance of aberrant E2F activity in cancer was reaffirmed during a search for the regulatory programs linking transcription factors to the target genes found upregulated in specific cancer types (Rhodes, D. R. et al. Mining for regulatory programs in the cancer transcriptome. *Nat. Genet.* 37, 579-583 (2005)). It was shown that E2F target genes were disproportionately upregulated in more than half of the gene expression profiles examined, which were obtained from a multitude of different cancer types. It was thus proposed that integrative bioinformatics analyses have the potential to generate new hypotheses about cancer progression.

In some aspects, the present invention is based on the discovery that the elucidation of disease-specific transcriptional programs allows construction of synthetic conditional promoter elements that can be used in gene therapy to drive restricted gene expression in pathologic sites of interest. Provided are methods that use integrative computational approaches to identify transcriptional programs active in specific diseases, in certain eukaryotic cell types, and/or under particular environmental conditions, for example, cancer indications.

Such methods are useful for the design synthetic promoter elements to drive gene expression in the particular diseases, cell types, tissue types, and/or one or more environmental conditions, for example, for use in therapeutic approaches.

In one example, provided are methods for rational design of synthetic promoter elements that drive highly cytotoxic genes, and anti-cancer therapeutic approaches employing the same. In one aspect, microarray data obtained by experimentation, or taken from publicly available resources such as Oncomine, may be used in order to identify the regulatory sequences over-represented in clusters of genes found to be upregulated in cancer stem cells.

Bioinformatics Tools

Different bioinformatics tools, examples of which are given in table 1, may be used to screen for TFREs, e.g., cis-regulatory elements. In general, such tools function by comparing gene expression profiles between differentially regulated genes and examining upstream sequences, available through genome sequence resources. For the phylogenetic footprinting tools, the untranslated regions of specific genes are compared between species and the most highly conserved sequences are returned and proposed to be potential cis-elements. A combination of all available approaches may be employed in order to identify regulatory sequences that predominate in the profile of specific cell or tissue types, for example in cancer stem cells. The most common sequences identified are then used as the building blocks employed in the design of synthetic promoters.

Typically the data used for the identification of genes aberrantly regulated in cancer cells is derived from microarray data. These methods can provide detailed information on the regulation of specific genes. It may further be necessary to screen the genes identified for false positives, e.g. the overexpression may be a result of altered transcription factor activation instead of chromosomal amplification.

Cells or Tissues of Interest

The invention relates in certain aspects to assays carried out on a cell or tissue type of interest. In particular, the provided methods and compositions relate to TFREs associated with gene expression in the context of one or more diseases, conditions, environmental conditions, cell type, e.g., eukaryotic cell type, tissue types, and/or following exposure to a particular agent, such as a biological agent, e.g., ligand, chemical agent, or microbial pathogen.

The cell types can include any type of cell, or plurality of cells such as a tissue. Cells and tissues for use with the provided methods include prokaryotic cells and tissues, typically eukaryotic cell, cells and tissues. A suitable eukaryotic cell may be derived from an organism, such as an animal, such as a mammal and preferably a human, or another eukaryotic organism, such as a plant. Such a cell or tissue may have been taken directly from such an organism or may be derived therefrom. For example, the cell or tissue may be from a primary, secondary or immortalised cell line or culture that is derived from such an organism.

The cell or tissue may be a naturally occurring cell or tissue or may have been artificially manipulated. For example, a cell or tissue may be manipulated by exposure to altered environmental or disease-specific conditions. For example, a cell or tissue may be manipulated by exposing it to an agent, such as a biological ligand, chemical agent or microbial pathogen.

The biological ligand may be any biological molecule that is capable of having an effect on the cell, particularly an effect on gene transcription. A biological ligand may be a molecule that is capable of binding to the cell or acting within the cell. A biological ligand may, for example, be a polypeptide, protein, nucleic acid or carbohydrate molecule. Suitable biological ligands include hormones, growth factors and neurotransmitters.

The chemical agent may be any agent capable of acting on the cell, preferably leading to a change in gene transcription within the cell. The chemical agent may, for example, be a chemotherapeutic drug or a therapeutic small molecular drug.

The microbial pathogen may be any virus, bacteria, fungus or other infectious agent capable of causing disease in mammals.

The cell or tissue may from an abnormal or disease source. For example, the cell or tissue may be taken from, or derive from, an organism suffering from a disease. Preferably the cell or tissue is from a tissue or organ that is affected by the disease. For example, where the disease is cancer, the cell or tissue may be taken from a tumour. The cell may be from, or derived from, a tumour cell line in vitro.

Among the cell and tissue types are eukaryotic cells, including animals, plants, fungi, and other eukaryotic cells. For example, the cell or tissue type can be from a mammal, yeast, insect, bovine, porcine, murine, equine, canine, feline, avian, piscine, ovine, insect, simian, and/or human.

In some aspects, the cell or tissue type is a tissue or cell from the cerebrum, cerebellum, adrenal gland, ovary, pancreas, parathyroid gland, hypophysis, testis, thyroid gland, breast, spleen, tonsil, thymus, lymph node, bone marrow, lung, cardiac muscle, esophagus, stomach, small intestine, colon, liver, salivary gland, kidney, prostate, blood, or other cell or tissue type.

In some aspects, the condition is a disease condition, such as a cancer, inflammatory disease, infectious disease, genetic defect, or other disease. The cancer can be cancer of the cerebrum, cerebellum, adrenal gland, ovary, pancreas, parathyroid gland, hypophysis, testis, thyroid gland, breast, spleen, tonsil, thymus, lymph node, bone marrow, lung, cardiac muscle, esophagus, stomach, small intestine, colon, liver, salivary gland, kidney, prostate, blood, or other cell or tissue type, and can include multiple cancers. For example, in some cases, each of the plurality of genes is aberrently regulated or differentially expressed in a number of different cancers.

In some aspects, the condition is in the presence of a genetic defect, such as in the absence of a gene or portion thereof, in the presence of a particular genetic mutation, or in the absence of the function of a particular genetic pathway, such as in a genetically engineered cell or organism or in the presence of a naturally occurring mutation or genetic defect.

In other cases, the condition is an environmental condition. In some aspects, the environmental condition is exposure to a particular drug, biological agent, chemical agent, or microbial pathogen. Such agents can include biologics, small molecules, antibodies and antibody fragments, fusion protein, recombinant proteins, nucleic acids, cytokines, ligands, and/or stimulatory materials derived or secreted from a particular cell culture or organism, such as from a tissue or fluid (e.g., blood or other bodily fluid) from a subject with a particular disease.

Transcription Factor Regulatory Elements

Among the provided methods are those that involve the identification of transcription factor regulatory elements (TFREs) that are active in a cell, cells, tissue, and/or disease or condition (e.g., environmental condition or disease condition, exposure to a particular agent, such as a biological agent, e.g., ligand, chemical agent, or microbial pathogen) of interest. Also provided are the TFREs, and promoters and libraries containing the same.

A suitable transcription factor regulatory element (TFRE) for use or selection in the provided methods, compositions, promoters, and libraries is a nucleic acid molecule that is recognised by a transcription factor. For example, a TFRE may comprise a sequence to which a transcription factor can bind. A TFRE may comprise a cis-acting region. By transcription factor is meant any factor, such as a protein, that can bind to such a cis-acting region and regulate either positively or negatively the expression of a gene. For example, a transcription factor may bind upstream of the coding sequence of a gene to either enhance or repress transcription of the gene by assisting or blocking RNA polymerase binding. Many transcription factors are well known in the art and include STAT, E2F, Oct-4, Nanog, Brachury, Pax genes, Sox2 and MCEF.

A TFRE comprises a nucleic acid sequence preferably, a double stranded DNA sequence. The TFRE may comprise a cis-acting region and may also comprise additional nucleic acids. The core six to eight nucleotides of promoter and enhancer elements may be sufficient for the binding of their corresponding transactivating factors. Indeed, in some cases this short oligonucleotide element is sufficient to drive gene expression alone. Thus, a transcription factor binding site may consist of 6 to 8 nucleic acids. A TFRE comprising that site will be at least 6 to 8 nucleic acids in length. In some embodiments, a TFRE of the invention is preferably 6 or more, 8 or more, 10 or more, 15 or more, 20 or more, 25 or more, or 30 or more nucleic acids in length. In some aspects, the provided embodiments provide synthetic promoters that are shorter compared to available synthetic promoters. In some embodiments, the TFRE is 100 or less, 75 or less, 50 or less, less than 50, 30 or less, 25 or less, 20 or less or 15 or less nucleic acids in length, preferably any combination of the given upper and lower values, preferably 6 to 100 or 6 to 25 nucleic acids.

Identification of TFREs

A suitable TFRE is one that is active in the cell or tissue of interest or under the condition of interest. Such a TFRE may be identified as being associated with a gene that is expressed in the cell or tissue of interest.

For example, a TFRE may be associated with a gene that is differentially expressed in that cell, tissue, or condition, when compared with another cell, tissue or condition. For example, differential expression of a gene may be seen by comparing the expression of the gene in two different cells, tissues, or conditions, and/or in the same cells or tissues under different conditions. Expression in one cell or tissue type may be compared with that in a different, but related, tissue type. For example, where the cell or tissue of interest is a disease cell or tissue or has been artificially manipulated as described herein, the expression of genes in that cell or tissue may be compared with the expression of the same genes in an equivalent normal or untreated cell or tissue. This may allow the identification of genes that are differentially regulated between the two cell or tissue types or under different conditions.

A TFRE that is associated with such a gene is generally located close to the coding sequence of the gene within the genome of the cell. For example, such a TFRE may be located in the region immediately upstream or downstream of that coding sequence. Such a TFRE may be located close to a promoter or other regulatory sequence that regulates expression of the gene. The location of a TFRE may be determined by the skilled person using his knowledge of this field and the methods described herein.

Suitable TFREs may thus be identified by analysis of the cell or tissue of interest and/or under the particular condition of interest. Genes that are differentially expressed in the cell or tissue of interest may be identified by routine methods. For example, routine methods may be used to compare the expression profile of genes in the cell or tissue of interest with that in other cell or tissue types which may act as a control. Genes that are up-regulated or down-regulated in the cell or tissue of interest may thus be identified. Such an analysis may make use of, for example, microarray analysis or serial analysis of gene expression (SAGE).

Such an analysis may be carried out using a sample of expressed molecules from the cell or tissue of interest or using all the expressed molecules from the cell or tissue of interest. For example, in one embodiment, such an analysis may be carried out using the total RNA content of the cell or tissue of interest. Thus, in some embodiments, the methods of the invention may be used to analyse expression from the entire genome of the cell or tissue of interest.

Such an analysis may be used to assess the expression of a wide variety of genes, or a subgroup of genes. Thus, in accordance with embodiments of the present invention, a selection of genes may be used that is known to be regulated by a wide variety of different transcription factors or each gene by only one or two transcription factors.

The ability to use gene expression data to identify gene modules, which mediate specific responses to environmental stimuli (or to a diseased state) and to correlate their regulation to the cis-regulatory elements present upstream of the genes in each module, has transformed the way in which microarray data are interpreted. For instance, by using the modular approach it is possible to examine whether particular gene modules are active in a variety of different cancers, or whether individual cancers require the function of unique gene modules. This allows screening for transcriptional commonalties between different cancers, which should aid in the design of widely applicable anti-cancer therapeutic strategies. In Gene expression data from 1975 microarrays, spanning 22 different cancers, was used to identify gene modules that were activated or deactivated in specific types of cancer (Segal, E., Friedman, N., Koller, D., & Regev, A. A module map showing conditional activity of expression modules in cancer. *Nat. Genet.* 36, 1090-1098 (2004)). A bone osteoblastic module was active in a number of cancers whose primary metastatic site was known to be the bone. Id. Thus, a common mechanism of bone metastasis between varieties of different cancers was identified, which could be targeted in the development of anticancer therapies.

It is also possible to identify the higher-level regulator that controls the expression of the genes in each module (Segal, E. et al. Module networks: identifying regulatory modules and their condition-specific regulators from gene expression data. *Nat. Genet.* 34, 166-176 (2003)). Examination of the upstream regulatory sequences of each gene in a module may reveal the presence of common cis-regulatory elements that are known to be the target of the module's regulator. Therefore, by identifying specific regulatory proteins that control the activation of gene modules in different cancers, it should be possible to extrapolate the important cis-elements that mediate transcription in the transformed cell. Thereby, allowing, for example, the design and construction of tumour-specific promoters based on the most active cis-regulatory elements in a number of tumour-specific gene modules.

Thus, once the differential expression of genes in a cell or tissue of interest or under certain conditions has been established, the sequences proximate to the differentially-expressed genes, such as those upstream of the differentially expressed genes, may be screened for TFREs, such as cis-regulatory elements. Those cis-regulatory elements which control expression of differentially expressed genes are considered to be active in the cell or tissue of interest. Thus, for those cis-elements to be active, the transcription factor(s) which control their activity must be present in that cell type. This therefore allows the identification of TFREs that are active in the cell or tissue of interest.

TFREs, e.g., cis-elements, may be identified using known methods, for example by screening using known bioinformatics techniques.

The ability to identify specific transcriptional elements in the human genome that control the expression of functionally related genes is transforming the application of functional genomics. Until recently the interpretation of data from microarray analysis has been limited to the identification of genes whose function may be important in a single pathway or response. How this related to global changes in the cellular phenotype had been largely ignored, as the necessary tools to examine this simply did not exist. With the advancement of bioinformatics we are now in a position to utilize all the data that is obtained from large-scale gene expression analysis and combine it with knowledge of the completed sequence of the human genome and with transcription factor, gene ontology and molecular function databases, thereby more fully utilizing the large datasets that are generated by global gene expression studies.

For nearly two decades scientists have been compiling databases that catalogue the trans-factors and cis-elements that are responsible for gene regulation (Wingender, E. Compilation of transcription regulating proteins. *Nucleic Acids Res* 16, 1879-1902 (1988)). This has resulted in the emergence of useful tools, such as TRANSCompel (Kel-Margoulis, O. V., Kel, A. E., Reuter, I., Deineko, I. V., & Wingender, E. TRANSCompel: a database on composite regulatory elements in eukaryotic genes. *Nucleic Acids Res* 30, 332-334 (2002)), ABS (Blanco, E., Farre, D., Alba, M. M., Messeguer, X., & Guigo, R. ABS: a database of Annotated regulatory Binding Sites from orthologous promoters. *Nucleic Acids Res* 34, D63-D67 (2006)), JASPAR (Sandelin, A., Alkema, W., Engstrom, P., Wasserman, W. W., & Lenhard, B. JASPAR: an open-access database for eukaryotic transcription factor binding profiles. *Nucleic Acids Res* 32, D91-D94 (2004)), HTPSELEX (Jagannathan, V., Roulet, E., Delorenzi, M., & Bucher, P. HTPSELEX—a database of high-throughput SELEX libraries for transcription factor binding sites. *Nucleic Acids Res* 34, D90-D94 (2006)) and TRANSFAC (Matys, V. et al. TRANSFAC: transcriptional regulation, from patterns to profiles. *Nucleic Acids Res* 31, 374-378 (2003)) that index transcription factors and their target sequences based on experimental data, and TRED (Zhao, F., Xuan, Z., Liu, L., & Zhang, M. Q. TRED: a Transcriptional Regulatory Element Database and a platform for in silico gene regulation studies. *Nucleic Acids Res* 33, D103-D107 (2005)), which indexes based on both experimental and automated data.

Databases of known transcription factor binding sites can be used to detect the presence of protein-recognition elements in a given promoter, but only when the binding site of the relevant DNA-binding protein and its tolerance to mismatches in vivo is already known. Because this knowledge is currently limited to a small subset of transcription factors, it can be advantageous to discover regulatory motifs by comparative analysis of the DNA sequences of promoters. By finding conserved regions between multiple promoters, motifs can be identified with no prior knowledge of transcription factor binding sites.

A number of models have emerged that achieve this by statistical overrepresentation. These algorithms function by aligning multiple untranslated regions from the entire genome and identifying sequences that are statistically significantly over-represented in comparison to what it expected by random, e.g. YMF (Sinha, S. & Tompa, M. YMF: A program for discovery of novel transcription factor binding sites by statistical overrepresentation. *Nucleic Acids Res* 31, 3586-3588 (2003); Sinha, S. & Tompa, M. Discovery of novel transcription factor binding sites by statistical overrepresentation. *Nucleic Acids Res* 30, 5549-5560 (2002)) and SCORE (Rebeiz, M., Reeves, N. L., & Posakony, J. W. SCORE: a computational approach to the identification of cis-regulatory modules and target genes in whole-genome sequence data. Site clustering over random expectation. *Proc. Natl. Acad. Sci. U.S.A* 99, 9888-9893 (2002)). At present these tools are mainly applied in the study of lower eukaryotes where the genome is less complex and regulatory elements are easier to identify, extending these algorithms to the human genome has proven somewhat more difficult.

In order to redress this issue a number of groups have shown that it is possible to mine the genome of higher eukaryotes by searching for conserved regulatory elements adjacent to transcription start site motifs such as TATA and CAAT boxes, e.g. as catalogued in the DBTSS resource (Suzuki, Y., Yamashita, R., Sugano, S., & Nakai, K. DBTSS, DataBase of Transcriptional Start Sites: progress report 2004. *Nucleic Acids Res* 32, D78-D81 (2004); Suzuki, Y., Yamashita, R., Nakai, K., & Sugano, S. DBTSS: DataBase of human Transcriptional Start Sites and full-length cDNAs. *Nucleic Acids Res* 30, 328-331 (2002)), or one can search for putative cis-elements in CpG rich regions that are present in higher proportions in promoter sequences (Davuluri, R. V., Grosse, I., & Zhang, M. Q. Computational identification of promoters and first exons in the human genome. *Nat. Genet.* 29, 412-417 (2001)).

Alternatively, with the co-emergence of microarray technology and the complete sequence of the human genome, it is now possible to search for potential transcription factor binding sites by comparing the upstream non-coding regions of multiple genes that show similar expression profiles under certain conditions. Gene sets for comparative analysis can be chosen based on clustering, e.g. hierarchical and k-means (Roth, F. P., Hughes, J. D., Estep, P. W., & Church, G. M. Finding DNA regulatory motifs within unaligned noncoding sequences clustered by whole-genome mRNA quantitation. *Nat. Biotechnol.* 16, 939-945 (1998)), from simple expression ratio (Bussemaker, H. J., Li, H., & Siggia, E. D. Regulatory element detection using correlation with expression. *Nat. Genet.* 27, 167-171 (2001)) or functional analysis of gene products (Jensen, L. J. & Knudsen, S. Automatic discovery of regulatory patterns in promoter regions based on whole cell expression data and functional annotation. *Bioinformatics.* 16, 326-333 (2000)). This provides scientists with the opportunity to identify promoter elements that are responsive to certain environmental conditions, or those that play a key role in mediating the differentiation of certain tissues or those that may be particularly active in mediating pathologic phenotypes.

Phylogenetic footprinting, or comparative genomics, is now being applied to identify novel promoter elements by comparing the evolutionary conserved untranslated elements proximal to known genes from a variety of organisms. The availability of genome sequences between species has notably advanced comparative genomics and the understanding of evolutionary biology in general. The neutral theory of molecular evolution provides a framework for the identification of DNA sequences in genomes of different species.

Its central hypothesis is that the vast majority of mutations in the genome are neutral with respect to the fitness of an organism. Whilst deleterious mutations are rapidly removed by selection, neutral mutations persist and follow a stochastic process of genetic drift through a population. Therefore, non-neutral DNA sequences (functional DNA sequences) must be conserved during evolution, whereas neutral mutations accumulate. Initial studies sufficiently demonstrated that the human genome could be adequately compared to the genomes of other organisms allowing for the efficient identification of homologous regions in functional DNA sequences.

Subsequently, a number of bioinformatics tools have emerged that operate by comparing non-coding regulatory sequences between the genomes of various organisms to enable the identification of conserved transcription factor binding sites that are significantly enriched in promoters of candidate genes or from clusters identified by microarray analysis.

Examples of these software suites include TRAFAC (Jegga, A. G. et al. Detection and visualization of compositionally similar cis-regulatory element clusters in orthologous and coordinately controlled genes. *Genome Res* 12, 1408-1417 (2002)), CORG (Dieterich, C., Wang, H., Rateitschak, K., Luz, H., & Vingron, M. CORG: a database for Comparative Regulatory Genomics. *Nucleic Acids Res* 31, 55-57 (2003)), CONSITE (Lenhard, B. et al. Identification of conserved regulatory elements by comparative genome analysis. *J. Biol.* 2, 13 (2003)), CONFAC (Karanam, S. & Moreno, C. S. CONFAC: automated application of comparative genomic promoter analysis to DNA microarray datasets. *Nucleic Acids Res* 32, W475-W484 (2004)), VAMP (La Rosa, P. et al. VAMP: visualization and analysis of array-CGH, transcriptome and other molecular profiles. *Bioinformatics.* 22, 2066-2073 (2006)) and CisMols Analyser (Jegga, A. G. et al. CisMols Analyzer: identification of compositionally similar cis-element clusters in ortholog conserved regions of coordinately expressed genes. *Nucleic Acids Res* 33, W408-W411 (2005)). Typically these tools work by aligning the upstream sequences of target genes between species thus identifying conserved regions that could potentially function as cis-regulatory elements and have consequently been applied in the elucidation of transcription regulatory networks in a variety of models.

A significant amount of effort has been dedicated to the cataloguing of transcription factors and their corresponding cis-elements. More recently, these databases have been compiled with the aim to utilise them to unravel regulatory networks active in response to diverse stimuli. Some examples of these resources include PreMod (Blanchette, M.

et al. Genome-wide computational prediction of transcriptional regulatory modules reveals new insights into human gene expression. *Genome Res* 16, 656-668 (2006); Ferretti, V. et al. PReMod: a database of genome-wide mammalian cis-regulatory module predictions. *Nucleic Acids Res* 35, D122-D126 (2007)), CisView (Sharov, A. A., Dudekula, D. B., & Ko, M. S. CisView: a browser and database of cis-regulatory modules predicted in the mouse genome. *DNA Res* 13, 123-134 (2006)), BEARR (Vega, V. B., Bangarusamy, D. K., Miller, L. D., Liu, E. T., & Lin, C. Y. BEARR: Batch Extraction and Analysis of cis-Regulatory Regions. *Nucleic Acids Res* 32, W257-W260 (2004)), VISTA (Diihchak, I. & Ryaboy, D. V. VISTA family of computational tools for comparative analysis of DNA sequences and whole genomes. *Methods Mol. Biol.* 338, 69-89 (2006)), PromAn (Lardenois, A. et al. PromAn: an integrated knowledge-based web server dedicated to promoter analysis. *Nucleic Acids Res* 34, W578-W583 (2006)), CRSD (Liu, C. C. et al. CRSD: a comprehensive web server for composite regulatory signature discovery. *Nucleic Acids Res* 34, W571-W577 (2006)) and MPromDb (Sun, H. et al. MPromDb: an integrated resource for annotation and visualization of mammalian gene promoters and ChIP-chip experimental data. *Nucleic Acids Res* 34, D98-103 (2006)).

Table 1 lists some of the currently available databases that can be used when searching for potential regulatory sequences. This table provides an example of the type of resource utilised when identifying potential cis-acting sequences.

Thus, any of the databases listed in Table 1, or any equivalent publicly available resource, may be used to identify TFREs, such as cis-regulatory elements, that are associated with genes that are expressed in the cell or tissue of interest, preferably genes that are differentially expressed in the cell or tissue of interest. Preferably at least one database selected from Pubmed, DBTSS, TRAFAC, TRANSCompel, TRANSFAC, Phylofoot, CORG, CONSITE, CONFAC, CisMols, TRED, ABS, JASPAR, HTPSELEX, PAINT, PreMOD, CisView, BEARR, VISTA, PromAn, CRSD, MPromDb, VAMP and Oncomine is used.

In the provided methods, the transcription regulatory elements are identified within the sequences in proximity of the plurality of genes, for example, genes whose expression is associated with the cell type, tissue type, or condition of interest. Typically the sequences are within a region of 20 kbases up- or downstream of each gene selected, preferably 10 kbases, more preferably 5 kbases, most preferred upstream within each of these regions.

In some embodiments of the provided methods, to facilitate the rational selection of transcription regulatory elements and their ranking in order of importance, the frequency of occurrence of each sequence is calculated.

As used herein, frequency is defined as the number of occurrences of a given transcription factor regulatory element (TFRE) being associated with any of the plurality of genes (i.e., the number of times a TFRE is associated with any of the plurality of genes), divided by the total number of transcription factor regulatory elements associated with any of the plurality of genes. In some embodiments, the TFRE is considered associated with a given gene for purposes of calculating frequency whether it is present in the sense or antisense strand, i.e., whether it is in the forward or reverse direction. In another embodiment the TFRE is considered associated with a given gene only if it is present in the sense strand or only if it is present in the antisense strand. In one embodiment, the TFRE is considered associated with a given gene for purposes of calculating frequency only if it is present in the sense strand. Unless otherwise specified, the TFRE is considered associated if present in either strand. In some embodiments, the frequency is defined in terms of the desired proximity to the plurality of genes. In such cases, the frequency is the number of occurrences of a given TFRE within the desired proximity, e.g., 20, 10, or 5 kilobases of any of the plurality of genes, divided by the total number of all the TFREs within such proximity to the plurality of genes. For example, if a transcription regulatory element occurs 150 times within the desired regions (e.g., within 20, 10, or 5 kb up or downstream of any of the plurality of genes) and a total number of 5000 sites of transcription regulatory elements were identified within that proximity for the plurality of genes, the frequency of this transcription regulatory element would be 150/5000. Again, in some embodiments, the occurrence is on the sense or antisense strand, i. e. in the forward or reverse direction; in other embodiments, the occurrence is only on the sense strand or only on the antisense strand.

Given that conservation of longer sequences is a good indication of their importance in mediating expression, weight is added to longer cis-regulatory elements using the relation frequency$^{(1/length)}$, with frequency being defined as described above and length being the length in nucleotides of the transcription regulatory element The calculated value (which is the nth root of the frequency, wherein n is the length) is also called SYN-value herein.

The SYN-value generally is used as a selection criterion, together with a threshold value, to allow the rational selection of TFREs, e.g., input cis-regulatory elements. The threshold SYN value can be any number between 0.1 and 0.9. Preferably the SYN-value has to be larger than the threshold; thus, in certain embodiments, TFREs are selected which have SYN values greater than or at least 0.1, 0.2, 0.3, 0.4, 0.5, 0.6, 0.7, 0.8, or 0.9 or about 0.1, 0.2, 0.3, 0.4, 0.5, 0.6, 0.7, 0.8, or 0.9. It is also possible to select a predefined number of TFREs, e.g., cis-acting sequences, e.g. 1 to 10 genes, which have the largest SYN-values. Thus, in some embodiments, among a plurality of TFREs identified as proximate to the plurality of genes, those selected are those having the top 1, 2, 3, 4, 5, 6, 7, 8, 9, or 10 highest SYN values, as defined by the formula above.

In a preferred embodiment a threshold value is larger than 0.3, preferably larger of 0.4, more preferred larger of 0.5. In another preferred embodiment the threshold value has the value of 0.5.

Construction of Synthetic Promoters

In recent years some efforts have been made to construct synthetic promoters for tissue specific transcription based on the linking of short oligonucleotide promoter and enhancer elements in a random fashion.

In one approach, which aimed to identify synthetic promoters for muscle-specific expression, duplex oligonucleotides from the binding sites of muscle-specific and non-specific transcription factors were randomly ligated and cloned upstream of a minimal muscle promoter driving luciferase (Li, X., Eastman, E. M., Schwartz, R. J., & Draghia-Akli, R. Synthetic muscle promoters: activities exceeding naturally occurring regulatory sequences. *Nat. Biotechnol.* 17, 241-245 (1999)). Approximately 1000 plasmid clones were individually tested by transient transfection into muscle cells and luciferase activity was determined in 96-well format by luminometry. By this approach several highly active and muscle specific promoters were identified that displayed comparable strength to the most commonly used viral promoters such as CMV.

In an effort to examine one million clones, Sutton and coworkers adopted a different screening approach based on the establishment of a lentiviral vector-based library (Dai, C., McAninch, R. E., & Sutton, R. E. Identification of synthetic endothelial cell-specific promoters by use of a high-throughput screen. *J. Virol.* 78, 6209-6221 (2004)). In this study duplex oligonucleotides from binding sites of endothelial cell-specific and non-specific transcription factors were cloned in a random manner upstream of a minimal promoter driving expression of eGFP in a HIV self-inactivating expression vector. A pool of one million clones was then transfected into endothelial cells and the highest expressers were selected by FACS sorting. Synthetic promoters were then rescued from stable transfectants by PCR from the genomic DNA where the HIV vectors had integrated.

The results from this study also demonstrated the possibility of isolating several highly active endothelial cell-specific synthetic promoter elements from a random screen.

When adopting this type of methodology in the design of synthetic tissue-specific promoters it is important to use well-designed duplex oligonucleotides. For example, each element has to be spaced in such a way that the regulatory elements appear on the same side of the DNA helix when reassembled, relevant minimal promoter elements have to be employed so that the screen produces promoters capable of expressing efficiently only in the tissue of interest and there must be some sort of mechanism, such as the addition of Sp1 sites, for the protection against promoter silencing through methylation.

The random nature of this approach actually increases the chance of finding active tissue-specific promoters, given that in some studies, where synthetic promoters were designed rationally by the linking of whole promoter regions rather than individual promoter elements, actually result in the identification of less efficient tissue-specific promoters. Therefore, the ability to carefully select relevant promoter/enhancer elements that will yield efficient tissue-specific promoters by these methods is paramount to the success of this approach.

Thus, in embodiments of the present invention, two or more selected TFREs as described above may be combined together as part of a synthetic promoter. A promoter element includes a DNA sequence that includes components that allow for the transcription of a gene.

A promoter element may include one or more transcription regulatory elements, a minimum promoter region and sequences from the 5' untranslated region of the gene or introns. In one embodiment, a promoter element may also comprise one or more cis-elements that allow the binding of one or more ubiquitously expressed transcription factors. A promoter element may comprise one or more regulatory elements that allow for transient gene expression. A promoter element may comprise one or more regulatory elements that allow for inducible gene expression.

As used herein, a minimal promoter refers to a DNA sequence which is inactive alone, but can mediate gene transcription when combined with other transcription regulatory elements. Minimal promoter sequences can be derived from various sources, such as prokaryotic and eukaryotic genes. Examples of minimal promoters include the dopamine beta-hydroxylase promoter and the cytomegalovirus (CMV) immediate early gene minimal promoter.

According to one aspect of the present invention, two or more TFREs are combined with a minimal promoter in a single promoter element. This may be achieved by mixing a number of TFREs as described herein under ligation reaction conditions. The TFREs may be directly linked to each other. The TFREs may be separated by spacer nucleotides. For example, the TFREs may be separated by 1 or more, 2 or more, 5 or more, 10 or more or 20 or more nucleotides. These spacer nucleotides may be for example 1 to 20 nucleotides.

In an embodiment of the invention the oligonucleotides encoding the TRFEs further comprise a short overhang of single stranded nucleotides, which is able to hybridize with the overhang of another oligonucleotide. Such an overhang may be also between 1 to 20 nucleotides long.

The TFREs combined in this way may be identified by a method described herein or may already have been identified as being active in the cell or tissue of interest.

A promoter element preferably contains two or more TFREs. The number of TFREs in each promoter element may be variable, or each promoter element may comprise the same number of TFREs. A promoter element may comprise 2 or more, 3 or more, 4 or more, 5 or more, or 6 or more TFREs. Preferably the ligated oligonucleotides from 0.1 to 1 kB are selected for the library, e.g. from an agarose gel. The sequence of a TFRE in the promoter element may be present in the sense or the antisense strand (i.e., in the forward or reverse direction) of the promoter element. The same TFRE may be present multiple times.

The promoter element may be arranged so that the TFREs are located upstream to the minimal promoter. Alternatively, the TFREs may be located downstream to the minimal promoter.

Expression Vectors

A plurality of promoter elements as described herein is used to create a library of expression vectors. Each expression vector comprises an antibiotic resistance gene. For example, expression of the gene may confer resistance to neomycin, zeocin, hygromycin or puromycin. A promoter element as described herein is included in a vector such that it is operably linked to the gene. That is, the promoter element is located such that it is capable of expressing the coding sequence of the gene in a cell of interest. The vector preferably includes no promoter or regulatory sequences other than those present in the promoter element. This ensures that any gene transcription from the promoter must have been regulated by the promoter element introduced into the vector.

The vector may be any vector capable of expression of an antibiotic resistance gene in the cell or tissue of interest. For example, the vector may be a plasmid or a viral vector. The vector may be a vector that integrates into the host genome, or a vector that allows gene expression while not integrated.

A plurality of different vectors as described herein may be provided. These may form a library. For example, where analysis of differential expression as described above has led to the identification of multiple TFREs for a cell or tissue type of interest, a plurality of promoter elements may be produced which comprise those TFREs. A mixture of multiple copies of the TFREs may be combined to produce a variety of different promoter elements. These may each be included in a vector to produce a library of vectors for the cell or tissue type of interest.

Assay Methods

A library of vectors as described herein may be assayed for vectors that are capable of expressing the antibiotic resistance gene in the cell or tissue of interest. Briefly, such an assay will comprise the steps of: transfecting cells of the cell or tissue of interest with vectors from the library; culturing said cells under conditions suitable for gene expression; and screening the cells for antibiotic resistance.

Transfection may be achieved using any suitable method. A variety of transfection methods are known in the art and the skilled person will be able to select a suitable method depending on the type of vector and type of cell or tissue that it is desired to use.

The culturing step may involve maintaining the transfected cells under suitable conditions to allow gene expression to occur. Where an inducible regulatory sequence has been included in the promoter elements, it may also be necessary to expose the cells or tissues to the relevant inducing agent.

The relevant antibiotic should then be added to the medium. In those cells where the promoter element does contain a suitable combination of TFREs to allow gene expression, the antibiotic resistance gene will be expressed and the cells will be resistant to the application of the antibiotic. For example, where the cell or tissue of interest includes the particular combination of transcription factors needed to activate the cis-acting factors within the promoter element, that promoter element may be capable of regulating expression of the antibiotic resistance gene.

In those cells where the promoter element does not contain a suitable combination of TFREs to allow gene expression, the cell will not have antibiotic resistance and will be killed by the presence of antibiotic. For example, where the cell or tissue of interest does not include the correct transcription factors, or does not include those transcription factors at sufficient levels to allow the cis-acting elements to regulate gene expression, the antibiotic resistance gene may not be expressed.

This will allow the selection of those cells in which the promoter element is capable of regulating gene expression in the cell or tissue type of interest. It is possible that mutations are introduced to the cis-acting elements during this step.

In one embodiment, the method may comprise a further step. In order to determine whether the activity of such a promoter element is specific to the cell or tissue type of interest, a further assay step may be carried out to determine whether the antibiotic resistance gene will also be expressed when the vector is transfected into a different cell type. For example, where the cell or tissue of interest has been treated with a particular biological ligand, chemical agent or microbial pathogen, the activity of the promoter element may also be assessed in untreated cells to determine whether the promoter element will be generally active in that cell type or only on those cells following such a treatment. Similarly, where the cell or tissue type is a diseased tissue, such as a cancer cell type, the activity of the promoter element in a "normal" equivalent tissue type may be assessed to determine whether the promoter element is generally active in that tissue type, or only in the disease state.

Two examples of strategies that may be adopted in the design and construction of synthetic promoter elements are as follows:

Bacterial Library Approach.

Regulatory elements corresponding to the transcription programs found to be upregulated in cancer cells using comparative genomics and integrative bioinformatics approaches detailed above are randomly ligated together with a minimal promoter upstream of the antibiotic selection gene in a promoterless mammalian expression vector. Duplex oligonucleotides are designed so that when linked together the regulatory elements are present on the same face of the double helix and contain Sp1-elements to prevent promoter silencing by methylation. The oligonucleotides that represent promoter elements are ligated together using different ratios and each ligation mix typically comprises five or six different cis-elements. Resultant plasmid constructs are then used to transfect corresponding cancer cell lines in 96-well format in order to find the optimal promoters by antibiotic selection, and promising candidate promoters are isolated and sequenced before being further transfected into control cell lines in order to ascertain tumour cell specificity. Clones containing synthetic promoters that display restricted expression in cancer cell lines are then selected.

Retroviral Library Approach.

Duplex oligonucleotides are designed as described above and are ligated into a self-inactivating (SIN) mouse moloney retroviral vector containing a minimal promoter driving the expression of the antibiotic selection gene. Bacterial clones are pooled and a mixed library of retroviral vectors is constructed and used to stably transduce selected cancer cell lines. Cancer cells are infected so that only 50% of the cells express the antibiotic selection gene and very high concentrations of antibiotic are used to sort the strongest expressing cells from the remaining population. Single clones of cancer cell lines transduced with the optimal synthetic promoter elements are then isolated by dilution cloning approaches. Genomic DNA is isolated, the synthetic promoter rescued by PCR and cloned into a promoter-less mammalian expression vector containing eGFP to evaluate expression in control cell lines thus confirming tumour specificity.

Uses for Identified Promoter Elements

The invention also extends to promoter elements and vectors of the invention, such as promoter elements and vectors that have been identified by the methods of the invention and to their uses.

Promoter elements or vectors identified by the methods of the invention as being active in a cell or tissue type of interest may be used to target genes to that cell or tissue type. For example, where the methods of the invention show that a promoter element is active specifically in a particular cell type, but not in a control cell type, then that promoter element may be used to specifically direct expression in the cell type or tissue type, or under the condition, of interest.

Thus, a promoter element of the invention may be combined with a gene that it is desired to express in a particular cell type. For example, a vector may be produced in which a promoter element of the invention is operably linked to the coding sequence of a gene. That vector may then be used to transfect a cell of interest. The vector may be any vector type as described herein, for example a plasmid or a viral vector. Alternatively, such a vector may be produced by replacing the antibiotic resistance gene in a vector identified by a method of the invention with the gene of interest.

Thus, provided is a method of expressing a gene in a cell or tissue of interest or under a particular condition, comprising the steps of: identifying a promoter element capable of regulating gene expression in the cell or tissue or under the particular condition, for example, using the provided methods for identifying promoter elements; generating an expression vector comprising said promoter element operably linked to a gene; and transfecting the cell or tissue with the vector and allowing gene expression to occur.

These methods may be used in vitro to manipulate cells in culture. For example, gene expression in an in vitro cell population may be manipulated using a promoter element of the invention.

These methods may be used in vivo to manipulate cells in a human or animal body or other eukaryotic organism, such as a plant. For example, a promoter element or vector of the invention, such as a promoter element or vector that has been identified as described herein as being capable of regulating gene expression in a cell or tissue of interest, may be provided for use in a method of therapy or diagnosis to be carried out on the human or animal body or organism. Such a promoter element or vector may be used in the manufacture of a medicament for the therapeutic treatment of the cell or tissue of interest. For example, where the cell or tissue of interest is from a disease tissue such as cancer, then the promoter element or vector may be used for the treatment of that disease, such as cancer. For example, the promoter element or vector may be used to direct expression in the particular disease tissue of a polypeptide having a therapeutic effect. Thus, in some embodiments, the invention may be used to provide a method of treating a disease such as cancer, the method comprising delivering a promoter element or vector of the invention, such as a promoter element or a vector that has been identified by a method of the invention, to a patient suffering from said disease, wherein the promoter element or vector directs expression in the disease cells or tissue of a therapeutic agent.

Another object of the invention is to provide a method of selecting multiple promoter elements whose combination is capable of specifically regulating gene expression under a particular condition or in a particular cell or tissue, for example, in a cancer cell, by performing the selection steps for the transcriptional regulatory elements described in the previous described method.

In one aspect of such methods, in the first step, a plurality of transcription factor regulatory elements (TRFEs) that are associated with any of a plurality of genes whose expression is identified as being aberrantly regulated in a particular cell or tissue type or under a particular condition, for example, in cancer cells, such as in cancer cells from a number of different sources, are provided or are identified.

From this plurality of transcription factor regulatory elements, particular TFREs are selected according to a number of pre-defined criteria. One criterion generally is that the selected transcription factor regulatory elements have to be in close proximity to more than fifty percent of the plurality of genes (for example, within 20, 10, or 5 kb of more than 50% of the genes and typically within the upstream region of such genes). The term proximity is thereby defined as the transcription factor regulatory element being located within the region of 20 kbases up- or downstream of the gene associated with, preferably 10 kbases, even more preferably 5 kbases, most preferably within the upstream region. The TFRE may be considered associated with a given gene whether its sequence is present on the sense or antisense strand (i.e., in the forward or reverse direction). In one embodiment only TFREs on the sense strand (i.e., in the forward direction) are considered to be associated with a given gene.

Another criterion generally relates to the frequency of occurrence of the TFREs. The frequency is defined as described herein above. Selection generally also relates to the length in nucleotides of each transcription factor regulatory element. Frequency and length generally are used to identify candidate regulatory elements (selected TFREs) according to the following relationship:

$$\text{frequency}^{(1/\text{length})}.$$

As discussed above, the calculated value (which is the nth root of the frequency, wherein n is the length) is also called SYN-value, which generally is used as a selection criterion and/or to rank the TFREs. The threshold SYN value can be any number between 0.1 and 0.9. Preferably the SYN-value of selected TFREs has to be larger than the threshold; thus, in certain embodiments, selected TFREs have SYN values greater than or at least 0.1, 0.2, 0.3, 0.4, 0.5, 0.6, 0.7, 0.8, or 0.9 or about 0.1, 0.2, 0.3, 0.4, 0.5, 0.6, 0.7, 0.8, or 0.9. It is also possible to select a predefined number of TFREs, e.g., cis-acting sequences, e.g. 1 to 10 genes, which have the largest SYN-values. Thus, in some embodiments, among a plurality of TFREs identified as proximate to the plurality of genes, those selected are those having the top 1, 2, 3, 4, 5, 6, 7, 8, 9, or 10, or 11, 12, 13, 14, 15, 16, 17, 18, 19, or 20 highest SYN values, typically within the top 10 SYN values.

Another object of the invention is vector comprising the combined promoter cassette obtained the prescribed methods, wherein the vector is a plasmid, viral, transiently expressed or integrated into the genome of a host cell.

Such a combined promoter cassette contains 2 or more, 3 or more, 4 or more, 5 or more, or 6 or more TFREs, originally selected for the method, wherein the sequence of each TFRE within the promoter cassette have a homology of more than 70%, preferably more than 80% to the sequence of the TFRE originally selected. The TFRE can be present in the sense or in the antisense strand of the promoter cassette. In a preferred embodiment the promoter cassette also contains a minimum promoter. In a preferred embodiment the TFREs in the sequence are selected from the TFREs shown in table 3 and/or their complements.

Another object of the invention is a host cell comprising the prescribed a vector. The preferred embodiment the host cell is a prokaryotic or a eukaryotic cell, preferably a mammalian cell.

Another object of the invention is an isolated promoter capable of driving and/or regulating expression, comprising:
    (a) an isolated nucleic acid as given in one of the SEQ ID Nos. 130 to 191 or the complement of one of the SEQ ID Nos. 130 to 191; or
    (b) an isolated nucleic acid having at least 90% sequence identity with the DNA sequence as given in one of the SEQ ID Nos. 130 to 191 or the complement of one of the SEQ ID Nos. 130 to 191; or
    (c) an isolated nucleic acid specifically hybridising under stringent conditions with the DNA sequence as given in one of the SEQ ID Nos. 130 to 191 or the complement of one of the SEQ ID Nos. 130 to 191; or
    (d) an isolated nucleic acid as defined in any one of (a) to (c), which is interrupted by an intervening sequence; or (e) a fragment of any of the nucleic acids as defined in (a) to (d), which fragment is capable of driving and/or regulating expression.

The isolated promoter may further contain a minimal promoter, such as any known minimal promoter, e.g., one of the minimal promoters described herein. In some embodiments, the isolated promoter further containing a minimal promoter contains:
    (a) an isolated nucleic acid as given in one of the SEQ ID Nos. 5 to 66 or the complement of one of the SEQ ID Nos. 5 to 66; or
    (b) an isolated nucleic acid having at least 90% sequence identity with the DNA sequence as given in one of the SEQ ID Nos. 5 to 66 or the complement of one of the SEQ ID Nos. 5 to 66; or
    (c) an isolated nucleic acid specifically hybridising under stringent conditions with the DNA sequence as given in one of the SEQ ID Nos. 5 to 66 or the complement of one of the SEQ ID Nos. 5 to 66; or
    (d) an isolated nucleic acid as defined in any one of (a) to (c), which is interrupted by an intervening sequence; or
    (e) a fragment of any of the nucleic acids as defined in (a) to (d), which fragment is capable of driving and/or regulating expression.

The term "isolated" as used herein means being removed from its original source. Preferably, the "isolated" promoter is free of sequences (such as protein encoding sequences or other sequences at the 3' end) that naturally flank the promoter in the genomic DNA of the organism from which the promoter is derived. Further preferably, the "isolated" promoter is also free of sequences that naturally flank it at the 5' end. Further preferably, the "isolated" promoter may comprise less than about 5 kb, 4 kb, 3 kb, 2 kb, 1.5 kb, 1.2 kb, 1 kb, 0.8 kb, 0.5 kb or 0.1 kb of nucleotide sequences that naturally occur with the promoter in genomic DNA from the organism of which the promoter is derived.

The present invention is not limited to the nucleic acids as presented by one of the SEQ ID Nos. 130 to 191, or SEQ ID No. 5 to 66. A person skilled in the art will recognize that variants or fragments of a nucleic acid may occur, whilst maintaining the same functionality. These variants or fragments may be man made (e.g. by genetic engineering) or may even occur in nature. Therefore the present invention extends to variant nucleic acids and fragments of one of the SEQ ID Nos. 130 to 191 or their complements, or SEQ ID Nos. 5 to 66 or their complements, which variants or fragments are useful in the methods of the present invention. Such variants and fragments include:

(a) an isolated nucleic acid as given in one of the SEQ ID Nos. 130 to 191, or SEQ ID Nos. 5 to 66 or the complement of one of the SEQ ID Nos. 130 to 191 or SEQ ID Nos. 5 to 66; or (b) an isolated nucleic acid having at least 90% sequence identity with any of the DNA sequences as given in one of the SEQ ID Nos. 130 to 191, or SEQ ID Nos. 5 to 66, or the complement of one of the SEQ ID Nos. 130 to 191 or SEQ ID Nos. 5 to 66; or (c) an isolated nucleic acid specifically hybridizing under stringent conditions with any of the DNA sequences as given in one of the SEQ ID Nos. 130 to 191, or SEQ ID Nos. 5 to 66, or the complement of one of the SEQ ID Nos. 130 to 191 or SEQ ID Nos. 5 to 66; or (d) an isolated nucleic acid as defined in any one of (a) to (c), which is interrupted by an intervening sequence; or (e) a fragment of any of the nucleic acids as defined in (a) to (d), which fragment is capable of driving and/or regulating expression.

Suitable variants of one of the SEQ ID Nos. 130 to 191, or SEQ ID Nos. 5 to 66, encompass homologues which have in increasing order of preference at least 90%, 91%, 92%, 93%, 94%, 95%, 96%, 97%, 98% or 99% sequence identity with the nucleic acid acids as represented in one of the SEQ ID Nos. 130 to 191, or SEQ ID Nos. 5 to 66. The same is valid for the complements of the SEQ ID Nos. 130 to 191 or SEQ ID Nos. 5 to 66.

The percentage of identity may be calculated using an alignment program. Preferably a pair wise global alignment program may be used, which implements the algorithm of Needleman-Wunsch (J. Mol. Biol. 48: 443-453, 1970). This algorithm maximizes the number of matches and minimizes the number of gaps. Such programs are for example GAP, Needle (EMBOSS package), stretcher (EMBOSS package) or Align X (Vector NTI suite 5.5) and may use the standard parameters (for example gap opening penalty 15 and gap extension penalty 6.66). Alternatively, a local alignment program implementing the algorithm of Smith-Waterman may be used. Such programs are for example Water (EMBOSS package) or matcher (EMBOSS package). "Sequence identity" as used herein is preferably calculated over the entire length of the promoters as represented by one of the SEQ ID Nos. 130 to 191 or SEQ ID Nos. 5 to 66.

Search and identification of homologous nucleic acids, would be well within the realm of a person skilled in the art. Such methods, involve screening sequence databases with the sequences provided by the present invention, for example SEQ ID No. 5, preferably in a computer readable form. Useful sequence databases, include but are not limited to Genbank (http:/www.ncbi.nim.nih.gov/web/Genbank), the European Molecular Biology Laboratory Nucleic acid Database (EMBL) (http://w.ebi.ac.uk/ebi-docs/embl-db.html) or versions thereof, or the MIPS database (http://mips.gsf.de/). Different search algorithms and software for the alignment and comparison of sequences are well known in the art. Such software includes, for example GAP, BEST-FIT, BLAST, FASTA and TFASTA. Preferably BLAST software is used, which calculates percent sequence identity and performs a statistical analysis of the similarity between the sequences. The suite of programs referred to as BLAST programs has five different implementations: three designed for nucleotide sequence queries (BLASTN, BLASTX, and TBLASTX) and two designed for protein sequence queries (BLASTP and TBLASTN). The software for performing BLAST analysis is publicly available through the National Centre for Biotechnology Information. In case of SEQ ID No. 5 no homologues could be found using BLAST.

Examples of homologues having at least 90% sequence identity with one of the SEQ ID Nos. 130 to 191, or SEQ ID Nos. 5 to 66, are allelic variants of one of the SEQ ID Nos. 130 to 191, or of the SEQ ID Nos. 5 to 66. Allelic variants are variants of the same gene occurring in two different individuals of the same species and usually allelic variants differ by slight sequence changes. Allelic variants may encompass Single Nucleotide Polymorphisms (SNPs) as well as Small Insertion/Deletion Polymorphisms (INDELs). The size of INDELs is usually less than 100 bp. SNPs and INDELs form the largest set of sequence variants in naturally occurring polymorphic strains of most organisms. The same is valid for the complements of the SEQ ID Nos. 130 to 191 or SEQ ID Nos. 5 to 66.

Homologues suitable for use in the methods according to the invention may readily be isolated from their source organism via the technique of PCR or hybridization. Their capability of driving and/or regulating expression may readily be determined, for example, by following the methods described in the Examples section by simply substituting the sequence used in the actual example with the homologue.

Other suitable variants of one of the SEQ ID Nos. 130 to 191, or of one of SEQ ID Nos. 5 to 66 or their complements, encompassed by the present invention are nucleic acids specifically hybridising under stringent conditions to any one of the nucleic acids of one of the SEQ ID Nos. 130 to 191, or of the SEQ ID Nos. 5 to 66 or their complements. The term "hybridising" means annealing to substantially homologous complementary nucleotide sequences in a hybridization process. Tools in molecular biology relying on such a hybridization process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination, Northern blotting (RNA blotting), Southern blotting (DNA blotting). The hybridisation process can also occur with one of the complementary nucleic acids immobilised to a matrix such as magnetic beads, Sepharose beads or any other resin. Tools in molecular biology relying on such a process include the isolation of poly (A+) mRNA. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. Conventional hybridisation conditions are described in, for example, Sambrook (2001) Molecular Cloning: a laboratory manual, 3rd Edition Cold Spring Harbor Laboratory Press, CSH, New York, but the skilled craftsman will appreciate that numerous different hybridisation conditions can be designed in function of the known or the expected homology and/or length of the nucleic acid sequence. High stringency conditions for hybridisation include high temperature and/or low sodium/salt concentration (salts include sodium as for example in NaCl and Nacitrate) and/or the inclusion of formamide in the hybridisation buffer and/or lowering the concentration of compounds such as SDS (sodium dodecyl sulphate detergent) in the hybridisation buffer and/or exclusion of compounds such as dextran sulphate or polyethylene glycol (promoting molecular crowding) from the hybridisation buffer. Specifically hybridising under stringent conditions means that the sequences have to be very similar. Specific hybrisization under stringent conditions is preferably carried out at a temperature of 60° C. followed by washes in 0.1 to 1×SSC, 0.1×SDS, and 1×SSC, 0.1×SDS.

The invention also relates in certain embodiments to a nucleic acid molecule of at least 15 nucleotides in length hybridizing specifically with any of the nucleic acids of the invention, especially one of the SEQ ID Nos. 130 to 191 or their complement SEQ ID Nos. 192 to 253, or SEQ ID Nos. 5 to 66 or one of their complements SEQ ID Nos. 68 to 129. The invention also relates in some embodiments to a nucleic acid molecule of at least 15 nucleotides in length specifically amplifying a nucleic acid of the invention by polymerase chain reaction.

Another variant of any of one of the SEQ ID Nos. 130 to 191, or SEQ ID Nos. 5 to 66, encompassed by the present invention are nucleic acids corresponding to one of the SEQ ID Nos. 130 to 191, or SEQ ID Nos. 5 to 66 or variants thereof as described hereinabove, which are interrupted by an intervening sequence. For example, any of the nucleic acids as presented in one of the SEQ ID Nos. 130 to 191, or of the SEQ ID Nos. 5 to 66, may be interrupted by an intervening sequence. With "intervening sequences" is meant any nucleic acid or nucleotide, which disrupts another sequence. Examples of intervening sequences comprise introns, nucleic acid tags, T-DNA and mobilizable nucleic acids sequences such as transposons or nucleic acids that can be mobilized via recombination. Examples of particular transposons comprise Ac (activator), Ds (Dissociation), Spm (suppressor-Mutator) or En. The introduction of introns into promoters is now widely applied. The methods according to the present invention may also be practised using a nucleic acid sequence according to one of the SEQ ID Nos. 130 to 191, or SEQ ID Nos. 5 to 66, provided with an intron. In case the intervening sequence is an intron, alternative splice variants of the nucleic acids according to the invention may arise. The term "alternative splice variant" as used herein encompasses variants of a nucleic acid sequence in which intervening introns have been excised, replaced or added. Such splice variants may be found in nature or may be manmade. Methods for making such promoters with an intron or for making the corresponding splice variants are well known in the art.

Variants interrupted by an intervening sequence, suitable for use in the methods according to the invention may readily be determined for example by following the methods described in the examples section by simply substituting the sequence used in the actual example with the variant.

The variant nucleic acids as described hereinabove may be found in nature (for example allelic variants or splice variants). Additionally and/or alternatively, variants of one of the SEQ ID Nos. 130 to 191, or SEQ ID Nos. 5 to 66, as described hereinabove may be manmade via techniques well known in the art involving for example mutation, substitution, insertion, deletions or derivation. The present invention also encompasses such variants, as well as their use in the methods of the present invention.

A "mutation variant" of a nucleic acid may readily be made using recombinant DNA manipulation techniques or nucleotide synthesis. Examples of such techniques include site directed mutagenesis via M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols. Alternatively, the nucleic acid of the present invention may be randomly mutated.

A "substitutional variant" refers to those variants in which at least one residue in the nucleic acid sequence has been removed and a different residue inserted in its place. Nucleic acid substitutions are typically of single residues, but may be clustered depending upon functional constraints placed upon the nucleic acid sequence; insertions usually are of the order of about 1 to about 10 nucleic acid residues, and deletions can range from about 1 to about 20 residues.

An "insertional variant" of a nucleic acid is a variant in which one or more nucleic acid residues are introduced into a predetermined site in that nucleic acid. Insertions may comprise 5'-terminal and/or 3'-terminal fusions as well as intrasequence insertions of single or multiple nucleotides. Generally, insertions within the nucleic acid sequence will be smaller than 5'- or 3'-terminal fusions, of the order of about 1 to 10 residues. Examples of 5'- or 3'-terminal fusions include the coding sequences of binding domains or activation domains of a transcriptional activator as used in the yeast two-hybrid system or yeast one-hybrid system, or of phage coat proteins, (histidine)$_6$-tag, glutathione S-transferase-tag, protein A, maltose-binding protein, dihydrofolate reductase, Tag 100 epitope, c-myc epitope, FLAG®-epitope, lacZ, CMP (calmodulin-binding peptide), HA epitope, protein C epitope and VSV epitope.

The term "derivative" of a nucleic acid may comprise substitutions, and/or deletions and/or additions of naturally and non-naturally occurring nucleic acid residues compared to the natural nucleic acid. Derivatives may, for example, comprise methylated nucleotides, or artificial nucleotides.

Also encompassed within the present invention are promoters, comprising a fragment of any of the nucleic acids as presented by one of the SEQ ID Nos. 130 to 191, or SEQ ID Nos. 5 to 66, or variants thereof as described hereinabove. A "fragment" as used herein means a portion of a nucleic acid sequence. Suitable fragments useful in the methods of the present invention are functional fragments, which retain at least one of the functional parts of the promoter and hence are still capable of driving and/or regulating expression.

Examples of functional fragments of a promoter include the minimal promoter, the upstream regulatory elements, or any combination thereof.

Suitable fragments may range from at least about 20 base pairs or about 50, 100, 150, 200, 250, 300, 350, 400, 450, 500, 550, 600, 650, 700, 750, 800, 850, 900, 950 or 1000 base pairs, up to about the full length sequence of the invention. These base pairs are typically immediately upstream of the transcription initiation start, but alternatively may be from anywhere in the promoter sequence.

Suitable fragments useful in the methods of the present invention may be tested for their capability of driving and/or regulating expression by standard techniques well known to the skilled person, or by the following method described in the Example section.

The term "promoter" as used herein is taken in a broad context and refers to regulatory nucleic acid sequences capable of effecting (driving and/or regulating) expression of the sequences to which they are operably linked. A "promoter" encompasses transcriptional regulatory sequences derived from a classical genomic gene. Usually a promoter comprises a TATA box, which is capable of directing the transcription initiation complex to the appropriate transcription initiation start site. However, some promoters do not have a TATA box (TATA-less promoters), but are still fully functional for driving and/or regulating expression. A promoter may additionally comprise a CCAAT box sequence and additional regulatory elements (i.e. upstream activating sequences or cis-elements such as enhancers and silencers).

"Driving expression" as used herein means promoting the transcription of a nucleic acid.

"Regulating expression" as used herein means influencing the level, time or place of transcription of a nucleic acid. The promoters of the present invention may thus be used to increase, decrease or change in time and/or place transcription of a nucleic acid. For example, they may be used to limit the transcription to certain cell types, tissues or organs, or during a certain period of time, or in response to certain environmental conditions.

According to a particular embodiment, the invention provides an isolated promoter as mentioned hereinabove, which is a hybrid promoter. The term "hybrid promoter" as used herein refers to a chimeric promoter made, for example, synthetically, for example by genetic engineering. Preferred hybrid promoters according to the present invention comprise a part, preferably a functional part, of one of the promoters according to the present invention and at least another part, preferably a functional part of a promoter. The latter part may be a part of any promoter, including any one of the promoters according to the present invention and other promoters. One example of a hybrid promoter comprises regulatory element(s) of a promoter according to the present invention combined with the minimal promoter of another promoter. Another example of a hybrid promoter is a promoter comprising additional regulatory elements to further enhance its activity and/or to alter its spatial and/or temporal expression pattern.

The present invention also provides in some aspects use of a functional fragment of one of the SEQ ID Nos. 130 to 191, or SEQ ID Nos. 5 to 66, or variant thereof for changing the expression pattern of a promoter. In such methods, at least part of the nucleic acid of one of the SEQ ID Nos. 130 to 191, or SEQ ID Nos. 5 to 66, according to the present invention is combined with at least one fragment of another promoter.

Further, the invention provides a genetic construct comprising:
(a) an isolated promoter as defined hereinabove
(b) a heterologous nucleic acid sequence operably linked to isolated promoter of (a), and optionally
(c) a 3' transcription terminator The term "genetic construct" as used herein means a nucleic acid made by genetic engineering.

The term "operably linked" to a promoter as used herein means that the transcription is driven and/or regulated by that promoter. A person skilled in the art will understand that being operably linked to a promoter preferably means that the promoter is positioned upstream (i.e. at the 5'-end) of the operably linked nucleic acid. The distance to the operably linked nucleic acid may be variable, as long as the promoter of the present invention is capable of driving and/or regulating the transcription of the operably linked nucleic acid. For example, between the promoter and the operably linked nucleic acid, there might be a cloning site, an adaptor, and/or a transcription or translation enhancer.

The operably linked nucleic acid may be any coding or noncoding nucleic acid. The operably linked nucleic acid may be in the sense or in the anti-sense direction. Typically in the case of genetic engineering of host cells, the operably linked nucleic acid is to be introduced into the host cell and is intended to change the phenotype of the host cell. Alternatively, the operably linked nucleic acid is an endogenous nucleic acid from the host cell.

The term "heterologous" as used herein is intended to be "heterologous to a promoter of the present invention". A nucleic acid that is heterologous to a promoter of the present invention is not naturally occurring in the nucleic acid sequences flanking the promoter of the present invention when it is in its biological genomic environment. While the nucleic acid may be heterologous to a promoter of the present invention, it may be homologous or native or heterologous or foreign to the host cell. The heterologous operably linked nucleic acid may be any nucleic acid (for example encoding any protein), provided that it comprises or it is flanked by at least one nucleotide which is normally not flanking the promoter of the present invention.

The term "transcription terminator" as used in (c) refers to a DNA sequence at the end of a transcriptional unit which signals termination of transcription. Terminators are 3'-non-translated DNA sequences usually containing a polyadenylation signal, which facilitates the addition of polyadenylate sequences to the 3'-end of a primary transcript. Terminators active in and/or isolated from viruses, yeasts, moulds, bacteria, insects, birds, mammals and plants are known and have been described in literature. Examples of terminators suitable for use in the genetic constructs of the present invention include any eukaryotic terminator or viral terminator, e.g. Bovine Growth Hormone poly A or SV40 poly A. These polyadenylation signals are known in the art.

Furthermore, the present invention encompasses a host cell comprising an isolated promoter or a genetic construct according to the invention as described hereinabove. In particular embodiments of the invention, the host cell is selected from bacteria, algae, fungi, yeast, plants, insect or animal host cells.

In a preferred embodiment the host cell is a cell in a disease state, preferably a cancer cell.

The invention further provides a method for driving and/or regulating expression of a nucleic acid in a cell, comprising:
(a) operably linking a nucleic acid to an isolated nucleic acid according to the invention as described hereinabove, such as to one of the SEQ ID Nos. 130 to 191, or SEQ ID Nos. 5 to 66, or a variant or fragment thereof, and (b) introducing the resultant genetic construct into a cell, preferably a cell in a disease state, more preferably a cancer cell.

Preferably the operably linked nucleic acid of (a) is heterologous to the nucleic acids according to the present invention.

This method may further comprise cultivating the transformed cell under conditions promoting growth, promoting regeneration and/or promoting maturation.

Furthermore, the expression of the operably linked nucleic acid may be driven and/or regulated in particular cells, tissues or organs of an organism, preferably a mammal. Accordingly, the invention in some embodiments provides a method as described above, wherein the expression is constitutive expression or tissue-specific expression. For these embodiments, reference is made to the example section where the specific expression patterns of the promoters according to the invention are described and where different types of tissue-specific expression are detailed.

The present invention further encompasses the use of an isolated nucleic acid as defined hereinabove to drive and/or regulate expression of an operably linked nucleic acid.

BRIEF DESCRIPTION OF THE DRAWINGS

Other objects and advantages of the present invention may be ascertained from a reading of the specification and appended claims in conjunction with the drawings therein. For a more complete understanding of the present invention, reference is established to the following description made in connection with accompanying drawings in which:

FIG. 1 shows a flow diagram of one example of the method for making and selecting a transcription enhancing combined promoter cassette.

Figure 1:
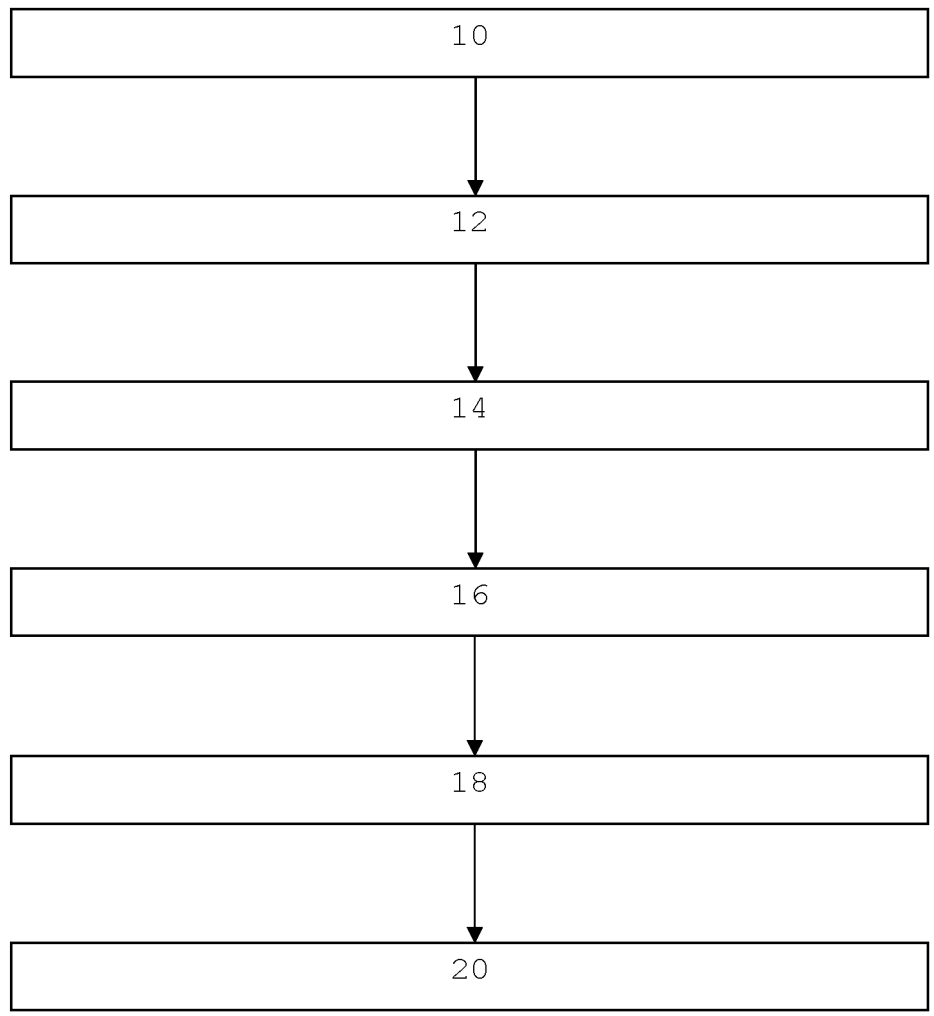
FIG. 1 Schematic representation of an embodiment of the method of the invention.

In this exemplary method, in a first step (10) a plurality of transcription factor regulatory elements that are associated with any of a plurality of genes whose expression is identified as being aberrantly regulated in cancer cells isolated from a number of different sources is provided.

In a second step (12) of this exemplary method, said transcription factor regulatory elements are selected according to a number of pre-defined criteria. In this example, as a first criterion said transcription factor regulatory elements have to be in close proximity to more than fifty percent of the genes found to be aberrantly regulated in cancer cells. As a second criterion in this example, the frequency of occurrence and as a third criterion is the length in nucleotides of the said transcription factor regulatory elements are both used to identify candidate regulatory elements according to the following relationship: frequency$^{(1/length)}$, with frequency defined as above.

In a preferred embodiment, the candidate regulatory elements in the case of colon cancer are the sequences listed in table 3.

In the next step (14) of this exemplary method, a library of randomly combined transcription factor regulatory elements selected in step (12) is constructed.

In the next step (16) of this exemplary method, the combined transcription factor regulatory elements are inserted upstream of a minimum promoter followed by a reporter gene in a vector. Preferably one combined transcription factor regulatory element is inserted in each vector.

In the next step (18) of this exemplary method, the vector is inserted into a host cells.

In the next step (20) the cells are screened for cells showing enhanced expression of the reporter gene, and identify the cells comprising the combined promoter cassette from the library.

EXAMPLE

1. Selection of Genes Upregulated in Colorectal Cancer

Table 2 represents a selection of genes identified by a meta-analysis of microarray data from colon cancer sources from a study conducted by Rhodes et al (Rhodes et al (2004) PNAS 2004; 101; 9309-14). This resulted in the identification of the 17 genes listed in table 2 shown to be upregulated in colorectal cancer biopsies.

These genes were then screened to ensure that overexpression was a result of altered transcription factor activation, instead of chromosomal amplification, in order to select cis-regulatory elements that will be active in the context of an altered transcription factor environment. This resulted in the exclusion of three genes: TOP2A, SMARCA4 and TRAF4 (indicated by *).

Further the literature was searched using pubmed in order to find genes whose overexpression in colorectal cancer had previously been shown by independent methods. Depending on the expression levels and assays used for detection, genes were scored as '+++'; Substantial evidence to support their overexpression, '++'; Significant evidence to support their overexpression, and '+'; Evidence to support their overexpression.

Due to improved computing power, an aim of the invention is to analyse all regulatory sequences of all differentially regulated genes. Therefore this selection step is only optionally.

Genes, where no further evidence regarding their overexpression in colorectal cancer was found, were excluded. Finally, the regulatory regions of the following seven genes with a view to select cis-regulatory elements to form a synthetic promoter active specifically in colon cancer cells were examined: PLK, G3BP, E2-EPF, MMP9, MCM3, PRDX4 and CDC2.

2. Identification of Regulatory Elements from Upregulated Genes

Upon deciding on the genes upregulated in colorectal cancer, the nucleotide sequence of each gene (a total of seven genes) was obtained with 5 kb upstream/downstream from UCSC GoldenPath (www.genome.ucsc.edu) with the use of the UCSC Genome Browser on Human March 2006 Assembly (http://genome.ucsc.edu/cgi-bin/hgTracks?org=human). Using the BIOBASE Biological Databases (www.generegulation.com), each retrieved sequence was BLASTed against the TRANSFAC Factor Table by using the BLASTX search tool (version 2.0.13) of the TFBLAST program (www.generegulation.com/cgi-bin/pub/programs/tfblast/tfblast.cgi) for searches against nucleotide sequences in order to identify regulatory elements. The selection of regulatory elements was based on sequence homology with significantly high (0.7-1.0) corresponding consensus sequences (identity threshold), while no restriction on score or length threshold was imposed. The BLAST results for the genes of interest were cross-referenced in order to obtain common regulatory element lists with significant e-values (<1e-03) as well as belonging to the species of choice (*Homo Sapiens*). Upon further review, the colon cancer gene list showed good evidence of regulatory elements since (a) significant e-values were present in all seven genes (b) multiple common regulatory elements were present in all seven genes, (c) the majority of genes present in the colon cancer gene list are also present in other cancer gene lists (data not shown), and (d) substantial/significant evidence to support the genes overexpression were established from expression levels and assays used for detection.

The seven gene sequences of interest from the colon cancer gene list were further investigated with the use of the PATCH public 1.0 (Pattern Search for Transcription Factor Binding Sites) (http://www.gene-regulation.com/cgibin/pub/programs/patch/bin/patch.cgi), from the BIOBASE Biological Databases. The search was conducted for all sites with a minimum site length of 7 bases, maximum number of mismatches of 0, mismatch penalty of 100, and lower score boundary of 100. The results of all seven gene sequences were further analyzed by grouping them all together, excluding all transcription factor binding sites except *Homo sapiens*.

It was then proceeded to examine the frequency that each transcription factor binding site occurred in close proximity to the seven genes that were originally identified as being upregulated in colon cancer cells. In some cases one sequence was present multiple times in proximity to a single gene under evaluation. Thus, in order to determine the frequency of occurrence of a transcription factor binding site; the sum of each time a binding site was detected in all genes was calculated and then used the sum of all binding sites present in all genes as the common denominator.

3. Selection of Regulatory Elements for Introduction into Screening Library

A total of 328 cis-regulatory sequences were identified that were present 5854 times in the seven gene sequences that were identified as being upregulated in colorectal cancer. Then those cis-regulatory sequences were identified, which were present at the highest proportion and which displayed the highest level of conservation between genes.

To accomplish this, sequences were selected for library construction according to the following two criteria:

A: They were present in four or more of the seven genes identified by the gene expression profile screen, i.e. present in the regulatory regions of more than fifty percent of the candidate genes.

B: The cis-regulatory sequences that were present at the highest frequency in gene regulatory regions were then subsequently analyzed using the following selection criterion (SYN value):

$$(\text{frequency of cis-sequence})^{(1/length\ at\ cis\text{-}sequence\ in\ bp)} > 0.5$$

The SYN value selection criterion has the advantage to take into account that longer sequences, which may be present at lower frequencies, may actually represent a higher degree of conservation and may therefore by important in specifically driving gene expression in colon cancer cells.

The ten cis regulatory sequences (listed in table 3) with the highest SYN value were then synthesized and used to create a retroviral vector library for selection of synthetic promoters in a colorectal cancer cell line.

Figure 2:
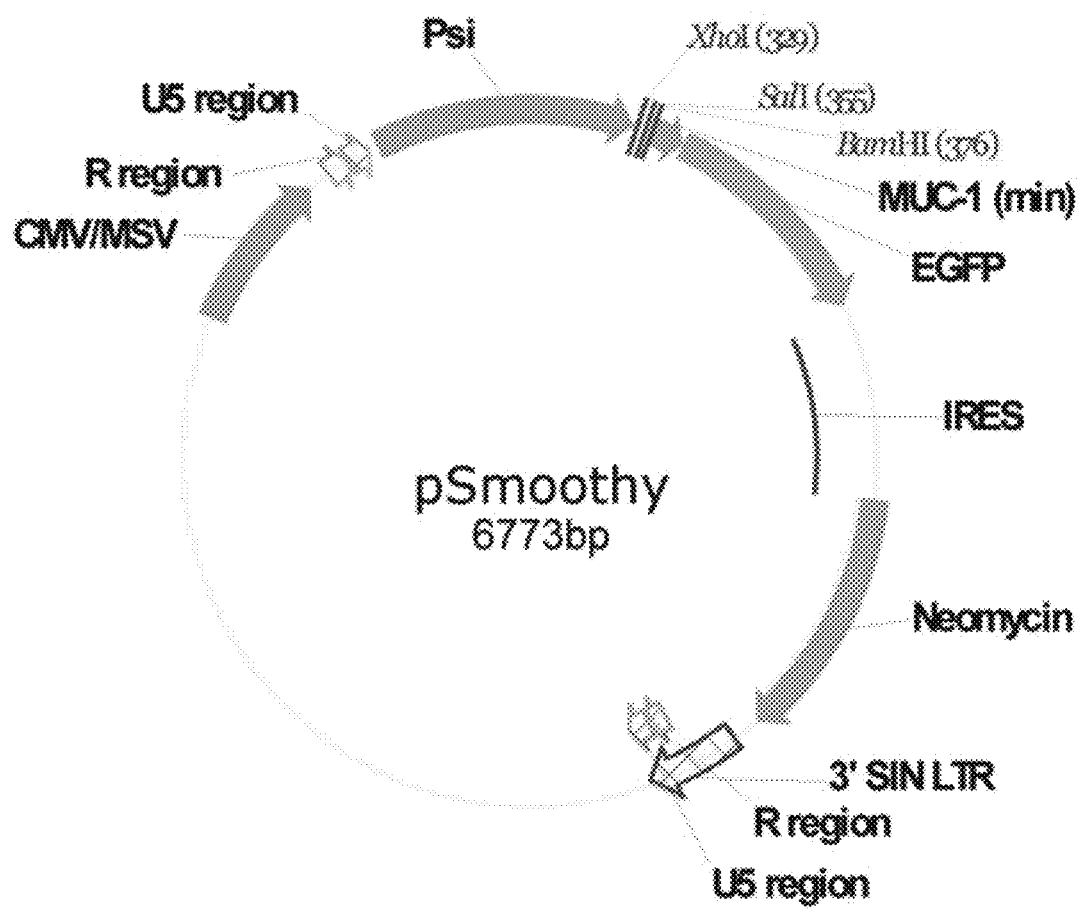
FIG. 2 Vector diagram of the vector pSmoothy. The sequence of this vector is SEQ ID No. 4.

4. Construction of the Retroviral Screening Library and Screening in Colon Cancer Cells In order to select the promoters with the optimal activity in colorectal cancer cells a similar protocol was used to that described by Edelman et al (2000) [PNAS 97 (7), 3038-43]. In brief, sense and antisense oligonucleotides corresponding to the ten selected cis elements were designed to contain a TOGA 5' overhang after annealing. Annealed oligonucleotides were then randomly ligated together using T4 ligase and ligated oligonucleotides in the range of 0.3-1.0 kb were selected for by extraction from a 1.0% agarose gel. It is also possible to use Gateway cloning techniques. These randomly ligated oligonucleotides were then subsequently ligated to the retroviral library pSmoothy vector (FIG. 2; SEQ-ID No. 4), which had been treated with Xho I restriction enzyme and library complexity was measured by transforming ⅕0th of the ligation reaction in supercompetent Top10 bacteria using an electroporator. Plasmid DNA from pSmoothy libraries with a complexity greater than 104 colonies was then expanded and used to create retroviral vectors.

pSmoothy was constructed in order to select potential synthetic promoter sequences by their ability to express both GFP and neomycin in target cells (FIG. 2). It was constructed as a self-inactivating (SIN) retroviral vector so that upon integration into the genome of transduced cells its 3'-UTR can no longer act as a promoter. The vector comprises the mucin minimal promoter which is located within the proviral genome and immediately downstream of the polylinker, where randomly ligated oligonucleotides are inserted. GFP and neomycin coding sequences are located immediately downstream of the minimal promoter and it is expression of these two genes which is used to select the potential synthetic promoter sequences with optimal activity. The sequence of pSmoothy-1 is shown in SEQ-ID No. 4.

Figure 3A:
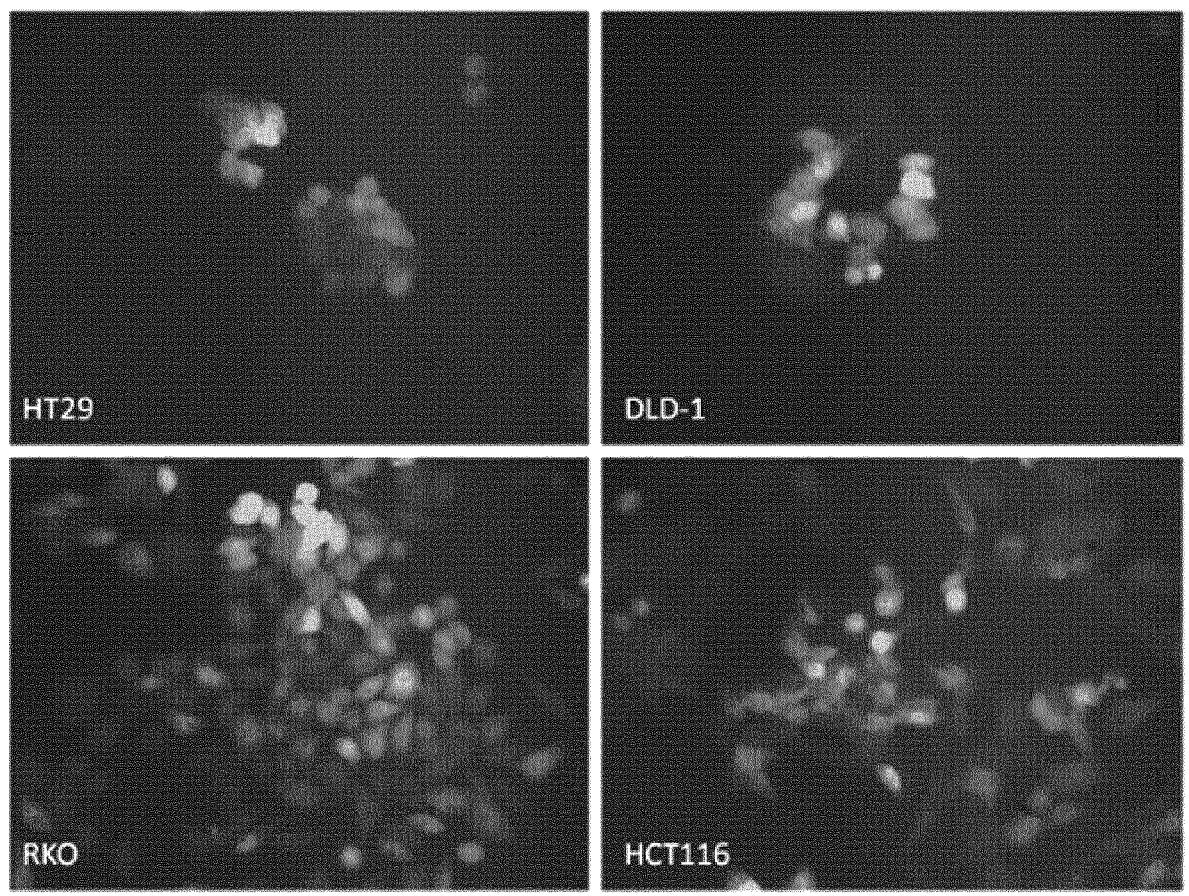
FIG. 3 Fluorescence sorting data of HT29 cells ((a) HT29; (b) HT29-SYN pre-sort; (c) HT29-SYN post-sort).
Figure 3B:
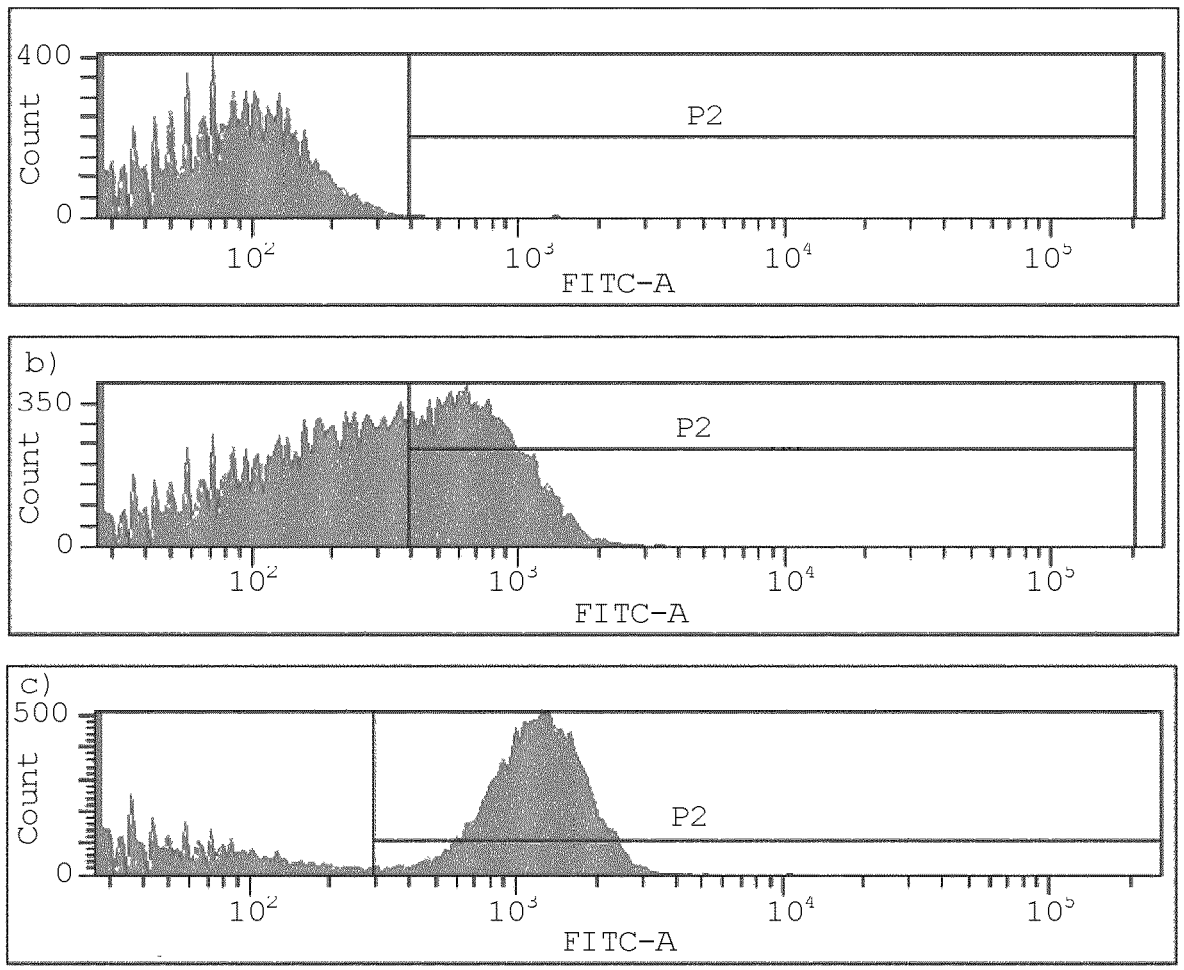

Retroviral vectors were constructed by transfecting the pSmoothy library with a retroviral VSV-G envelop construct into 293 cells stably expressing Gag and Pol and allowing viral vector to be produced over a period of 48 hours. This retroviral vector library was then used to transduce HT29, DLD-1, HCT-116 and RKO colorectal cancer cells at various titers and the transduced cells were subjected to selection with 1 mg/ml G418 for a period of several weeks. FIG. 3A demonstrates efficacy of GFP expression in each cell line. The colorectal cancer cells expressing the highest amounts of GFP were then sorted using a FACS Aria cell sorter (BD) by selecting the 10% cells expressing the highest amount of GFP. This sorted population was then subject to further selection with 1 mg/ml G418 and then sorted a second time, again selecting the 10% cells expressing the highest amount of GFP (FIG. 3B; (a) HT29; (b) HT29-SYN pre-sort; (c) HT29-SYN post-sort). Genomic DNA was then prepared from sorted colorectal cancer cells and promoter sequences were rescued by PCR using the following primers that specifically hybridize to the pSmoothy vector:

```
SYN1S
SEQ-ID No. 2:
5'-TAT CTG CAG TAG GCG CCG GAA TTC-3'

SYN1AS
SEQ-ID No. 3:
5'-GCA ATC CAT GGT GGT GGT GAA ATG-3'
```

Figure 4:
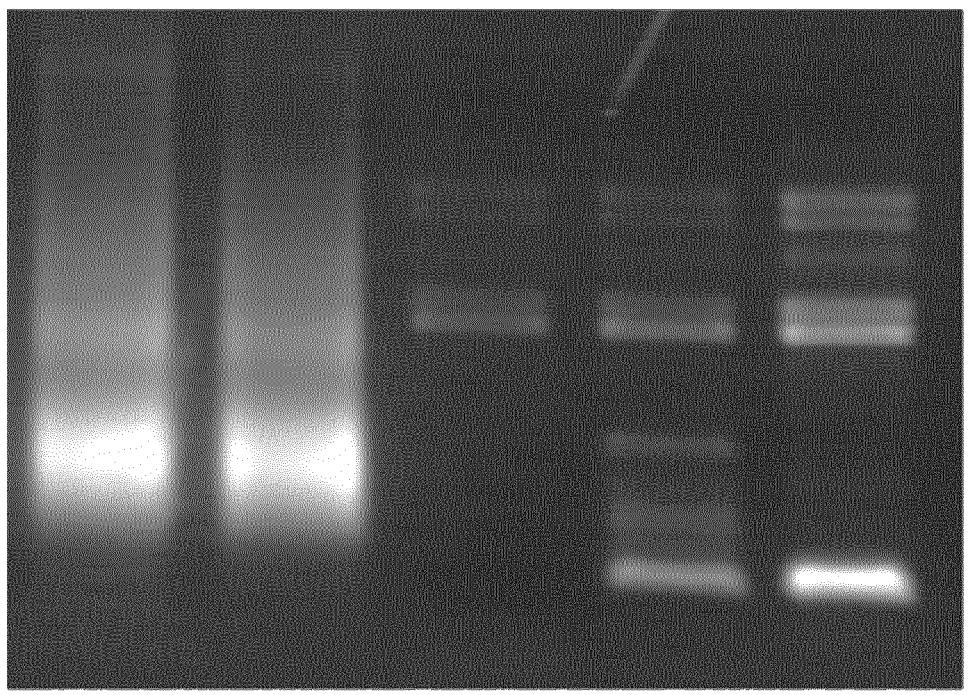
FIG. 4 Agarose gel of the PCR product amplified with the primers SYN1S and SYN1AS. The different lanes show L1: pSmoothy retroviral library 1 prior to transduction into CRC cells; L2: pSmoothy retroviral library 2 prior to transduction into CRC cells; HT29: control; S1: first sort of HT29-transduced cells; S2: second sort of HT29-transduced cells.

FIG. 4 shows a typical PCR from the genomic DNA of retrovirally-transduced HT29 cells using these primers, where amplification of several species occurs after the first sort (S1) with the FACS Aria. After the second sort (S2) a single product at 290 bp was amplified.

This process was then repeated using genomic DNA isolated from pSmoothy-transduced DLD-1, HCT-116 and RKO cell lines and isolated a total of 250 sequences with the potential to drive gene expression specifically in colorectal cancer cells.

Figure 5A:
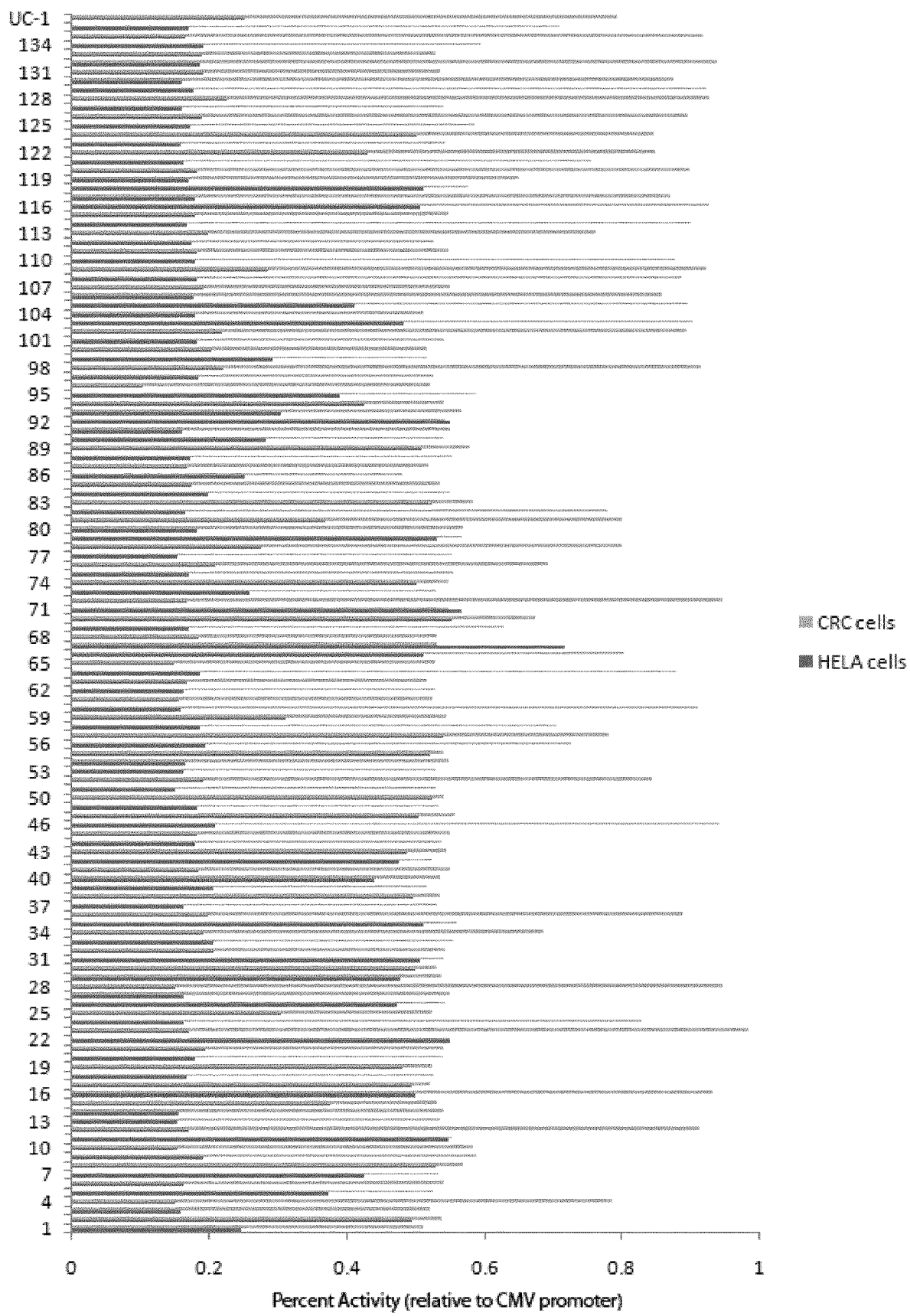
FIG. 5A Level of LacZ gene expression that was achieved in colorectal cancer cells (average of HT29, DLD-1, HCT-116 and RKO cells; upper column for each promoter; light gray) versus HELA control cells (lower column for each promoter; dark gray) from each of the 140 potential synthetic promoters (normalised to the level of expression obtained with the pCMV-beta control plasmid).

Then the ability of the 140 potential colon cancer-specific synthetic enhancer elements (CRCSE) to drive expression of the LacZ reporter gene was evaluated in all colorectal cancer cell lines under investigation: HT29, DLD1, RKO and HCT116 cells. 24 synthetic promoter elements were identified that were broadly able to drive a varying degree of LacZ expression across the four different colorectal cancer cell lines; ten of which were deemed to drive high expression and were chosen for further analysis. FIG. 5A shows the level of LacZ gene expression that was achieved in colorectal cancer cells (average of HT29, DLD-1, HCT-116 and RKO cells) versus HELA control cells from each of the 140 potential synthetic promoters (normalised to the level of expression obtained with the pCMV-beta control plasmid). From these cell lines 5 lines showing activity by two independent means of testing, i.e. betagalactosidase and staining of cells were selected. They correspond to numbers 001, 102, 103, 105, 106, 108 in FIG. 5A. The corresponding SEQ-IDs are shown in table 5. The sequences of the promoters without the mucin-1 minimum promoter are given in the SEQ-ID Nos. 130 to 135 for the sense and SEQ-ID Nos. 192 to 197 for the antisense strands.

Overall the results illustrated that the synthetic promoters constructed in this study only drive efficient gene expression in cell lines derived from patients with colorectal cancer. Specifically, high levels of beta-galactosidase expression was detected in HT29, RKO, HCT116, Dld-1 and Caco-2 cells, and minimal levels of gene expression was detected in Hela, Neuro2A, MCF-7, Panc-1, CV-1 and 3T3 cells. The results were further compared with cells transfected with vectors pCMV-beta (CMV promoter) and pDRIVE-Muc1 (Mucin-1 promoter; Invitrogen).

The results from one synthetic promoter CRCSE-1 (SEQ-ID No. 5, anti-sense strand SEQ-ID No. 11) are summarised in table 4 ((+++) high expression, (++) medium expression, (+) low expression, (+/−) very low expression, (−) no expression). These results clearly demonstrate that the selection procedure outlined in this example is capable of generating synthetic promoters with specific activity in colon cancer cells.

Figure 5B:
FIG. 5B LacZ expression of HT29 and NEURO2A cells transfected with different promoters (CMV-beta; Mucin-1; CRCSE SEQ ID No. 5).
Figure 5B:
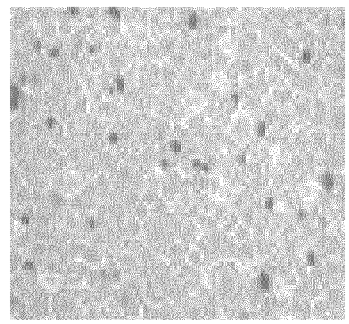
Figure 5B:
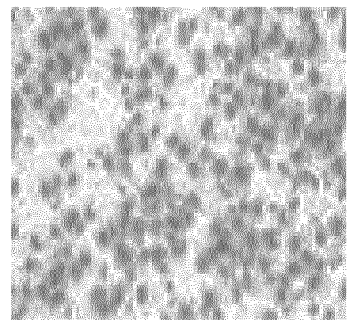
Figure 5B:
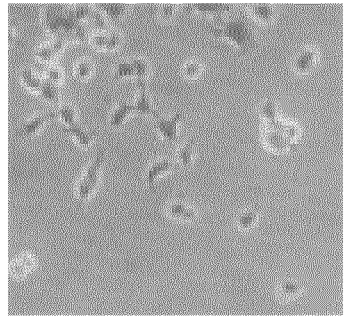
Figure 5B:
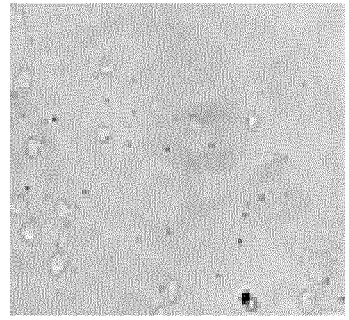
Figure 5B:
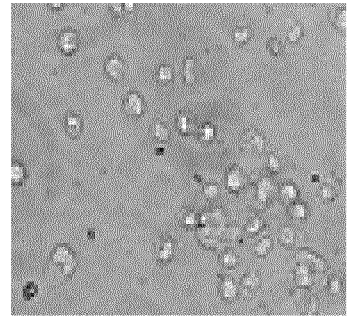

FIG. 5B shows representative expression levels of Lac Z mediated by CRCSE-1 (SEQ-ID No. 5; anti-sense strand SEQ-ID No. 68) in HT29 and Neuro2A cells transfected using Lipofectamine 2000 and stained for LacZ expression 48 hours posttransfection. Notably, control cell lines, including NEURO2A, NIH3T3, CV1, HELA and COS-7 cells, did not exhibit any expression of Lac Z when transfected with CRCSE-1 (table 4).

Within these sequences the following TFES could be identified using 86% homology as criteria. In total all the sequences used show a homology of approx. 72%. Table 5 shows the identified elements. The mutation was most likely introduced during the Neomycin selection procedure. Since the minimum promoter is an essential binding site there are less mutations within this region of each sequence.

It then was assessed whether the number of cis-elements present in each promoter is an important indicator of promoter strength and specificity. A process was carried out to select promoter sequences with a higher degree of stringency; i.e. to select promoters containing cis-elements with 100% homology to the input oligonucleotides. A further 82 sequences thus were subcloned from the promoter library isolated from CRC cell genomic DNA (described above) into pBluescript II KSM; the sequences of each clone were analysed prior to expression analysis. From these 82 sequences 55 were identified containing cis-regulatory elements with 100% homology to input oligonucleotides (SEQ-ID No. 11 to SEQ-ID No. 66; antisense strands SEQ-ID No. 68 to SEQ-ID No. 129, Tables 6 and 7; All these sequences comprise a Mucin-1 minimum promoter. The sequences without this promoter are also given in table 6). As controls, sequences were sub-cloned from the random ligation products of all ten cis-regulatory elements prior to selection in CRC cell lines. The results showed that on average, only 2.2 cis-regulatory elements per sequence were found in unselected sequences, compared to 4.0 elements per promoter subjected to selection through the CRC cell lines ($p<0.001$; Mann-Whitney non-parametric test). Indeed, only 3/22 sequences in the control group contained four or more cis-regulatory elements, compared to over 31/55 promoters containing four or more cis-elements from the group subjected to selection. Moreover, cis-elements with a SYN value greater than 0.6 represented 70.0% of all the elements in the 55 identified promoters, thus confirming the importance of the SYN selection formula. To correlate the presence of specific cis-regulatory elements to level and specificity of expression, 28/31 promoters were inserted into the pSmoothy retroviral vector and their ability to drive GFP expression in CRC cells compared to the HELA control cell line was monitored.

Figure 6A:
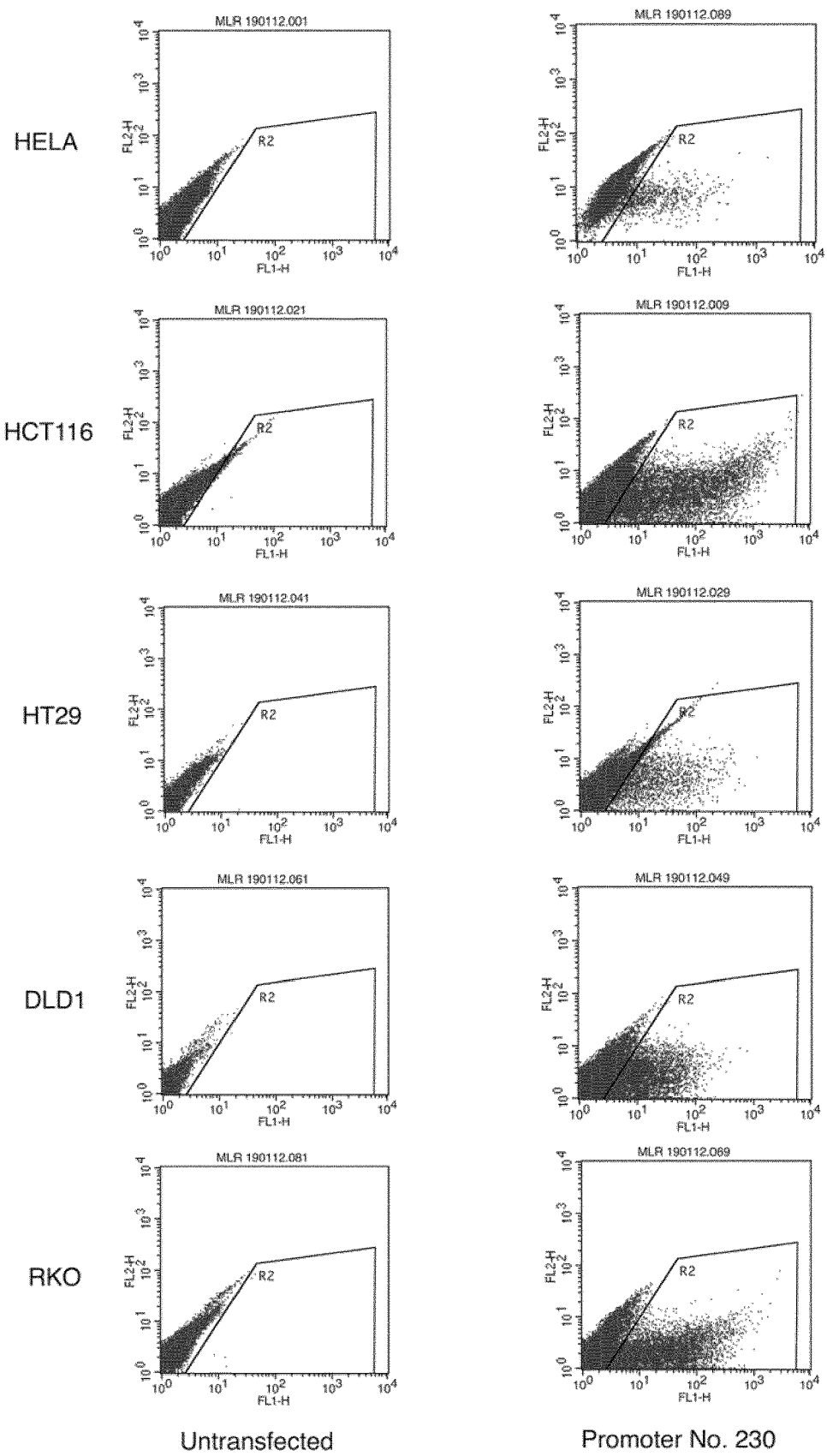
FIG. 6A FACS analysis demonstrating the proportion of cells expressing GFP from a promoter with average activity in control HELA cells and CRC Cell lines; HCT116, HT29, DLD1 and RKO. GFP cells are present in the R2 gate.
Figure 6B:
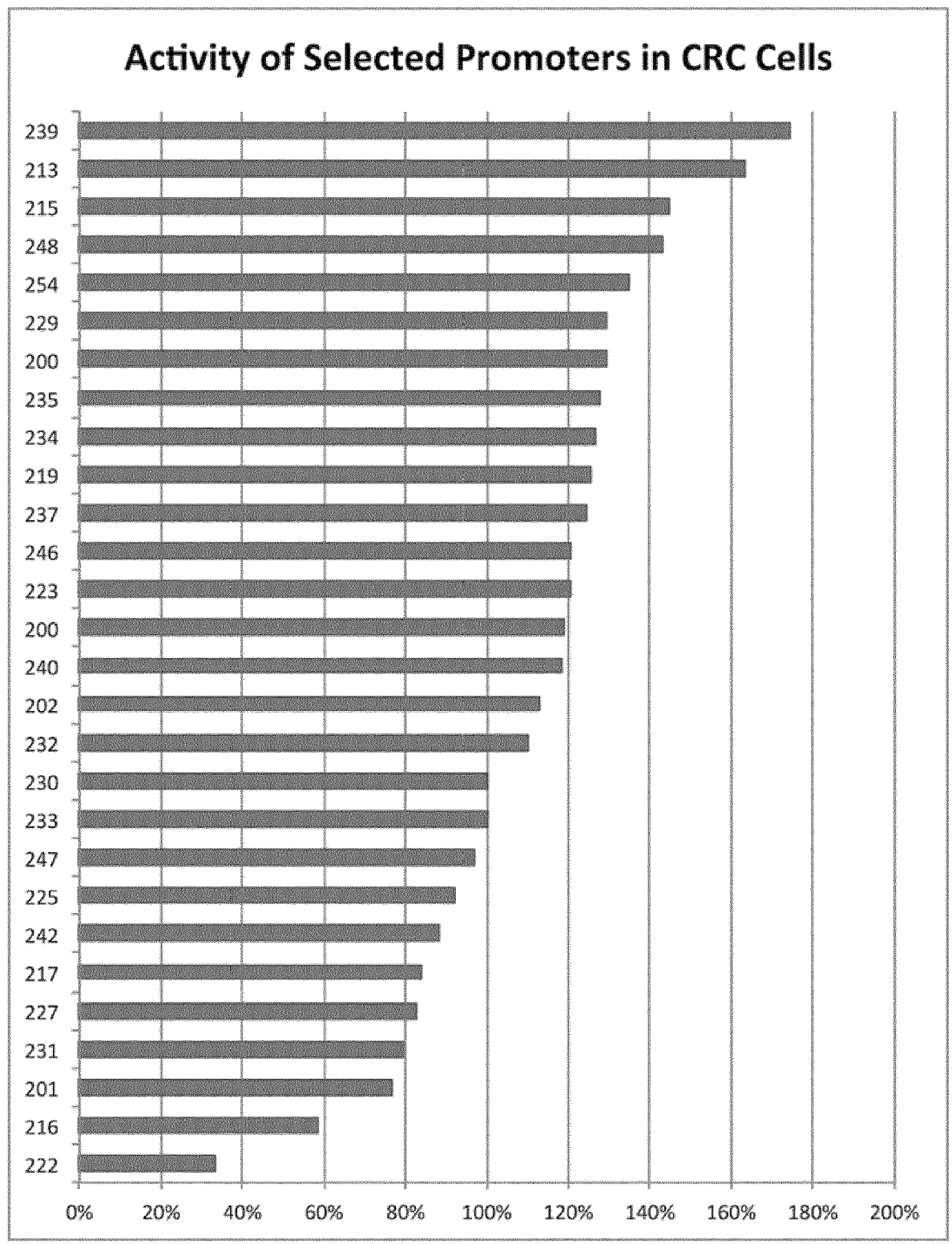
FIG. 6B Activity measurements on different promoters generated by an embodiment of the method of the invention.

Efficiency of GFP expression was determined by FACS analysis and the proportion of cells fluorescing above a threshold value of 200 units on the FL1 channel was determined for all promoters. Depending on the cell line, an average 1.0-10.0% of the cells expressing GFP demonstrated fluorescence above this level. All promoters analysed generated significantly higher levels of expression in CRC cell lines (HCT116, HT29, DLD1 and RKO) when compared to the HELA control cell line; where only a small proportion of cells were GFP positive. This is illustrated in FIG. 6A, which comprises the FACS results from promoter 230; a synthetic promoter that expressed GFP to average levels in all CRC cell lines; see FIG. 6B. To identify which promoters were the most efficient, an expression ratio for each promoter in all cell lines was determined; this expression ratio was defined as the proportion of cells expressing GFP above the threshold value for each individual promoter divided by the average proportion above the threshold for all promoters. The results of this analysis are shown in FIG. 6B, which illustrates that promoters 239, 213, 215, 248 and 254 show the highest activity in all CRC cell lines compared to the other promoters.

We further examined which cis-elements constituted these more efficient promoters and found that on average the five cis-elements with the highest SYN value represented 64% of all the regulatory elements in each promoter. Thus further demonstrating the importance of the SYN value for selecting the optimal elements to maximise efficient and selective expression.

Taken together the results demonstrate that the SYN selection formula and the methods provided herein represent a useful tool in selecting cis-regulatory elements (i.e., TFREs) for inclusion in synthetic promoter libraries. Several promoters were constructed using the described methodology that could efficiently express GFP or Lac Z specifically in CRC cell lines, whilst showing no or limited activity in control cells. It is proposed that this method can be applied in the construction of any eukaryotic promoter designed to be active in specific environmental or diseased conditions.

While the present inventions have been described and illustrated in conjunction with a number of specific embodiments, those skilled in the art will appreciate that variations and modifications may be made without departing from the principles of the inventions as herein illustrated, as described and claimed. The present inventions may be embodied in other specific forms without departing from their spirit or essential characteristics. The described embodiments are considered in all respects to be illustrative and not restrictive. The scope of the inventions is, therefore, indicated by the appended claims, rather than by the foregoing description. All changes which come within the meaning and range of equivalence of the claims are to be embraced within their scope.

REFERENCES CITED

Rhodes, D. R. et al. Mining for regulatory programs in the cancer transcriptome. *Nat. Genet.* 37, 579-583 (2005);

Segal, E., Friedman, N., Koller, D., & Regev, A. A module map showing conditional activity of expression modules in cancer. *Nat. Genet.* 36, 1090-1098 (2004);

Segal, E. et al. Module networks: identifying regulatory modules and their condition-specific regulators from gene expression data. Nat. Genet. 34, 166-176 (2003);

Wingender, E. Compilation of transcription regulating proteins. *Nucleic Acids Res* 16, 1879-1902 (1988);

Kel-Margoulis, O. V., Kel, A. E., Reuter, I., Deineko, I. V., & Wingender, E. TRANSCompel: a database on composite regulatory elements in eukaryotic genes. *Nucleic Acids Res* 30, 332-334 (2002);

Blanco, E., Farre, D., Alba, M. M., Messeguer, X., & Guigo, R. ABS: a database of Annotated regulatory Binding Sites from orthologous promoters. *Nucleic Acids Res* 34, D63-D67 (2006);

Sandelin, A., Alkema, W., Engstrom, P., Wasserman, W. W., & Lenhard, B. JASPAR: an open-access database for eukaryotic transcription factor binding profiles. *Nucleic Acids Res* 32, D91-D94 (2004);

Jagannathan, V., Roulet, E., Delorenzi, M., & Bucher, P. HTPSELEX—a database of high-throughput SELEX libraries for transcription factor binding sites. *Nucleic Acids Res* 34, D90-D94 (2006);

Matys, V. et al. TRANSFAC: transcriptional regulation, from patterns to profiles. *Nucleic Acids Res* 31, 374-378 (2003);

Zhao, F., Xuan, Z., Liu, L., & Zhang, M. Q. TRED: a Transcriptional Regulatory Element Database and a platform for in silico gene regulation studies. *Nucleic Acids Res* 33, D103-D107 (2005);

Sinha, S. & Tompa, M. YMF: A program for discovery of novel transcription factor binding sites by statistical overrepresentation. *Nucleic Acids Res* 31, 3586-3588 (2003);

Sinha, S. & Tompa, M. Discovery of novel transcription factor binding sites by statistical overrepresentation. *Nucleic Acids Res* 30, 5549-5560 (2002);

Rebeiz, M., Reeves, N. L., & Posakony, J. W. SCORE: a computational approach to the identification of cis-regulatory modules and target genes in whole-genome sequence data. Site clustering over random expectation. *Proc. Natl. Acad. Sci. U.S.A* 99, 9888-9893 (2002);

Suzuki, Y., Yamashita, R., Sugano, S., & Nakai, K. DBTSS, DataBase of Transcriptional Start Sites: progress report 2004. *Nucleic Acids Res* 32, D78-D81 (2004);

Suzuki, Y., Yamashita, R., Nakai, K., & Sugano, S. DBTSS: DataBase of human Transcriptional Start Sites and full-length cDNAs. *Nucleic Acids Res* 30, 328-331 (2002);

Davuluri, R. V., Grosse, I., & Zhang, M. Q. Computational identification of promoters and first exons in the human genome. *Nat. Genet.* 29, 412-417 (2001);

Roth, F. P., Hughes, J. D., Estep, P. W., & Church, G. M. Finding DNA regulatory motifs within unaligned noncoding sequences clustered by whole-genome mRNA quantitation. *Nat. Biotechnol.* 16, 939-945 (1998);

Bussemaker, H. J., Li, H., & Siggia, E. D. Regulatory element detection using correlation with expression. *Nat. Genet.* 27, 167-171 (2001);

Jensen, L. J. & Knudsen, S. Automatic discovery of regulatory patterns in promoter regions based on whole cell expression data and functional annotation. *Bioinformatics.* 16, 326-333 (2000);

Jegga, A. G. et al. Detection and visualization of compositionally similar cis-regulatory element clusters in orthologous and coordinately controlled genes. *Genome Res* 12, 1408-1417 (2002);

Dieterich, C., Wang, H., Rateitschak, K., Luz, H., & Vingron, M. CORG: a database for Comparative Regulatory Genomics. *Nucleic Acids Res* 31, 55-57 (2003);

Lenhard, B. et al. Identification of conserved regulatory elements by comparative genome analysis. *J. Biol.* 2, 13 (2003);

Karanam, S. & Moreno, C. S. CONFAC: automated application of comparative genomic promoter analysis to DNA microarray datasets. *Nucleic Acids Res* 32, W475-W484 (2004);

La Rosa, P. et al. VAMP: visualization and analysis of array-CGH, transcriptome and other molecular profiles. *Bioinformatics.* 22, 2066-2073 (2006);

Jegga, A. G. et al. CisMols Analyzer: identification of compositionally similar cis-element clusters in ortholog conserved regions of coordinately expressed genes. *Nucleic Acids Res* 33, W408-W411 (2005);

Blanchette, M. et al. Genome-wide computational prediction of transcriptional regulatory modules reveals new insights into human gene expression. *Genome Res* 16, 656-668 (2006);

Ferretti, V. et al. PReMod: a database of genome-wide mammalian cis-regulatory module predictions. *Nucleic Acids Res* 35, D122-D126 (2007);

Sharov, A. A., Dudekula, D. B., & Ko, M. S. CisView: a browser and database of cis-regulatory modules predicted in the mouse genome. *DNA Res* 13, 123-134 (2006);

Vega, V. B., Bangarusamy, D. K., Miller, L. D., Liu, E. T., & Lin, C. Y. BEARR: Batch Extraction and Analysis of cis-Regulatory Regions. *Nucleic Acids Res* 32, W257-W260 (2004);

Dubchak, I. & Ryaboy, D. V. VISTA family of computational tools for comparative analysis of DNA sequences and whole genomes. *Methods Mol. Biol.* 338, 69-89 (2006);

Lardenois, A. et al. PromAn: an integrated knowledge-based web server dedicated to promoter analysis. *Nucleic Acids Res* 34, W578-W583 (2006);

Liu, C. C. et al. CRSD: a comprehensive web server for composite regulatory signature discovery. *Nucleic Acids Res* 34, W571-W577 (2006);

Sun, H. et al. MPromDb: an integrated resource for annotation and visualization of mammalian gene promoters and ChIP-chip experimental data. *Nucleic Acids Res* 34, D98-103 (2006);

Li, X., Eastman, E. M., Schwartz, R. J., & Draghia-Akli, R. Synthetic muscle promoters: activities exceeding naturally occurring regulatory sequences. *Nat. Biotechnol.* 17, 241-245 (1999);

Dai, C., McAninch, R. E., & Sutton, R. E. Identification of synthetic endothelial cell-specific promoters by use of a high-throughput screen. *J. Virol.* 78, 6209-6221 (2004);

Needleman-Wunsch, J. Mol. Biol. 48, 443-453, (1970);

Sambrook (2001) Molecular Cloning: a laboratory manual, 3rd Edition Cold Spring Harbor Laboratory Press, CSH, New York Rhodes et al (2004) PNAS 2004; 101; 9309-14;

Edelman et al (2000) [PNAS 97 (7), 3038-43;

TABLE 1

| Resource | Description | Citation |
|---|---|---|
| DBTSS | Database of transcriptional start sites | Suzuki, Y., Yamashita, R., Nakai, K., & Sugano, S. DBTSS: DataBase of human Transcriptional Start Sites and full-length cDNAs. *Nucleic Acids Res* 30, 328-331 (2002). |
| TRAFAC | Conserved cis-element search tool | Jegga, A. G. et al. Detection and visualization of compositionally similar cis-regulatory element clusters in orthologous and coordinately controlled genes. *Genome Res* 12, 1408-1417 (2002). |
| TRANSCompel | Database of composite regulatory elements | Kel-Margoulis, O. V., Kel, A. E., Reuter, I., Deineko, I. V., & Wingender, E. TRANSCompel: a database on composite regulatory elements in eukaryotic genes. *Nucleic Acids Res* 30, 332-334 (2002). |
| TRANSFAC | Eukaryotic transcription factor database | Matys, V. et al. TRANSFAC: transcriptional regulation, from patterns to profiles. *Nucleic Acids Res* 31, 374-378 (2003). |
| Phylofoot | Tools for phylogenetic footprinting purposes | Lenhard, B. et al. Identification of conserved regulatory elements by comparative genome analysis. *J. Biol.* 2, 13 (2003). |
| CORG | Multi-species DNA comparison and annotation | Dieterich, C., Wang, H., Rateitschak, K., Luz, H., & Vingron, M. CORG: a database for COmparative Regulatory Genomics. *Nucleic Acids Res* 31, 55-57 (2003). |

TABLE 1-continued

| Resource | Description | Citation |
|---|---|---|
| CONSITE | Explores trans-factor binding sites from two species | Lenhard, B. et al. Identification of conserved regulatory elements by comparative genome analysis. *J. Biol.* 2, 13 (2003). |
| CONFAC | Conserved transcription factor binding site finder | Karanam, S. & Moreno, C. S. CONFAC: automated application of comparative genomic promoter analysis to DNA microarray datasets. *Nucleic Acids Res* 32, W475-W484 (2004). |
| CisMols | Identifies cis-regulatory modules from inputed data | Jegga, A. G. et al. CisMols Analyzer: identification of compositionally similar cis-element clusters in ortholog conserved regions of coordinately expressed genes. *Nucleic Acids Res* 33, W408-W411 (2005). |
| TRED | Catalogue of transcription regulatory elements | Zhao, F., Xuan, Z., Liu, L., & Zhang, M. Q. TRED: a Transcriptional Regulatory Element Database and a platform for in silico gene regulation studies. *Nucleic Acids Res* 33, D103-D107 (2005). |
| Oncomine | Repository and analysis of cancer microarray data | Rhodes, D. R. et al. Mining for regulatory programs in the cancer transcriptome. *Nat. Genet.* 37, 579-583 (2005). |
| ABS | Database of regulatory elements | Blanco, E., Farre, D., Alba, M. M., Messeguer, X., & Guigo, R. ABS: a database of Annotated regulatory Binding Sites from orthologous promoters. *Nucleic Acids Res* 34, D63-D67 (2006). |
| JASPAR | Database of regulatory elements | Sandelin, A., Alkema, W., Engstrom, P., Wasserman, W. W., & Lenhard, B. JASPAR: an open-access database for eukaryotic transcription factor binding profiles. *Nucleic Acids Res* 32, D91-D94 (2004). |
| HTPSELEX | Database of composite regulatory elements | Jagannathan, V., Roulet, E., Delorenzi, M., & Bucher, P. HTPSELEX--a database of high-throughput SELEX libraries for transcription factor binding sites. *Nucleic Acids Res* 34, D90-D94 (2006). |
| PReMod | Database of transcriptional regulatory modules in the human genome | Blanchette, M. et al. Genome-wide computational prediction of transcriptional regulatory modules reveals new insights into human gene expression. *Genome Res* 16, 656-668 (2006). |
| CisView | Browser of regulatory motifs and regions in the genome | Sharov, A. A., Dudekula, D. B., & Ko, M. S. CisView: a browser and database of cis-regulatory modules predicted in the mouse genome. *DNA Res* 13, 123-134 (2006). |

TABLE 1-continued

| Resource | Description | Citation |
|---|---|---|
| BEARR | Batch extraction algorithm for microarray data analysis | Vega, V. B., Bangarusamy, D. K., Miller, L. D., Liu, E. T., & Lin, C. Y. BEARR: Batch Extraction and Analysis of cis-Regulatory Regions. *Nucleic Acids Res* 32, W257-W260 (2004). |
| VISTA | Align and compare sequences from multiple species | Dubchak, I. & Ryaboy, D. V. VISTA family of computational tools for comparative analysis of DNA sequences and whole genomes. *Methods Mol. Biol.* 338, 69-89 (2006). |
| PromAn | Promoter analysis by integrating a variety of databases | Lardenois, A. et al. PromAn: an integrated knowledge-based web server dedicated to promoter analysis. *Nucleic Acids Res* 34, W578-W583 (2006). |
| CRSD | Composite regulatory signature database | Liu, C. C. et al. CRSD: a comprehensive web server for composite regulatory signature discovery. *Nucleic Acids Res* 34, W571-W577 (2006). |
| MPromDb | Portal for genome-wide promoter analysis | Sun, H. et al. MPromDb: an integrated resource for annotation and visualization of mammalian gene promoters and ChIP-chip experimental data. *Nucleic Acids Res* 34, D98-103 (2006). |

TABLE 2

| | Accesion Number | Chromosome Location | Expression Levels |
|---|---|---|---|
| TOP2A* | NM_001067 | 17q21-q22 | |
| E2F5 | NM_001951 | 8q21.2 | |
| PRDX4 | NM_006406 | Xp22.11 | + |
| SMARCA4* | NM_003072 | 19p13.2 | |
| PLK | NM_005030 | 16p12.1 | +++ |
| KPNA2 | NM_002266 | 17q24.2 | |
| CCT5 | NM_012073 | 5p15.2 | |
| TRAF4* | NM_004295 | 17q11-q12 | |
| E2-EPF | M91670 | 19q13.43 | +++ |
| G3BP | NM_005754 | 5q33.1 | ++ |
| PSME2 | NM_002818 | 14q11.2 | |
| CDC2 | NM_001786 | 10q21.1 | ++ |
| MCM3 | NM_002388 | 6p12 | + |
| LDHA | NM_005566 | 11p15.4 | |
| MMP9 | NM_004994 | 20q11.2-q13.1 | + |
| HDAC1 | NM_004964 | 1p34 | |
| COL1A2 | NM_000089 | 7q22.1 | |

TABLE 3

| Frequency | SYN value | Sequence | Identifiers | Gene % | Trans Factors |
|---|---|---|---|---|---|
| 90/5852 | 0.593426961 | ATGCAAAT | TFE1: gg-5, gg-7, gg-9, gg-10, gg-11, il3-11, igh-2, u2sn-6, u2sn-1 | 4/7 | POU2F1, POU2F2, gamma-OBP, GATA-1, NF-A, Octa-factor |
| 154/5852 | 0.594724494 | TGACTCA | TFE2: gm-csf-16, ag-10, cycd1-01, bg-41, gfap-04, MT-2A-08, ag-07 | 7/7 | Ap-1, c-fos, c-jun, NF-E2, AP-2alphaA, Fra-1, v-Jun |
| 80/5852 | 0.58475401 | ATTTGCAT | TFE3: h2b-01, igkl-5, igkl-6, m2dra-4, u4csn-1, m2dra-5, m2dra-6, lpl-3 | 4/7 | POU2F1, POU2F2, CREN, NF-A, Oct-B2, |
| 165/5852 | 0.600616265 | AACAAAG | TFE4: sry-01, ada-08, cd3e-01 | 7/7 | SRY, LEF-1, Mat1-Mc, Sox-13, Sox-5, TCF-1, TCF-1A, TCF-1B, TCF-1C, TCF-1E, TCF-1F, TCF-1G |
| 88/5852 | 0.549031051 | TGAGTCA | TFE5: bg-50, il3-02, ag-11, mmp3-02 | 7/7 | Ap-1, c-fos, c-jun, MafG, NF-E2 |
| 89/5852 | 0.628072127 | CCTCCCAAA | TFE6: cd8a-03 | 7/7 | LyF-1 |
| 45/5852 | 0.544174923 | TGACATCA | TFE7: pth-01, cjun-12, act2-01 | 6/7 | CREB, c-jun, AP-1 |
| 90/5852 | 0.550796498 | TTCAAAG | TFE8: cd3E-02, mmp7-02, tcf1-01 | 7/7 | TCF-4, SRY, TCF-1A |

TABLE 3-continued

| Frequency | SYN value | Sequence | Identifiers | Gene % | Trans Factors |
|---|---|---|---|---|---|
| 69/5852 | 0.530281402 | CTTTGAT | TFE9: c-myc-19, c-myc-20, cycD1 | 5/7 | TCF-4E |
| 9/5852 | 0.723347374 | GCTGGGATTA CAGGTGTGAG | TFE10: plod1-02 | 5/7 | PITX2 (SEQ ID No. 1) Anti-sense: SEQ ID No. 67 |

TABLE 4

| | | Level of beta-galactoside activity | | |
|---|---|---|---|---|
| Cell Line | Source | CMV-beta | Mucin Promoter | CRCSEs (synthetic) |
| HT29 | Human Colon Adenocarcinoma | +++ | ++ | +++ |
| HCT116 | Human Colon Carcinoma | ++ | + | ++ |
| DLD-1 | Human Colon Adenocarcinoma | ++ | + | ++ |
| RKO | Human Colon Carcinoma | + | +/− | +/− |
| NEURO2A | Mouse Neuroblastoma | +++ | − | − |
| NIH3T3 | Mouse Fibroblasts | +++ | − | − |
| CV1 | Monkey Fibroblasts | ++ | − | − |
| HELA | Human Ovarian Cancer | ++ | − | − |
| COS-7 | Monkey Fibroblasts | ++ | − | − |
| MCF-7 | Human Breast Cancer | +++ | − | − |
| Panc-1 | Human Pancreatic Cancer | ++ | − | − |

TABLE 5

| Promotor Sense strand (S) Anti-sense strand (AS) | TFES (homology) | Position |
|---|---|---|
| No. 001 (CRCSE-1): S: SEQ-ID No. 5 AS: SEQ-ID No. 68 | TFE4 (86%) TFE4 (86%) TFE10 (100%) | 224-230 (AS) 51-57 (S) 184-203 (AS) |
| No. 102 S: SEQ-ID No. 6 AS: SEQ-ID No. 69 | TFE9 (100%) TFE10 (95%) TFE8 (100%) TFE5 (100%) TFE1 (100%) | 68-74 (S) 236-256 (AS) 107-113 (S) 120-126 (S) 146-153 (S) |
| No. 103 S: SEQ-ID No. 7 AS: SEQ-ID No. 70 | TFE6 (100%) TFE5 (100%) TFE8 (100%) | 208-216 (AS) 195-201 (AS) 182-188 (AS) |
| No. 105 S: SEQ-ID No. 8 AS: SEQ-ID No. 71 | TFE8 (100%) TFE1 (100%) TFE9 (100%) TFE1 (100%) TFE9 (100%) | 250-256 (AS) 222-230 (AS) 136-142 (S) 196-203 (AS) 184-190 (AS) |
| No. 106 S: SEQ-ID No. 9 AS: SEQ-ID No. 72 | TFE4 (86%) TFE4 (86%) TFE4 (86%) | 288-294 (AS) 198-204 (AS) 103-109 (S) |
| No. 108 S: SEQ-ID No. 10 AS: SEQ-ID No. 73 | TFE4 (86%) TFE4 (86%) | 198-204 (AS) 48-54 (S) |

TABLE 6

| Promoter | Seq-ID No. Sense/Antisense | Seq-ID No. without MUC-1 min. prom. Sense/Antisense | No. TFE |
|---|---|---|---|
| Pro_200 | 11/74 | 136/198 | 5 |
| Pro_201 | 12/75 | 137/199 | 4 |
| Pro_202 | 13/76 | 138/200 | 9 |
| Pro_203 | 14/77 | 139/201 | 1 |
| Pro_204 | 15/78 | 140/202 | 3 |
| Pro_205 | 16/79 | 141/203 | 2 |
| Pro_206 | 17/80 | 142/204 | 3 |
| Pro_207 | 18/81 | 143/205 | 1 |
| Pro_208 | 19/82 | 144/206 | 2 |
| Pro_209 | 20/83 | 145/207 | 3 |
| Pro_210 | 21/84 | 146/208 | 1 |
| Pro_211 | 22/85 | 147/209 | 2 |
| Pro_212 | 23/86 | 148/210 | 1 |
| Pro_213 | 24/87 | 149/211 | 6 |
| Pro_214 | 25/88 | 150/212 | 4 |
| Pro_215 | 26/89 | 151/213 | 5 |
| Pro_216 | 27/90 | 152/214 | 4 |
| Pro_217 | 28/91 | 153/215 | 5 |
| Pro_218 | 29/92 | 154/216 | 1 |
| Pro_219 | 30/93 | 155/217 | 5 |
| Pro_220 | 31/94 | 156/218 | 1 |
| Pro_221 | 32/95 | 157/219 | 2 |
| Pro_222 | 33/96 | 158/220 | 4 |
| Pro_223 | 34/97 | 159/221 | 8 |
| Pro_224 | 35/98 | 160/222 | 2 |
| Pro_225 | 36/99 | 161/223 | 6 |
| Pro_226 | 37/100 | 162/224 | 7 |
| Pro_227 | 38/101 | 163/225 | 5 |
| Pro_228 | 39/102 | 164/226 | 3 |
| Pro_229 | 40/103 | 165/227 | 4 |
| Pro_230 | 41/104 | 166/228 | 4 |
| Pro_231 | 42/105 | 167/229 | 5 |
| Pro_232 | 43/106 | 168/230 | 4 |
| Pro_233 | 44/107 | 169/231 | 4 |
| Pro_234 | 45/108 | 170/232 | 6 |
| Pro_235 | 46/109 | 171/233 | 5 |
| Pro_236 | 47/110 | 172/234 | 3 |
| Pro_237 | 48/111 | 173/235 | 11 |
| Pro_238 | 49/112 | 174/236 | 3 |
| Pro_239 | 50/113 | 175/237 | 6 |
| Pro_240 | 51/114 | 176/238 | 4 |
| Pro_241 | 52/115 | 177/239 | 1 |
| Pro_242 | 53/116 | 178/240 | 6 |
| Pro_243 | 54/117 | 179/241 | 2 |
| Pro_244 | 55/118 | 180/242 | 2 |
| Pro_245 | 56/119 | 181/243 | 3 |
| Pro_246 | 57/120 | 182/244 | 4 |
| Pro_247 | 58/121 | 183/245 | 6 |
| Pro_248 | 59/122 | 184/246 | 8 |
| Pro_249 | 60/123 | 185/247 | 2 |
| Pro_250 | 61/124 | 186/248 | 5 |
| Pro_251 | 62/125 | 187/249 | 1 |
| Pro_252 | 63/126 | 188/250 | 4 |
| Pro_253 | 64/127 | 189/251 | 3 |
| Pro_254 | 65/128 | 190/252 | 4 |
| Pro_255 | 66/129 | 191/253 | 2 (86%) |

TABLE 7

| Promoter Name | cis Element | Sequence | Start | End | [bp] | Direction |
|---|---|---|---|---|---|---|
| Pro_200 | TFE2 | TGACTCA | 72 | 78 | 7 | reverse |
| Pro_200 | TFE2(AS) | TGAGTCA | 72 | 78 | 7 | forward |
| Pro_200 | TFE3 | ATTTGCAT | 58 | 65 | 8 | forward |
| Pro_200 | TFE3(AS) | ATGCAAAT | 58 | 65 | 8 | reverse |
| Pro_200 | TFE4 | AACAAAG | 45 | 51 | 7 | forward |
| Pro_200 | TFE4 | AACAAAG | 85 | 91 | 7 | reverse |
| Pro_200 | TFE4(AS) | CTTTGTT | 45 | 51 | 7 | reverse |
| Pro_200 | TFE4(AS) | CTTTGTT | 85 | 91 | 7 | forward |
| Pro_200 | TFE7 | TGACATCA | 98 | 105 | 8 | forward |
| Pro_200 | TFE7(AS) | TGATGTCA | 98 | 105 | 8 | reverse |
| Pro_201 | TFE1 | ATGCAAAT | 72 | 79 | 8 | forward |
| Pro_201 | TFE1 | ATGCAAAT | 86 | 93 | 8 | reverse |
| Pro_201 | TFE1(AS) | ATTTGCAT | 72 | 79 | 8 | reverse |
| Pro_201 | TFE1(AS) | ATTTGCAT | 86 | 93 | 8 | forward |
| Pro_201 | TFE4 | AACAAAG | 59 | 65 | 7 | forward |
| Pro_201 | TFE4(AS) | CTTTGTT | 59 | 65 | 7 | reverse |
| Pro_201 | TFE7 | TGACATCA | 45 | 52 | 8 | reverse |
| Pro_201 | TFE7(AS) | TGATGTCA | 45 | 52 | 8 | forward |
| Pro_202 | TFE1 | ATGCAAAT | 84 | 91 | 8 | reverse |
| Pro_202 | TFE1(AS) | ATTTGCAT | 84 | 91 | 8 | forward |
| Pro_202 | TFE2 | TGACTCA | 58 | 64 | 7 | reverse |
| Pro_202 | TFE2 | TGACTCA | 71 | 77 | 7 | forward |
| Pro_202 | TFE2 | TGACTCA | 113 | 119 | 7 | forward |
| Pro_202 | TFE2(AS) | TGAGTCA | 58 | 64 | 7 | forward |
| Pro_202 | TFE2(AS) | TGAGTCA | 71 | 77 | 7 | reverse |
| Pro_202 | TFE2(AS) | TGAGTCA | 113 | 119 | 7 | reverse |
| Pro_202 | TFE4 | AACAAAG | 45 | 51 | 7 | forward |
| Pro_202 | TFE4 | AACAAAG | 126 | 132 | 7 | forward |
| Pro_202 | TFE4(AS) | CTTTGTT | 45 | 51 | 7 | reverse |
| Pro_202 | TFE4(AS) | CTTTGTT | 126 | 132 | 7 | reverse |
| Pro_202 | TFE6 | CCTCCCAAA | 98 | 106 | 9 | forward |
| Pro_202 | TFE6(AS) | TTTGGGAGG | 98 | 106 | 9 | reverse |
| Pro_202 | TFE8 | TTCAAAG | 152 | 158 | 7 | reverse |
| Pro_202 | TFE8(AS) | CTTTGAA | 152 | 158 | 7 | forward |
| Pro_202 | TFE9 | CTTTGAT | 139 | 145 | 7 | forward |
| Pro_202 | TFE9(AS) | ATCAAAG | 139 | 145 | 7 | reverse |
| Pro_203 | TFE4 | AACAAAG | 45 | 51 | 7 | forward |
| Pro_203 | TFE4(AS) | CTTTGTT | 45 | 51 | 7 | reverse |
| Pro_204 | TFE1 | ATGCAAAT | 60 | 67 | 8 | forward |

TABLE 7-continued

| Promoter Name | cis Element | Sequence | Start | End | [bp] | Direction |
|---|---|---|---|---|---|---|
| Pro_204 | TFE1(AS) | ATTTGCAT | 60 | 67 | 8 | reverse |
| Pro_204 | TFE2 | TGACTCA | 74 | 80 | 7 | reverse |
| Pro_204 | TFE2(AS) | TGAGTCA | 74 | 80 | 7 | forward |
| Pro_204 | TFE6 | CCTCCCAAA | 45 | 53 | 9 | reverse |
| Pro_204 | TFE6(AS) | TTTGGGAGG | 45 | 53 | 9 | forward |
| Pro_205 | TFE2 | TGACTCA | 45 | 51 | 7 | forward |
| Pro_205 | TFE2(AS) | TGAGTCA | 45 | 51 | 7 | reverse |
| Pro_205 | TFE10 | GCTGGGATTACAGGTGTGAG | 58 | 77 | 20 | reverse |
| Pro_205 | TFE10(AS) | CTCACACCTGTAATCCCAGC | 58 | 77 | 20 | forward |
| Pro_206 | TFE4 | AACAAAG | 58 | 64 | 7 | forward |
| Pro_206 | TFE4(AS) | CTTTGTT | 58 | 64 | 7 | reverse |
| Pro_206 | TFE8 | TTCAAAG | 45 | 51 | 7 | reverse |
| Pro_206 | TFE8(AS) | CTTTGAA | 45 | 51 | 7 | forward |
| Pro_206 | TFE10 | GCTGGGATTACAGGTGTGAG | 71 | 90 | 20 | reverse |
| Pro_206 | TFE10(AS) | CTCACACCTGTAATCCCAGC | 71 | 90 | 20 | forward |
| Pro_207 | TFE10 | GCTGGGATTACAGGTGTGAG | 45 | 64 | 20 | reverse |
| Pro_207 | TFE10(AS) | CTCACACCTGTAATCCCAGC | 45 | 64 | 20 | forward |
| Pro_208 | TFE6 | CCTCCCAAA | 45 | 53 | 9 | reverse |
| Pro_208 | TFE6(AS) | TTTGGGAGG | 45 | 53 | 9 | forward |
| Pro_208 | TFE7 | TGACATCA | 60 | 67 | 8 | reverse |
| Pro_208 | TFE7(AS) | TGATGTCA | 60 | 67 | 8 | forward |
| Pro_209 | TFE8 | TTCAAAG | 37 | 43 | 7 | forward |
| Pro_209 | TFE8(AS) | CTTTGAA | 37 | 43 | 7 | reverse |
| Pro_209 | TFE9 | CTTTGAT | 50 | 56 | 7 | forward |
| Pro_209 | TFE9(AS) | ATCAAAG | 50 | 56 | 7 | reverse |
| Pro_209 | TFE10 | GCTGGGATTACAGGTGTGAG | 63 | 82 | 20 | forward |
| Pro_209 | TFE10(AS) | CTCACACCTGTAATCCCAGC | 63 | 82 | 20 | reverse |
| Pro_210 | TFE1 | ATGCAAAT | 58 | 65 | 8 | reverse |
| Pro_210 | TFE1(AS) | ATTTGCAT | 58 | 65 | 8 | forward |
| Pro_211 | TFE2 | TGACTCA | 45 | 51 | 7 | forward |
| Pro_211 | TFE2(AS) | TGAGTCA | 45 | 51 | 7 | reverse |
| Pro_211 | TFE4 | AACAAAG | 58 | 64 | 7 | reverse |
| Pro_211 | TFE4(AS) | CTTTGTT | 58 | 64 | 7 | forward |
| Pro_212 | TFE6 | CCTCCCAAA | 45 | 53 | 9 | forward |

TABLE 7-continued

| Promoter Name | cis Element | Sequence | Start | End | [bp] | Direction |
|---|---|---|---|---|---|---|
| Pro_212 | TFE6(AS) | TTTGGGAGG | 45 | 53 | 9 | reverse |
| Pro_213 | TFE2 | TGACTCA | 125 | 131 | 7 | forward |
| Pro_213 | TFE2(AS) | TGAGTCA | 125 | 131 | 7 | reverse |
| Pro_213 | TFE4 | AACAAAG | 45 | 51 | 7 | forward |
| Pro_213 | TFE4 | AACAAAG | 58 | 64 | 7 | reverse |
| Pro_213 | TFE4(AS) | CTTTGTT | 45 | 51 | 7 | reverse |
| Pro_213 | TFE4(AS) | CTTTGTT | 58 | 64 | 7 | forward |
| Pro_213 | TFE6 | CCTCCCAAA | 71 | 79 | 9 | reverse |
| Pro_213 | TFE6(AS) | TTTGGGAGG | 71 | 79 | 9 | forward |
| Pro_213 | TFE9 | CTTTGAT | 112 | 118 | 7 | reverse |
| Pro_213 | TFE9(AS) | ATCAAAG | 112 | 118 | 7 | forward |
| Pro_213 | TFE10 | GCTGGGATTACAGGTGTGAG | 86 | 105 | 20 | forward |
| Pro_213 | TFE10(AS) | CTCACACCTGTAATCCCAGC | 86 | 105 | 20 | reverse |
| Pro_214 | TFE1 | ATGCAAAT | 72 | 79 | 8 | forward |
| Pro_214 | TFE1(AS) | ATTTGCAT | 72 | 79 | 8 | reverse |
| Pro_214 | TFE2 | TGACTCA | 86 | 92 | 7 | reverse |
| Pro_214 | TFE2(AS) | TGAGTCA | 86 | 92 | 7 | forward |
| Pro_214 | TFE7 | TGACATCA | 45 | 52 | 8 | forward |
| Pro_214 | TFE7(AS) | TGATGTCA | 45 | 52 | 8 | reverse |
| Pro_214 | TFE8 | TTCAAAG | 59 | 65 | 7 | forward |
| Pro_214 | TFE8(AS) | CTTTGAA | 59 | 65 | 7 | reverse |
| Pro_215 | TFE1 | ATGCAAAT | 71 | 78 | 8 | reverse |
| Pro_215 | TFE1 | ATGCAAAT | 99 | 106 | 8 | reverse |
| Pro_215 | TFE1(AS) | ATTTGCAT | 71 | 78 | 8 | forward |
| Pro_215 | TFE1(AS) | ATTTGCAT | 99 | 106 | 8 | forward |
| Pro_215 | TFE4 | AACAAAG | 58 | 64 | 7 | forward |
| Pro_215 | TFE4(AS) | CTTTGTT | 58 | 64 | 7 | reverse |
| Pro_215 | TFE6 | CCTCCCAAA | 113 | 121 | 9 | forward |
| Pro_215 | TFE6(AS) | TTTGGGAGG | 113 | 121 | 9 | reverse |
| Pro_215 | TFE7 | TGACATCA | 85 | 92 | 8 | forward |
| Pro_215 | TFE7(AS) | TGATGTCA | 85 | 92 | 8 | reverse |
| Pro_216 | TFE1 | ATGCAAAT | 45 | 52 | 8 | forward |
| Pro_216 | TFE1(AS) | ATTTGCAT | 45 | 52 | 8 | reverse |
| Pro_216 | TFE5 | TGAGTCA | 59 | 65 | 7 | forward |
| Pro_216 | TFE5 | TGAGTCA | 85 | 91 | 7 | forward |
| Pro_216 | TFE5(AS) | TGACTCA | 59 | 65 | 7 | reverse |
| Pro_216 | TFE5(AS) | TGACTCA | 85 | 91 | 7 | reverse |
| Pro_216 | TFE8 | TTCAAAG | 72 | 78 | 7 | forward |

TABLE 7-continued

| Promoter Name | cis Element | Sequence | Start | End | [bp] | Direction |
|---|---|---|---|---|---|---|
| Pro_216 | TFE8(AS) | CTTTGAA | 72 | 78 | 7 | reverse |
| Pro_217 | TFE2 | TGACTCA | 84 | 90 | 7 | reverse |
| Pro_217 | TFE2(AS) | TGAGTCA | 84 | 90 | 7 | forward |
| Pro_217 | TFE4 | AACAAAG | 71 | 77 | 7 | forward |
| Pro_217 | TFE4(AS) | CTTTGTT | 71 | 77 | 7 | reverse |
| Pro_217 | TFE6 | CCTCCCAAA | 110 | 118 | 9 | reverse |
| Pro_217 | TFE6(AS) | TTTGGGAGG | 110 | 118 | 9 | forward |
| Pro_217 | TFE8 | TTCAAAG | 97 | 103 | 7 | reverse |
| Pro_217 | TFE8(AS) | CTTTGAA | 97 | 103 | 7 | forward |
| Pro_217 | TFE10 | GCTGGGATTACAGGTGTGAG | 45 | 64 | 20 | forward |
| Pro_217 | TFE10(AS) | CTCACACCTGTAATCCCAGC | 45 | 64 | 20 | reverse |
| Pro_218 | TFE4 | AACAAAG | 58 | 64 | 7 | reverse |
| Pro_218 | TFE4(AS) | CTTTGTT | 58 | 64 | 7 | forward |
| Pro_219 | TFE6 | CCTCCCAAA | 72 | 80 | 9 | reverse |
| Pro_219 | TFE6(AS) | TTTGGGAGG | 72 | 80 | 9 | forward |
| Pro_219 | TFE7 | TGACATCA | 45 | 52 | 8 | forward |
| Pro_219 | TFE7(AS) | TGATGTCA | 45 | 52 | 8 | reverse |
| Pro_219 | TFE8 | TTCAAAG | 100 | 106 | 7 | forward |
| Pro_219 | TFE8(AS) | CTTTGAA | 100 | 106 | 7 | reverse |
| Pro_219 | TFE9 | CTTTGAT | 59 | 65 | 7 | reverse |
| Pro_219 | TFE9 | CTTTGAT | 89 | 95 | 7 | forward |
| Pro_219 | TFE9(AS) | ATCAAAG | 59 | 65 | 7 | forward |
| Pro_219 | TFE9(AS) | ATCAAAG | 89 | 95 | 7 | reverse |
| Pro_220 | TFE2 | TGACTCA | 45 | 51 | 7 | forward |
| Pro_220 | TFE2(AS) | TGAGTCA | 45 | 51 | 7 | reverse |
| Pro_221 | TFE1 | ATGCAAAT | 58 | 65 | 8 | forward |
| Pro_221 | TFE1(AS) | ATTTGCAT | 58 | 65 | 8 | reverse |
| Pro_221 | TFE2 | TGACTCA | 45 | 51 | 7 | reverse |
| Pro_221 | TFE2(AS) | TGAGTCA | 45 | 51 | 7 | forward |
| Pro_222 | TFE1 | ATGCAAAT | 123 | 130 | 8 | forward |
| Pro_222 | TFE1(AS) | ATTTGCAT | 123 | 130 | 8 | reverse |
| Pro_222 | TFE2 | TGACTCA | 97 | 103 | 7 | reverse |
| Pro_222 | TFE2(AS) | TGAGTCA | 97 | 103 | 7 | forward |
| Pro_222 | TFE8 | TTCAAAG | 84 | 90 | 7 | forward |
| Pro_222 | TFE8(AS) | CTTTGAA | 84 | 90 | 7 | reverse |
| Pro_222 | TFE9 | CTTTGAT | 45 | 51 | 7 | forward |
| Pro_222 | TFE9(AS) | ATCAAAG | 45 | 51 | 7 | reverse |

TABLE 7-continued

| Promoter Name | cis Element | Sequence | Start | End | [bp] | Direction |
|---|---|---|---|---|---|---|
| Pro_223 | TFE2(AS) | TGAGTCA | 126 | 132 | 7 | forward |
| Pro_223 | TFE3 | ATTTGCAT | 98 | 105 | 8 | forward |
| Pro_223 | TFE3 | ATTTGCAT | 112 | 119 | 8 | reverse |
| Pro_223 | TFE3(AS) | ATGCAAAT | 98 | 105 | 8 | reverse |
| Pro_223 | TFE3(AS) | ATGCAAAT | 112 | 119 | 8 | forward |
| Pro_223 | TFE5 | TGAGTCA | 72 | 78 | 7 | reverse |
| Pro_223 | TFE5 | TGAGTCA | 85 | 91 | 7 | forward |
| Pro_223 | TFE5 | TGAGTCA | 126 | 132 | 7 | forward |
| Pro_223 | TFE5(AS) | TGACTCA | 72 | 78 | 7 | forward |
| Pro_223 | TFE5(AS) | TGACTCA | 85 | 91 | 7 | reverse |
| Pro_223 | TFE7 | TGACATCA | 45 | 52 | 8 | reverse |
| Pro_223 | TFE7(AS) | TGATGTCA | 45 | 52 | 8 | forward |
| Pro_223 | TFE9 | CTTTGAT | 59 | 65 | 7 | forward |
| Pro_223 | TFE9(AS) | ATCAAAG | 59 | 65 | 7 | reverse |
| Pro_224 | TFE2 | TGACTCA | 72 | 78 | 7 | reverse |
| Pro_224 | TFE2(AS) | TGAGTCA | 72 | 78 | 7 | forward |
| Pro_224 | TFE7 | TGACATCA | 45 | 52 | 8 | reverse |
| Pro_224 | TFE7(AS) | TGATGTCA | 45 | 52 | 8 | forward |
| Pro_225 | TFE1 | ATGCAAAT | 71 | 78 | 8 | forward |
| Pro_225 | TFE1(AS) | ATTTGCAT | 71 | 78 | 8 | reverse |
| Pro_225 | TFE4 | AACAAAG | 58 | 64 | 7 | reverse |
| Pro_225 | TFE4(AS) | CTTTGTT | 58 | 64 | 7 | forward |
| Pro_225 | TFE5 | TGAGTCA | 85 | 91 | 7 | reverse |
| Pro_225 | TFE5(AS) | TGACTCA | 85 | 91 | 7 | forward |
| Pro_225 | TFE6 | CCTCCCAAA | 98 | 106 | 9 | reverse |
| Pro_225 | TFE6(AS) | TTTGGGAGG | 98 | 106 | 9 | forward |
| Pro_225 | TFE8 | TTCAAAG | 45 | 51 | 7 | reverse |
| Pro_225 | TFE8(AS) | CTTTGAA | 45 | 51 | 7 | forward |
| Pro_225 | TFE9 | CTTTGAT | 38 | 44 | 7 | forward |
| Pro_225 | TFE9(AS) | ATCAAAG | 38 | 44 | 7 | reverse |
| Pro_226 | TFE2 | TGACTCA | 123 | 129 | 7 | reverse |
| Pro_226 | TFE2(AS) | TGAGTCA | 123 | 129 | 7 | forward |
| Pro_226 | TFE4 | AACAAAG | 58 | 64 | 7 | reverse |
| Pro_226 | TFE4 | AACAAAG | 110 | 116 | 7 | forward |
| Pro_226 | TFE4(AS) | CTTTGTT | 58 | 64 | 7 | forward |
| Pro_226 | TFE4(AS) | CTTTGTT | 110 | 116 | 7 | reverse |
| Pro_226 | TFE8 | TTCAAAG | 45 | 51 | 7 | forward |
| Pro_226 | TFE8 | TTCAAAG | 71 | 77 | 7 | forward |
| Pro_226 | TFE8 | TTCAAAG | 97 | 103 | 7 | forward |

TABLE 7-continued

| Promoter Name | cis Element | Sequence | Start | End | [bp] | Direction |
|---|---|---|---|---|---|---|
| Pro_226 | TFE8(AS) | CTTTGAA | 45 | 51 | 7 | reverse |
| Pro_226 | TFE8(AS) | CTTTGAA | 71 | 77 | 7 | reverse |
| Pro_226 | TFE8(AS) | CTTTGAA | 97 | 103 | 7 | reverse |
| Pro_226 | TFE9 | CTTTGAT | 136 | 142 | 7 | reverse |
| Pro_226 | TFE9(AS) | ATCAAAG | 136 | 142 | 7 | forward |
| Pro_227 | TFE1 | ATGCAAAT | 45 | 52 | 8 | reverse |
| Pro_227 | TFE1(AS) | ATTTGCAT | 45 | 52 | 8 | forward |
| Pro_227 | TFE3 | ATTTGCAT | 99 | 106 | 8 | forward |
| Pro_227 | TFE3(AS) | ATGCAAAT | 99 | 106 | 8 | reverse |
| Pro_227 | TFE4 | AACAAAG | 72 | 78 | 7 | reverse |
| Pro_227 | TFE4(AS) | CTTTGTT | 72 | 78 | 7 | forward |
| Pro_227 | TFE5 | TGAGTCA | 59 | 65 | 7 | forward |
| Pro_227 | TFE5(AS) | TGACTCA | 59 | 65 | 7 | reverse |
| Pro_227 | TFE7 | TGACATCA | 85 | 92 | 8 | reverse |
| Pro_227 | TFE7(AS) | TGATGTCA | 85 | 92 | 8 | forward |
| Pro_228 | TFE6 | CCTCCCAAA | 44 | 52 | 9 | forward |
| Pro_228 | TFE6(AS) | TTTGGGAGG | 44 | 52 | 9 | reverse |
| Pro_228 | TFE7 | TGACATCA | 85 | 92 | 8 | forward |
| Pro_228 | TFE7(AS) | TGATGTCA | 85 | 92 | 8 | reverse |
| Pro_228 | TFE8 | TTCAAAG | 59 | 65 | 7 | forward |
| Pro_228 | TFE8(AS) | CTTTGAA | 59 | 65 | 7 | reverse |
| Pro_229 | TFE1 | ATGCAAAT | 71 | 78 | 8 | reverse |
| Pro_229 | TFE1(AS) | ATTTGCAT | 71 | 78 | 8 | forward |
| Pro_229 | TFE5 | TGAGTCA | 45 | 51 | 7 | forward |
| Pro_229 | TFE5 | TGAGTCA | 58 | 64 | 7 | forward |
| Pro_229 | TFE5(AS) | TGACTCA | 45 | 51 | 7 | reverse |
| Pro_229 | TFE5(AS) | TGACTCA | 58 | 64 | 7 | reverse |
| Pro_229 | TFE8 | TTCAAAG | 85 | 91 | 7 | forward |
| Pro_229 | TFE8(AS) | CTTTGAA | 85 | 91 | 7 | reverse |
| Pro_230 | TFE3 | ATTTGCAT | 45 | 52 | 8 | forward |
| Pro_230 | TFE3 | ATTTGCAT | 59 | 66 | 8 | forward |
| Pro_230 | TFE3 | ATTTGCAT | 86 | 93 | 8 | reverse |
| Pro_230 | TFE3(AS) | ATGCAAAT | 45 | 52 | 8 | reverse |
| Pro_230 | TFE3(AS) | ATGCAAAT | 59 | 66 | 8 | reverse |
| Pro_230 | TFE3(AS) | ATGCAAAT | 86 | 93 | 8 | forward |
| Pro_230 | TFE5 | TGAGTCA | 73 | 79 | 7 | forward |
| Pro_230 | TFE5(AS) | TGACTCA | 73 | 79 | 7 | reverse |
| Pro_231 | TFE1 | ATGCAAAT | 72 | 79 | 8 | forward |

TABLE 7-continued

| Promoter Name | cis Element | Sequence | Start | End | [bp] | Direction |
|---|---|---|---|---|---|---|
| Pro_231 | TFE1(AS) | ATTTGCAT | 72 | 79 | 8 | reverse |
| Pro_231 | TFE4 | AACAAAG | 59 | 65 | 7 | reverse |
| Pro_231 | TFE4(AS) | CTTTGTT | 59 | 65 | 7 | forward |
| Pro_231 | TFE5 | TGAGTCA | 86 | 92 | 7 | reverse |
| Pro_231 | TFE5(AS) | TGACTCA | 86 | 92 | 7 | forward |
| Pro_231 | TFE6 | CCTCCCAAA | 99 | 107 | 9 | reverse |
| Pro_231 | TFE6(AS) | TTTGGGAGG | 99 | 107 | 9 | forward |
| Pro_231 | TFE7 | TGACATCA | 45 | 52 | 8 | reverse |
| Pro_231 | TFE7(AS) | TGATGTCA | 45 | 52 | 8 | forward |
| Pro_232 | TFE1 | ATGCAAAT | 53 | 60 | 8 | reverse |
| Pro_232 | TFE1(AS) | ATTTGCAT | 53 | 60 | 8 | forward |
| Pro_232 | TFE3 | ATTTGCAT | 67 | 74 | 8 | forward |
| Pro_232 | TFE3(AS) | ATGCAAAT | 67 | 74 | 8 | reverse |
| Pro_232 | TFE5 | TGAGTCA | 107 | 113 | 7 | reverse |
| Pro_232 | TFE5(AS) | TGACTCA | 107 | 113 | 7 | forward |
| Pro_232 | TFE8 | TTCAAAG | 94 | 100 | 7 | reverse |
| Pro_232 | TFE8(AS) | CTTTGAA | 94 | 100 | 7 | forward |
| Pro_233 | TFE1 | ATGCAAAT | 58 | 65 | 8 | forward |
| Pro_233 | TFE1(AS) | ATTTGCAT | 58 | 65 | 8 | reverse |
| Pro_233 | TFE4 | AACAAAG | 45 | 51 | 7 | forward |
| Pro_233 | TFE4 | AACAAAG | 72 | 78 | 7 | forward |
| Pro_233 | TFE4(AS) | CTTTGTT | 45 | 51 | 7 | reverse |
| Pro_233 | TFE4(AS) | CTTTGTT | 72 | 78 | 7 | reverse |
| Pro_233 | TFE8 | TTCAAAG | 85 | 91 | 7 | reverse |
| Pro_233 | TFE8(AS) | CTTTGAA | 85 | 91 | 7 | forward |
| Pro_234 | TFE5 | TGAGTCA | 49 | 55 | 7 | forward |
| Pro_234 | TFE5 | TGAGTCA | 62 | 68 | 7 | reverse |
| Pro_234 | TFE5 | TGAGTCA | 103 | 109 | 7 | forward |
| Pro_234 | TFE5(AS) | TGACTCA | 49 | 55 | 7 | reverse |
| Pro_234 | TFE5(AS) | TGACTCA | 62 | 68 | 7 | forward |
| Pro_234 | TFE5(AS) | TGACTCA | 103 | 109 | 7 | reverse |
| Pro_234 | TFE6 | CCTCCCAAA | 88 | 96 | 9 | forward |
| Pro_234 | TFE6(AS) | TTTGGGAGG | 88 | 96 | 9 | reverse |
| Pro_234 | TFE7 | TGACATCA | 116 | 123 | 8 | forward |
| Pro_234 | TFE7 | TGACATCA | 130 | 137 | 8 | reverse |
| Pro_234 | TFE7(AS) | TGATGTCA | 116 | 123 | 8 | reverse |
| Pro_234 | TFE7(AS) | TGATGTCA | 130 | 137 | 8 | forward |
| Pro_235 | TFE3 | ATTTGCAT | 45 | 52 | 8 | forward |
| Pro_235 | TFE3(AS) | ATGCAAAT | 45 | 52 | 8 | reverse |

TABLE 7-continued

| Promoter Name | cis Element | Sequence | Start | End | [bp] | Direction |
|---|---|---|---|---|---|---|
| Pro_235 | TFE4 | AACAAAG | 72 | 78 | 7 | reverse |
| Pro_235 | TFE4(AS) | CTTTGTT | 72 | 78 | 7 | forward |
| Pro_235 | TFE5 | TGAGTCA | 59 | 65 | 7 | forward |
| Pro_235 | TFE5 | TGAGTCA | 85 | 91 | 7 | forward |
| Pro_235 | TFE5 | TGAGTCA | 98 | 104 | 7 | forward |
| Pro_235 | TFE5(AS) | TGACTCA | 59 | 65 | 7 | reverse |
| Pro_235 | TFE5(AS) | TGACTCA | 85 | 91 | 7 | reverse |
| Pro_235 | TFE5(AS) | TGACTCA | 98 | 104 | 7 | reverse |
| Pro_236 | TFE1 | ATGCAAAT | 72 | 79 | 8 | forward |
| Pro_236 | TFE1(AS) | ATTTGCAT | 72 | 79 | 8 | reverse |
| Pro_236 | TFE2 | TGACTCA | 59 | 65 | 7 | reverse |
| Pro_236 | TFE2(AS) | TGAGTCA | 59 | 65 | 7 | forward |
| Pro_236 | TFE7 | TGACATCA | 45 | 52 | 8 | reverse |
| Pro_236 | TFE7(AS) | TGATGTCA | 45 | 52 | 8 | forward |
| Pro_237 | TFE2 | TGACTCA | 99 | 105 | 7 | forward |
| Pro_237 | TFE2(AS) | TGAGTCA | 99 | 105 | 7 | reverse |
| Pro_237 | TFE3 | ATTTGCAT | 57 | 64 | 8 | forward |
| Pro_237 | TFE3 | ATTTGCAT | 71 | 78 | 8 | forward |
| Pro_237 | TFE3(AS) | ATGCAAAT | 57 | 64 | 8 | reverse |
| Pro_237 | TFE3(AS) | ATGCAAAT | 71 | 78 | 8 | reverse |
| Pro_237 | TFE4 | AACAAAG | 18 | 24 | 7 | forward |
| Pro_237 | TFE4(AS) | CTTTGTT | 18 | 24 | 7 | reverse |
| Pro_237 | TFE5 | TGAGTCA | 31 | 37 | 7 | reverse |
| Pro_237 | TFE5 | TGAGTCA | 44 | 50 | 7 | forward |
| Pro_237 | TFE5(AS) | TGACTCA | 31 | 37 | 7 | forward |
| Pro_237 | TFE5(AS) | TGACTCA | 44 | 50 | 7 | reverse |
| Pro_237 | TFE6 | CCTCCCAAA | 165 | 173 | 9 | forward |
| Pro_237 | TFE6(AS) | TTTGGGAGG | 165 | 173 | 9 | reverse |
| Pro_237 | TFE7 | TGACATCA | 85 | 92 | 8 | forward |
| Pro_237 | TFE7 | TGACATCA | 112 | 119 | 8 | forward |
| Pro_237 | TFE7(AS) | TGATGTCA | 85 | 92 | 8 | reverse |
| Pro_237 | TFE7(AS) | TGATGTCA | 112 | 119 | 8 | reverse |
| Pro_237 | TFE8 | TTCAAAG | 126 | 132 | 7 | forward |
| Pro_237 | TFE8(AS) | CTTTGAA | 126 | 132 | 7 | reverse |
| Pro_237 | TFE10 | GCTGGGATTACAGGTGTGAG | 139 | 158 | 20 | reverse |
| Pro_237 | TFE10 (AS) | CTCACACCTGTAATCCCAGC | 139 | 158 | 20 | forward |
| Pro_238 | TFE1 | ATGCAAAT | 58 | 65 | 8 | forward |

TABLE 7-continued

| Promoter Name | cis Element | Sequence | Start | End | [bp] | Direction |
|---|---|---|---|---|---|---|
| Pro_238 | TFE1(AS) | ATTTGCAT | 58 | 65 | 8 | reverse |
| Pro_238 | TFE8 | TTCAAAG | 45 | 51 | 7 | reverse |
| Pro_238 | TFE8(AS) | CTTTGAA | 45 | 51 | 7 | forward |
| Pro_238 | TFE9 | CTTTGAT | 38 | 44 | 7 | forward |
| Pro_238 | TFE9(AS) | ATCAAAG | 38 | 44 | 7 | reverse |
| Pro_239 | TFE1 | ATGCAAAT | 96 | 103 | 8 | reverse |
| Pro_239 | TFE1 | ATGCAAAT | 124 | 131 | 8 | forward |
| Pro_239 | TFE1(AS) | ATTTGCAT | 96 | 103 | 8 | forward |
| Pro_239 | TFE1(AS) | ATTTGCAT | 124 | 131 | 8 | reverse |
| Pro_239 | TFE4 | AACAAAG | 18 | 24 | 7 | reverse |
| Pro_239 | TFE4 | AACAAAG | 44 | 50 | 7 | forward |
| Pro_239 | TFE4(AS) | CTTTGTT | 18 | 24 | 7 | forward |
| Pro_239 | TFE4(AS) | CTTTGTT | 44 | 50 | 7 | reverse |
| Pro_239 | TFE5 | TGAGTCA | 31 | 37 | 7 | forward |
| Pro_239 | TFE5(AS) | TGACTCA | 31 | 37 | 7 | reverse |
| Pro_239 | TFE9 | CTTTGAT | 57 | 63 | 7 | reverse |
| Pro_239 | TFE9(AS) | ATCAAAG | 57 | 63 | 7 | forward |
| Pro_240 | TFE1 | ATGCAAAT | 78 | 85 | 8 | reverse |
| Pro_240 | TFE1(AS) | ATTTGCAT | 78 | 85 | 8 | forward |
| Pro_240 | TFE7 | TGACATCA | 92 | 99 | 8 | forward |
| Pro_240 | TFE7(AS) | TGATGTCA | 92 | 99 | 8 | reverse |
| Pro_240 | TFE10 | GCTGGGATTACAGGTGTGAG | 14 | 33 | 20 | forward |
| Pro_240 | TFE10 | GCTGGGATTACAGGTGTGAG | 52 | 71 | 20 | forward |
| Pro_240 | TFE10(AS) | CTCACACCTGTAATCCCAGC | 14 | 33 | 20 | reverse |
| Pro_240 | TFE10(AS) | CTCACACCTGTAATCCCAGC | 52 | 71 | 20 | reverse |
| Pro_241 | TFE9 | CTTTGAT | 58 | 64 | 7 | reverse |
| Pro_241 | TFE9(AS) | ATCAAAG | 58 | 64 | 7 | forward |
| Pro_242 | TFE2 | TGACTCA | 121 | 127 | 7 | reverse |
| Pro_242 | TFE2(AS) | TGAGTCA | 121 | 127 | 7 | forward |
| Pro_242 | TFE3 | ATTTGCAT | 71 | 78 | 8 | reverse |
| Pro_242 | TFE3(AS) | ATGCAAAT | 71 | 78 | 8 | forward |
| Pro_242 | TFE5 | TGAGTCA | 58 | 64 | 7 | reverse |
| Pro_242 | TFE5 | TGAGTCA | 85 | 91 | 7 | forward |
| Pro_242 | TFE5 | TGAGTCA | 98 | 104 | 7 | reverse |
| Pro_242 | TFE5(AS) | TGACTCA | 58 | 64 | 7 | forward |
| Pro_242 | TFE5(AS) | TGACTCA | 85 | 91 | 7 | reverse |
| Pro_242 | TFE5(AS) | TGACTCA | 98 | 104 | 7 | forward |

TABLE 7-continued

| Promoter Name | cis Element | Sequence | Start | End | [bp] | Direction |
|---|---|---|---|---|---|---|
| Pro_242 | TFE7 | TGACATCA | 111 | 118 | 8 | reverse |
| Pro_242 | TFE7(AS) | TGATGTCA | 111 | 118 | 8 | forward |
| Pro_243 | TFE1 | ATGCAAAT | 45 | 52 | 8 | reverse |
| Pro_243 | TFE1 | ATGCAAAT | 59 | 66 | 8 | forward |
| Pro_243 | TFE1(AS) | ATTTGCAT | 45 | 52 | 8 | forward |
| Pro_243 | TFE1(AS) | ATTTGCAT | 59 | 66 | 8 | reverse |
| Pro_244 | TFE1 | ATGCAAAT | 60 | 67 | 8 | reverse |
| Pro_244 | TFE1(AS) | ATTTGCAT | 60 | 67 | 8 | forward |
| Pro_244 | TFE6 | CCTCCCAAA | 45 | 53 | 9 | reverse |
| Pro_244 | TFE6(AS) | TTTGGGAGG | 45 | 53 | 9 | forward |
| Pro_245 | TFE7 | TGACATCA | 45 | 52 | 8 | reverse |
| Pro_245 | TFE7(AS) | TGATGTCA | 45 | 52 | 8 | forward |
| Pro_245 | TFE8 | TTCAAAG | 59 | 65 | 7 | forward |
| Pro_245 | TFE8 | TTCAAAG | 72 | 78 | 7 | reverse |
| Pro_245 | TFE8(AS) | CTTTGAA | 59 | 65 | 7 | reverse |
| Pro_245 | TFE8(AS) | CTTTGAA | 72 | 78 | 7 | forward |
| Pro_246 | TFE1 | ATGCAAAT | 58 | 65 | 8 | reverse |
| Pro_246 | TFE1(AS) | ATTTGCAT | 58 | 65 | 8 | forward |
| Pro_246 | TFE3 | ATTTGCAT | 87 | 94 | 8 | reverse |
| Pro_246 | TFE3(AS) | ATGCAAAT | 87 | 94 | 8 | forward |
| Pro_246 | TFE5 | TGAGTCA | 101 | 107 | 7 | reverse |
| Pro_246 | TFE5(AS) | TGACTCA | 101 | 107 | 7 | forward |
| Pro_246 | TFE6 | CCTCCCAAA | 72 | 80 | 9 | reverse |
| Pro_246 | TFE6(AS) | TTTGGGAGG | 72 | 80 | 9 | forward |
| Pro_247 | TFE1 | ATGCAAAT | 100 | 107 | 8 | reverse |
| Pro_247 | TFE1(AS) | ATTTGCAT | 100 | 107 | 8 | forward |
| Pro_247 | TFE4 | AACAAAG | 45 | 51 | 7 | reverse |
| Pro_247 | TFE4 | AACAAAG | 127 | 133 | 7 | forward |
| Pro_247 | TFE4(AS) | CTTTGTT | 45 | 51 | 7 | forward |
| Pro_247 | TFE4(AS) | CTTTGTT | 127 | 133 | 7 | reverse |
| Pro_247 | TFE6 | CCTCCCAAA | 71 | 79 | 9 | reverse |
| Pro_247 | TFE6(AS) | TTTGGGAGG | 71 | 79 | 9 | forward |
| Pro_247 | TFE8 | TTCAAAG | 58 | 64 | 7 | reverse |
| Pro_247 | TFE8(AS) | CTTTGAA | 58 | 64 | 7 | forward |
| Pro_247 | TFE9 | CTTTGAT | 114 | 120 | 7 | reverse |
| Pro_247 | TFE9(AS) | ATCAAAG | 114 | 120 | 7 | forward |
| Pro_248 | TFE1 | ATGCAAAT | 45 | 52 | 8 | reverse |
| Pro_248 | TFE1(AS) | ATTTGCAT | 45 | 52 | 8 | forward |

TABLE 7-continued

| Promoter Name | cis Element | Sequence | Start | End | [bp] | Direction |
|---|---|---|---|---|---|---|
| Pro_248 | TFE4 | AACAAAG | 98 | 104 | 7 | forward |
| Pro_248 | TFE4 | AACAAAG | 137 | 143 | 7 | forward |
| Pro_248 | TFE4(AS) | CTTTGTT | 98 | 104 | 7 | reverse |
| Pro_248 | TFE4(AS) | CTTTGTT | 137 | 143 | 7 | reverse |
| Pro_248 | TFE5 | TGAGTCA | 111 | 117 | 7 | forward |
| Pro_248 | TFE5 | TGAGTCA | 124 | 130 | 7 | reverse |
| Pro_248 | TFE5(AS) | TGACTCA | 111 | 117 | 7 | reverse |
| Pro_248 | TFE5(AS) | TGACTCA | 124 | 130 | 7 | forward |
| Pro_248 | TFE8 | TTCAAAG | 85 | 91 | 7 | reverse |
| Pro_248 | TFE8(AS) | CTTTGAA | 85 | 91 | 7 | forward |
| Pro_248 | TFE9 | CTTTGAT | 150 | 156 | 7 | reverse |
| Pro_248 | TFE9(AS) | ATCAAAG | 150 | 156 | 7 | forward |
| Pro_248 | TFE10 | GCTGGGATTACAGGTGTGAG | 59 | 78 | 20 | forward |
| Pro_248 | TFE10(AS) | CTCACACCTGTAATCCCAGC | 59 | 78 | 20 | reverse |
| Pro_249 | TFE2 | TGACTCA | 58 | 64 | 7 | reverse |
| Pro_249 | TFE2(AS) | TGAGTCA | 58 | 64 | 7 | forward |
| Pro_249 | TFE9 | CTTTGAT | 71 | 77 | 7 | forward |
| Pro_249 | TFE9(AS) | ATCAAAG | 71 | 77 | 7 | reverse |
| Pro_250 | TFE2 | TGACTCA | 58 | 64 | 7 | forward |
| Pro_250 | TFE2(AS) | TGAGTCA | 58 | 64 | 7 | reverse |
| Pro_250 | TFE4 | AACAAAG | 84 | 90 | 7 | reverse |
| Pro_250 | TFE4(AS) | CTTTGTT | 84 | 90 | 7 | forward |
| Pro_250 | TFE8 | TTCAAAG | 45 | 51 | 7 | forward |
| Pro_250 | TFE8(AS) | CTTTGAA | 45 | 51 | 7 | reverse |
| Pro_250 | TFE9 | CTTTGAT | 71 | 77 | 7 | forward |
| Pro_250 | TFE9(AS) | ATCAAAG | 71 | 77 | 7 | reverse |
| Pro_250 | TFE10 | GCTGGGATTACAGGTGTGAG | 97 | 116 | 20 | reverse |
| Pro_250 | TFE10(AS) | CTCACACCTGTAATCCCAGC | 97 | 116 | 20 | forward |
| Pro_251 | TFE10 | GCTGGGATTACAGGTGTGAG | 44 | 63 | 20 | reverse |
| Pro_251 | TFE10(AS) | CTCACACCTGTAATCCCAGC | 44 | 63 | 20 | forward |
| Pro_252 | TFE1 | ATGCAAAT | 122 | 129 | 8 | forward |
| Pro_252 | TFE1(AS) | ATTTGCAT | 122 | 129 | 8 | reverse |
| Pro_252 | TFE2 | TGACTCA | 96 | 102 | 7 | reverse |
| Pro_252 | TFE2(AS) | TGAGTCA | 96 | 102 | 7 | forward |
| Pro_252 | TFE8 | TTCAAAG | 83 | 89 | 7 | forward |
| Pro_252 | TFE8(AS) | CTTTGAA | 83 | 89 | 7 | reverse |

TABLE 7-continued

| Promoter Name | cis Element | Sequence | Start | End | [bp] | Direction |
|---|---|---|---|---|---|---|
| Pro_252 | TFE9 | CTTTGAT | 44 | 50 | 7 | forward |
| Pro_252 | TFE9(AS) | ATCAAAG | 44 | 50 | 7 | reverse |
| Pro_253 | TFE2 | TGACTCA | 60 | 66 | 7 | reverse |
| Pro_253 | TFE2(AS) | TGAGTCA | 60 | 66 | 7 | forward |
| Pro_253 | TFE6 | CCTCCCAAA | 45 | 53 | 9 | reverse |
| Pro_253 | TFE6(AS) | TTTGGGAGG | 45 | 53 | 9 | forward |
| Pro_253 | TFE8 | TTCAAAG | 73 | 79 | 7 | reverse |
| Pro_253 | TFE8(AS) | CTTTGAA | 73 | 79 | 7 | forward |
| Pro_254 | TFE1 | ATGCAAAT | 84 | 91 | 8 | reverse |
| Pro_254 | TFE1 | ATGCAAAT | 111 | 118 | 8 | reverse |
| Pro_254 | TFE1(AS) | ATTTGCAT | 84 | 91 | 8 | forward |
| Pro_254 | TFE1(AS) | ATTTGCAT | 111 | 118 | 8 | forward |
| Pro_254 | TFE8 | TTCAAAG | 58 | 64 | 7 | reverse |
| Pro_254 | TFE8(AS) | CTTTGAA | 58 | 64 | 7 | forward |
| Pro_254 | TFE9 | CTTTGAT | 98 | 104 | 7 | forward |
| Pro_254 | TFE9 | CTTTGAT | 124 | 130 | 7 | reverse |
| Pro_254 | TFE9(AS) | ATCAAAG | 98 | 104 | 7 | reverse |
| Pro_254 | TFE9(AS) | ATCAAAG | 124 | 130 | 7 | forward |
| Pro_255 | TFE4 | AACAAAG | 26 | 32 | 7 | forward |
| Pro_255 | TFE4(AS) | CTTTGTT | 26 | 32 | 7 | reverse |
| Pro_255 | TFE4 | AACAAAG | 18 | 24 | 7 | reverse |
| Pro_255 | TFE4(AS) | CTTTGTT | 18 | 24 | 7 | forward |

The invention claimed is:

1. A method for making a transcription-enhancing combined promoter cassette, the method comprising:
   (a) identifying a plurality of transcription factor regulatory elements (TFREs), wherein each of the plurality of TFREs is associated with a plurality of genes, each of which is differentially expressed in a particular cell type or tissue type, or under a particular condition;
   (b) determining the frequency, length and SYN value for each of said plurality of TFREs provided in step (a), and selecting TFREs from among the plurality of TFREs provided in step (a), wherein each of the selected TFREs (1) is within 20 kilobases of more than fifty percent of the plurality of genes defined in step (a), and (2) has a SYN value larger than 0.3, wherein the SYN value of a TFRE is defined as frequency$^{(1/length)}$, wherein frequency is defined as the number of occurrences of a given TFRE being associated with any of the plurality of genes, divided by the total number of all TFREs associated with any of the plurality of genes, and wherein the frequency is its frequency within 20 kilobases of any of the plurality of the genes and length is the length in nucleotides of the TFRE;
   (c) constructing a library of randomly combined elements by randomly combining TFREs selected in step (b); and
   (d) inserting combined elements from the library of (c) in a vector with a minimum promoter and a reporter gene, thereby generating a transcription-enhancing combined promoter cassette.

2. The method of claim 1, further comprising step (e): inserting the vector into a host cell.

3. The method of claim 2, wherein step (e) produces a plurality of host cells and the method further comprises step (f): screening for a host cell produced in step (e) that shows enhanced expression of the reporter gene.

4. The method of claim 3, further comprising identifying the combined promoter cassette in the host cell produced in step (e) or the host cell selected in step (f).

5. The method of claim 1, wherein the library of randomly combined selected TFREs in step (c) is made by mixing individual double stranded DNA sequence elements encoding at least the selected TFREs together under ligation reaction conditions.

6. The method of claim 1, wherein the reported gene in step (d) is LacZ or GFP.

7. The method of claim 1, wherein each of the plurality of genes is differentially expressed under the particular condition, which is a disease condition.

8. The method of claim 7, wherein the disease condition is cancer.

9. The method of claim 1, wherein each of the plurality of genes is differentially expressed under the particular condition, which is exposure to a particular biological agent, chemical agent, or microbial pathogen.

10. The method of claim 1, wherein a plurality of combined promoter cassettes are generated in step (d) and the method further comprises selecting one or more of the combined promoter cassettes so produced, wherein:
the number of TFREs per promoter in each of the selected combined promoter cassettes is greater than the average number of TFREs per promoter for the plurality of combined promoter cassettes generated in step (d); or
the number of TRFEs per promoter in each of the selected combined promoter cassettes is greater than 2.

11. The method of claim 1, wherein the frequency of occurrence of the TFRE within 20 kilobases of any of the plurality of the genes is the frequency of occurrence of the TFRE within 20 kilobases in the sense strand of any of the plurality of the genes.

* * * * *

UNITED STATES PATENT AND TRADEMARK OFFICE
CERTIFICATE OF CORRECTION

Page 1 of 1

PATENT NO. : 10,508,275 B2
APPLICATION NO. : 13/981894
DATED : December 17, 2019
INVENTOR(S) : Michael L. Roberts It is certified that error appears in the above-identified patent and that said Letters Patent is hereby corrected as shown below:

In the Claims

At Column 224, Line 13:
"TRFEs"

Should be replaced with:
-- TFREs" --

Signed and Sealed this
Fifth Day of January, 2021

Andrei Iancu
*Director of the United States Patent and Trademark Office*